(12) United States Patent
El-Sayed et al.

(10) Patent No.: US 11,045,548 B2
(45) Date of Patent: Jun. 29, 2021

(54) METHODS FOR INHIBITING CANCER CELL MIGRATION WITH GOLD NANOMATERIALS AND PHOTOTHERMAL THERAPY

(71) Applicant: Georgia Tech Research Corporation, Atlanta, GA (US)

(72) Inventors: Mostafa A. El-Sayed, Atlanta, GA (US); Moustafa R. K. Ali, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 16/029,193

(22) Filed: Jul. 6, 2018

(65) Prior Publication Data

US 2019/0008964 A1    Jan. 10, 2019

Related U.S. Application Data

(60) Provisional application No. 62/529,956, filed on Jul. 7, 2017.

(51) Int. Cl.
| | |
|---|---|
| *A61K 9/08* | (2006.01) |
| *A61K 47/64* | (2017.01) |
| *A61K 41/00* | (2020.01) |
| *A61K 47/69* | (2017.01) |
| *A61K 9/00* | (2006.01) |
| *A61N 5/06* | (2006.01) |
| *A61K 47/62* | (2017.01) |
| *A61K 33/242* | (2019.01) |
| *A61N 5/067* | (2006.01) |

(52) U.S. Cl.
CPC ........ *A61K 41/0052* (2013.01); *A61K 9/0019* (2013.01); *A61K 9/08* (2013.01); *A61K 33/242* (2019.01); *A61K 47/62* (2017.08); *A61K 47/64* (2017.08); *A61K 47/6923* (2017.08); *A61K 47/6929* (2017.08); *A61N 5/062* (2013.01); *A61N 5/0613* (2013.01); *A61N 2005/067* (2013.01); *A61N 2005/0658* (2013.01)

(58) Field of Classification Search
CPC .... A61K 33/24; A61K 41/0052; A61K 47/62; A61K 47/64; A61K 47/6923; A61K 47/6929; A61K 9/0019; A61K 9/08; A61N 2005/0658; A61N 2005/067; A61N 5/0613; A61N 5/062
See application file for complete search history.

(56) References Cited

U.S. PATENT DOCUMENTS

2013/0177523 A1* 7/2013 Ghandehari ....... A61K 41/0052
424/78.27

OTHER PUBLICATIONS

Dickerson et al. (Cancer Lett. 2008;269(1):57-66) (Year: 2008).*
Li et al. (Molecular Pharmaceutics 2010 (published online Nov. 5, 2009); 7(1):94-104). (Year: 2009).*
Ali et al. (JACS 2014;136:4464-4467) (Year: 2014).*

(Continued)

*Primary Examiner* — Ernst V Arnold
(74) *Attorney, Agent, or Firm* — Troutman Pepper Hamilton Sanders LLP; Ryan A. Schneider

(57) ABSTRACT

A method of inhibiting migration of a cancer cell of a tumor in a subject comprising the steps of: (a) contacting the tumor with a gold nanomaterial; and (b) irradiating the tumor with an irradiation source.

54 Claims, 84 Drawing Sheets

(56) References Cited

OTHER PUBLICATIONS

Ali et al. (International Jouranl of Nanomedicine 2016;11:4849-4863) (Year: 2016).*
Arvizo, R. R.; Saha, S.; Wang, E.; Robertson, J. D.; Bhattacharya, R.; Mukherjee, P. Inhibition of Tumor Growth and Metastasis by a Self-Therapeutic Nanoparticle. Proc. Natl. Acad. Sci. U. S. A. 2013, 110, 6700-6705.
Tay, C. Y.; Cai, P.; Setyawati, M. I.; Fang, W.; Tan, L. P.; Hong, C. H.; Chen, X.; Leong, D. T. Nanoparticles Strengthen Intracellular Tension and Retard Cellular Migration. Nano Lett. 2014, 14, 83-8.
Zhou, T.; Yu, M. F.; Zhang, B.; Wang, L. M.; Wu, X. C.; Zhou, H. J.; Du, Y. P.; Hao, J. F.; Tu, Y. P.; Chen, C. Y.; et al. Inhibition of Cancer Cell Migration by Gold Nanorods: Molecular Mechanisms and Implications for Cancer Therapy. Adv. Funct. Mater. 2014, 24, 6922-6932.
Kong, L.; Schafer, G.; Bu, H. J.; Zhang, Y.; Zhang, Y. X.; Klocker, H. Lamin A/C Protein Is Overexpressed in Tissue-Invading Prostate Cancer and Promotes Prostate Cancer Cell Growth, Migration and Invasion Through the PI3K/AKT/PTEN Pathway. Carcinogenesis 2012, 33, 751-759.
Ali, M. R. K.; Snyder, B.; El-Sayed, M. A. Synthesis and Optical Properties of Small Au Nanorods Using A Seedless Growth Technique. Langmuir 2012, 28, 9807-9815.
Chen PS, et al. (2007) CTGF Enhances The Motility Of Breast Cancer Cells Via An Integrin-Alphavbeta3-ERK1/2-Dependent S100A4-Upregulated Pathway. J Cell Sci 120:2053-2065.

* cited by examiner

Ctrl

50 μm

AuNRs@PEG

AuNRs@PEG@RGD

Ctrl

AuNSs@NLS

AuNRs@NLS

Surgery only

Photo-micrograph of tumor bed vasculature

Surgery after PPTT

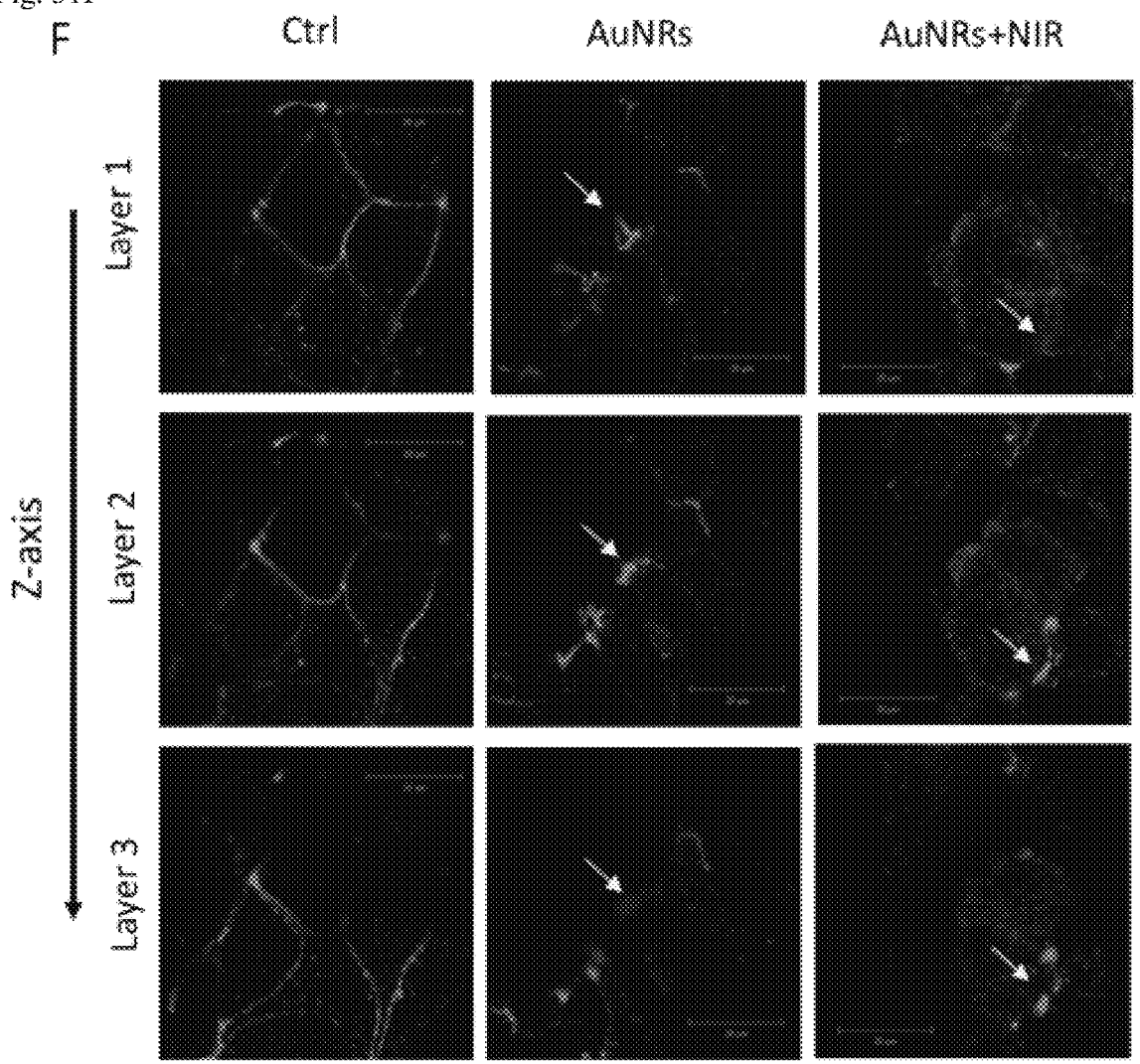

Hela

MCF-7

Fig. 35A
Fig. 35B
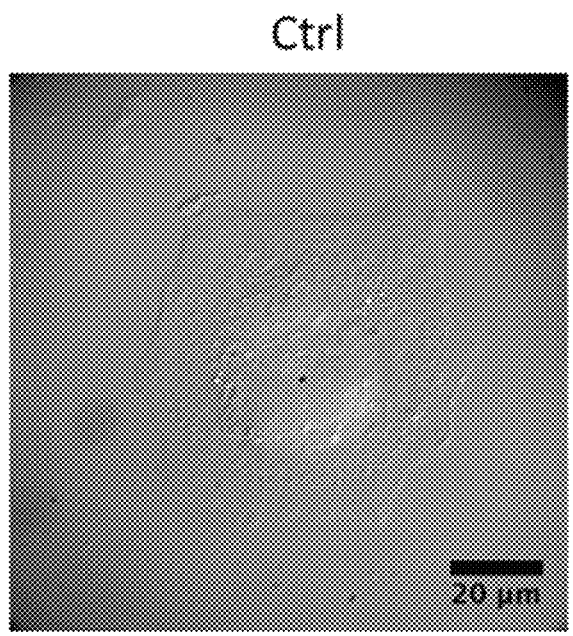
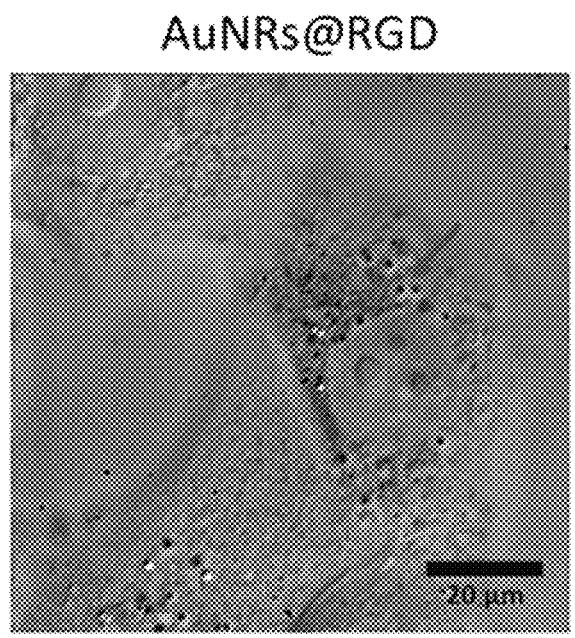
Fig. 35C
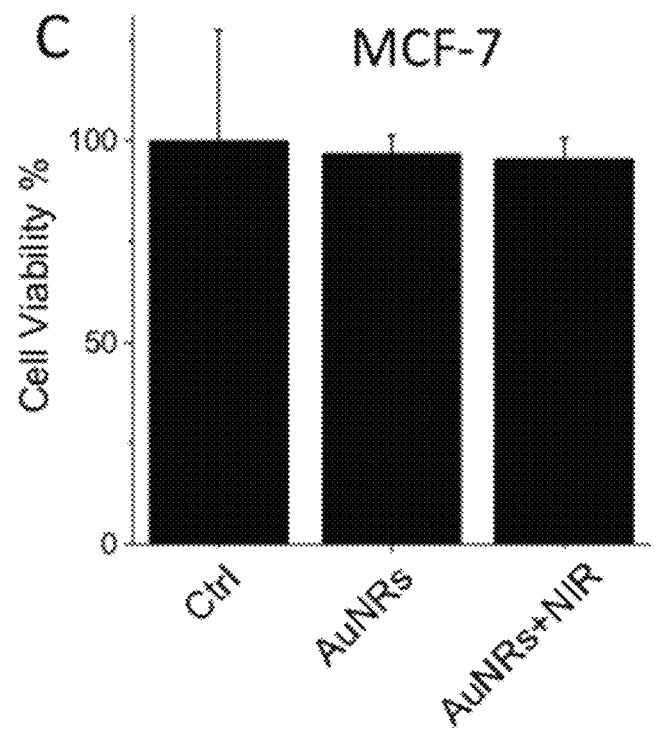

Differentially Phosphorylated Proteins Identified in Each Experiment (MCF7)

Differentially Phosphorylated Proteins Identified in Each Experiment (HeLa)

Fig. 42D
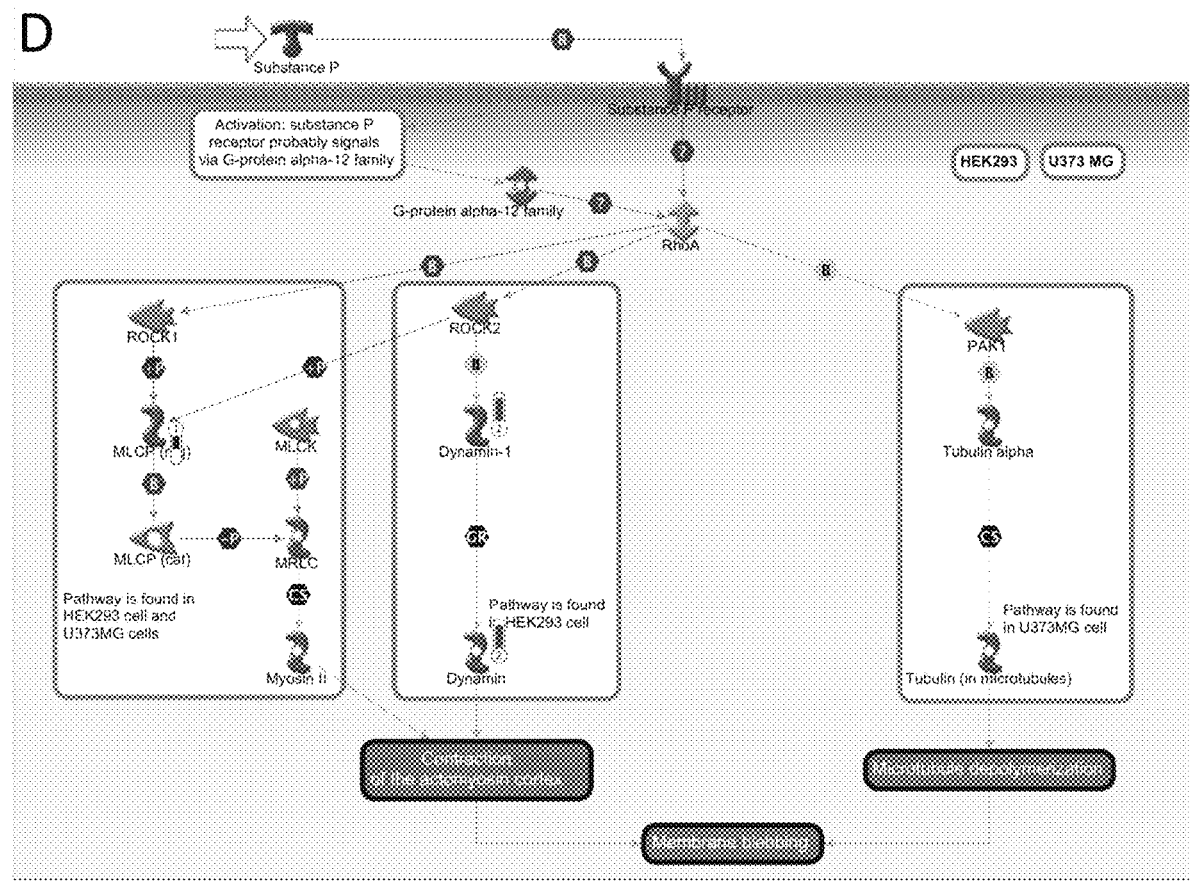
Fig. 43A                    Fig. 43B
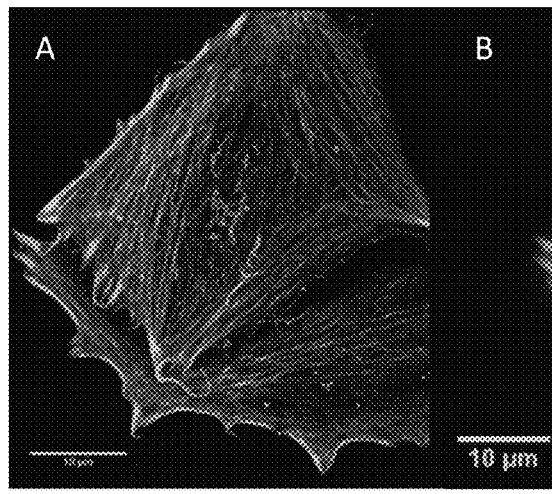 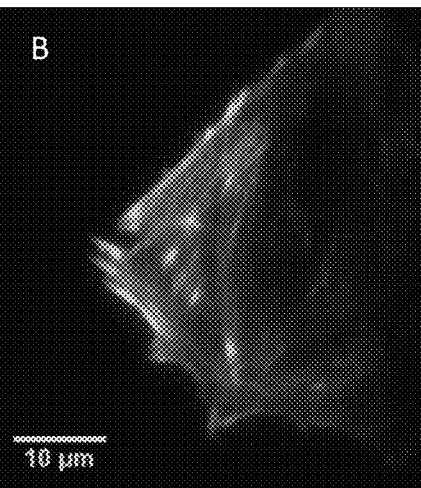

A    Ctrl

B    AuNRs

C    AuNRs+NIR

METHODS FOR INHIBITING CANCER CELL MIGRATION WITH GOLD NANOMATERIALS AND PHOTOTHERMAL THERAPY

CROSS-REFERENCE TO RELATED APPLICATIONS

This application, filed 6 Jul. 2018, claims the benefit of U.S. Provisional Patent Application No. 62/529,956, filed 7 Jul. 2017, entitled "Different Methods for Inhibiting Cancer Cell Migration Based on Gold Nanoparticles" the entire contents and substance of which are hereby incorporated by reference as if fully set forth below.

GOVERNMENT SPONSORSHIP

This invention was made with government support under Grant Nos. 1608801 awarded by the National Science Foundation and GM115763 from the National Institutes of Health. The government has certain rights in the invention.

BACKGROUND OF THE INVENTION

Metastasis is a process that enables cancer cells to spread to other sites of the body and is responsible for most cancer-related deaths. The migration of cancer cells from one site to another requires dramatic remodeling of the cellular cytoskeleton. Studies on the changes of cytoskeletal components could provide novel therapeutic approaches to prevent cancer cell migration and metastasis. The targeting of cytoskeletal components, such as actin or tubulin, or regulatory proteins, such as Rho-ROCK or LIM kinases, has been shown to inhibit the invasive and metastatic behavior of cancer cells. However, the pharmacological inhibitors of cytoskeleton have not been very effective in clinical trials due to their nonspecific targeting of cytoskeleton in normal cells, which might cause side effects, such as cardiotoxicity. Moreover, in many cases, the anticancer drugs that target specific proteins might lose their efficacy after several months of treatment due to mutations of the proteins that result in the rise of drug resistance in cancer cells.

Recent advancements in nanomedicine provide us with great opportunities to avoid the drawbacks of commonly used drugs. Due to their small size and surface modifications, nanoparticles, in general, are able to target tumors selectively and have been widely used in cancer diagnosis and therapy. However, high concentrations of nontargeted nanoparticles (in μM) were used in these previous studies, which might be an obstacle when considering the translation to clinical use. Additionally, several types of nanoparticles, including $TiO_2$, $SiO_2$, iron oxide, etc., have been found to exhibit toxicity when used in relatively high concentrations.

Gold nanomaterial (AuNPs, including for example and not limitation gold nanorods (AuNRs) and gold nanospheres (AuNSs)) based plasmonic photothermal therapy (PPTT) is a therapy in which AuNPs are injected into the tumor before exposure to the near-infrared (NIR) light. The NIR light which has the ability to deeply penetrate the tissue, is transiently applied to the tumor producing localized heat which could lead to tumor apoptosis. The high efficiency of PPTT in getting rid of cancer cells has been accomplished in vivo and in vitro. For large tumors (volume ≥20 $cm^3$), PPTT could be ineffective due to an uneven distribution of injected AuNRs which causes inhomogeneity of the heat in the tumor. In these cases, surgery is frequently recommended to remove primary solid tumors. However, the surgical resection of primary breast tumors commonly has a risk for metastatic recurrence. It has been recognized that the tumors contain large amount of blood vessels, which provides nutrients that supports tumoral growth. Blood vessels are critical for metastasis as extensive and highly permeable blood vessels provide ways for cancer cells to exit primary tumor sites and go to the blood stream. Surgery usually disrupts the blood and lymphatic vessels, releasing cancer cells in the vasculature which promotes the process of metastasis.

Therefore, the development of novel therapies that aid in the surgical process to prevent tumor recurrences and metastasis are of great importance. Moreover, there is a need for low or non-toxic targeted nanotherapy for the treatment of cancer and more specifically, for the inhibition of cancer cell migration.

BRIEF SUMMARY

In some embodiments, the present disclosure can be a method of inhibiting migration of a cancer cell of a tumor in a subject that can comprise the steps of: (a) contacting the tumor with a gold nanomaterial; and (b) irradiating the tumor with an irradiation source; wherein the nanomaterial can inhibit the migration of the cancer cell in the subject, and wherein the cancer cell can be present in the tumor in the subject. In some embodiments, the method of inhibiting migration of a cancer cell in a tumor in a subject can comprise the steps of: (a) providing a gold nanorod-arginylglycylaspartic acid (RGD) peptide conjugate to an integrin of the cancer cell; and (b) irradiating the tumor with an irradiation source comprising a wavelength range of from about 750 nm to about 1250 nm; wherein the gold nanorod-RGD peptide conjugate can inhibit the migration of the cancer cell in the subject. In some embodiments, the method of inhibiting migration of a cancer cell in a tumor in a subject can comprise the steps of: (a) providing a gold nanorod-nuclear localization signal (NLS) peptide conjugate to an integrin of the cancer cell; and (b) irradiating the tumor with an irradiation source comprising a wavelength range of from about 750 nm to about 1250 nm; wherein the gold nanorod-NLS peptide conjugate can inhibit the migration of the cancer cell in the subject.

BRIEF DESCRIPTION OF THE DRAWINGS

The accompanying Figures, which are incorporated in and constitute a part of this specification, illustrate several aspects described below.

(FIG. 1A) TEM image of AuNRs. (FIG. 1B) UV-Vis spectrum of AuNRs with different surface ligands. Black, the as-synthesized AuNRs with CTAB on the surface; blue, PEGylated AuNRs; red, AuNRs conjugated with PEG and RGD. (FIG. 1C) Zeta potential shows the surface charge before/after conjugations. (FIG. 1D-1F) DF image of cells without AuNRs, incubated with AuNRs@PEG or AuNRs@RGD, respectively (representative of replicated experiments, another two sets of results in FIG. 5). (FIG. 1G-1K) Cell viability/apoptosis/necrosis assay of cells under different treatments, using flow cytometry. Q1, necrotic cells; Q2, late apoptotic cells; Q3, early apoptotic cells; Q4, viable cells (representative of replicated experiments, statistical results in FIG. 7). (FIG. 1L) Western blotting for the BAX protein after four groups of treatments.

(FIG. 2A) Images of HSC cell movement using scratch assay (representative of replicated experiments, another set of results in FIG. 8A). (FIG. 2B) Changes in the cell shape using DIC images before and after AuNR or NIR treatments (representative of replicated experiments, another set of results in FIG. 8B). (FIG. 2C) Western-blot analysis of integrin- and migration-related proteins in AuNRs@PEG and AuNRs@RGD (with or without NIR light).

(FIG. 3A) Heatmap showing the expression levels of all of the quantified proteins. (FIG. 3B) Heatmap showing identified proteins contributing to migration inhibition. (FIG. 3C) Bar graph showing identified significant pathways related to migration. (FIG. 3D) Western-blot analysis of some integrin- and migration-related proteins.

(FIG. 6A) UV-Vis spectra of AuNRs before and after incubation with cells. (FIG. 6B-6D) DIC microscopy images of cells without nanoparticle incubation (FIG. 6B), incubated with AuNRs@PEG (FIG. 6C), and incubated with AuNRs@RGD (FIG. 6D). (Scale bar, 20 μm.).

(FIG. 8A) Images of HSC cell movement under different conditions using scratch assay (replicated experiment). (FIG. 8B) Changes in the cell shape using DIC images before and after gold AuNRs or NIR treatments (replicated experiments).

(FIG. 9A) Clustering analysis of samples: AuNRs@PEG, AuNRs@PEG+NIR, and control. (FIG. 9B) Clustering analysis of samples: AuNRs@RGD, AuNRs@RGD+NIR, and control. (FIG. 9C-9F) Volcano plots of proteins under perturbation by (FIG. 9C) AuNRs@PEG, (FIG. 9D) AuNRs@PEG+NIR, (FIG. 9E) AuNRs@RGD, and (FIG. 9F) AuNRs@RGD+NIR. (FIG. 9G) Numbers of regulated/unregulated proteins identified in each experiment. (FIG. 9H) Venn diagram showing the comparison of differentially expressed proteins identified in each experiment.

(FIG. 10A) Pathway map of "Cell adhesion_Integrin-mediated cell adhesion and migration. " (FIG. 10B) Pathway map of "Cytoskeleton remodeling_Cytoskeleton remodeling. " (FIG. 10C) Pathway map of "Cytoskeleton remodeling_Regulation of actin cytoskeleton by Rho GTPases. " (FIG. 10D) Pathway map of "Cytoskeleton remodeling_TGF, WNT and cytoskeletal remodeling."

(FIG. 11A) Transmission electron microscopic (TEM) image of gold nanorods (AuNRs) and (FIG. 11B) TEM image of gold nanospheres (AuNSs), Scale bar 100 nm. (FIG. 11C) Schematic figure of Au nanoparticle conjugation with PEG, RGD and NLS peptides. (11D) UV-vis extinction spectra of the unconjugated AuNRs (black spectrum), AuNRs@PEG (red spectrum), and AuNRs@PEG@RGD/NLS (green spectrum), (11E) UV-vis extinction spectra of the unconjugated AuNSs (black spectrum), AuNSs@PEG (red spectrum), and AuNSs@PEG@RGD/NLS (green spectrum).

FIG. 31A-31F. Immunofluorescence images of N-cadherin in HeLa cells before (31A) and after AuNRs (31B) and AuNRs/PPTT (31C) treatments (more images in FIG. 46). The fluorescence intensities in these images are normalized together. (31D) The fluorescence quantification of the N-cadherin (n=20 cells, ±SEM). (31E) Western blot results also indicate a decreased expression level of N-cadherin after treatments. (31F) Immunofluorescence images of tight junction protein ZO-2 in MCF-7 cells, before and after AuNR or AuNRs/PPTT treatments. The morphology of ZO-2 change from a normal and continuous line-like structure in the control group to a discontinuous dot-like structure after treatments. The figures showed 3D scanning of ZO-2, where Layer 1 is close to the bottom of the cells, and Layer 3 is close to the top of the cells.

FIG. 35A-35D. Cellular uptake and cytotoxicity of AuNRs treatments of MCF-7 cells. (35A-35B) Differential interference contrast (DIC) microscopic images of MCF-7 cells without (35A) and with AuNRs@RGD (35B). The red arrow indicates the locations of AuNRs. (35C) Cell viability of MCF-7 cells after AuNRs and AuNRs+NIR treatments (n=3). (35D) Western blotting for the BAX protein upon different treatments.

FIG. 42A-42D. Key pathways perturbed by AuNRs+PPTT (vs AuNRs group). 1 refers to AuNRs-PPTT (MCF-7), 2 refers to AuNRs-PPTT (HeLa). (42A) Pathway map of "Cytoskeleton remodeling_Regulation of actin cytoskeleton organization by the kinase effectors of Rho GTPases" (42B) Pathway map of "Development_Regulation of cytoskeleton proteins in oligodendrocyte differentiation and myelination" (42C) Pathway map of "Cell adhesion_Endothelial cell contacts by junctional mechanisms" (42D) Pathway map of "Cytoskeleton remodeling_Substance P mediated membrane blebbing".

FIG. 43A-43B. Comparison of the resolution of STORM (43A) and conventional fluorescence microscopy imaging (43B) for actin filaments.

DETAILED DESCRIPTION

Figure 1A:
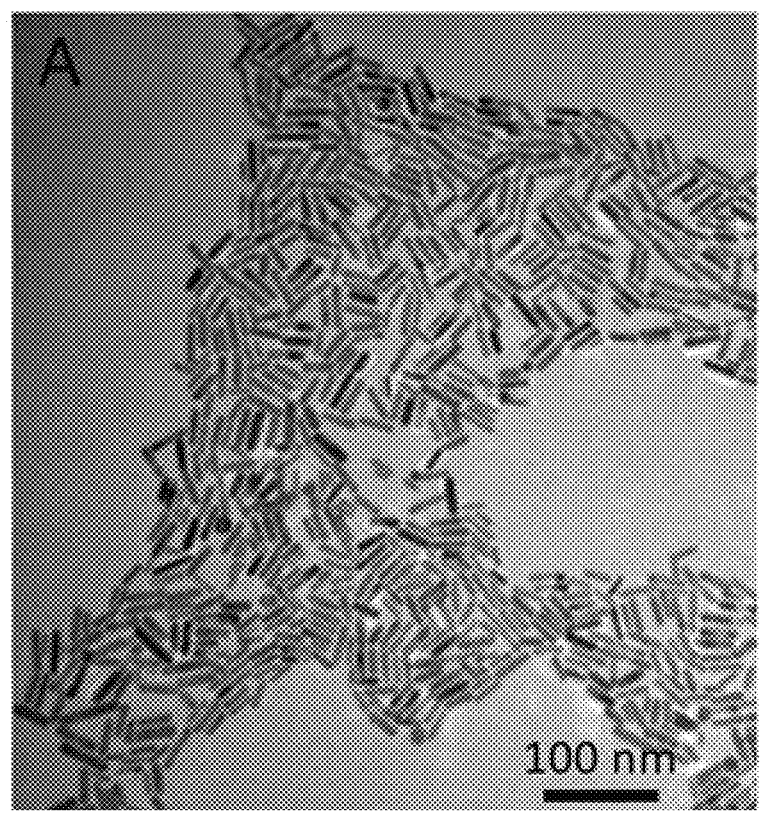
FIG. 1A-1L. AuNRs synthesis, characterization, HSC-3 cellular uptake, and cytotoxicity study.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Embodiments of the present disclosure can include compositions and methods of inhibiting migration of a cancer cell of a tumor in a subject. Some embodiments include a method of inhibiting migration of a cancer cell of a tumor in a subject. Advantages of some embodiments of the present disclosure include that ability to inhibit cancer cell migration while still (i) lowering the concentration of gold nanomaterials to nM dosage, as a means for lowering toxicity; (ii) enhancing the selectivity to the cancerous cells; (iii) applying NIR light to enhance the gold nanomaterial's effects on cytoskeletal proteins to inhibit migration; and (iv) enhancing the migration inhibition effect by targeting the gold nanomaterials to various cellular locations to remodel the cytoskeleton.

In some embodiments, the method can include contacting the tumor with a gold nanomaterial and irradiating the tumor with an irradiation source. In some embodiments, the nanomaterial can inhibit the migration of the cancer cell in the subject. In some embodiments, the nanomaterial can inhibit migration of from about 10% to about 100% of the cancer cells in the tumor, from about 20% to about 90%, from about 20% to about 80%, from about 20% to about 70%, from about 30% to about 70%, from about 40% to about 60%, from about 50% to about 100%, from about 50% to about 90%, or from about 60% to about 90% of the cancer cells in the tumor. In some embodiments, the gold nanomaterial can inhibit migration of at least about 40% of the cancer cells in the tumor, at least about 50% of the cancer cells in the tumor, at least about 60% of the cancer cells in the tumor, at least about 70% of the cancer cells in the tumor, at least about 80% of the cancer cells in the tumor, at least about 90% of the cancer cells in the tumor, or at least about 95% of the cancer cells in the tumor.

In some embodiments, the contacting step can comprise injecting into the tumor a solution that can comprise the gold nanomaterial. In some embodiments, the solution can comprise a plurality of gold nanorods. In some embodiments, the solution can comprise a plurality of gold nanospheres. In some embodiments, the solution can comprise a plurality of gold nanorods and a plurality of gold nanospheres. In some embodiments, the solution can comprise a plurality of gold nanomaterials, in which the plurality of gold nanomaterials can be conjugated to one or more moieties (i.e., ligands), such as targeting moieties and/or moieties that increase the bioavailability and/or biocompatibility of the gold nanomaterials. In some embodiments, the solution can comprise a plurality of gold nanomaterials that are conjugated to at least one type of moiety. In some embodiments the solution can comprise a first plurality of gold nanomaterials that are conjugated to a first type of moiety and a second plurality of gold nanomaterials that are conjugated to a second type of moiety. For example, in some embodiments, the solution can comprise a first plurality of gold nanorods that are conjugated to at least one targeting moiety and a second plurality of gold nanorods that are targeted to at least one moiety that increases bioavailability of the gold nanorods. In some embodiments, the solution can comprise a first plurality of gold nanorods that are conjugated to at least one targeting moiety and at least one moiety that increases bioavailability of the gold nanorods, wherein each nanorod comprises the at least one targeting moiety and at least one moiety that increases bioavailability of the gold nanorods.

In some embodiments, the cancer cell can be present in the tumor in the subject. In some embodiments, the subject can be a mammal. In some embodiments, the subject can be a human. In some embodiments, the subject can be a non-human subject, including, but not limited to, a canine and/or a feline.

In some embodiments, the gold nanomaterial can be at least one of a gold nanorod and a gold nanosphere (AuNS). In some embodiments, the gold nanomaterial can be a gold nanorod (AuNR). Gold nanorods can be utilized in some embodiments where the irradiation source includes a particular emission wavelength or wavelength range that can be absorbed by nanorods.

In some embodiments, the gold nanomaterial can be a gold nanorod having a length dimension of from about 15 nm to about 50 nm, from about 20 nm to about 50 nm, from about 20 nm to about 40 nm, from about 20 nm to about 35 nm, from about 20 nm to about 30 nm, from about 22 nm to about 30 nm, or from 22 nm to about 28 nm. In some embodiments, the gold nanorod can have a length dimension of about 26 nm. In some embodiments, the gold nanorod can have a length dimension of about 25 (±3) nm.

In some embodiments, the gold nanomaterial can be a gold nanorod having a width dimension of from about 1 nm to about 15 nm, from about 2 nm to about 10 nm, from about 5 nm to about 15 nm, from about 5 nm to about 10 nm, or from about 5 nm to about 7 nm. In some embodiments, the gold nanorod can have a width dimension of about 5 nm. In some embodiments, the gold nanorod can have a width dimension of about 5 (±0.5) nm. In some embodiments, the gold nanorod can have a width dimension of about 6 (±1) nm.

In some embodiments, the gold nanomaterial can be a gold nanorod having an aspect ratio of from about 2 to about 10, from about 3 to about 10, from about 3 to about 8, from about 4 to about 7, from about 4 to about 10, from about 3 to about 5, from about 2 to about 6, or from about 3 to about 6. In some embodiments, the gold nanorod can have an aspect ratio of about 4.2.

In some embodiments, the gold nanomaterial can absorb wavelengths of light in the near-infrared (NIR) spectrum. In some embodiments, the gold nanomaterial can absorb wavelengths of light between about 750 nm and about 1250 nm. In some embodiments, the gold nanomaterial is a gold material that can have a maximum absorption peak of about 800 nm (in other words, the nanomaterial can have a UV-vis maximum absorption peak of about 800 nm). In some embodiments, the gold nanomaterial can be a gold nanorod that can absorb wavelengths of light in the NIR spectrum, e.g., from about 750 nm to about 1250 nm, with an absorption maximum of about 800 nm.

In some embodiments, the gold nanomaterial is a gold nanosphere with an average size of from about 20 nm to about 100 nm, from about 20 nm to about 90 nm, from about 20 nm to about 80 nm, from about 25 nm to about 75 nm, from about 25 nm to about 50 nm, from about 30 nm to about 50 nm, from 30 nm to about 40 nm, or from about 32 nm to about 36 nm. In some embodiments, the gold nanomaterial is a gold nanosphere with an average size of about 35 nm. In some embodiments, the gold nanosphere has an average size of about 35±2 nm.

In some embodiments, the gold nanomaterial is a gold nanosphere that can absorb wavelengths of light in the visible spectrum. In some embodiments, the gold nanosphere can absorb light from about 390 nm to about 700 nm. In some embodiments, the gold nanosphere can have a maximum absorption peak of about 535 nm (in other words, the nanomaterial can have a UV-vis maximum absorption peak of about 535 nm).

In some embodiments, the method can comprise targeting the gold nanomaterial to at least one of an integrin of the cancer cell and a cell nuclear membrane of the cancer cell. In some embodiments, the gold nanomaterial can be conjugated to a targeting moiety that can be configured to specifically target particular areas of the cell, including, but not limited to, surface integrins, cell nuclei, etc. In some embodiments, the gold nanomaterial can be conjugated to one or more Arg-Gly-Asp (RGD) peptides. RGD peptides can specifically bind to a wide number of surface integrins, including but not limited to $\alpha v \beta 3$, $\alpha 3 \beta 1$, and $\alpha 5 \beta 1$ integrins. In some embodiments, the gold nanomaterial can be conjugated to one or more Nuclear Localization Signals (NLS). A NLS is an amino acid sequence that 'tags' a protein for introduction into the cell nucleus. In some embodiments, the gold nanomaterial can be conjugated to one or more Bovine Serum Albumin (BSA) moieties. In some embodiments, the gold nanomaterial can be conjugated to one or more Rifampicin (RF) moieties. BSA and RF-conjugated gold nanomaterials can enhance the rate of endocytosis of gold nanomaterials and hence their concentration inside the cancer cell.

In some embodiments, the gold nanomaterial can be conjugated to a moiety (i.e., ligand) that can increase the biocompatibility of the gold nanomaterial. In some embodiments, the gold nanomaterial can be conjugated to one or more Poly-Ethylene Glycol (PEG) moieties. PEG is a polyether compound that can increase the biocompatibility of the gold nanomaterial.

In some embodiments, the gold nanomaterial can be conjugated to only one type of moiety. In some embodiments, the gold nanomaterial can be conjugated to more than one type of moiety, for example, the gold nanoparticle can be conjugated to a targeting moiety and a moiety that increases biocompatibility of the gold nanomaterial. In some embodiments, a single particle of gold nanomaterial (e.g., a single nanorod or nanosphere) can be conjugated to one or more types of moieties. In some embodiments, each particle of gold nanomaterial can be conjugated to a single type of moiety.

In some embodiments, the concentration of targeting moieties on the gold nanomaterial is from about 1,000 to about 75,000 moieties per particle of gold nanomaterial, from about 2,000 to about 75,000, from about 5,000 to about 50,000, from about 7,500 to about 75,000, from about 7,500 to about 50,000, from about 10,000 to about 50,000, from about 10,000 to about 75,000, from about 15,000 to about 50,000, from about 15,000 to about 30,000, or from about 10,000 to about 30,000 moieties per particle of gold nanomaterial.

In some embodiments, the irradiation source can comprise a single emission wavelength or a range of emission wavelengths. In some embodiments, the emission wavelength range can be a wavelength range that causes minimal or no cellular damage. In some embodiments, the emission wavelength range can be in the near-infrared wavelength range, e.g., from about 750 nm to about 1250 nm. In some embodiments, the irradiation source can comprise a single emission wavelength from about 750 nm to about 1250 nm. In some embodiments, the irradiation source can be a laser with a single emission wavelength of from about 750 nm to about 1250 nm. In some embodiments, the irradiation source can be a laser with an emission wavelength range of from about 750 nm to about 1250 nm. In some embodiments, the irradiation source can be an 808 nm diode laser.

In some embodiments, the dose of the gold nanomaterial administered to the subject can be dependent on a volume of the tumor in the subject. The volume of the tumor can be determined by the following calculation:

$$\text{Tumor volume} = (\text{tumor length} \times \text{tumor width} \times \text{tumor height})/2.$$

In some embodiments, for each 20 mm$^3$ of tumor volume, about 10 µL of about 2.5 nM gold nanomaterial solution is added. In some embodiments, the dose of the gold nanomaterial is between about 1 nM and about 25 nM gold nanomaterial per 100 cm$^3$ of tumor volume, between about 2 nM and about 20 nM, between about 2.5 nM and about 15 nM, between about 2.5 nM and about 10 nM, or between about 2.5 nM and about 5 nM gold nanomaterial per 100 cm$^3$ of tumor volume.

In some embodiments, the cancer cell for which migration is inhibited can be selected from at least one of human oral squamous cell carcinoma, e.g., HSC-3, breast cancer, e.g., cell line MCF-7, cervical cancer cells, e.g., HeLa, cellosaurus cells, e.g., cell line HEY A8, and the like. In some embodiments, the cancer cell can be a cancer stem cell.

In some embodiments, the irradiation step comprises irradiating the tumor for from about 30 seconds to about 10 minutes with the irradiation source, from about 30 seconds to about 5 minutes, from about 1 minute to about 10 minutes, from about 1 minute to about 10 minutes, from about 1 minute to about 5 minutes, from about 30 seconds to about 4 minutes, or from about 1 minute to about 4 minutes with the irradiation source. In some embodiments, the tumor can be irradiated for about 1 minute per dose.

In some embodiments, the method of inhibiting migration of a cancer cell in a tumor in a subject can comprise the steps of providing a gold nanorod-arginylglycylaspartic acid (RGD) peptide conjugate to an integrin of the cancer cell, irradiating the tumor with an irradiation source that can comprise a wavelength range of from about 750 nm to about 1250 nm, wherein the gold nanorod-RGD peptide conjugate can inhibit the migration of the cancer cell in the subject. While not wishing to be bound by theory, it is thought that integrins are major adhesion and signaling receptor proteins that play an important role in regulating cytoskeleton by providing a physical linkage between the cytoskeleton and the extracellular matrix (ECM) and receiving signals from the ECM. They could perturb the downstream cell adhesion and migration pathways and modulate the cytoskeleton, thus regulating cell motility and migration.

In some embodiments, the method of inhibiting migration of a cancer cell in a tumor in a subject can comprise the steps of providing a gold nanorod-nuclear localization signal (NLS) peptide conjugate to an integrin of the cancer cell, irradiating the tumor with an irradiation source that can comprise a wavelength range of from about 750 nm to about 1250 nm, wherein the gold nanorod-NLS peptide conjugate can inhibit the migration of the cancer cell in the subject.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1—Targeting Cancer Cell Integrins Using Gold Nanorods in Photothermal Therapy Inhibits Migration Through Affecting Cytoskeletal Proteins In this Example, RGD peptides were conjugated on the surface of AuNRs to achieve the selective targeting of integrin. NIR light was applied to the AuNRs to generate mild heat. The concentration of the AuNRs and heat were kept well below the threshold to avoid negative effects on cell viability or proliferation. The inventors compared both nontargeted and integrin-targeted AuNRs (AuNRs@RGD). Results indicated that although both types of AuNRs decreased the cell migration speed, the targeted ones did so with a surprisingly greater effect. After applying NIR light, cell motility was further decreased. The inventors have performed a proteomics study to understand the molecular mechanism, explaining how and why AuNRs have a wide range of effects in perturbing cytoskeletal proteins and cell migration pathways. Compared with the drugs composed of small molecules that target only a single protein, AuNRs exhibit surprisingly significant inhibition of cancer cell migration.

AuNR Fabrication, Characterization, Cell Uptake, and Cytotoxicity Study.

Figure 1B:
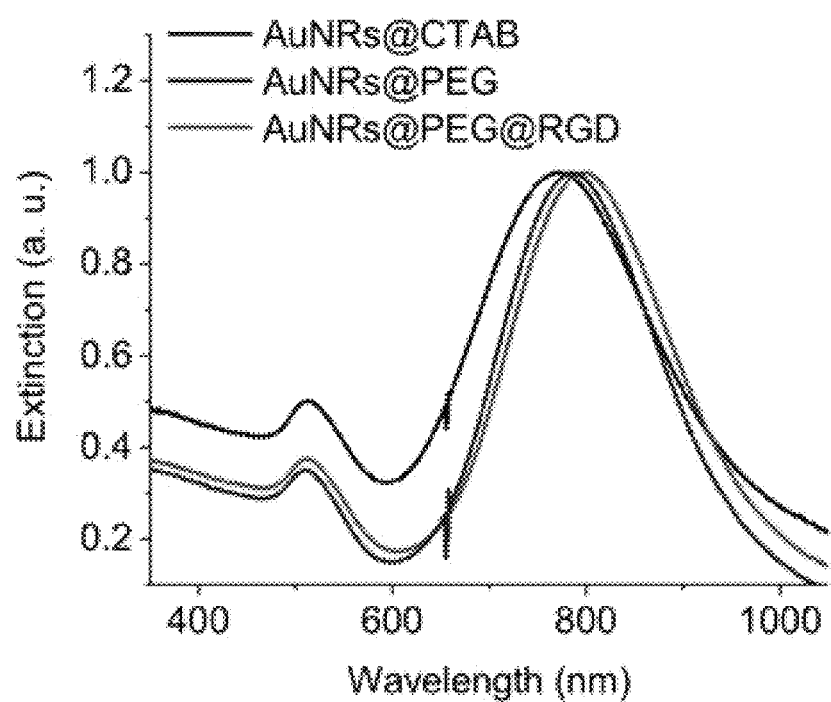
Figure 1C:
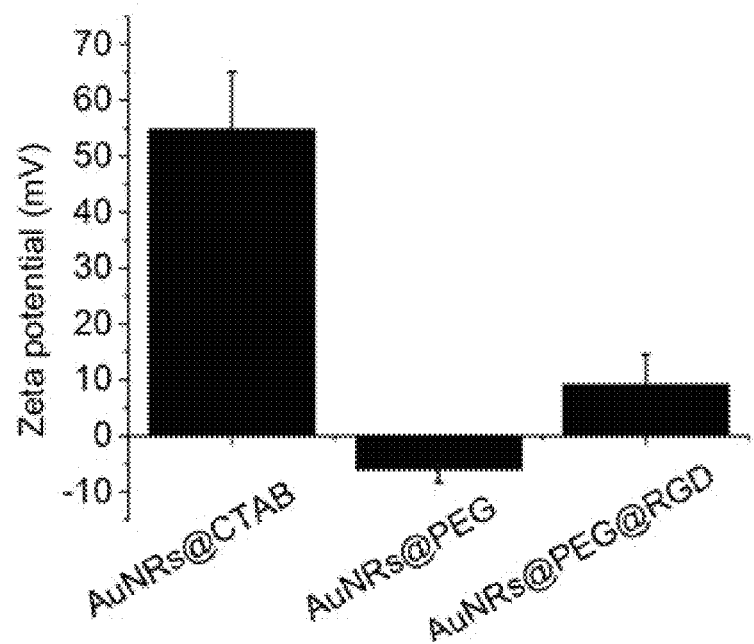
Figure 1D:
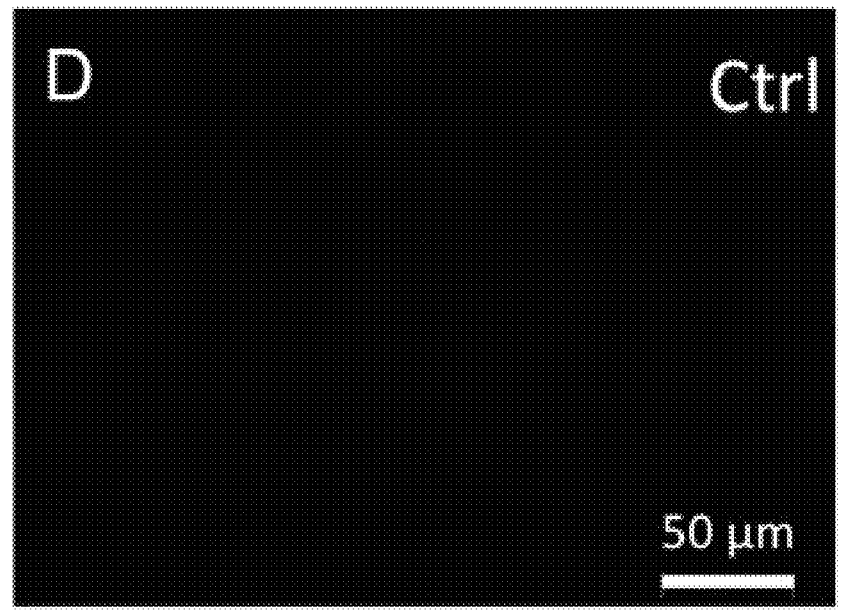
Figure 1E:
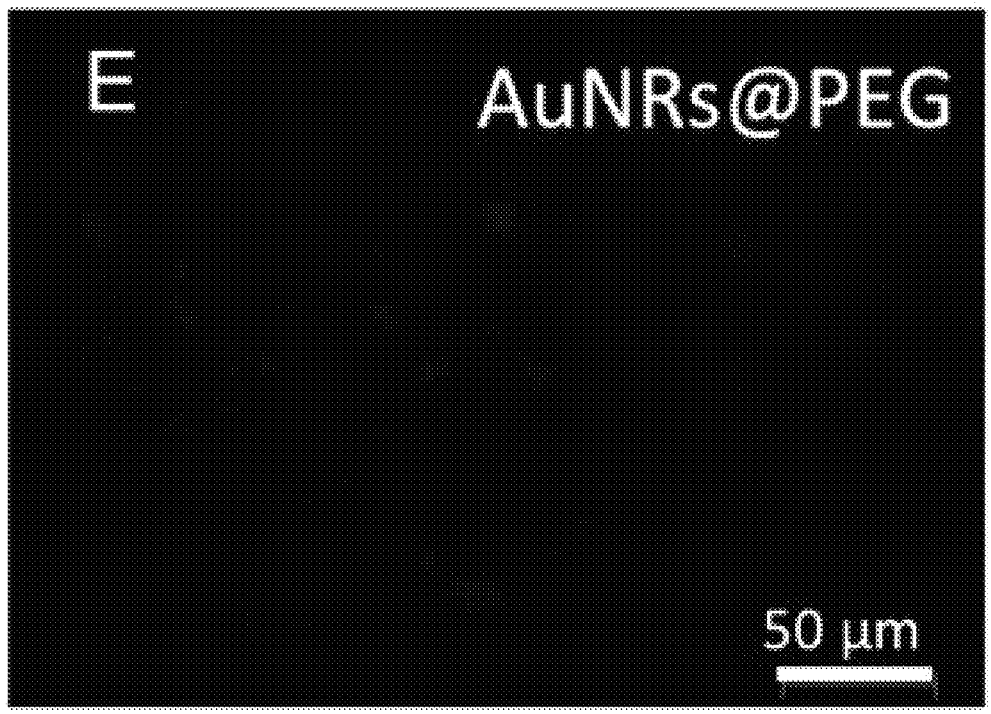
Figure 1F:
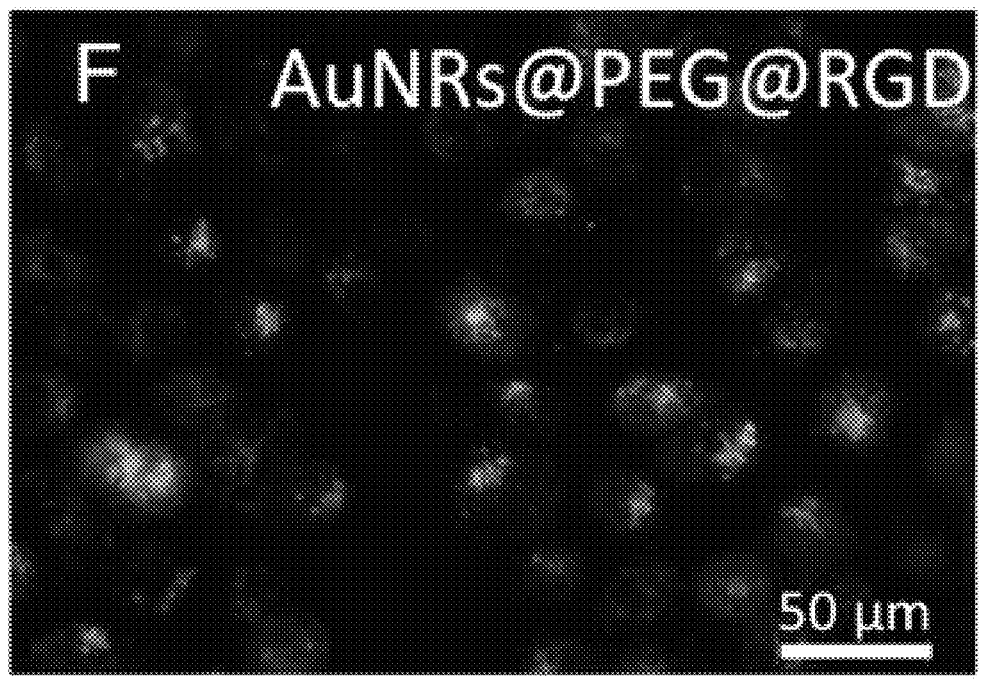

AuNRs with a size of 25 (±3)×6 (±1) nm (length×width) and aspect ratio of 4.2 were synthesized according the seedless method (49), as shown in the transmission electron microscope (TEM) in FIG. 1A. This size of AuNRs has shown better efficacy in heat generation in PPTT by the inventors' previous study (50). The as-synthesized AuNRs were washed twice with water to remove cetyltrimethylammonium bromide (CTAB) to decrease the cytotoxicity and for the next step of surface modification. The AuNPs were functionalized with polyethylene glycol thiol (PEG) and RGD peptides to increase the biocompatibility and achieve integrin targeting, respectively. Surface modification causes a red shift of the longitudinal surface plasmon resonance (SPR) band of AuNRs due to the change in the dielectric constant of the surrounding environment of AuNRs (as shown in the UV-Vis spectra in FIG. 1B). After PEGylation, the SPR band red-shifts to 785 nm for AuNRs@PEG (initially 771 nm). Further red-shift to 796 nm for AuNRs@RGD was observed, indicating the surface binding of RGD. In addition, the zeta potentials of the AuNRs at different stages were measured to confirm the surface modifications. As shown in FIG. 1C, the as-synthesized CTAB-coated AuNRs had a positive surface charge of 22.9±15.1 mV, as the CTAB is a highly cationic surfactant. After PEG modification, the AuNRs became negatively charged (−10.2±6.73 mV) and then became positive again after further modification of the RGD peptides. The characterization results are consistent with previous reports, which indicates the successful conjugation of the RGD peptides to the surface of AuNRs.

Figure 1G:
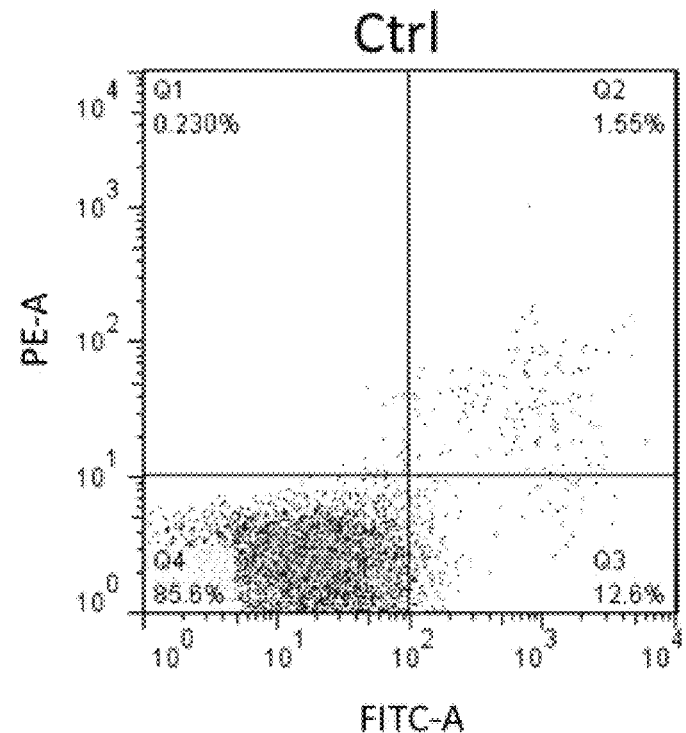
Figure 1H:
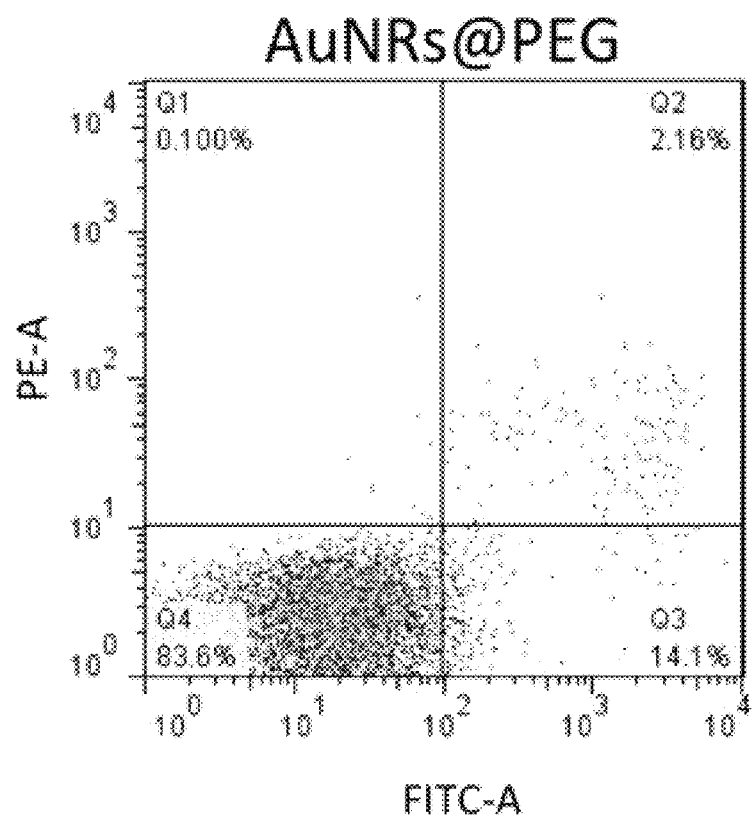
Figure 1I:
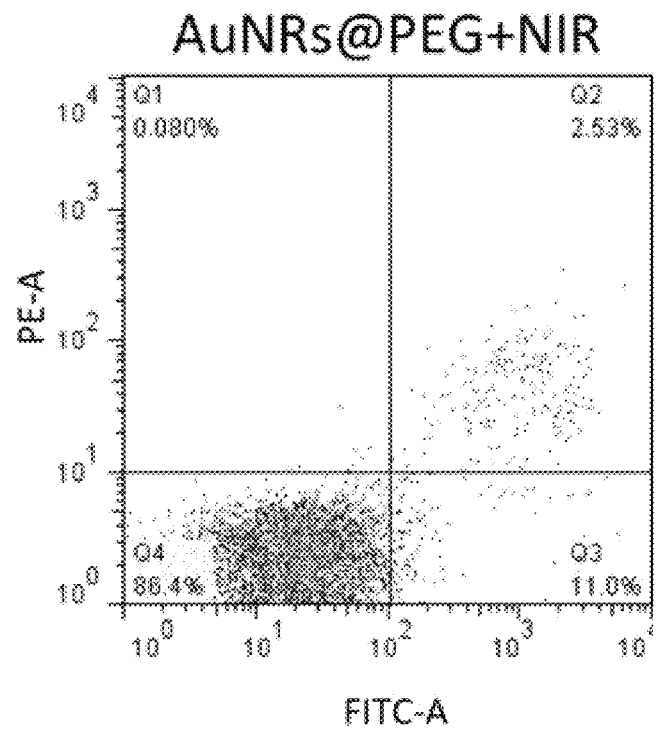
Figure 1J:
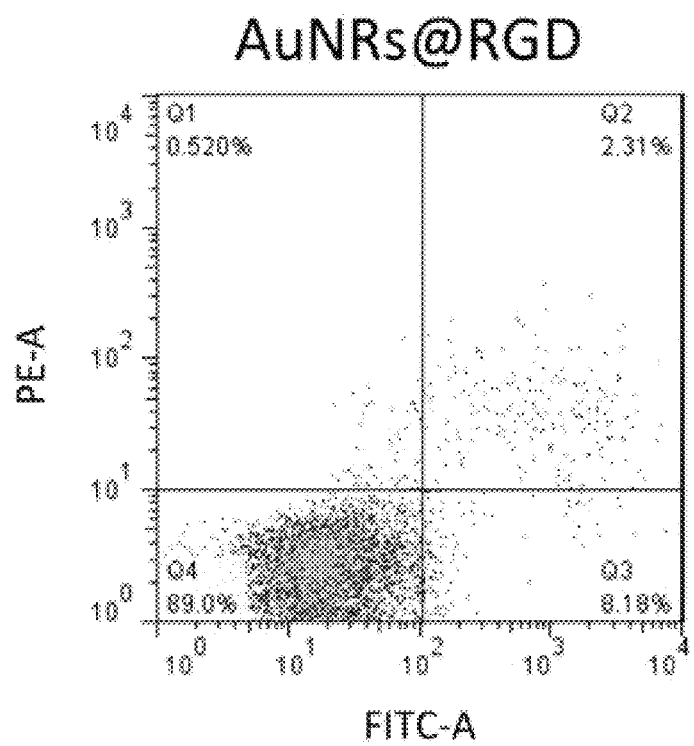
Figure 1K:
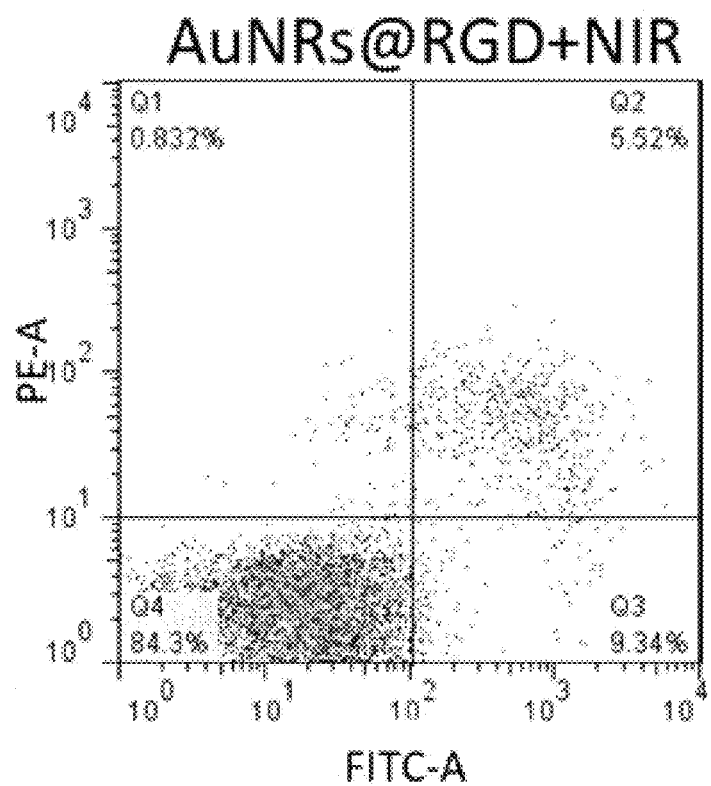
Figure 1L:
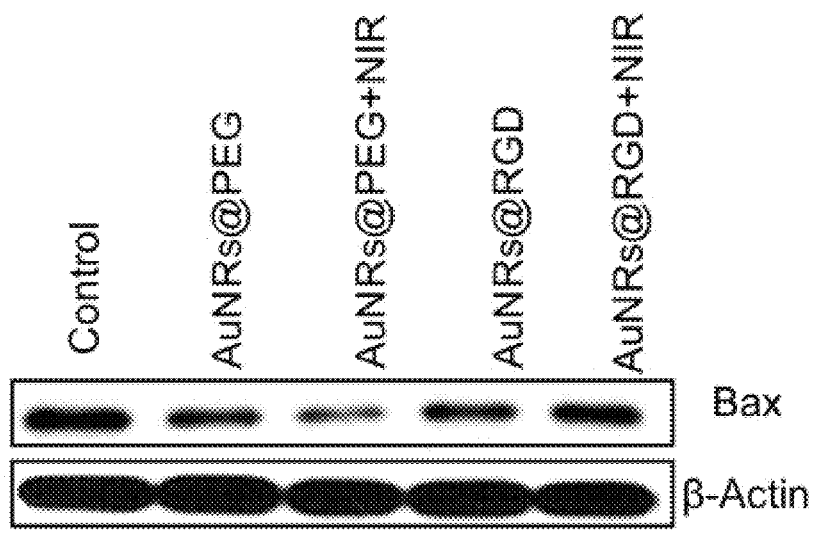
Figure 6A:
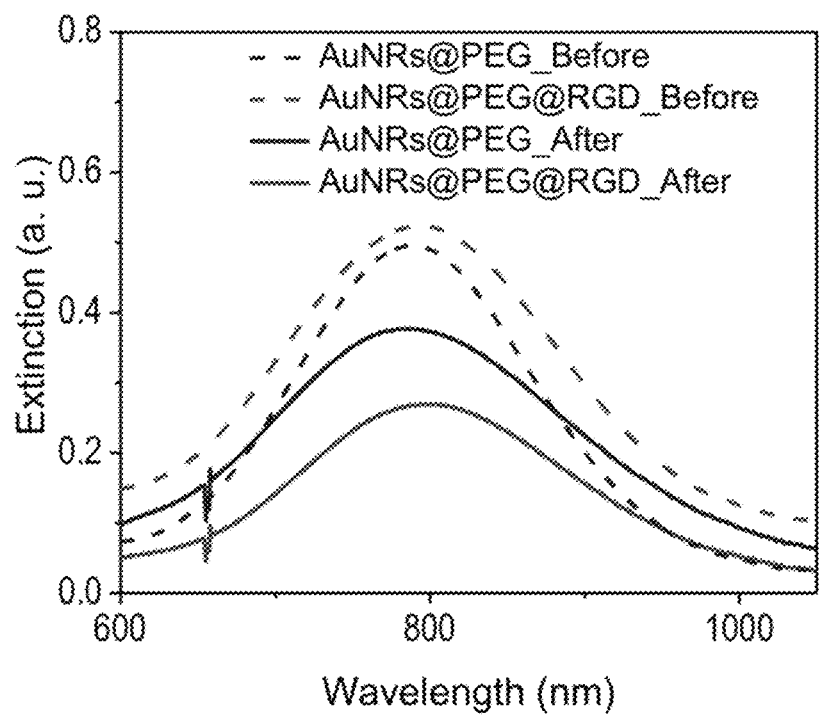
FIG. 6A-6D. HSC cell uptake of AuNRs.
Figure 6B:
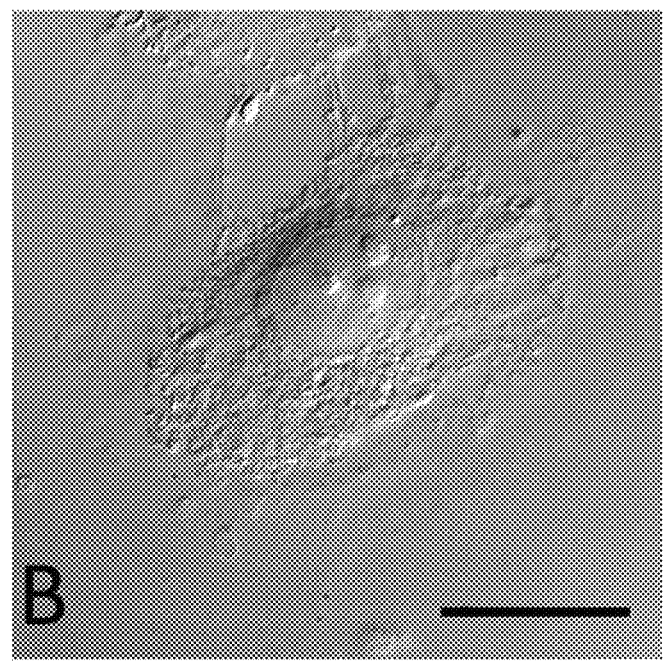
Figure 6C:
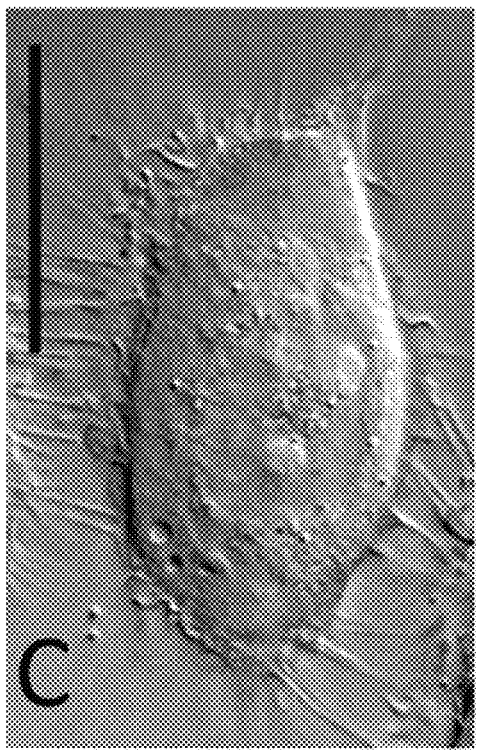
Figure 6D:
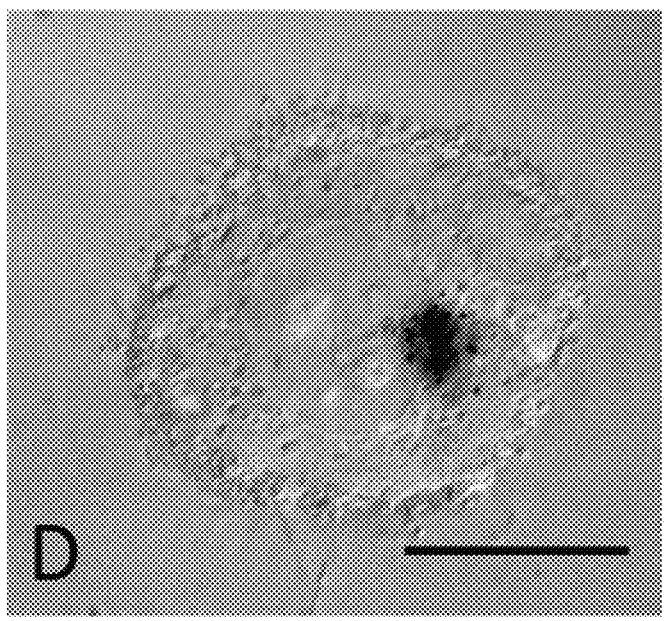
Figure 7:
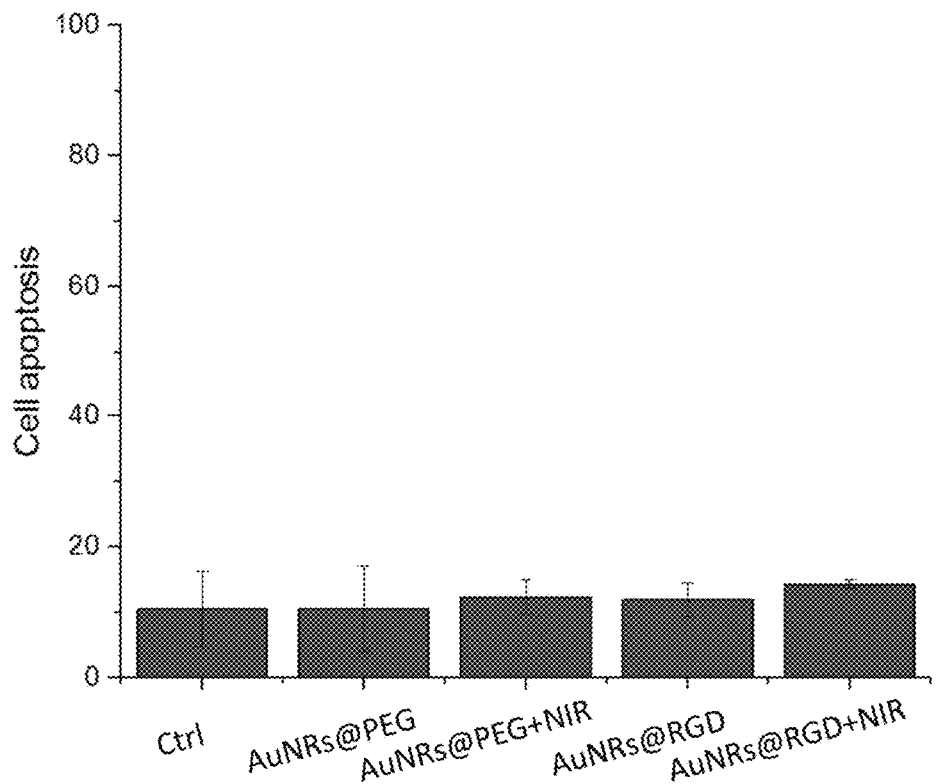
FIG. 7. Apoptosis populations of HSC cells under different treatments, using flow cytometry.

Successful internalization of AuNRs within the cells was observed as monitored under a dark-field (DF) microscope (FIGS. 1D-1F and FIG. 5A-5F), where the brightness of the scattering light from AuNRs indicates the internalized AuNR amount. The human oral squamous cell carcinoma (HSC-3) cells were incubated with 2.5 nM of AuNRs for 24 h. For AuNRs@RGD, clear scattering light of AuNRs was observed, whereas AuNRs@PEG did not show high uptake compared with the AuNRs@RGD. The difference in uptake of these two types of AuNRs is due to the binding of RGD to the surface integrin that enhances the endocytosis of AuNRs. For further confirmation, the internalization of AuNRs was also measured by UV-Vis spectra (FIG. 6A) and the differential interference contrast (DIC) microscopy (FIG. 6B-6D). In addition, the retention of the Gaussian-shape peaks in the UV-Vis spectra of AuNRs after incubation with cells indicates the colloidal stability. Flow cytometry was used to measure the cell viability and apoptosis status, and the results indicated 2.5 nM AuNRs@PEG and AuNRs@RGD did not affect the cell viability or cause apoptosis (FIG. 1G and FIG. 7). This result confirms that the functionalization of AuNRs has been well performed by ligand-ligand exchange to replace the CTAB with PEG and RGD. A 808-nm CW NIR laser was applied for 1 min to raise the temperature of the culture media to about 42±1° C. As the temperature increased, there was no obvious change in the cell viability and no sign of apoptosis/necrosis (FIGS. 1 G-1K and FIG. 7). In addition, no cell apoptosis occurred after AuNR incubation and slight NIR exposure, as confirmed by the Western-blot results (FIG. 1L). BAX, an important protein that participates in the initiation of apoptotic signaling, did not increase.

AuNRs Inhibit Cancer Cell Migration and Invasion Ability.

Figure 2A:
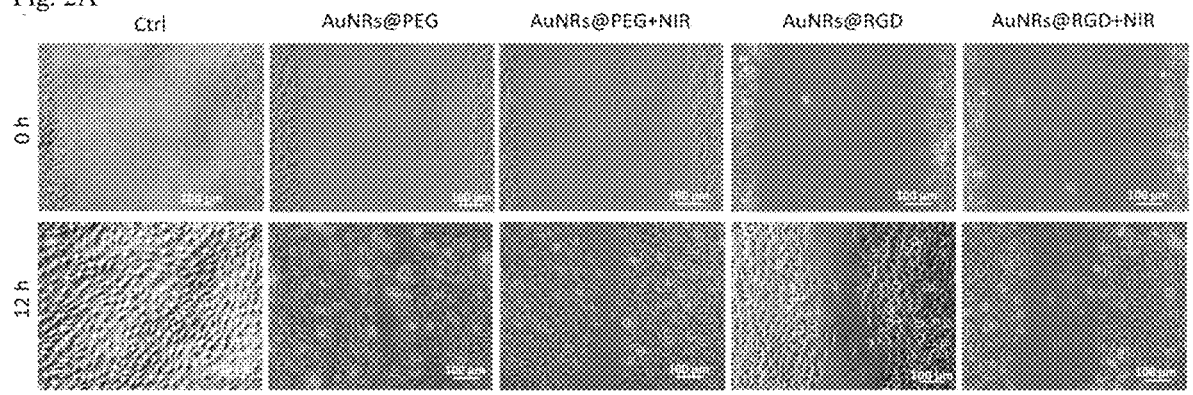
FIG. 2A-2C. Changes of cell migration rate and shapes upon AuNRs treatments.
Figure 8A:
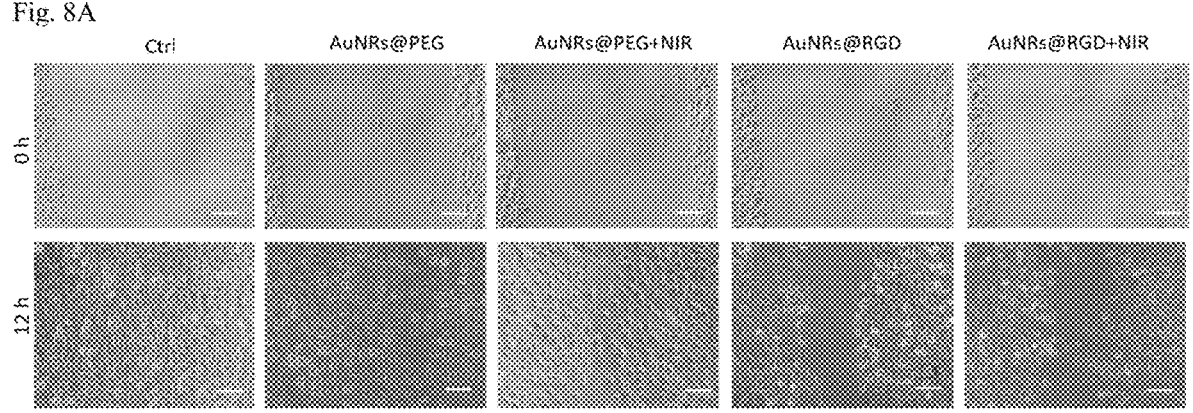
FIG. 8A-8B.

To evaluate the AuNRs' effect on cancer cell migration, the inventors conducted a scratch assay on the monolayers of cells that were incubated with or without AuNRs for 24 h. After introducing a "scratch" or "wound" into a cell culture, images were captured immediately and 12 h after the scratch. FIG. 2A and FIG. 8A indicate that cells in the control group had the wound completely healed, whereas cells treated with AuNRs were not completely healed. The integrin-targeting AuNRs (AuNRs@RGD) have a greater inhibition effect than the nontargeted AuNRs (AuNRs@PEG). In addition, NIR light exposure demonstrated an enhanced inhibition effect on cancer cell migration.

Figure 2B:
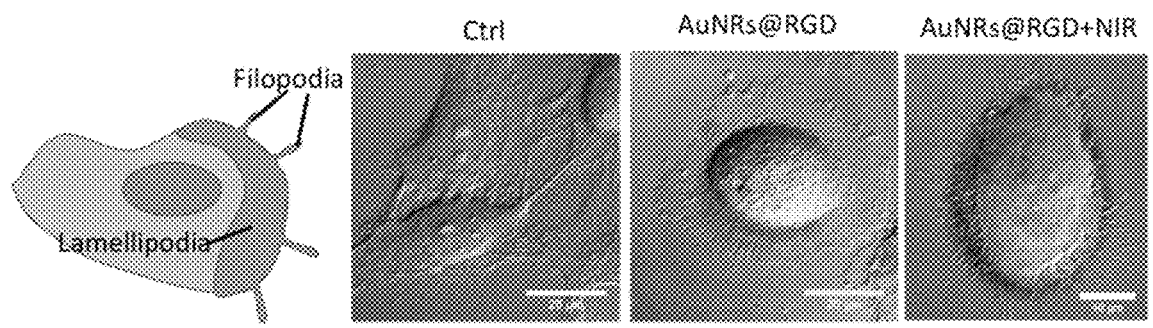
Figure 8B:
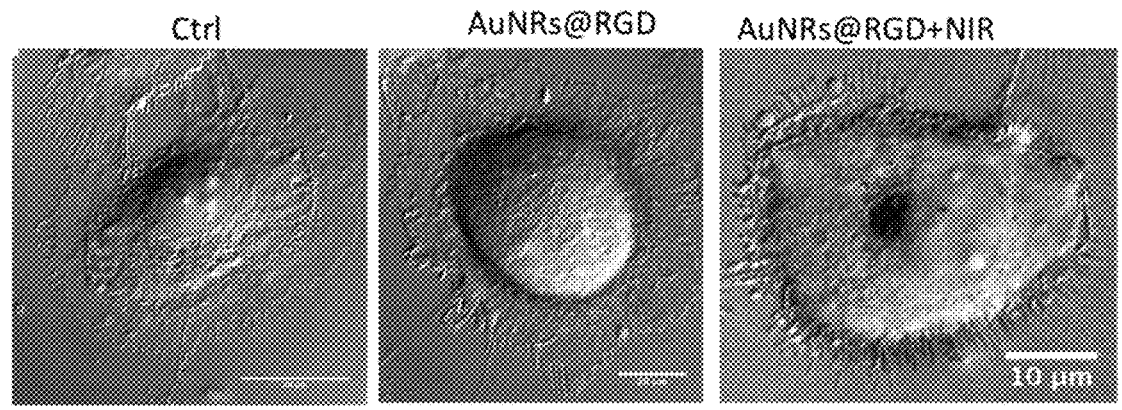

As mentioned herein, the cell motility decreased upon the AuNR treatment. It is well known that changes in cell morphology are closely related to cell motility, which is initiated through two types of membrane protrusions: flat, sheet-like lamellipodia and needle-like, actin-based filopodia (FIG. 2B). Both structures contain a large density of integrins and play major roles in leading cancer cell migration and invasion. To study the cell morphological changes (lamellipodia and filopodia), a DIC microscope was used. The control sample exhibited a normal and extended lamellipodia and filopodia. After treating with AuNRs@RGD alone, the cells tended to have a round shape with fewer lamellipodia and filopodia compared with the control. When the inventors applied AuNRs@RGD and NIR light together, the area of lamellipodia was further decreased, and many needle-like filopodia appear outside the cell (FIG. 8B). The morphological changes of integrin-rich lamellipodia and filopodia indicate that the integrin-targeted AuNRs with or without NIR light are effective in changing the cytoskeleton structures, a probable cause for the decrease in cell motility.

Figure 2C:
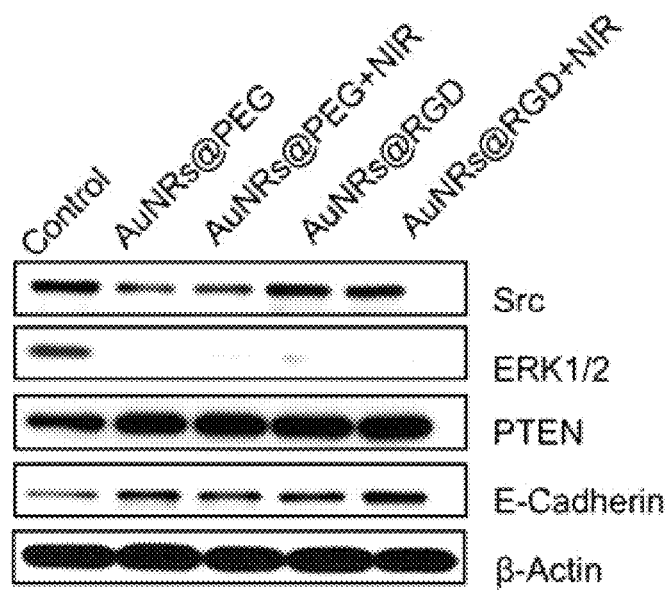

To study the molecular mechanism, the inventors checked the expression levels of several proteins that are closely associated with integrin and cell migration. Two important downstream regulators of integrin, Src and ERK½, were found to be down-regulated with the AuNR treatment compared with the control (FIG. 2C). Src is a critical protein that bridges between integrin and Rho (a main regulator of cytoskeleton) signaling, and ERK½ is a mitogen-activated protein kinase. The decrease of Src and ERK½ indicates that targeting the surface integrin using AuNRs@RGD might block the downstream regulators of integrin signaling, which contributes to the inhibition of cell migration by AuNRs. Moreover, in a further investigation of integrin-related proteins, FIG. 2C showed that epithelial cadherin (E-cadherin) and phosphatase and tensin homolog (PTEN) were up-regulated upon AuNR treatments. Recent discoveries have shown that E-cadherin has cross-talks with integrin signaling (64) that alter cytoskeletal organization. Loss of E-cadherin is often associated with tumor invasive progressing. In addition, the tumor suppressor protein PTEN has been reported to inhibit integrin-mediated cell migration, spreading, and adhesion and affect mitogen-activated protein kinase. The results indicated that the up-regulation of E-cadherins and PTEN contributes to the inhibition of cancer migrations.

Proteomics Analysis Reveals the Inhibition of Migration Pathways.

Figure 3A:
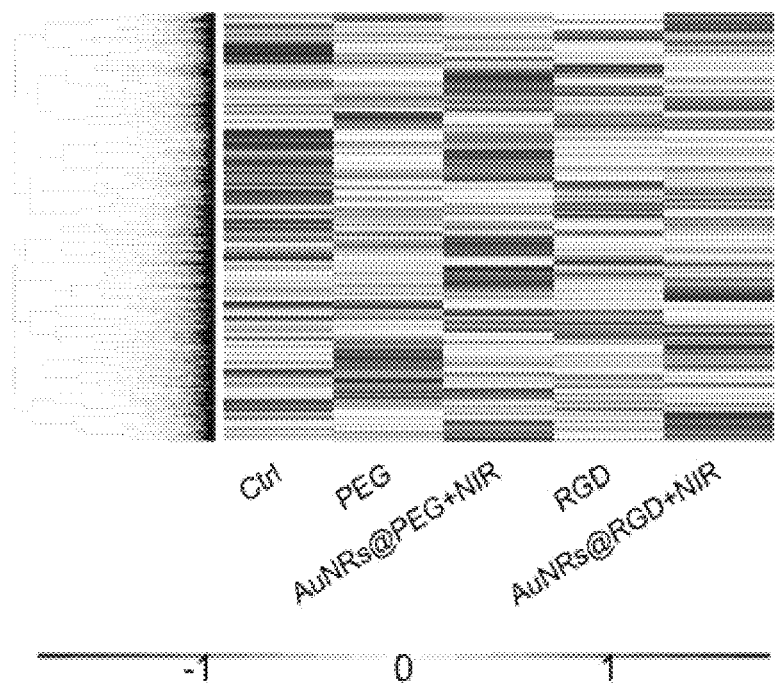
FIG. 3A-3D. Experimental results of proteomics in the four treatment groups (AuNRs@PEG, AuNRs@PEG+NIR, AuNRs@RGD, and AuNRs@RGD+NIR).
Figure 9A:
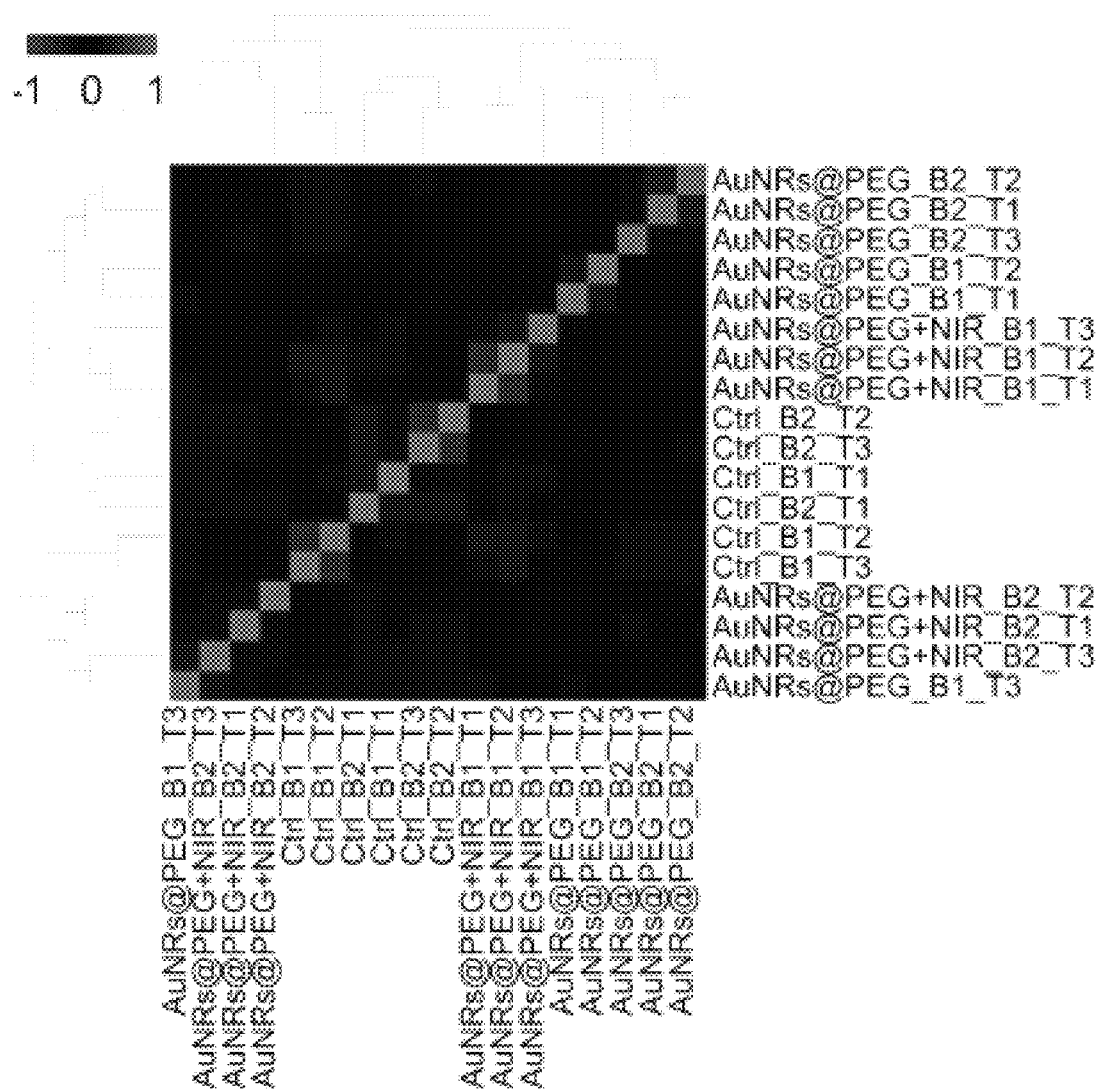
FIG. 9A-9H. Experimental results of proteomics and data analysis.
Figure 9B:
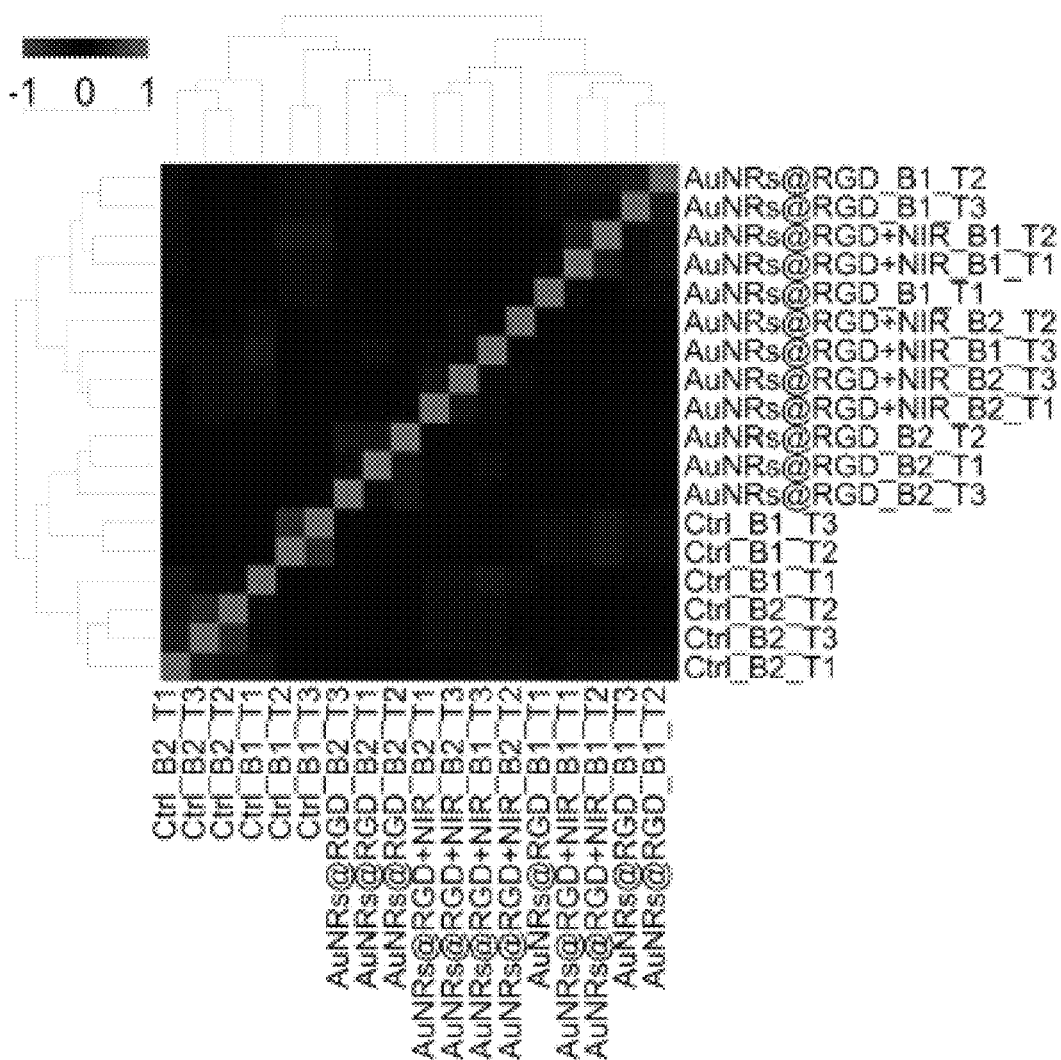
Figure 9C:
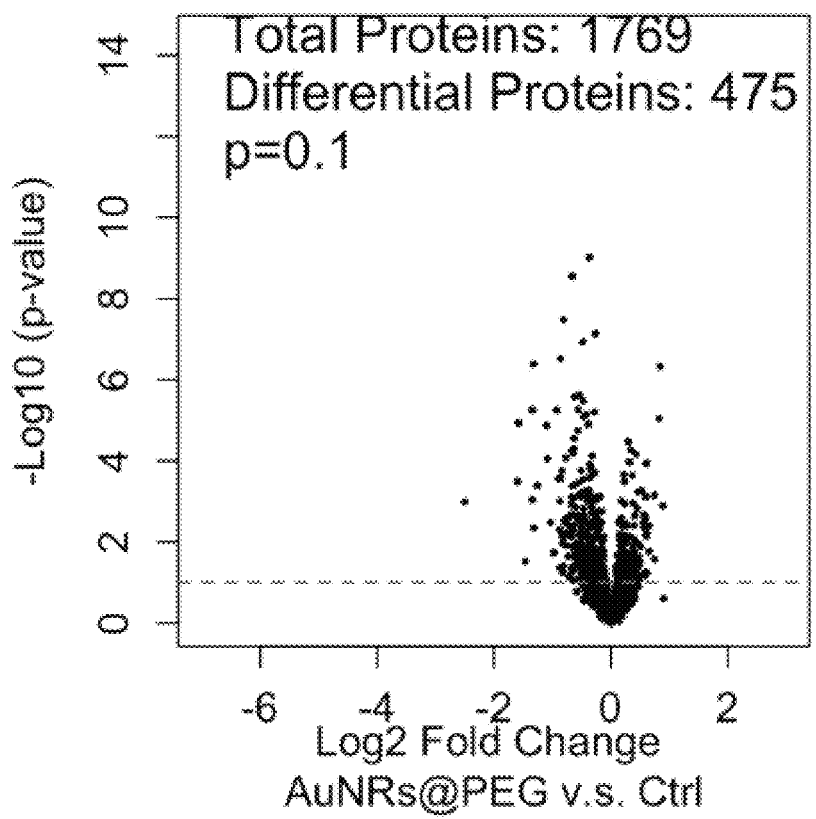
Figure 9D:
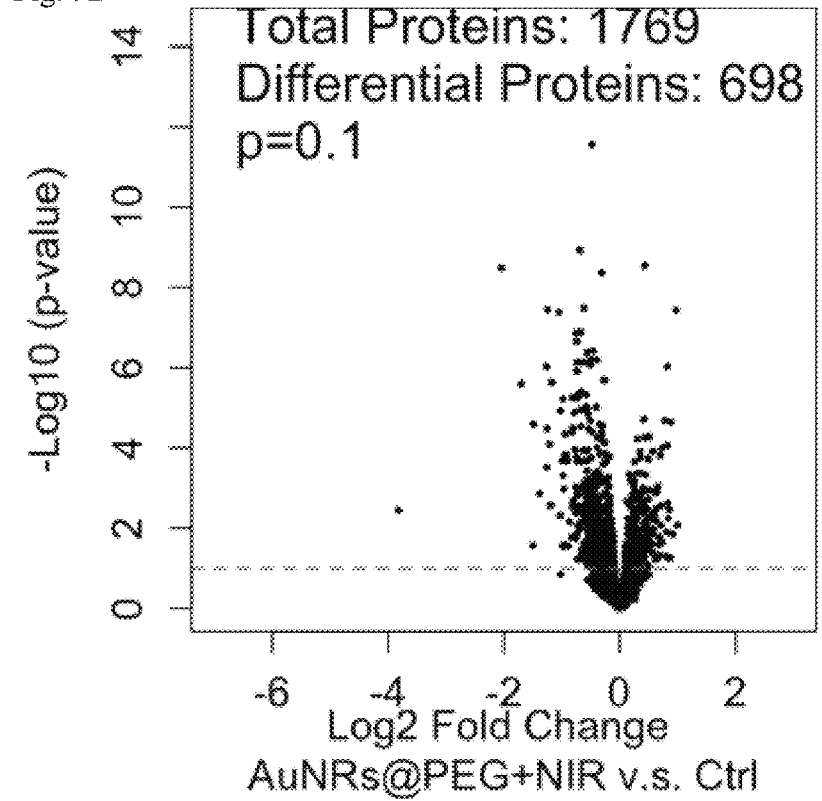
Figure 9E:
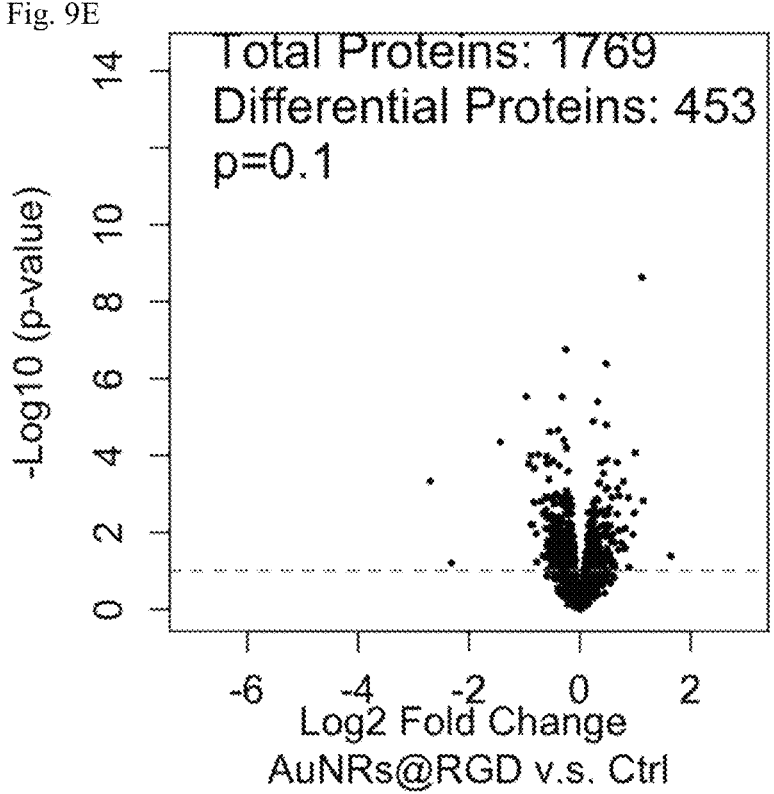
Figure 9F:
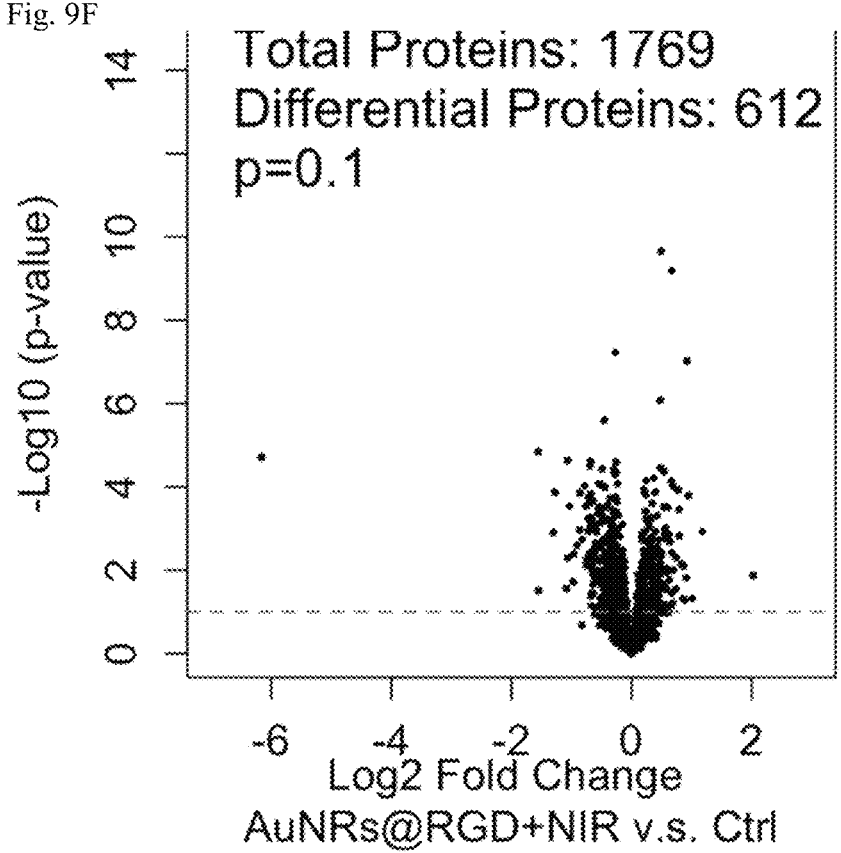
Figure 9G:
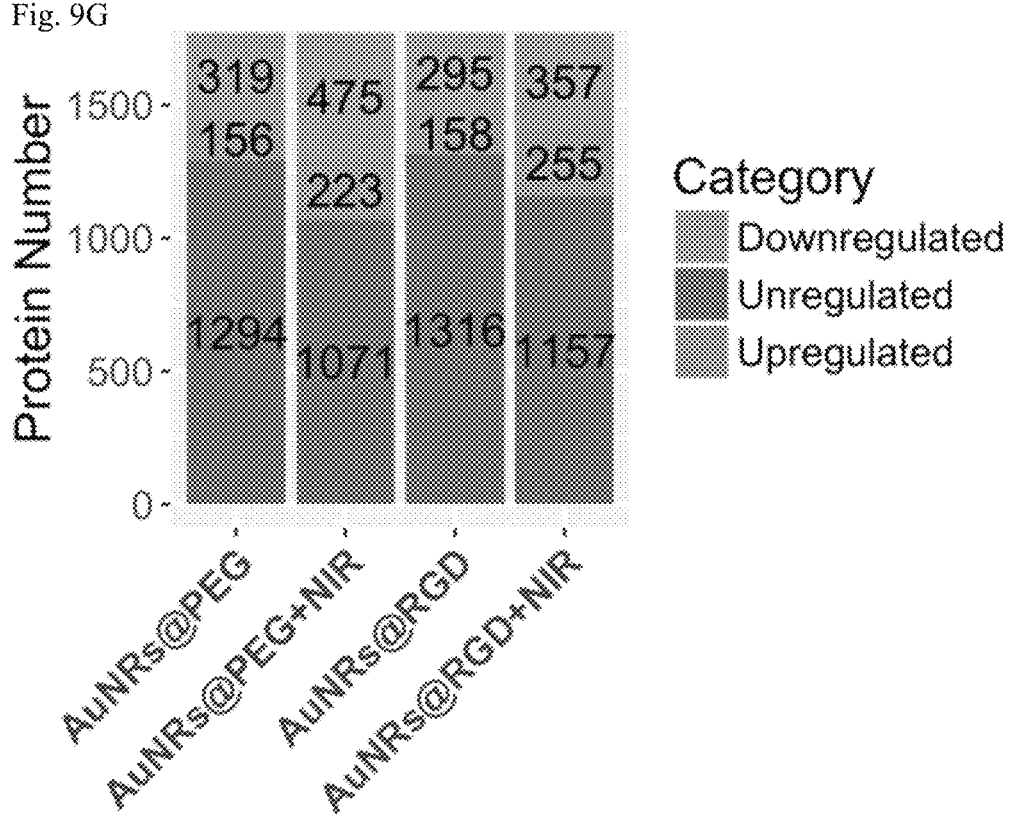
Figure 9H:
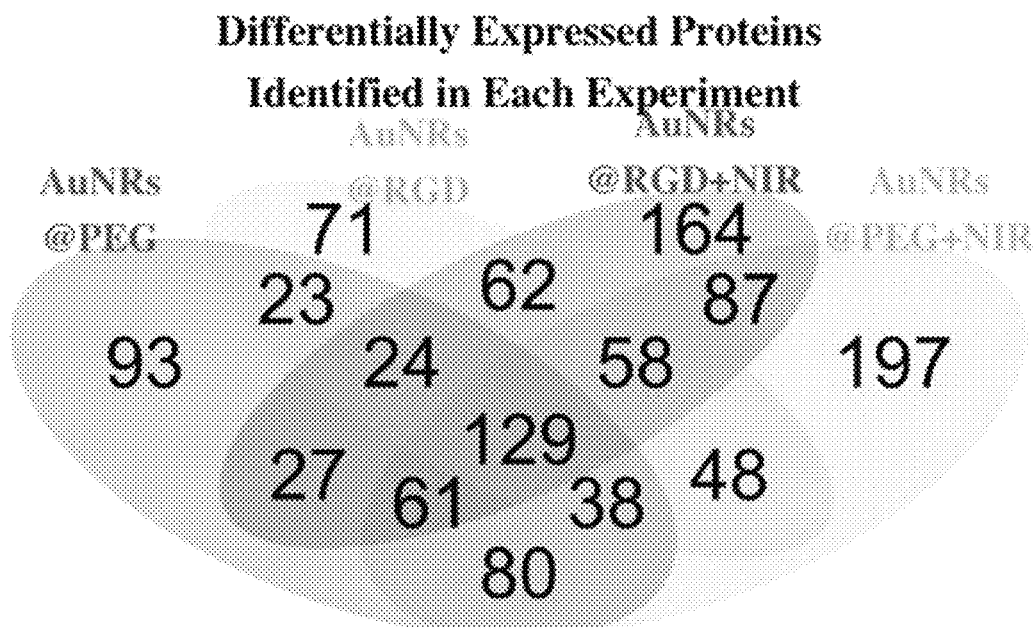
Figure 10A:
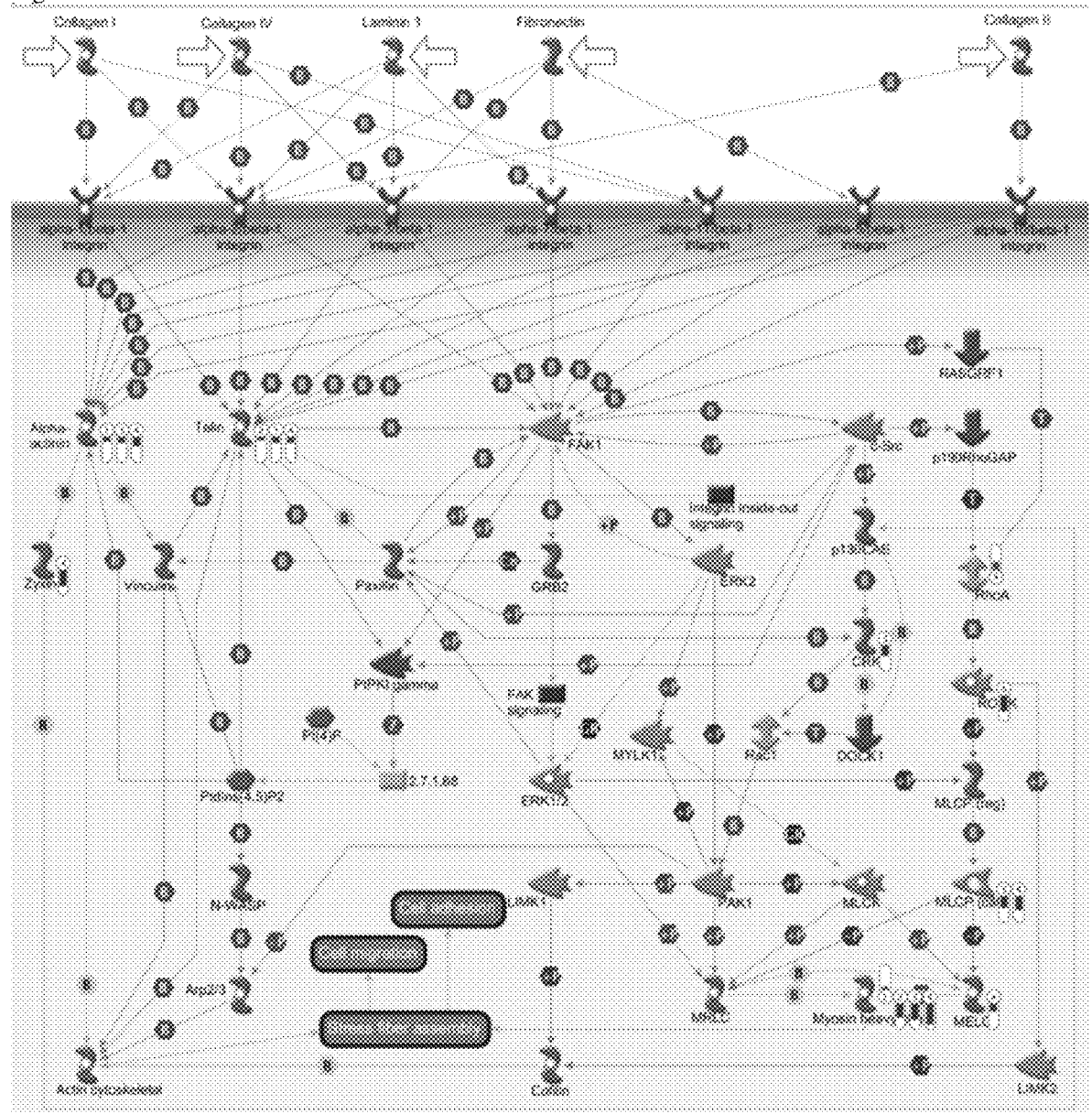
FIG. 10A-10D. Key pathways perturbed by AuNRs related to cytoskeleton identified with MetaCore from Thomson Reuters. (Red) Mean up-regulation compared with control; (blue) mean down-regulation compared with control. In the thermometer sign, 1 refers to AuNRs@PEG, 2 refers to AuNRs@PEG+NIR, 3 refers to AuNRs@RGD, and 4 refers to AuNRs@RGD+NIR. The thermometers are filled to various degrees, corresponding to the amount by which the markers were up-regulated or down-regulated.
Figure 10B:
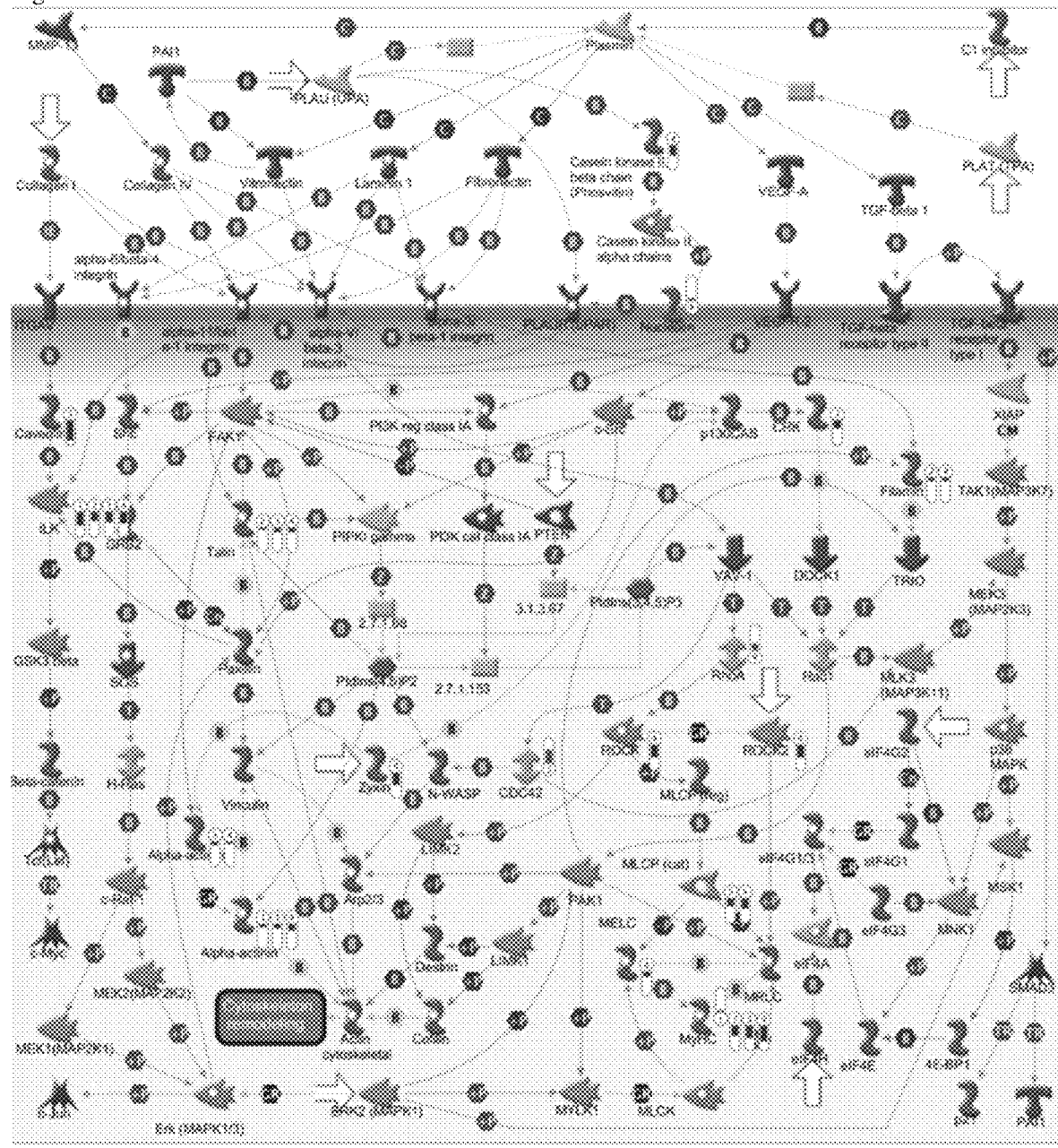
Figure 10C:
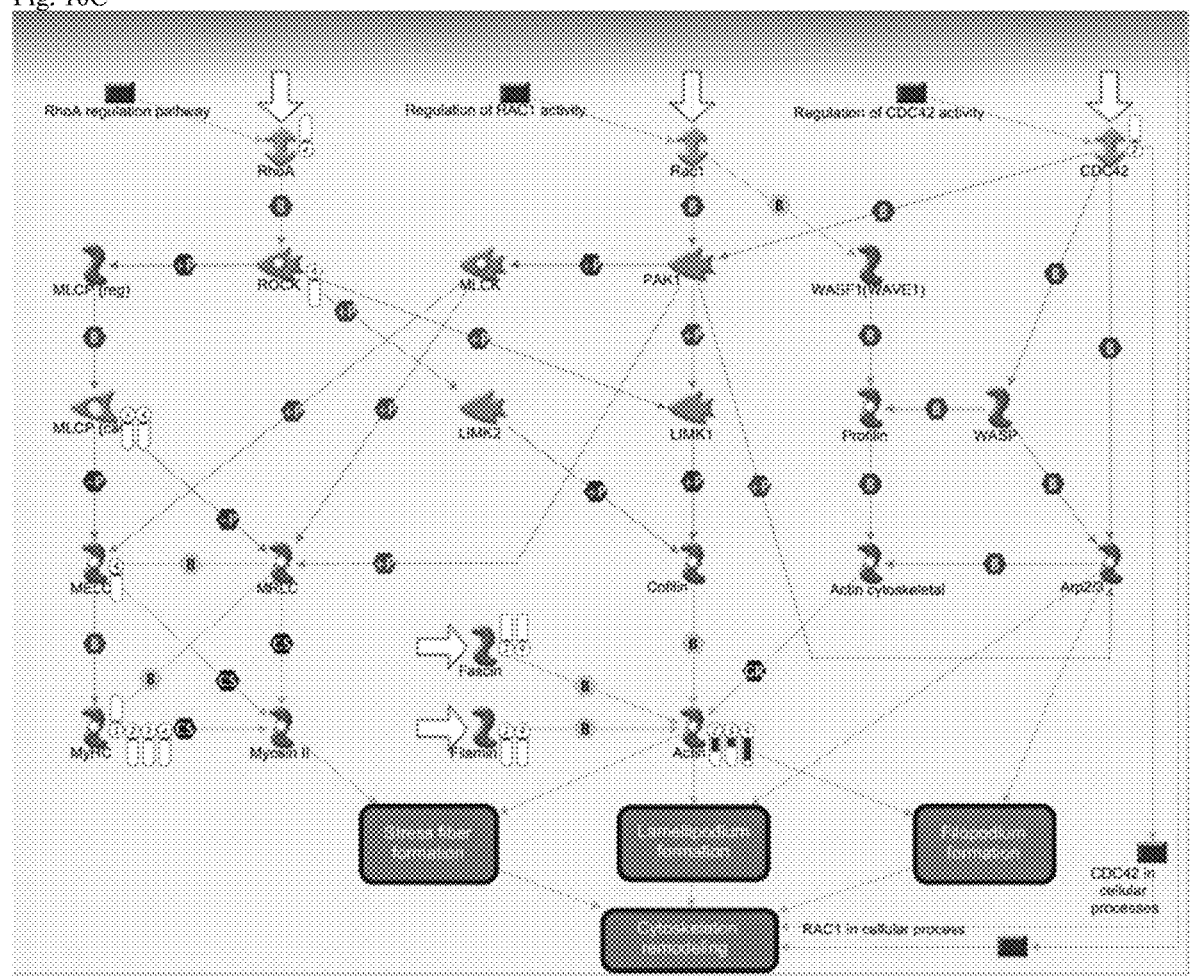
Figure 10D:
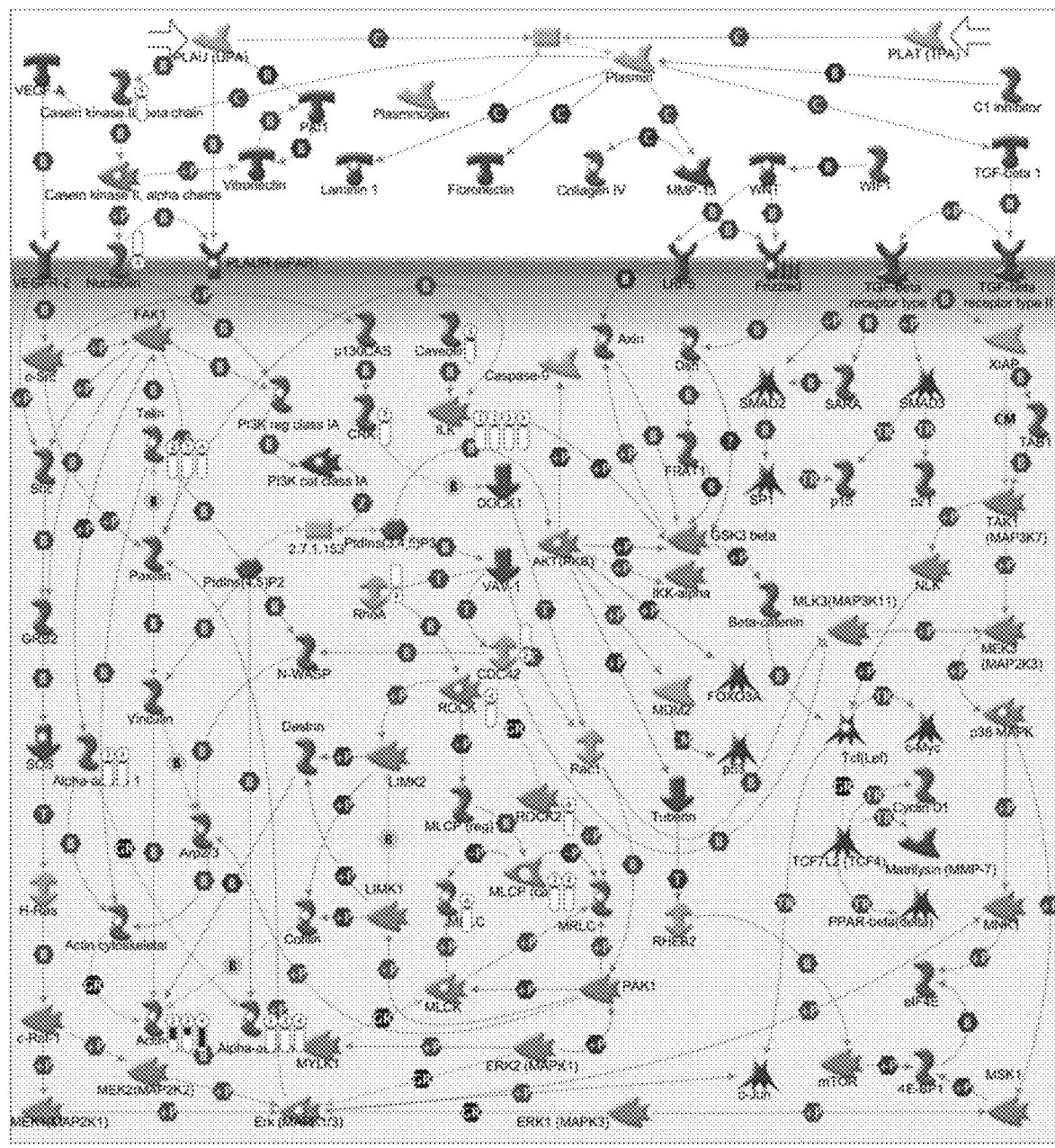

To gain a global view of proteome change, label-free quantitative proteomics was conducted to identify and quantify protein expression changes in HSC-3 cells after incubation with AuNRs. Proteomics results indicated a wide range of perturbations of proteins in migration-related pathways after AuNR treatment. In this experiment, cells were lysed and proteins were then extracted and digested. The purified peptides were analyzed by an online liquid chromatography-mass spectrometry (LC-MS) system. Two biological replications and three technical replications for each condition were conducted. In total, over 4,000 proteins were identified, and about 1,800 common proteins were quantified in four treatment groups (AuNRs@PEG, AuNRs@PEG+NIR, AuNRs@RGD, and AuNRs@RGD+NIR) (FIG. 3A). The clustering analysis (FIG. 9A-9B) shows that the control group and experimental groups were separately clustered, also indicating a good reproducibility of the proteomics experiments. Differential analysis identified proteins with significant changes in AuNR-treated groups compared with the control group (FIG. 9C-9F). The numbers of up- and down-regulated proteins in each group are shown in FIG. 9G. Comparison of differentially expressed proteins identified in the four treatments is shown in the Venn diagram (FIG. 9H). Expression levels of key proteins in migration-related pathways are shown in the heatmap (FIG. 3B), where a wide range of cytoskeletal proteins were observed to be affected in the four AuNR-treated groups. Pathway analysis using MetaCore (Thomson Reuters) revealed the perturbation of signaling pathways related to cell migration in all groups (FIG. 3C), including the cytoskeleton remodeling, Rho GTPase signaling, integrin-mediated cell migration and invasion, etc. Maps of these pathways are shown in FIG. 10 Per the pathway analysis results, AuNRs@RGD+NIR caused the greatest changes to the migration-related pathway and was considered the most effective for inhibiting cancer cell migration, followed by AuNRs@RGD and then AuNRs@PEG.

A scheme (FIG. 4) was concluded from the pathway maps (FIG. 10) to illustrate the changes of the key protein players in the migration-related pathways. AuNRs regulate the cell migration by affecting the cytoskeleton in four main ways: (i) Rho GTPases, (ii) actin, (iii) microtubule, and (iv) kinase-related signaling pathways.

Figure 3B:
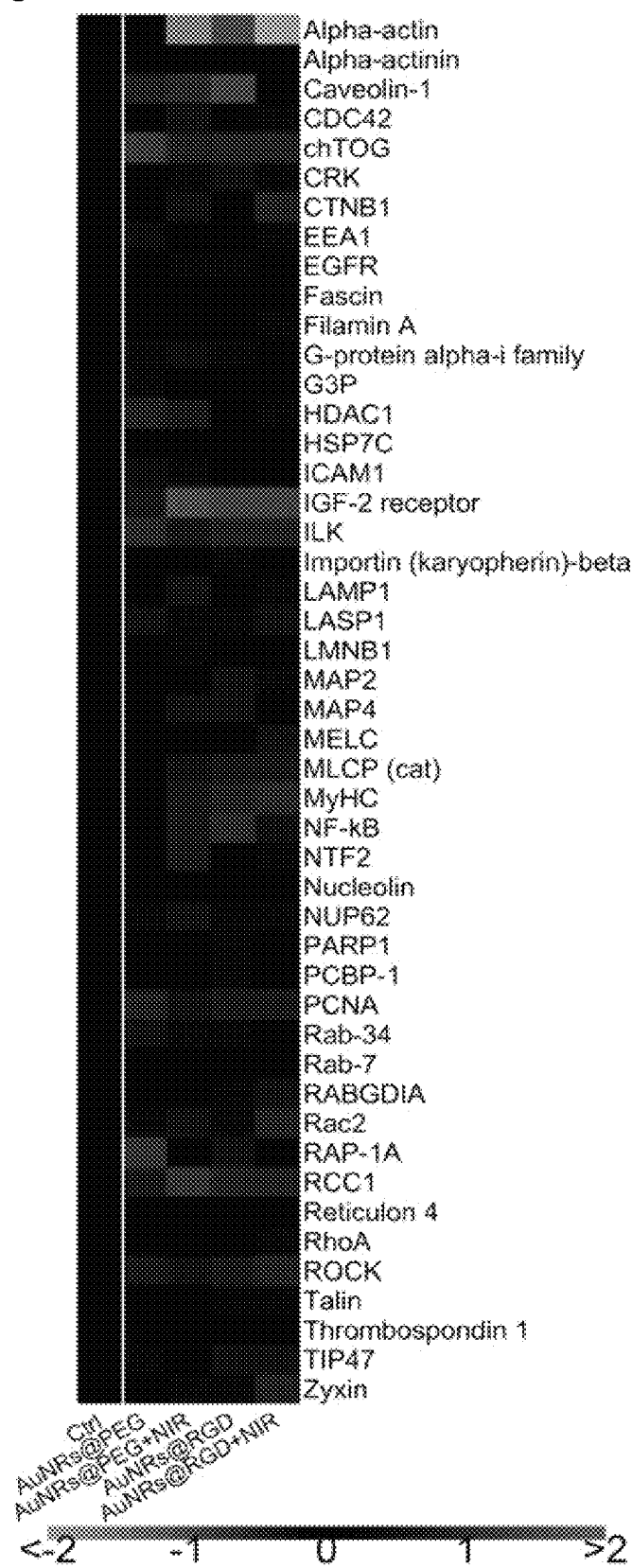
Figure 3C:
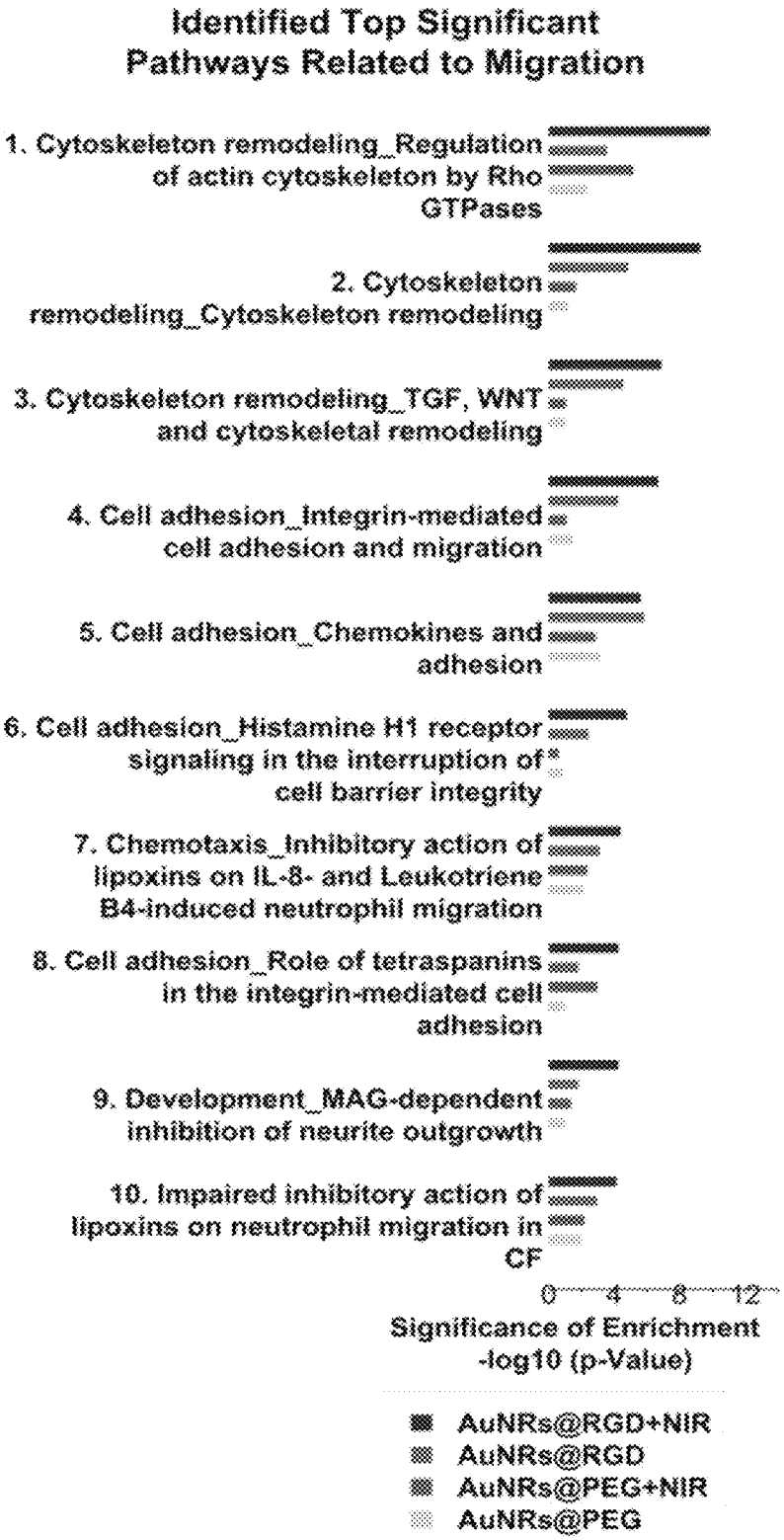
Figure 4:
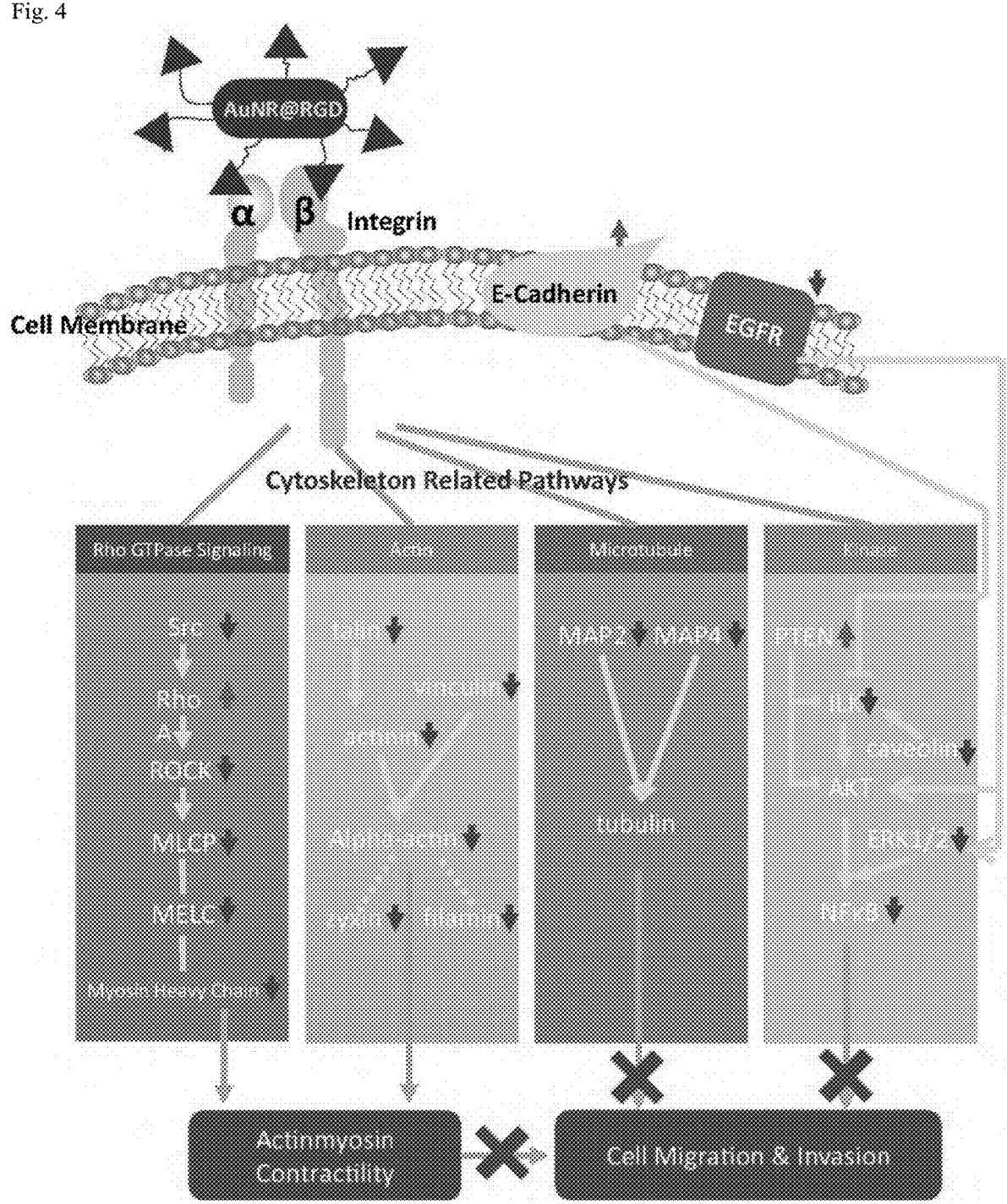
FIG. 4. Scheme representing the mechanisms involved in inhibiting cell migration upon AuNR treatments. When the AuNRs@RGD (in red) target the alpha/beta integrins, four different cytoskeletal proteins pathways are regulated, Rho (blue), Actin (yellow), Microtubule (green), and Kinase (pink), all of which affect the cell contractility and thus inhibit cell migration (shown in red at the bottom of the figure).

Rho GTPases regulate the actin cytoskeleton, which plays an important role in cellular contractility (actomyosin contraction) by directly controlling the balance between myosin II and actin and initiates the force needed for cell migration. Many key proteins in Rho GTPase signaling pathways were perturbed, including serine/threonine kinase ROCK, myosin heavy chain (MyHC), myosin essential light chain (MELC), myosin light-chain phosphorylation (MLCP), RhoA, α-actinin, talin, etc., as shown in FIG. 3B and FIG. 4. All four treatments exhibit the regulation of Rho GTPase signaling to different extents. The AuNRs@RGD+NIR group has the highest statistical significance with the lowest P value (1.5× 10-10), reflecting this group's highest efficacy in inhibiting the cancer cell migration-related pathways. These results indicate the disruption of actomyosin contraction, which might prevent the generation of traction force during the migration process.

In addition to disrupting actomyosin contraction, the effect of AuNRs on focal adhesions (or cell-matrix adhesion) was also observed. Focal adhesions are related to integrins and other associated proteins, which form links between intracellular actin cytoskeleton and ECM. The activated integrins couple to the actin cytoskeleton by recruiting actin-binding proteins. These results show that actin-binding proteins, including alpha-actinin, talin, and vinculin, were down-regulated after AuNRs incubation (FIG. 3B and FIG. 4), suggesting the connectivity between integrin and actin cytoskeleton was likely weakened due to the blocking effect of AuNRs on the migration pathways.

Although the actin cytoskeleton provides contractile forces, microtubules form a polarized network throughout the cell. The microtubule-associated proteins (MAPs) were significantly down-regulated (MAP2 and MAP4), indicating the rearrangement of microtubules. MAPs bind directly to the tubulin dimers of microtubules, which often leads to the stabilization and polymerization of microtubules. The disruption of the intracellular microtubule assembly could also limit the cell motility.

Figure 3D:
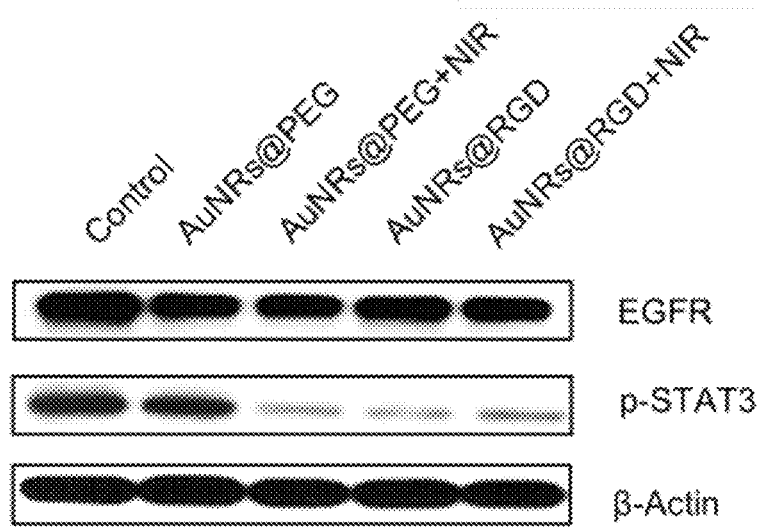

Furthermore, these results showed several kinases related to the integrin signaling pathways were perturbed, including integrin-linked kinase (ILK), nuclear factor-κB (NF-κB), the epidermal growth factor receptor (EGFR), caveolin, etc. These proteins are closely associated with integrin regulation and cell migration. It has been reported that the overexpression of ILK could promote the migration and invasion of colorectal cancer cells via NF-κB signaling. In the current results, the down-regulation of ILK and NF-κB is associated with reduced cancer cell migration ability. In addition, the expression level of EGFR, a surface receptor for epidermal growth factor, decreased. The down-regulation of EGFR was also confirmed in the Western-blot results. EGFR is regarded as an important target for anticancer therapeutics. Furthermore, STAT3, which is normally activated by tyrosine phosphorylation in response to the addition of EGFR and can promote cell migration, was also down-regulated in all of the AuNR-treated samples (FIG. 3D).

Discussion

Herein, the inventors have shown that targeting AuNRs to cancer cell surface integrins could surprisingly greatly rearrange the cytoskeleton proteins, thus enhancing the inhibition effect on cancer cell migration. Compared with nontargeted AuNRs, the integrin-targeted AuNRs are surprisingly more effective on cell migration inhibition with a nanoparticle concentration at the nM scale (1,000× lower than the literature values), which could be safer for future clinical use.

These results show that cancer cells incubated with integrin-targeted AuNRs (with or without NIR light exposure) exhibited impaired migration abilities. Morphological changes were observed in cytoskeleton protrusions by targeting surface integrins using AuNRs, namely lamellipodia and filopodia, that form the leading edge for cell movement. These cytoskeleton protrusions were reduced after treating the cells with AuNRs@RGD. Furthermore, greater morphological changes were observed after applying NIR light. Integrins are often found in the tips or alone in the shaft of filopodia and lamellipodia, which creates the "sticky fingers" and facilitates the migration and invasion. The reason for this morphological change has been explored in the Western blot and proteomics analysis, which indicated that the integrin-related proteins were obviously affected.

In addition to the morphological change through lamellipodia and filopodia, systematic molecular mechanisms have been studied, and many protein pathways exhibit changes after exposure to integrin-targeted AuNRs. This broad change of cytoskeletal proteins is possibly due to the ability of integrin in controlling cytoskeleton through many different ways as an up-stream surface receptor. Results show that by targeting surface integrins, the focal adhesion connecting the cytoskeleton to the ECM through integrin might be weakened. Moreover, the actomyosin contraction, which creates intracellular tension for migration, has been modulated through the Rho GTPase signaling. Although targeting integrins, both the changes of actin and microtubule were observed, as well as several protein kinases that related to cytoskeleton and cancer progression and metastasis. All of the above aspects could finally result in the inhibition of cancer cell migration.

In summary, the ability of targeting AuNRs to cancer cell surface integrins and the introduction of PPTT caused wide-range regulation on cytoskeletal proteins, observed as lamellipodia/filopodia morphological changes and four major groups of migration-related protein changes. Applying NIR light to generate mild heat further enhanced this effect.

Methods

Materials.

Tetrachloroauric acid trihydrate (HAuCl4.3H2O), NaBH4, ascorbic acid, CTAB, AgNO$_3$, 4-(2-hydroxyethyl)-1-piperazineethanesulfonic acid (Hepes), NaCl, sodium deoxycholate, SDS, and Triton×100 were purchased from Sigma-Aldrich. Methoxypolyethylene glycol-thiol (mPEG-SH, MW 5000) was purchased from Laysan Bio, Inc. Cell-penetrating peptide RGD (RGDRGDRGDRGDPGC) was obtained from GenScript, Inc. Dulbecco's PBS, DMEM, FBS, antibiotic solution, and 0.25% trypsin/2.2 mM EDTA solution were purchased from VWR. Mammalian cell protease inhibitors and phosphatase inhibitors were purchased from Roche Applied Sciences, and sequencing grade trypsin was purchased from Promega. Lysyl endopeptidase (Lys-C) was purchased from Wako.

Instrumentation.

AuNPs were imaged using a JEOL 100CX-2 TEM, and their average size was then measured by ImageJ software. UV-vis spectra were obtained using an Ocean Optics HR4000CG UV-NIR spectrometer. An inverted Nikon Eclipse Ti-E microscope equipped with Perfect Focus System (PFS, 25 nm z axial resolution) was used for imaging under a Nikon DIC microscope. Proteomics analysis was performed on a hybrid dual-cell quadrupole linear ion trap-Orbitrap mass spectrometer LTQ Orbitrap Elite (Thermo Fisher) with XCalibur 3.0.63 software. Flow cytometry experiments were conducted on a BD LSR II Flow Cytometer (BD Biosciences).

Synthesis, Conjugation, and Characterization of AuNRs.

AuNRs with an average size of 25×6 nm (length×width) were synthesized using a seedless growth method. The inventors added 5 mL of 1.0 mM HAuCl$_4$ to a solution of 5 mL of 0.2 M CTAB, 250 µL of 4.0 mM AgNO$_3$, and 8 µL of 37% HCl. Then, 70 µL of 78.8 mM ascorbic acid was added, followed by immediate injection of 15 µL of 0.01 M ice-cold NaBH$_4$. The solution was left undisturbed for 12 h. The particles were centrifuged at 21,000×g for 50 min and dispersed in DI water, followed by a second centrifugation at 19,000×g for 40 min to remove the extra CTAB. TEM was used to measure the sizes and homogeneity of the nanoparticles.

After rinsing them with water, AuNRs were then conjugated with different surface ligands (PEG and RGD). For AuNRs@PEG, mPEG-SH (1 mM) was added to the nanoparticles overnight to achieve about 5,000 ligands on each particle. For preparing AuNRs@RGD, first, mPEG-SH (1 mM) was added to the nanoparticles overnight to achieve about 1,000 ligands on each particle. Then, the PEGylated nanoparticles (1 nM) were treated with RGD (1 mM) to achieve 10,000 molar excess. The solution was then allowed to shake overnight at room temperature. Excess of ligands was removed by centrifugation. UV-vis spectrometer and zetasizer were used to test the conjugation.

Cell Culture, AuNR Treatments, and PPTT.

The human oral squamous cell carcinoma (HSC-3) cells were grown in DMEM (Mediatech) containing 10% (vol/vol) FBS (Mediatech) and 1% antimycotic solution (Mediatech) at 37° C. in a humidified incubator under 5% CO2. Cells were cultured in 60-mm dishes for 24 h followed by incubation with AuNRs for 24 h. Then, a CW 808-nm laser (5.8 W/cm2, spot size 5.6 mm) was applied to the cells for 1 min. To cover the entire area of the culture dish, the laser was applied spot by spot using scanning with each spot undergoing 1 min of laser exposure time. The cells were then harvested for MS analysis, with a final confluence of about 80-90%.

Sample Preparation for Proteomics Experiment.

After treatment for 24 h, cells were washed twice using PBS. Cell lysates were prepared by directly adding the lysis buffer (150 mM NaCl, 50 mM Hepes, pH 7.4, 0.1% SDC, 10 units per mL benzonase, protease inhibitor mixture) to the cells followed by scraping and collecting on ice. Lysates were vortexed for 90 s (30 s×3 times, 2 min pause), sonicated on ice, and centrifuged at 18,000×g for 15 min at 4° C. The supernatant solutions were saved, and proteins were precipitated by adding 4× excess volumes of ice-cold precipitation solvents (acetone:ethanol:acetic acid=50:50:0.1). After centrifugation, the protein pellet was redissolved in a solution with 8 M urea and 50 mM Hepes (pH 8).

Protein disulfide bonds were reduced using 1 mM DTT followed by alkylation with 5.5 mM iodoacetamide. After the lysates were diluted twice (final urea concentration of 4 M), endoproteinase Lys-C (1:100 wt/wt) was added to digest proteins for 4 h. Then, modified sequencing grade trypsin (1:100 wt/wt) was used for further digestion in a more diluted solution with the final urea concentration of 1 M overnight. Protein concentration was measured by Bradford assay.

RPLC-MS/MS Analysis for Label-Free Quantitative Proteomics.

The proteomics analysis was conducted using the previously reported method. Briefly, purified and dried peptide samples from the previous step were dissolved in 10 µL solvent with 5% acetonitrile and 4% FA, and 4 µL of the resulting solutions were loaded onto a microcapillary column packed with C18 beads (Magic C18AQ, 3 µm, 200 Å, 100 µm×16 cm, Michrom Bioresources) by a Dionex WPS-3000TPLRS autosampler (UltiMate 3000 thermostated Rapid Separation Pulled Loop Well Plate Sampler). A reversed-phase liquid chromatography (RPLC) was used for peptide separation with a 110-min gradient of 8-38% ACN (with 0.125% FA). Peptides were detected with a data-dependent Top20 method—that is, for each cycle, one full MS scan (resolution, 60,000) in the Orbitrap was followed by up to 20 MS/MS in the ion trap for the most intense ions. The selected ions were excluded from further analysis for 90 s. Ions with singly or unassigned charge were not sequenced. Maximum ion accumulation times were 1,000 ms for each full MS scan and 50 ms for MS/MS scans. The sample at each condition was repeated 6 times (2 biological and 3 technique replicates) for label-free quantification.

Apoptosis/Necrosis Assay.

After removing the cell culture media, cells were washed with PBS and collected after trypsinization followed by washing with cold PBS twice again. Then, the cells were dispersed in a mixture of 493 mL of annexin V binding buffer, 5 µL of annexin V FITC (BioLegend), and 2 µL of propidium iodide PI (BioLegend, 100 µg/mL) and incubated for 15 min at room temperature. The cells were then filtered and subjected to flow cytometry analysis using a BSR LSR II flow cytometer (BD Biosciences). A 488-nm laser was applied for excitation, and FITC was detected in FL-1 using a 525/30 BP filter, whereas PI was detected in FL-2 using a 575/30 BP filter. Standard compensation using unstained and single-stained cells was done before running actual experiments. FlowJo software (Tree Star Inc.) was used for analysis of the viable, apoptotic, and necrotic cells from at least 10,000 events.

Cell Imaging Using DIC Microscopy.

The Nikon DIC mode used a pair of polarizer and analyzer, a high-resolution 100×I-R Nomarski DIC slider, a high numerical aperture (N.A., 1.40) oil immersion condenser lens, a Nikon CFI Apo TIRF 100× (N.A., 1.49) oil immersion objective, and a 12 V/100 W halogen lamp as the light source. Appropriate bandpass filters were placed in the light path. Fixed HEYA8 cells on 22 mm×22 mm glass coverslips were rinsed with PBS at pH 7.4 and fabricated into a sandwiched chamber with two pieces of double-sided tape and a cleaned glass slide. PBS solution was then added into the chamber to fill the space, and the chamber was then sealed by clear nail polish. The so-formed sample slide was then placed under the microscope for observation. Two scientific CMOS cameras were used to capture the DIC images: a Hamamatsu C11440-22CU, ORCA-Flash 4.0 V2 with a 2048×2048 pixel array and a pixel size of 6.5 µm×6.5 µm and a Tucsen Dhyana 95 with a 2048×2048 pixel array and a pixel size of 11 µm×11 µm. These cameras performed similarly in our experiments.

Scratch Assay.

The scratch assay has been performed according to a former report. Cells were cultured in a six-well plate to a confluent monolayer. A p200 pipet tip was used to scrape the cell monolayer in a straight line to create an empty gap. The debris was then removed by washing the cells once with a culture medium and then replaced with 2 mL of fresh medium. Then, the cells were imaged immediately after scratch and 12 h after scratch.

Proteomics Data Analysis.

Two biological replications and three MS technical replications for each condition (control, AuNRs@PEG, AuNRs@PEG/NIR, AuNRs@RGD, AuNRs@RGD/NIR) were conducted. Raw data from proteomics was normalized using supervised normalization of the microarray (SNM). In the SNM procedure, variance due to biological and technical replicates was adjusted by setting them as variables in the model. Variance explained by different experimental treatments (control, AuNRs@PEG, and AuNRs@PEG+NIR for PEG-conjugated AuNR group; control, AuNRs@RGD, and AuNRs@RGD+NIR for RGD-conjugated AuNR group) was fitted as a biological variable in the model. Hierarchical clustering was done with statistical software R. Proteomics data were log 2-transformed before analysis of variance (ANOVA), which was used to detect differential expression of proteins between control and treatment groups, with treatment conditions set as fixed effects. P value threshold at 0.1 was set to select differential proteins. The proteins identified as being affected were subjected to pathway analysis using the MetaCore pathway analysis software ("MetaCore from Thomson Reuters").

Western Blot Analysis.

Briefly, cells were lysed in RIPA buffer (20 mM Tris, pH 7.4, 150 mM NaCl, 2 mM EDTA, 2 mM EGTA, 0.1% sodium deoxycholate, 1% Triton X-100, 0.1% SDS) containing protease inhibitors (Sigma-Aldrich). BCA assay (Pierce) was performed to measure the protein concentration, and equal amounts of protein were loaded on a SDS/PAGE gel. After the protein separation, the resulting gels were transferred to PVDF membranes (Millipore) overnight. Afterward, the gel was blocked with 5% milk in TBS (20 mM Tris, 150 mM NaCl). The primary antibodies (Bethyl Laboratories, Inc.) were incubated with the membrane overnight in 4° C. with shaking, followed by adding the secondary antibodies (Jackson Immuno Research Laboratories). Blots were washed three times for 20 m in TBS after primary and secondary antibodies.

Example 2—Nuclear Membrane-Targeted Gold Nanoparticles Inhibit Cancer Cell Migration and Invasion Here, targeted AuNPs were used to locate the AuNPs to the cells, because of their specific physical and chemical properties and better biocompatibility than other nanomaterials such as nanoceramics or silver nanoparticles. By targeting and locating the AuNPs to the cell in a manner to modulate the stiffness of its nucleus, the inventors could surprisingly improve the inhibition effect on cell migration and invasion. In these experiments, the inventors used three ligands, methoxy-polyethylene glycol thiol (PEG) for increasing the biocompatibility of AuNPs, RGD (RGDRGDR-GDRGDPGC) peptides for binding to the surface integrin of cancer cells and enhancing endocytosis, and nuclear localization signal (NLS, CGGGPKECICRICVGG) peptides for targeting the AuNPs to the nucleus. Cell migration or invasion abilities have been measured, and the results show a clear decrease in these functions after the nuclear targeting of the nanoparticles. For studying the cell mechanical response, atomic force microscope (AFM) showed that the two types of AuNPs (i.e., AuNRs and AuNSs) both significantly enhanced the nuclear stiffness. A high-resolution 3D optical imaging system showed the exact location of the nanoparticles, which were trapped at the nuclear membrane. The levels of lamin A/C were found to be surprisingly elevated upon nanoparticle incubation, which could be an explanation for the observed enhanced nuclear stiffness causing inhibition of cell motility upon gold nanoparticle treatment.

Results and Discussion

Au Nanoparticles Synthesis, Conjugation, Cellular Uptake and Cytotoxicity Measurement.

Figure 11A:
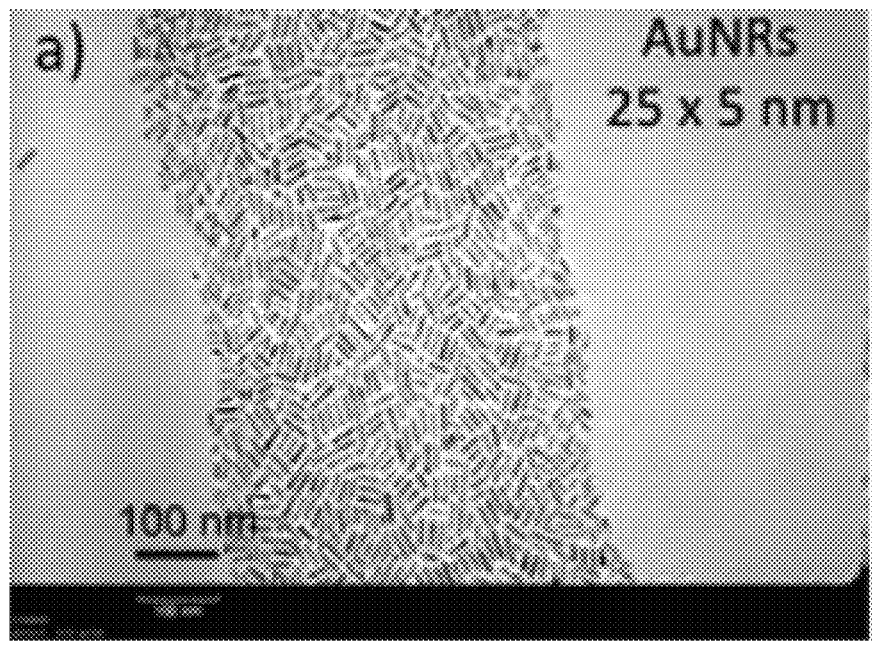
FIG. 11A-11E. Characterization of Au nanoparticles.
Figure 11B:
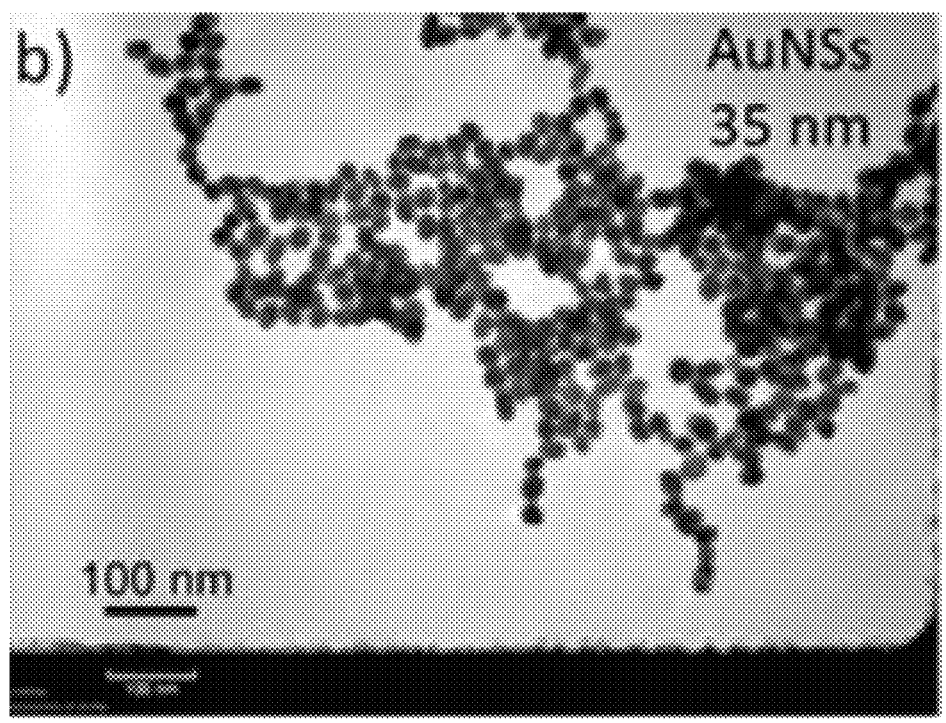
Figure 11C:
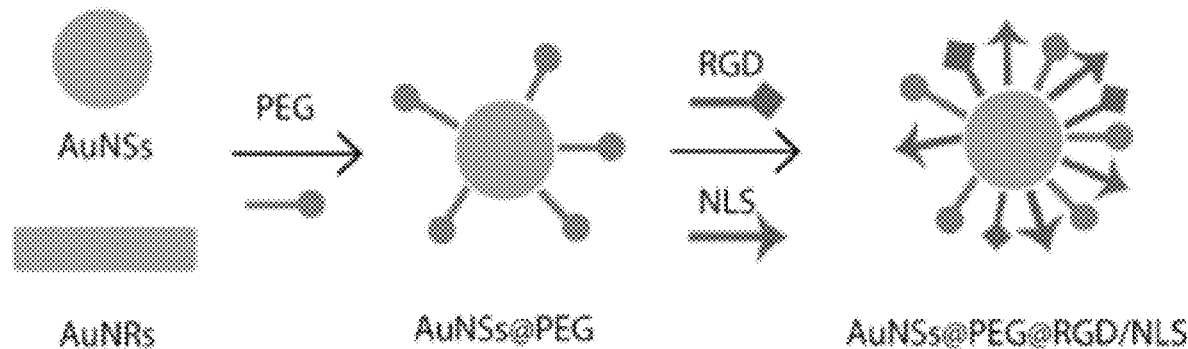
Figure 11D:
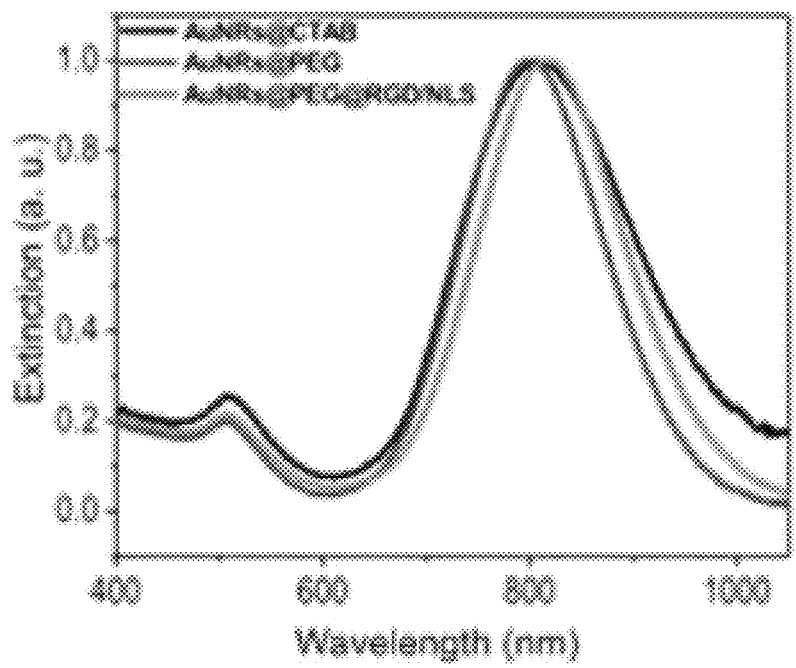

The AuNRs with an average size of 25 (±2)×5 (±0.5) nm were synthesized using a seedless method (35), as shown in FIG. 11A (TEM figure) and a surface plasmon resonance (SPR) peak centered ~800 nm (UV-vis spectrum in FIG. 11D). The AuNSs with an average size of 35±2 nm that absorb at 535 nm wavelength of light were synthesized using citrate reduction method and were shown in FIGS. 1B and 1E (TEM and UV-vis spectrum). Both of the two types of the nanoparticles are widely used in the biological studies.

Figure 11E:
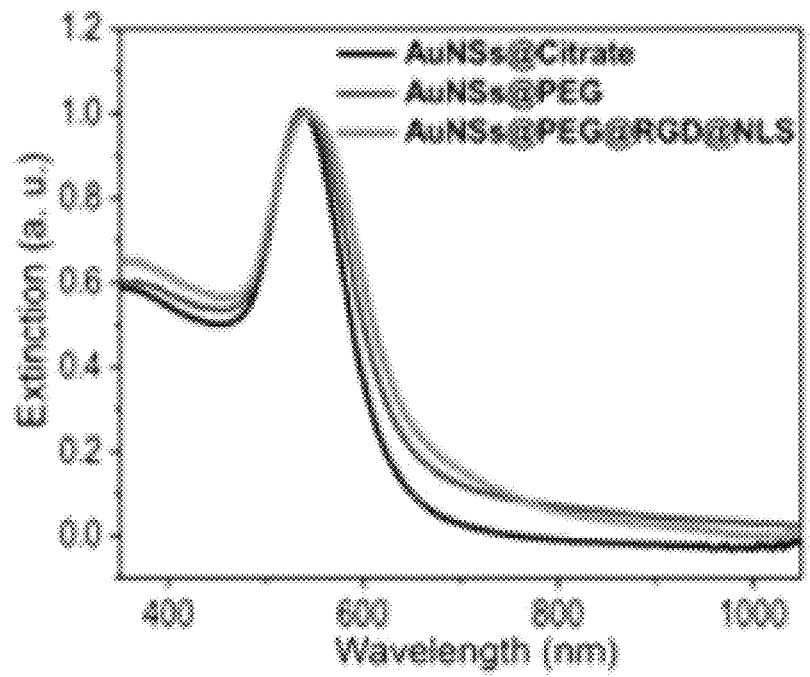

AuNPs were functioned with three ligands, methoxy-polyethylene glycol thiol (PEG), RGD peptides and nuclear localization signal (NLS) peptides, as shown in schematic FIG. 11C. First, the inventors conjugated the PEG to the surface of the AuNPs surface in order to enhance the biocompatibility. The second ligand, RGD bound to surface integrins, which are highly expressed on the surface of the cancer cells when compared to healthy cells to enhance the receptor-mediated endocytosis of the nanoparticles selectively to the cancer cells. The third ligand, NLS, was recognized by importin and translocate into the nucleus. Successful surface modification of AuNRs@PEG@RGD/NLS (AuNRs@NLS) is evident in the red-shift of the plasmon peak of AuNRs to longer wavelengths, from 800 nm for the as-synthesized cetyl-trimethyl ammonium bromide (CTAB) coated AuNRs to 805 nm for PEGylated AuNRs, and finally to 825 nm for the RGD and NLS modified AuNRs (FIG. 11D). Similarly, the surface plasma peak of AuNSs@PEG@RGD/NLS (AuNSs@NLS) was also red-shifted (FIG. 11E), which is in agreement with previous studies.

The zeta potential of the AuNRs at the different conjugating stages of the three livands were measured (Table 1) to confirm the surface modifications. The as-synthesized CTAB coated AuNRs has a highly positive surface charge (50.9±7.97 mV); this makes sense as CTAB is a highly cationic surfactant. After PEG modification, the AuNRs become negatively charged (−13.6±11.8 mV). The zeta potential of the AuNRs becomes positive again (14.9±3.13 mV) after further modification with RGD and NLS peptides (Table 1). Also, the zeta potential of the AuNSs@NLS proved their successful surface modification (Table 1), similar to previous studies.

TABLE 1

Zeta potential of AuNPs with different surface ligands.

| Au nancparticles with different surface ligands | Zeta potential (mV) |
|---|---|
| AuNRs@CTAB | 50.9 ± 7.97 |
| AuNRs@PEG | −13.6 ± 11.8 |
| AuNRs@PEG@RGD@NLS | 14.9 ± 3.13 |
| AuNSs@Citrate | −29.7 ± 4.72 |
| AuNSs@PEG | −12.1 ± 5.79 |
| AuNSs@PEG@RGD@NLS | 18.3 ± 7.55 |
| AuNRs@BSA | −19.6 ± 9.89 |
| AuNSs@BSA | −15.2 ± 12.5 |

To examine the cytotoxicity of the AuNPs, the XTT cell proliferation assay was conducted, and no significant change of the cell viability was observed for nanoparticles at frequently used concentrations 0.5, 2.5, and 5 nM (for AuNRs) (FIGS. 12A and 12B), and 0.05, 0.1, and 0.2 nM. Concentrations (for AuNSs)). Apoptosis/necrosis assay was also conducted for 5 nM of the AuNRs or 0.2 nM of the AuNSs (FIGS. 2C, 2D and 2E) using flow cytometry. The results indicate that the concentrations of the AuNRs used in this study are lower than those affecting cell viability or inducing apoptosis.

The mass concentration (gram/L) of the two types of particles are very similar (Equation 1).

$$\frac{C_{AuNSs}(g/L)}{C_{AuNRs}(g/L)} = \frac{M_{w(Au)}\rho_{(Au)}V_{AuNSs}C_{AuNSs}}{M_{w(Au)}\rho_{(Au)}V_{AuNRs}C_{AuNRs}} = \quad \text{(Equation 1)}$$

-continued $$\frac{V_{AuNSs}C_{AuNSs}}{V_{AuNRs}C_{AuNRs}} = \frac{4/3\pi R^3 C_{AuNSs}}{\pi\left(\frac{w}{2}\right)^2 l C_{AuNSs}} = 0.92 \approx 1,$$

where $C_{AuNSi(g/L)}$ or $C_{AuNRs(g/L)}$ is the mass concentration (in grain of gold/L), $M_{w(Au)}$ is the molar mass of gold, $\rho(Au)$ is the density, $V_{AnNSs}$ or $V_{AuNRs}$ is the volume of the gold nanoparticles (AuNSs or AuNR), $C_{AuNSs}$ or $C_{AuNRs}$ is the molar concentration of the gold nanoparticles (AuNSs or AuNRs), R is the average radius of the AuNSs, w and l are the width and length in the AuNRs.

Figure 16A:
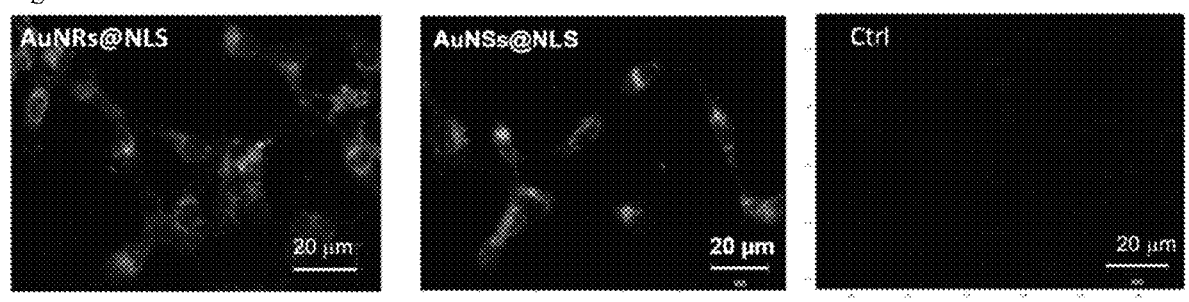
FIG. 16A-16C. HEY A8 cell uptake of AuNRs@NLS and AuNSs@NLS. (16A) Dark field images of cells without AuNPs incubation (Ctrl), with 2.5 nM of AuNRs@NLS and 0.1 nM of AuNSs@NLS incubation. (16B) UV-Vis spectra of 2.5 nM of AuNRs@NLS or 0.1 nM of AuNSs@NLS (16C) in culture media before incubation with cells (black spectrum), compared with the ones after 24 h cell incubation (red spectrum).
Figure 16B:
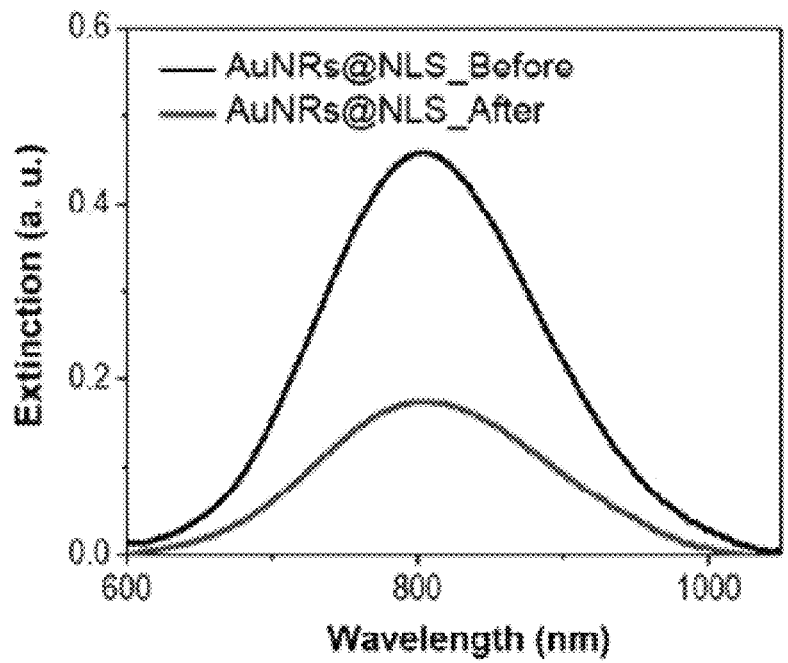
Figure 16C:
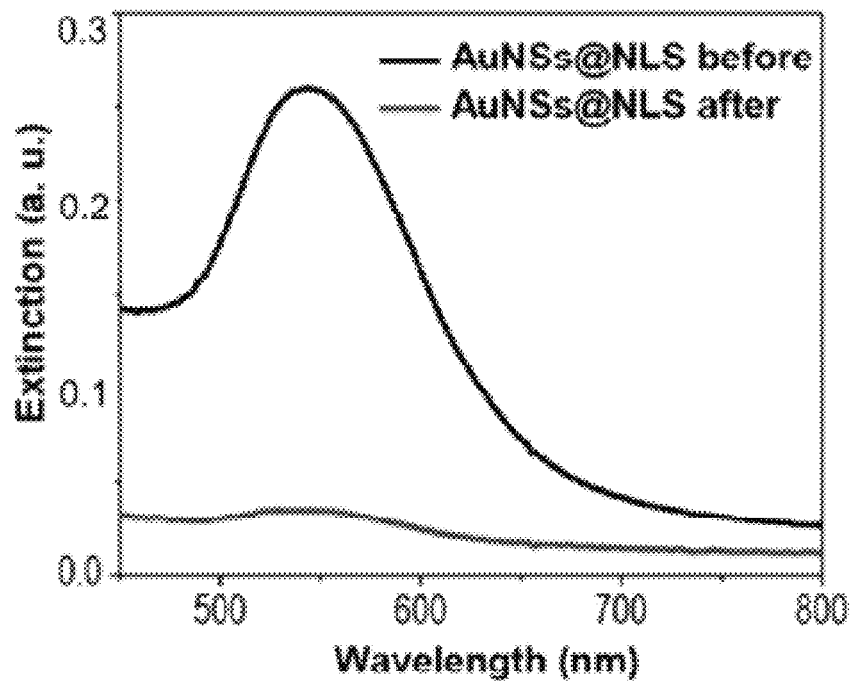

The uptake of AuNPs@NLS was monitored using darkfield (DF) microscopy and UV-vis absorption. The HEY A8 cells, which were previously identified to be highly invasive cell line, were incubated with 2.5 nM of AuNRs@NLS or 0.05 nM of AuNSs@NLS for 24 h. As shown in the DF image (FIG. 16A), clear internalization of both AuNPs (AuNRs@NLS and AuNSs@NLS) was observed. To evaluate the AuNPs uptake to the HEY A8 cells, UV-vis spectra were collected for the AuNPs in culture media before incubation with cells and compared with the ones after 24 h cell incubation (FIG. 16B-16C). According to the Beer's law, the concentration of gold nanoparticles is linearly correlated with the absorbance at their localized surface plasmon resonance (LSPR) wavelength. Therefore, the decrease of the absorbance indicates the portion of AuNRs internalized in cells.

Figure 17A:
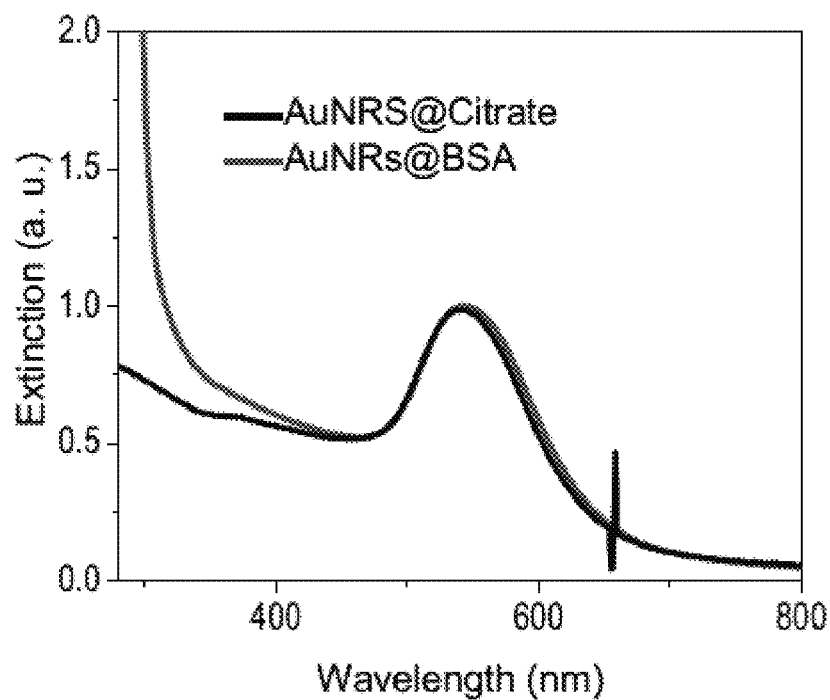
FIG. 17A-17D. Characterization for AuNPs@BSA and HEY A8 cell uptake. (17A) UV-Vis extinction spectra of the unconjugated AuNSs@Citrate (black spectrum) and AuNRs@BSA (red spectrum). (17B) UV-Vis extinction spectra of the unconjugated AuNRs@CTAB (black spectrum) and AuNSs@BSA (red spectrum). (17C) XTT assay of HEY-A8 cells after 24 h incubation with AuNSs@NLS at concentrations 0.05 nM (light blue), 0.1 nM (medium blue) and 0.2 nM (dark blue), n=3. (17D) XTT assay for cells after 1.5 nM (light blue), 2.5 nM (medium blue) and 5 nM (dark blue) of AuNRs@NLS incubation with HEY A8 cells for 24 h (n=3).
Figure 17B:
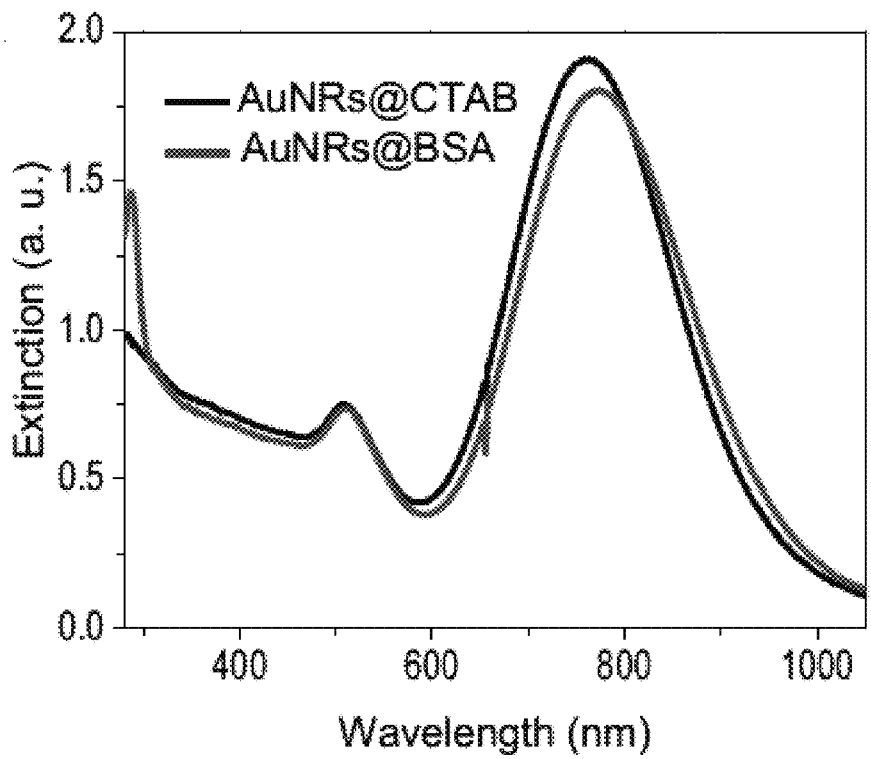
Figure 17C:
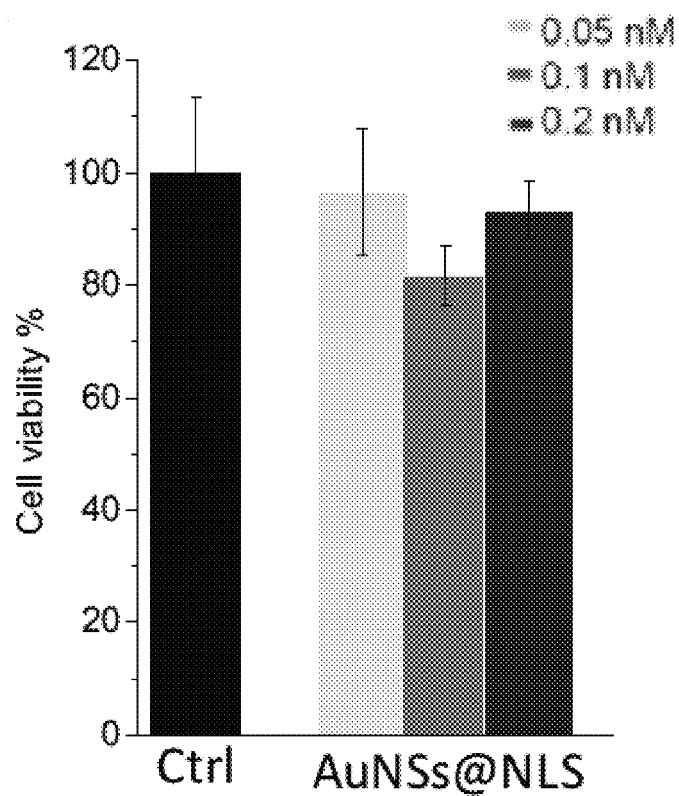
Figure 17D:
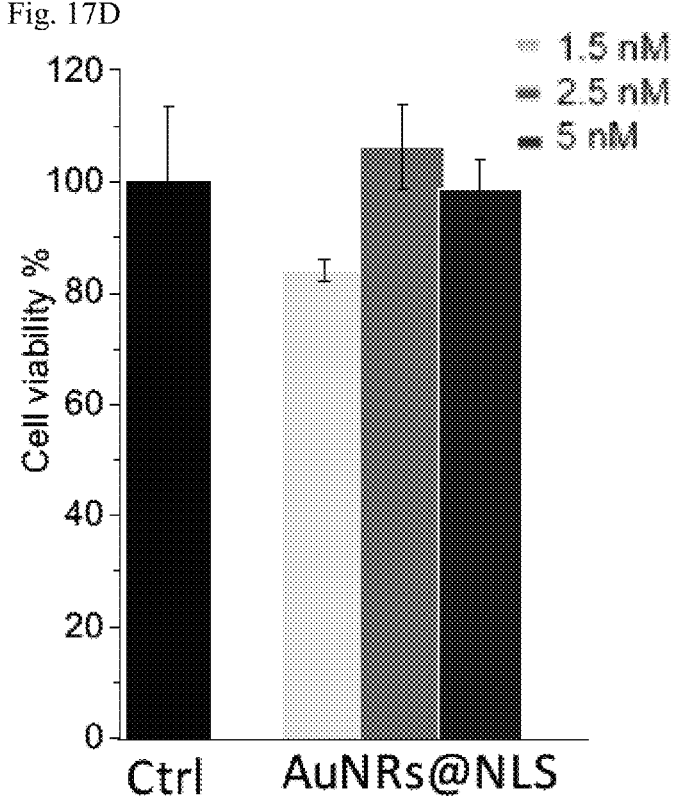

Nontargeted AuNPs with bovine serum albumin (BSA) coating were also fabricated. Successful surface modification of AuNPs@BSA (both AuNRs@BSA. and AuNSs@BSA) was evident in the red-shift of the surface plasmon peak of AuNPs to longer wavelengths (FIG. 17A-17B). Zeta potential of AuNRs after BSA modification became negatively charged (−19.6±9.89 mV, Table 1) due to the negative charge of BSA, while the as-synthesized CTAB coated AuNRs has highly positive surface charge (50.9±7.97 mV, Table 1). The AuNSs@BSA also has a negative zeta potential of −15.2±12.5 mV (Table 1). No toxicity effect of AuNPs@BSA was observed, as shown in FIG. 17C-D.

Nuclear Targeting Gold Nanoparticles Inhibit Cancer Cell Migration and Invasion.

Figure 12A:
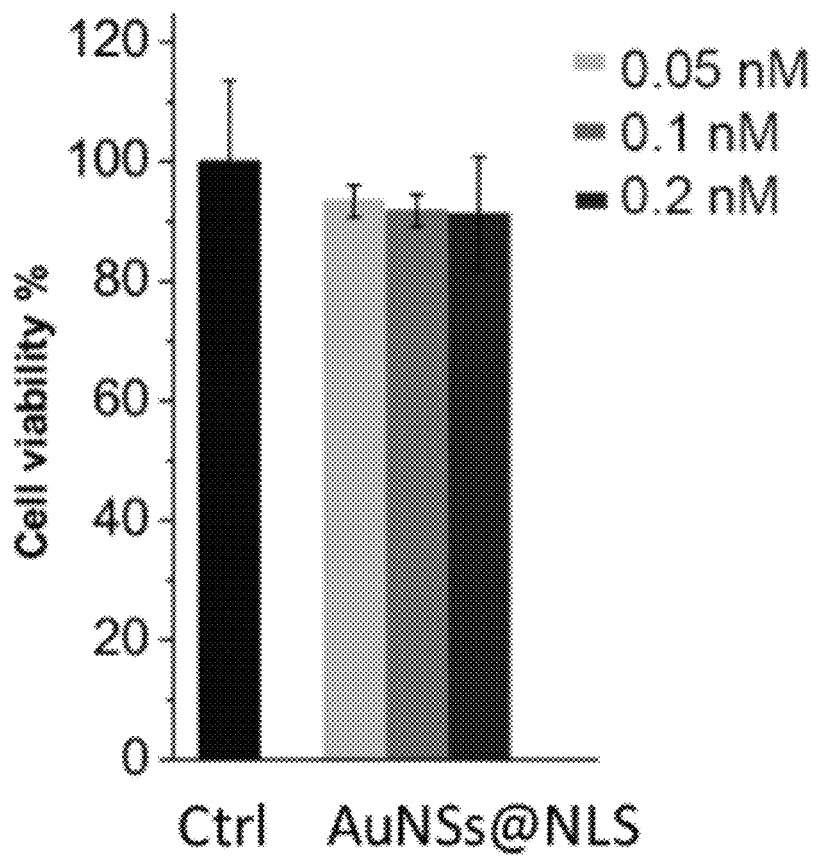
FIG. 12A-12E. Au nanoparticles cytotoxicity measurements and cellular uptake. (12A) Cell viability measurement (XTT assay, n=3) of HEY A8 cells after 24 h incubation with AuNSs@NLS at concentrations 0.05 nM (light blue), 0.1 nM (medium blue) and 0.2 nM (dark blue). (12B) Cell viability (XTT, n=3) assay for cells after 1.5 nM (light blue), 2.5 nM (medium blue) and 5 nM (dark blue) of AuNRs@NLS incubation with HEY A8 cells for 24 h. (12C-12E) Flow cytometry experiment for apoptosis/necrosis assay (12C, Ctrl; 12D, cells incubated with 0.2 nM of AuNSs@NLS; 12E, cells incubated with 5 nM of AuNRs@NLS).
Figure 12B:
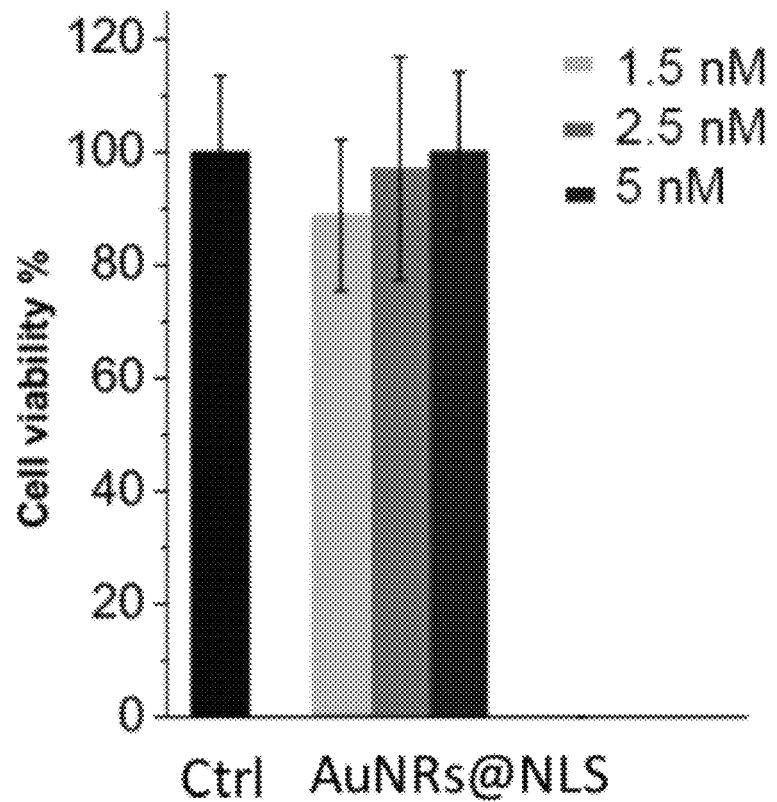
Figure 12C:
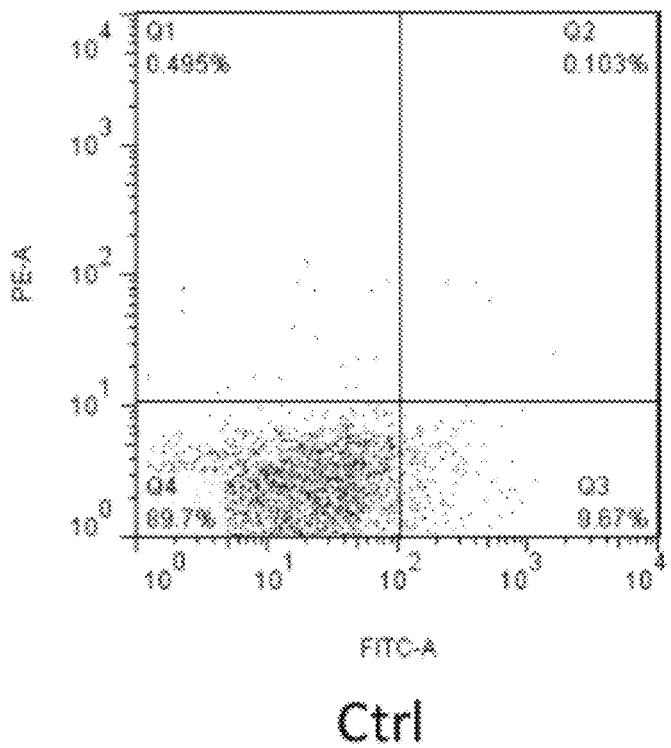
Figure 12D:
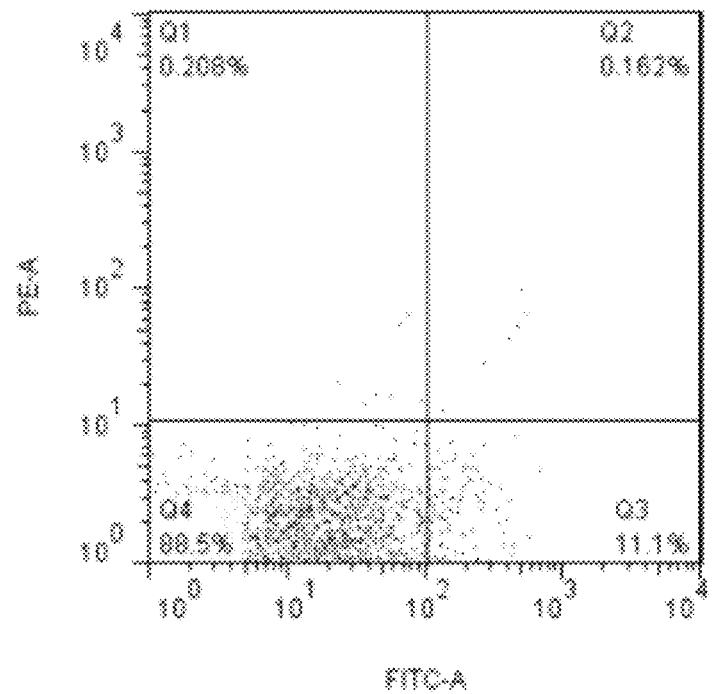
Figure 12E:
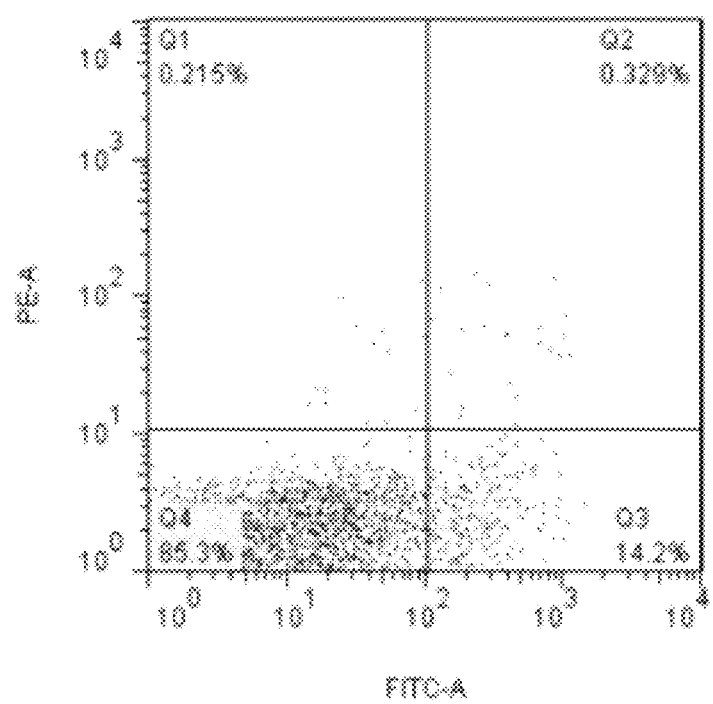
Figure 13A:
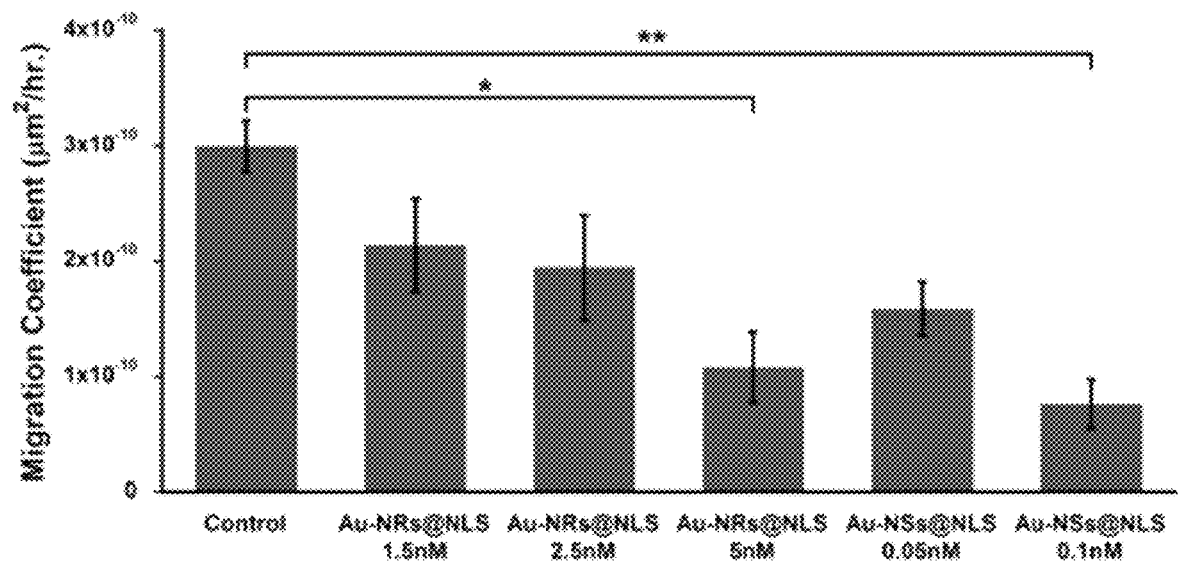
FIG. 13A-13D. Effect of AuNPs (2.5 nM AuNRs@NLS and 0.1 nM AuNSs@NLS if not mentioned) on motility and invasion of HEY A8 cells. Cell migration study was performed to determine the effects of both AuNRs@NLS and AuNSs@NLS (13A), and AuNRs@BSA (5 nM) and AuNSs@BSA (0.1 nM) (13B) on the HEY A8 cells motility (error bar±SEM, n=2). (12C) Scratch assay of cells incubated with AuNRs@NLS and AuNSs@NLS displayed arrested healing/closing of the scratch (representative pictures from 3 repeated experiments). (d) Invasion assay of cells without AuNPs or with AuNRs@NLS and AuNSs@NLS treatment (error bar±SD, n=3). *P<0.05, P<0.01, *P<0.001.
Figure 13B:
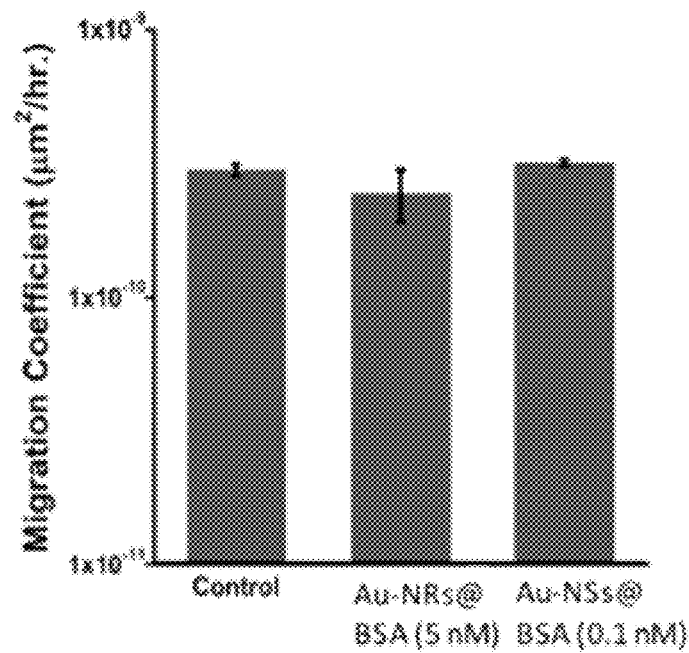
Figure 13C:
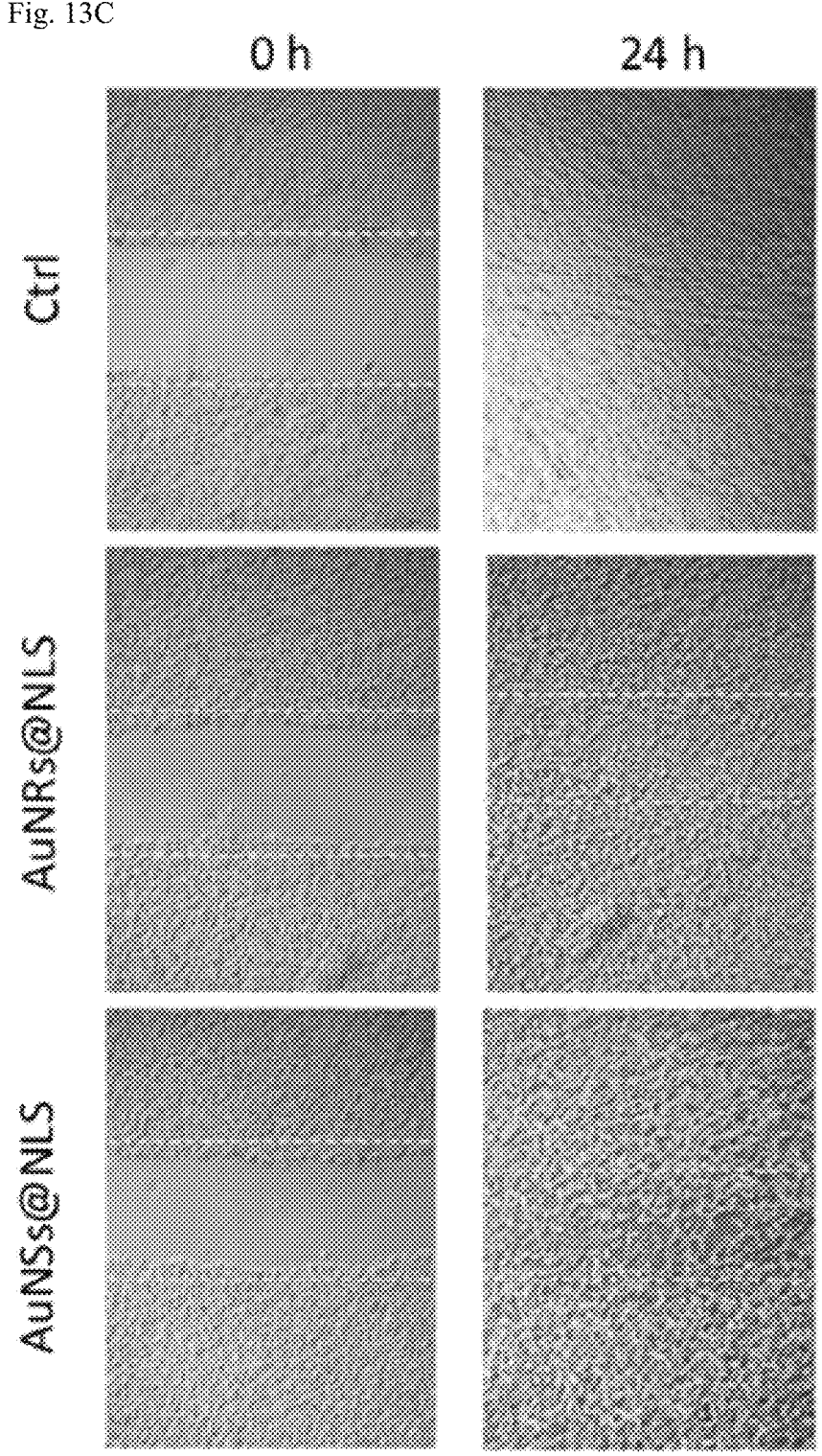

To test the cell motility, HEY A8 cells were incubated with AuNPs for 12 h before staining with fluorescent nuclear dye. Cells were then placed on an inverted epi-fluorescent microscope equipped with a cell culture chamber for continuous bright field and fluorescence imaging. The cell migration coefficients were then determined from the images. As shown in FIG. 13A, both nuclear-targeted AuNRs and AuNSs inhibit the motility of HEY A8 cells. The average migration coefficient of the cells decreases from $3 \times 10^{-10}$ by a factor of 3-10. (FIG. 12A). The inventors conducted a control experiment of nontargeted AuNPs coated with BSA, (AuNPs@BSA, FIG. 13). The motility assay shows that there is no apparent inhibition of AuNRs@BSA or AuNSs@BSA on cell migration (FIG. 13B).

The scratch assay was conducted to evaluate the migration ability. Results (FIG. 13C) indicate that the control cells had a completely healed "wound" after 24 h following AuNPs incubation, while the ones treated with AuNRs@NLS and AuNSs@NLS were not completely healed after 24 h. No obvious change in cell proliferation rate were observed after 24 h (FIGS. 12A and 12B), thus the scratch assay result merely reflects the migration ability of the cells.

Figure 13D:
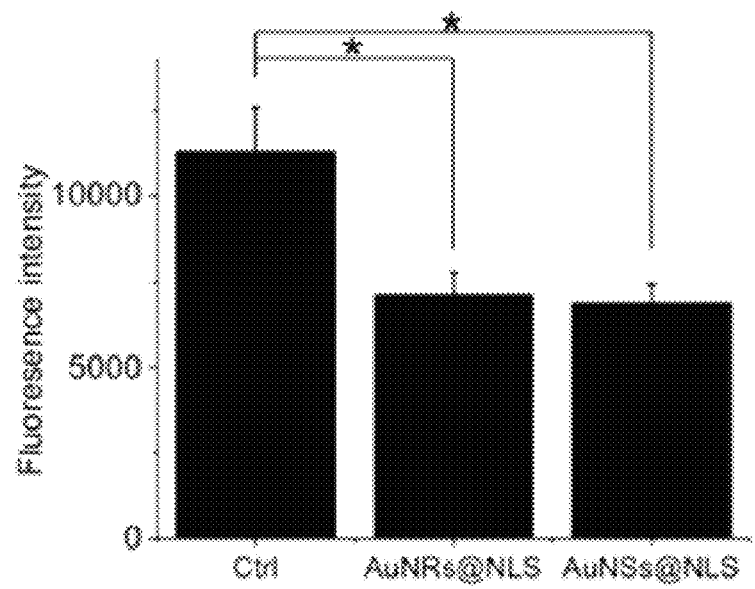
Figure 18:
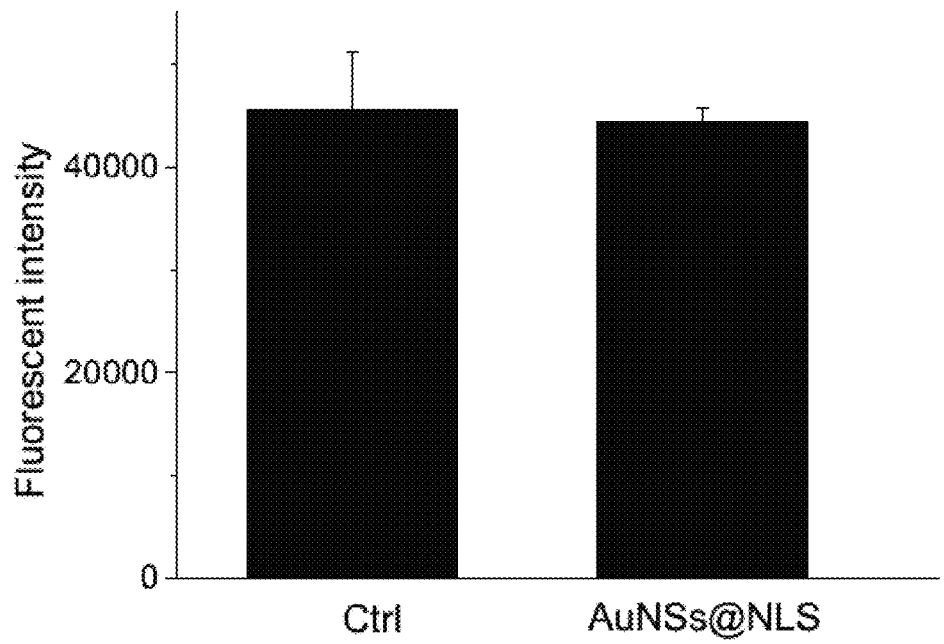
FIG. 18. The introduction of Au nanoparticles in cells does not affect the Fluorescent intensity of Calcein AM (n=3).

In order to examine the invasion ability of HEY A8 cells after their treatment with the nuclear membrane-targeted AuNPs, the transwell invasion assay was performed. The cells that invaded the basement membrane extract (BME) after 32 h were dissociated and stained with Calcein AM, a fluorescent dye that labels living cells. A control experiment has been performed to eliminate the possibility that gold nanoparticles could quench the fluorescence from Calcein AM (FIG. 18). A significant decrease in fluorescence intensity was observed in the AuNPs treated groups, indicating the inhibition of the invasion ability of HEY A8 cells particles (FIG. 13D).

In general, the cell migration and Invasion abilities of HEY A8 cells were inhibited effectively by both AuNRs@NLS and AuNSs@NLS.

Nuclear Targeting Gold Nanoparticles Enhance Nuclear Stiffness.

Figure 14A:
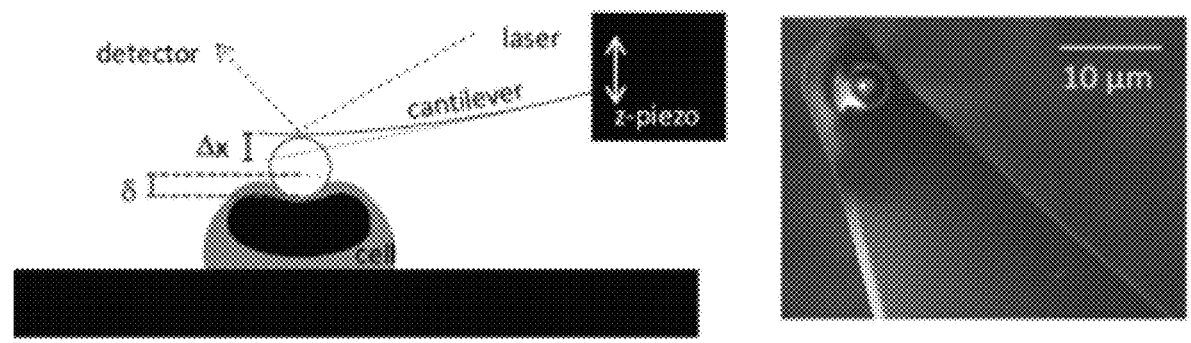
FIG. 14A-14D. Stiffness distribution of cells. (14A) Schematic of measurements on cells with AFM; δ is indentation, Δx is cantilever deflection. To measure bulk cellular stiffness, a beaded cantilever was used to increase cell-probe surface area. (14B) Overhead image of AFM cantilever tip next to HEY A8 cells with nanoparticles. (14C) Box-and-whisker plots of stiffness of single cells for different nanoparticles treatment, the percentiles are 10%, 25%, 50%, 75%, and 90%. Overall difference between means is significant (p-value calculated from ANOVA). (14D) Box-and-whisker plots of nuclear stiffness. *P<0.05, P<0.01, *P<0.001, n=3, cell counts>20 for each sample.
Figure 14B:
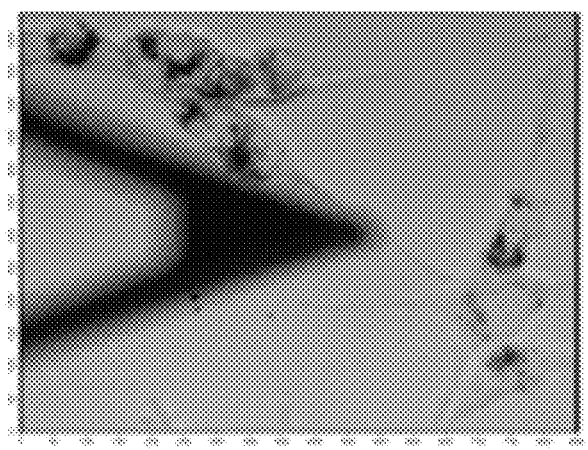
Figure 14C:
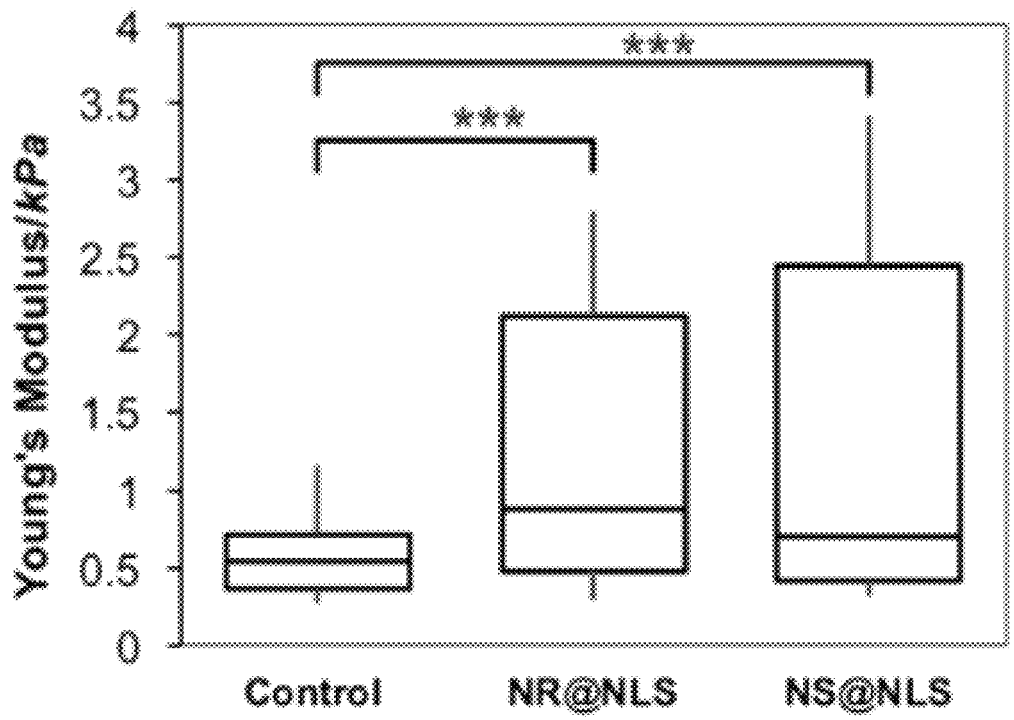
Figure 14D:
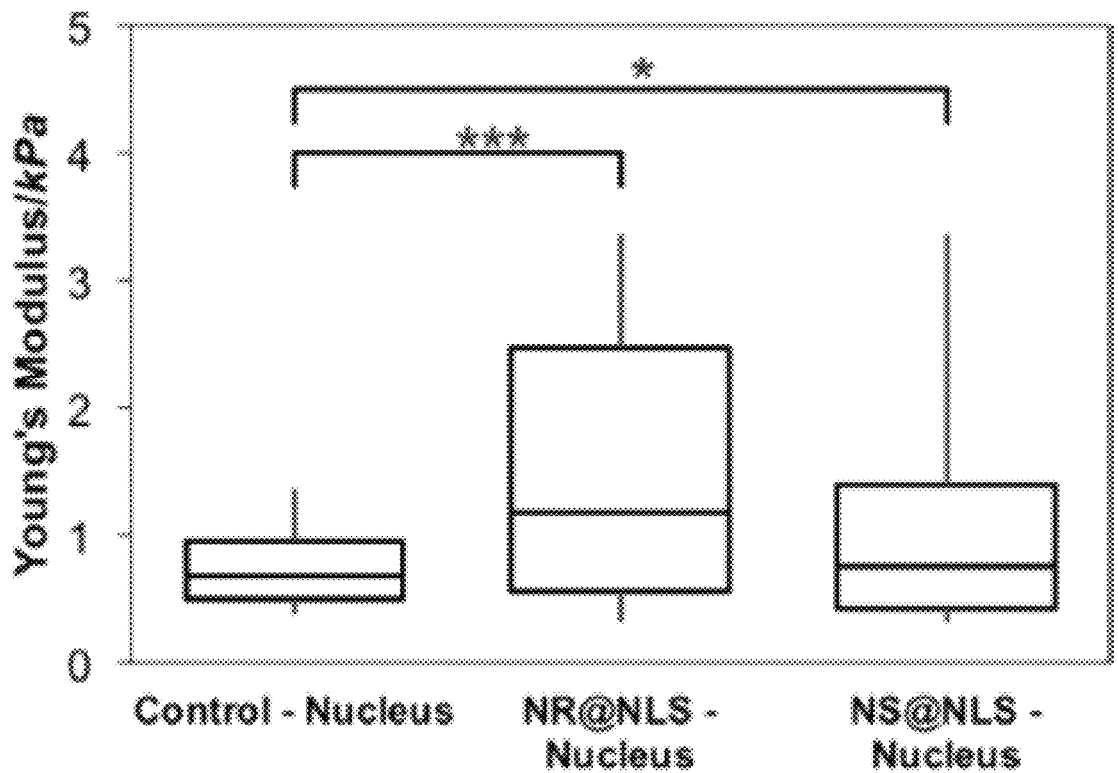
Figure 19:
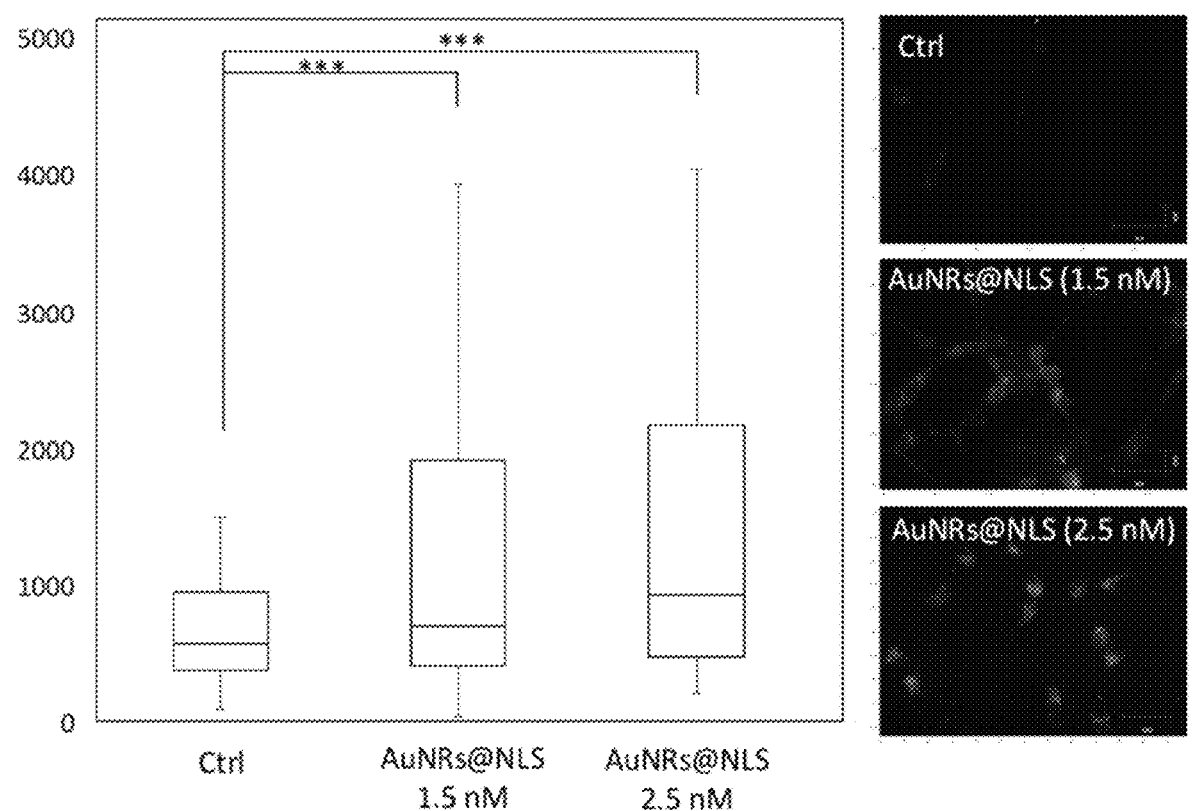
FIG. 19. Nuclear stiffness increased with the increased quantity of AuNRs. AFM result (left) and dark field images (right) show the stiffness and the nanoparticle uptake of AuNRs under different nanoparticle concentrations, respectively. n=3, cell counts>20 for each sample.
Figure 20A:
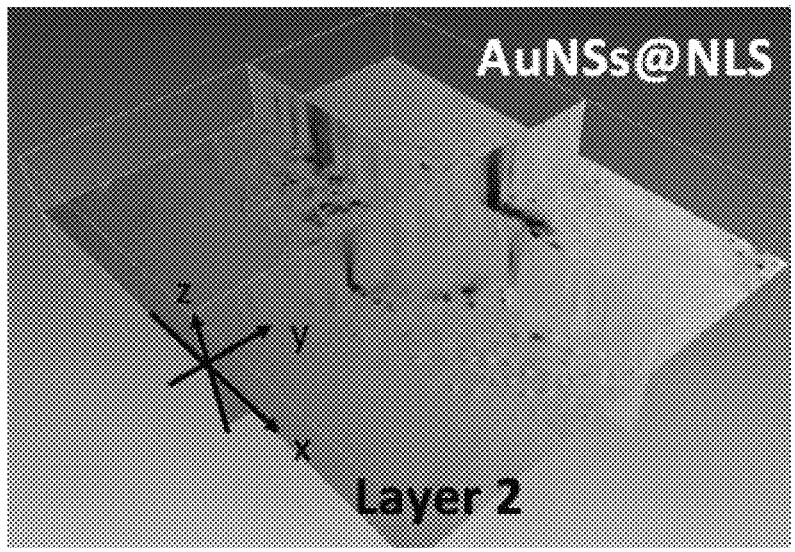
FIG. 20A-20D. 3-dimensional (3D) view of HEY A8 cells incubated with AuNPs. (20A and 20B) 3D figures of cells with 2.5 nM of AuNRs@NLS and 0.1 nM of AuNRs@NLS, showing xy, xz and yz planes (20C and 20D) showing the z-stacking of 3 layers from the bottom of the cell (close to the attached glass surface as shown in the scheme), the middle of the cell, and the top of the cell, respectively, for AuNSs@NLS (20C) and AuNRs@NLS (20D).
Figure 20B:
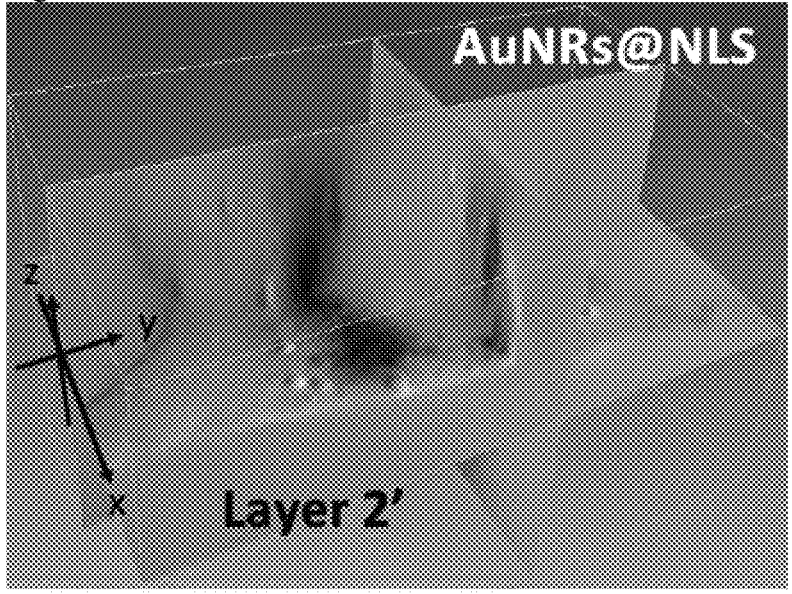
Figure 20C:
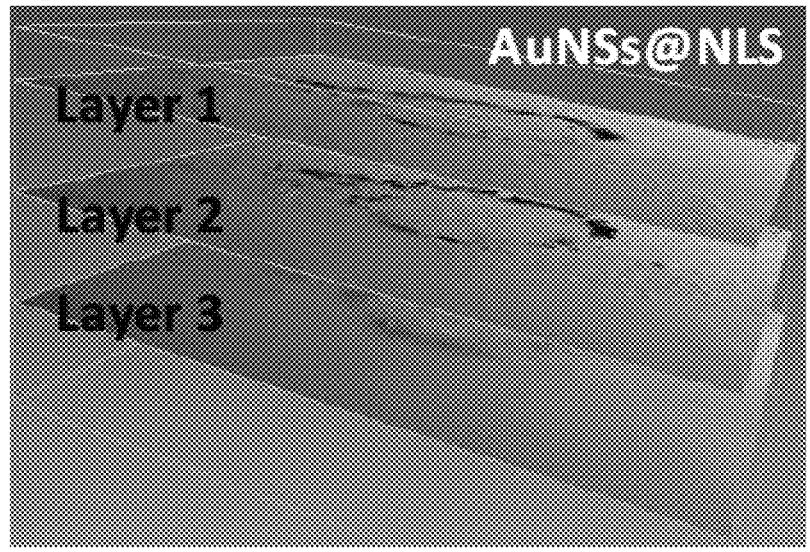
Figure 20D:
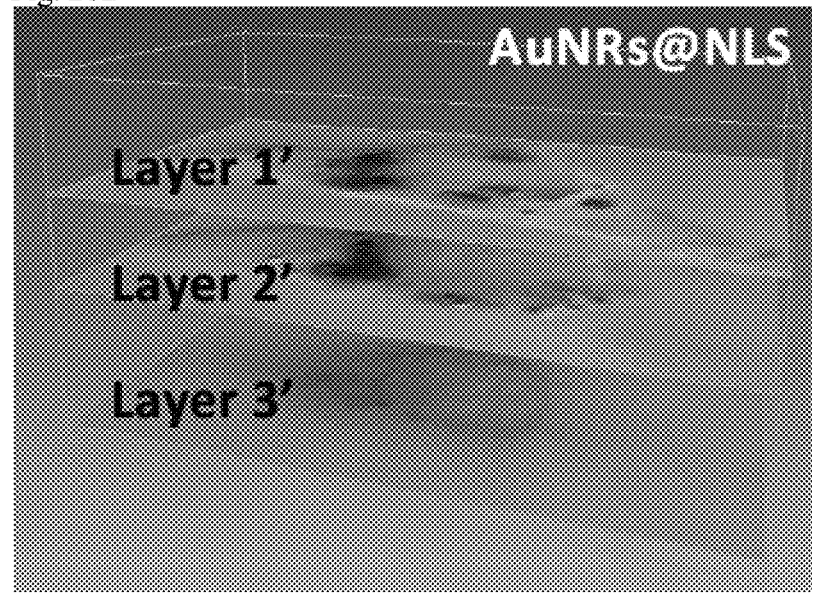

Next, the inventors tested the hypothesis that the nuclear-targeted AuNPs can enhance nuclear stiffness. Cell stiffness as quantified by the Young's modulus has been used as a biomarker of the metastatic potential of cancer cells. For AFM measurements (FIG. 14A), a beaded cantilever was lowered on top of the individual cells, producing an indentation in those cells and corresponding deflection of the AFM cantilever, which allowed for the measurement of cell stiffness. An overhead image of AFM cantilever tip nest to HEY A8 cells with nanoparticles was shown in FIG. 14B. The distribution of Young's moduli of individual cells, as well as that of the cell nucleus, from different nanoparticle treatments and the control is depicted in FIGS. 4C and 4D. In this study, both AuNSs@NLS and AuNRs@NLS exhibit significant increase in the cell stiffness (FIG. 4C), which is similar to previous observations that nanoparticles could increase cell stiffness. For the nuclear stiffness, as shown in FIG. 4D, the mean nuclear Young's modulus of the cells treated with AuNPs (AuNRs and AuNSs) were also significantly higher than the mean nuclear Young's modulus of the untreated cells, in agreement with the results of the overall cell stiffness. In addition, the inventors observed the increase of gold nanoparticle amount could increase the nuclear stiffness, as shown in FIG. 19.

AuNPs Accumulate at Nuclear Membrane Resolved by Three-Dimensional Microscopy.

Figure 15A:
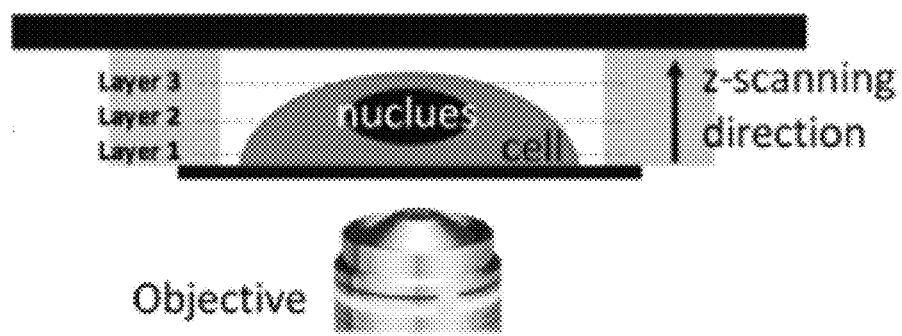
FIG. 15A-15E. Locations of AuNPs inside the HEY A8 cell (up) and lamin A/C protein location/expression (down) inside the HEY A8 cell. (15A) Scheme of the cell sample in sandwiched chamber for 3-dimensional DIC microscope imaging. Z-axis scanning step is 65 nm from the bottom (close to the attached glass surface) to the top of the cell. Three layers from the bottom, middle and the top of the cell, for cells incubated with 0.1 nM of AuNSs@NLS (15B) and 2.5 nM of AuNRs@NLS (15C) were imaged. (15D) Western-blot results of lamin A/C, with beta-actin as reference protein. (15E) Lamin A/C localization by confocal microscope of cells without (left panel) or with AuNSs@NLS (middle panel) or AuNRs@NLS (right panel) incubation. The red arrows in 15B and 15C indicate the nuclear membrane of the cells.
Figure 15B:
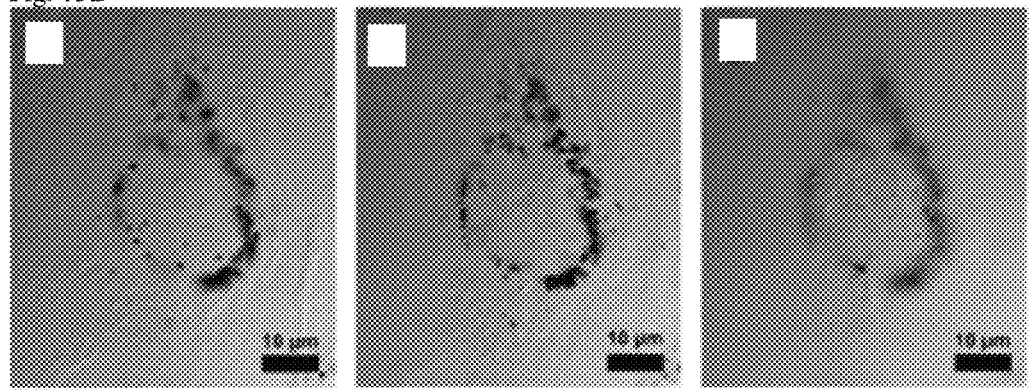

Resolving the exact localizations of AuNPs with regard to the nuclear membranes is a crucial, yet highly challenging, step in the inventors' attempt to understand the effects of AuNPs on the inhibition of cell migration/invasion. Most commonly used optical microscopy methods, such as confocal fluorescence microscopy and dark field (DF) microscopy, do not offer the accurate locations of the nuclear membranes and AuNPs simultaneously, and they usually suffer from high background. On the other hand, TEM, despite its high resolving power, is limited by the high costs and tedious sample preparation to gain the full 3D distribution of AuNPs inside the cells. To circumvent these challenges, the inventors employed a recently developed differential interference contrast (DIC) microscopy-based 3D imaging method to visualize and locate plasmonic AuNPs inside the cells. As shown in FIG. 15A, the cells were placed in a sandwiched chamber. DIC optical sectioning was performed on the whole cell thickness. The arrow indicates the scanning optical sectioning of the cell, directed from layer 1 (close to the surface of the cover glass) to layer 2 (middle of the cell) and to layer 3 (top of the cell) (FIG. 15 and FIG. 20A-20D). The DIC microscope, which was equipped with a set of high numerical aperture (NA=1.4), oil-immersion condenser and objective, featured a shallow depth of field in optical sectioning of a 3D specimen to generate sharply focused images. More importantly, the nuclear membranes were clearly visible under the DIC microscope to allow the determination of the relative positions of the nuclear membranes and AuNPs.

Figure 5A:
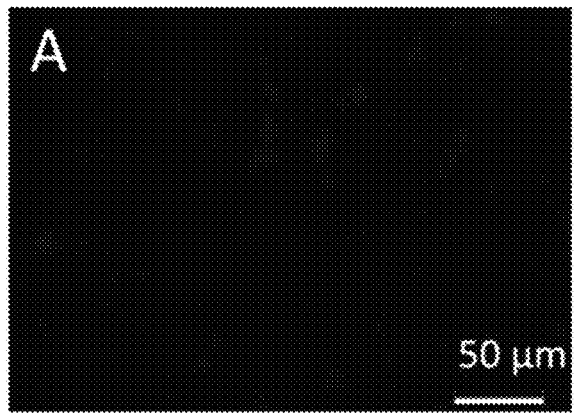
FIG. 5A-5F. Monitoring under dark field (DF) microscope. DF image of cells without AuNRs (FIG. 5A and FIG. 5D), incubated with AuNRs@PEG (FIG. 5B and FIG. 5E), or AuNRs@PEG@RGD (FIG. 5C and FIG. 5F), respectively (replicated experiments of FIG. 1D-FIG. 1F). (Scale bar, 50 μm.).
Figure 5D:
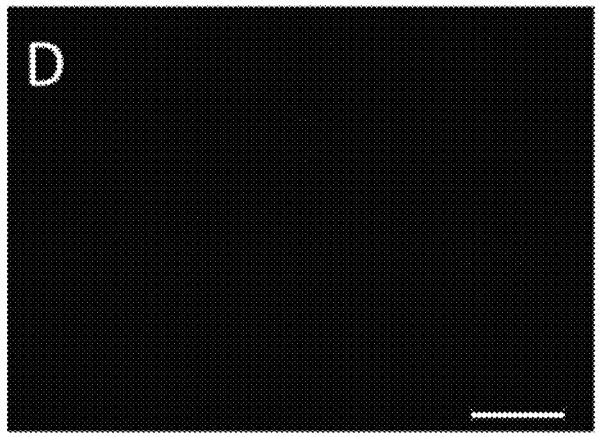
Figure 5B:
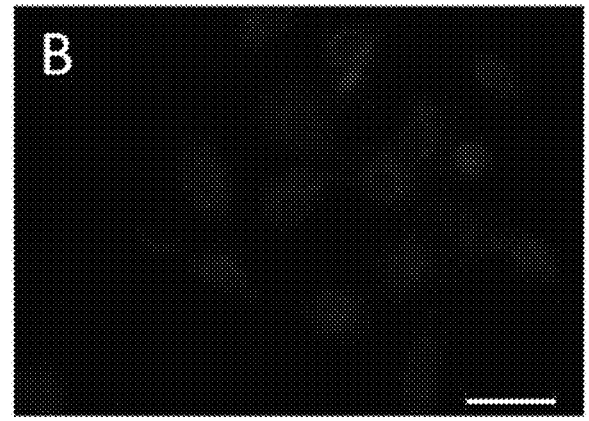
Figure 5E:
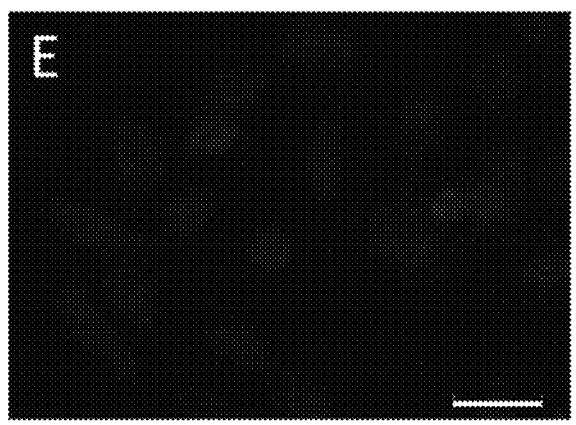
Figure 5C:
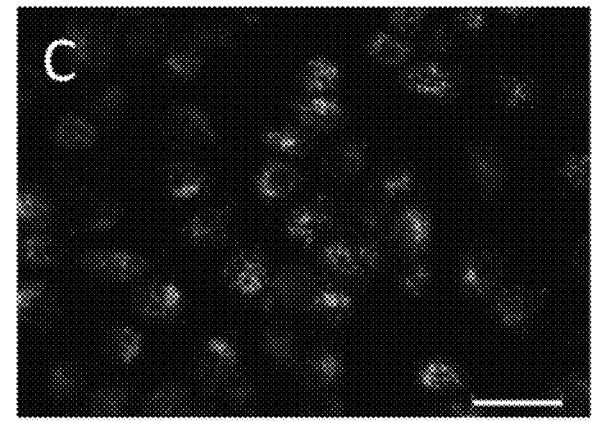
Figure 5F:
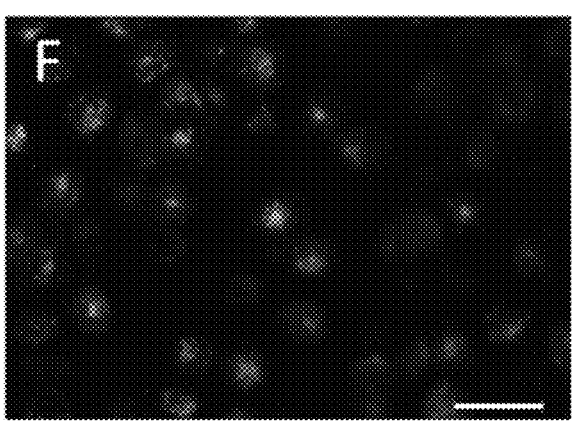
Figure 15C:
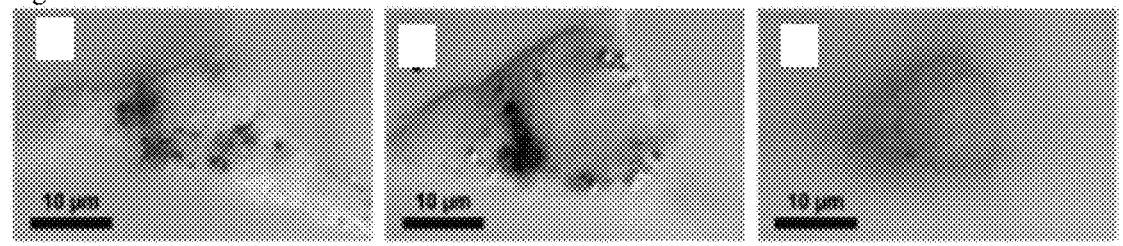
Figure 15D:
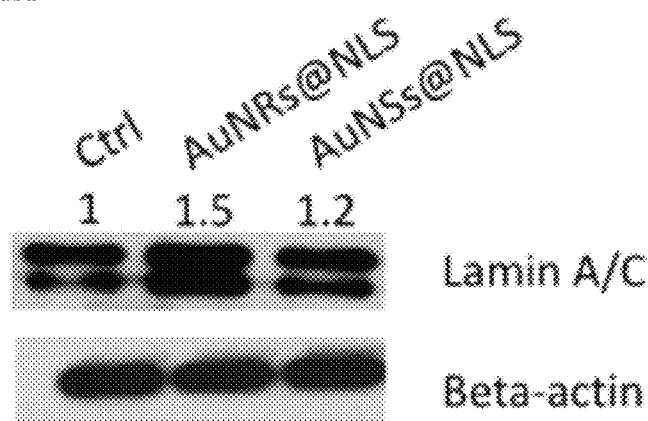
Figure 15E:
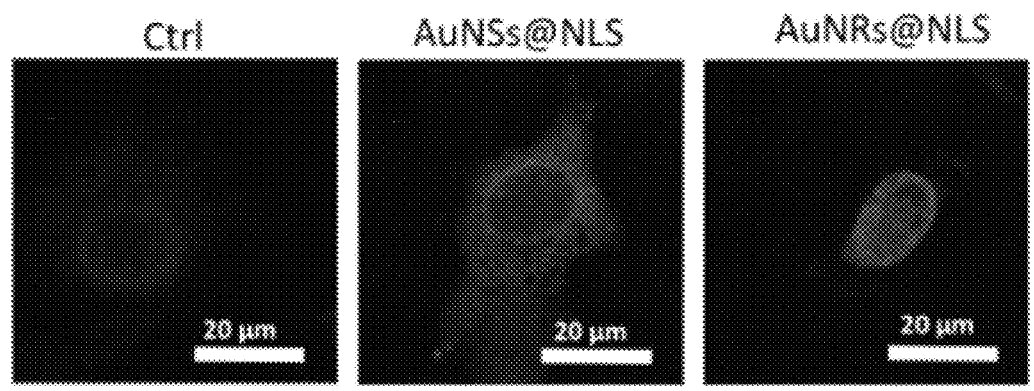
Figure 21A:
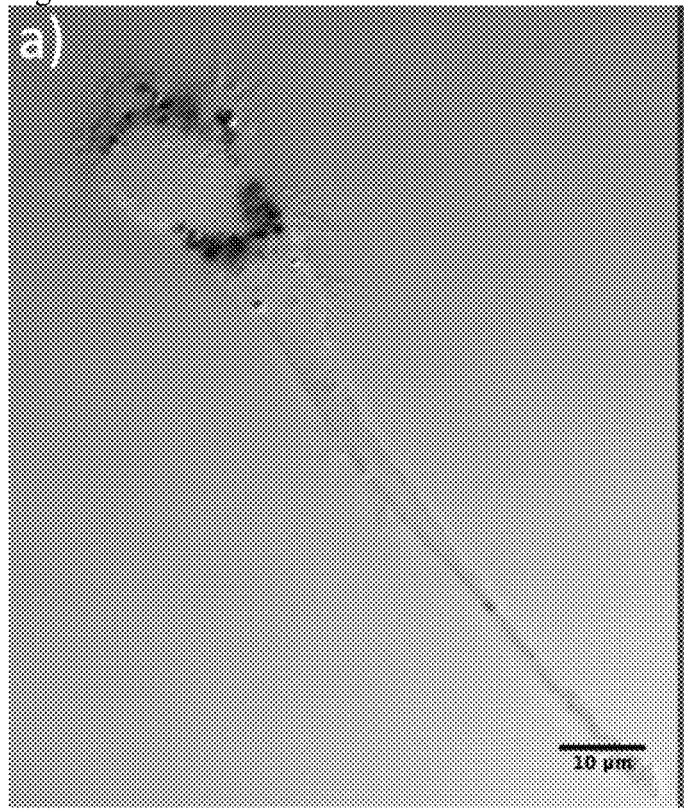
FIG. 21A-21B. The nuclear membrane targeting for AuNRs@NLS indicated by differential interference contrast (DIC) images.
Figure 21B:
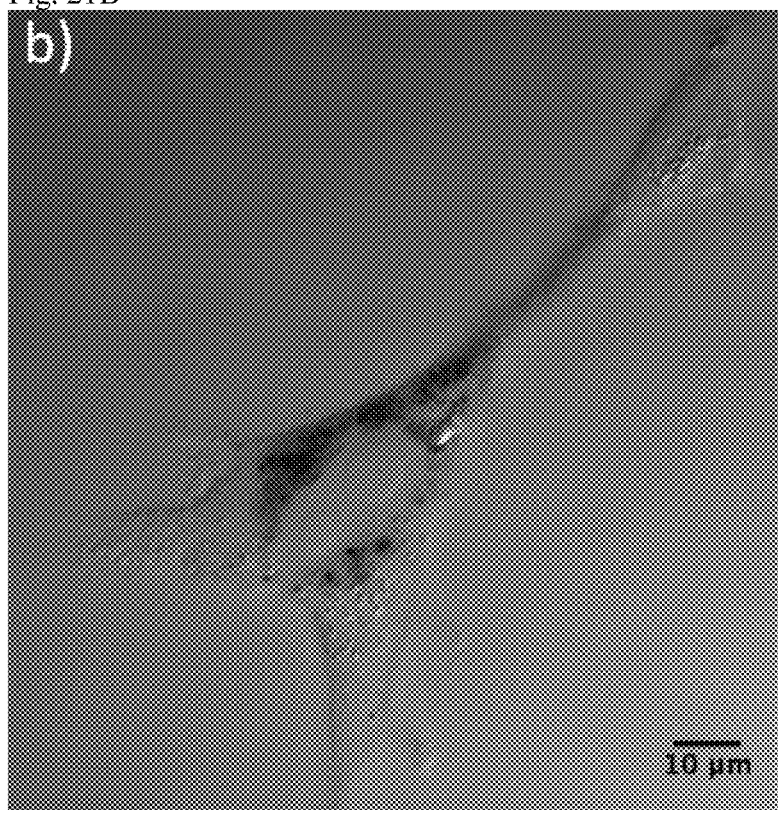

FIGS. 5B-5D show the AuNSs@NLS locations inside the HEY A8 cells. The black spots in the figures are the nanoparticle aggregates, which are shown clearly surrounding the nucleus from difference optical sections. Similarly, FIGS. 15E-G show a similar distribution of AuNRs@NLS inside HEY A8 cells. Both AuNRs@NLS and AuNSs@NLS aggregates were located predominantly on the nuclear membranes (indicated by the red arrows in FIGS. 15C and 15F, more evidence in FIG. 21A-21B), while the internalization of nanoparticles inside the nucleus was rarely found, which was likely due to the large sizes of the nanoparticles and their aggregates compared to the nuclear pores (around 9-12 nm).

Nuclear Targeting Gold Nanoparticles Cause Lamin A/C Protein Increase.

Lamins, especially lamin A/C, are intermediate filament proteins found at nearly all cell nuclei and contribute to nuclear stiffness and stability. Nuclear lamins interact with the membrane-associated proteins to form the nuclear lamina (30-100 nm thick), which is located in the interior of the nuclear membrane. It has been reported that lamin A/C-deficient cells exhibit severely reduced nuclear stiffness. To further understand the biological mechanism for why nuclear membrane-targeting AuNPs increase nuclear stiffness and inhibit cancer cell migration/invasion, the inventors measured the expression level of lamin A/C in Western blots (FIG. 15H) and confocal microscopy imaging after immunostaining (FIG. 15). The results indicate a clear overexpression of lamin A/C after incubation with AuNSs@NLS or AuNRs@NLS. As shown in FIGS. 15I, 15J, and 15K, the fluorescence signal from lamin A/C was increased as a circle-surrounding the nucleus, which is in agreement with the location of nuclear lamina.

AuNPs conjugated with a nuclear localization signal were thought to be able to internalize into the nucleus. In this study the inventors clearly observed most of the NLS conjugated gold nanoparticles aggregated around the nuclear membrane. Without NLS, the nanoparticles (AuNPs@RGD) spread in the cytoplasm, instead of accumulating around the cell nuclear region, which has been discussed in the inventors' previous reports. Western blot experiment showed that the endocytosis and nuclear transportation has been activated upon nanoparticle incubation (FIG. 22), due to the increased expression level of dynamin protein (a GTPase responsible for endocytosis in the eukaryotic cell) and GTP-binding nuclear protein Ran (involved in the transport into and out of the cell nucleus). Since the cellular and nuclear transportation are all activated, the trapping of AuNPs at the nuclear membrane was most likely due to the large size of the gold nanoparticles aggregates compared to the nuclear pores.

It has been widely reported that following the entry of nanoparticles, they traffic through early endosomes to late endosomes and lysosomes (endolysosomal trafficking). To achieve nuclear membrane targeting, nanoparticles need to escape from the endosome and/or lysosomes. There are several well-established mechanisms explaining the cytosolic release of the NPs from endosomes or lysosomes. One of the most popular mechanism is through the charge interactions. The cationic nanoparticles could interact with the negatively charged phospholipid membrane, followed by "proton sponge" effect, causing endosomal membrane rupturing and nanoparticle escaping. In this study, the positively charged AuNRs@NLS could have the similar mechanism to escape from the endosome. In these results, most of the nanoparticles were finally located surrounding the cell nucleolus after incubation with cells overnight (FIG. 15B-15G), indicating a good efficacy that gold nanoparticles escaped from the endosome/lysosomes and targeted the nuclear membrane. Meanwhile, the above results show that the effect of endosome degradation of the surface conjugated peptides might be very minor.

Figure 22:
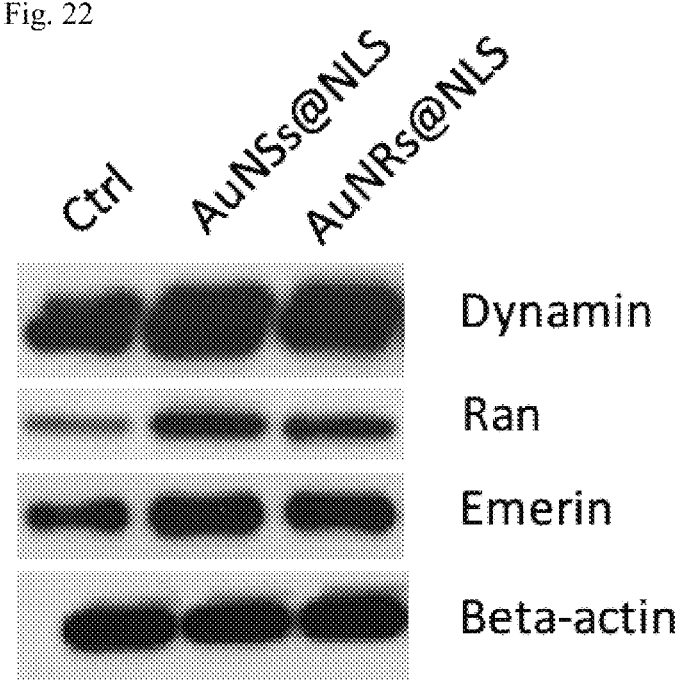
FIG. 22. Western blot of expression levels of Dynamin, Ran, emerin proteins and beta-actin from HEY A8 cells (without AuNPs), HEY A8 cells with 0.1 nM of AuNSs@NLS and 2.5 nM of AuNRs@NLS treatment for 24 h.

Coincident with the increased nuclear stiffness by the AuNPs is the aggregation of the AuNPs at the nuclear membrane and the increase of the Lamin A/C expression, which is located at the inner side of nuclear membrane. Lamin A/C is known to maintain the mechanical strength of the nucleus and is thus consistent with an inhibited cell migration or invasion. In these results, a clearly increased expression level of Lamin A/C was observed. Thus, without wishing to be bound by theory, it is suggested that the increase of nuclear stiffness is not only due to the mechanical contribution of the presence of gold nanoparticles, but could also be due to the increase of Lamin A/C. How AuNPs increase Lamin A/C is not yet well explored in literature. FIG. 15C shows AuNPs closely contacted with the nuclear membrane, which could potentially disturb the membrane integrity. Therefore, without wishing to be bound by theory, it is suggested that it could be a cellular defense mechanism as lamin is known to remain the mechanical strength of nucleus. Interestingly, nuclear lamin-associated proteins, such as emerin, which stabilizes nuclear architecture for maintaining the structural integrity are also increased as the AuNPs are added at the nuclear membrane as shown in FIG. 22. To investigate this mechanism, further studies such as proteomics and high-resolution imaging could be fruitful to elucidate the exact role of the AuNPs in inhibiting cell migration and invasion.

The clearance of nanoparticles from body after treatment has great importance to the evaluation of long-term effect of nanoparticles. While small nanoparticles (hydrodynamic diameter less than 5.5 nm) can be discarded rapidly and efficiently through renal/urinary excretion, big nanoparticles (over 18 nm) tend to accumulate in liver and spleen. Such body deposition of metallic NPs over a long time period raises significant concerns regarding their long-term safety. A decrease of the liver content of gold has been reported after 1 month from 0.54% to the 0.07%. The ultimate fate and the body elimination pattern of gold nanoparticles are not well studied. Future work will be focused on studying the effect of gold nanoparticles for preventing and treating the metastasis in animals.

Conclusion

This example shows that nuclear membrane-targeting AuNPs can increase nuclear stiffness and thereby inhibit cell migration and invasion. Compared with the previous studies with nontargeted AuNPs at relatively high amount (50-200 µM of AuNRs@BSA and 5-20 µg AuNSs@Citrate), the nuclear membrane-targeted AuNPs showed higher inhibition effects at significantly lower concentrations (0.1 nM for 35 nm AuNSs and 2.5 nM for 25×5 nm AuNRs). The AuNPs were found to be trapped on the nuclear membranes from mapping the 3D distributions of the AuNPs under a DIC microscope. The trapping of AuNPs at the nuclear membranes could possibly (1) add to the mechanical stiffness of the nucleus, and (2) stimulate the overexpression of lamin A/C, which is known to lead to nuclear stiffness and thus slows down cancer cell migration and invasion. This insight takes us one step closer to fully understanding the effects on AuNPs on the inhibition of metastasis.

Methods

Materials.

Tetrachloroauric acid trihydrate ($HAuCl_4 \cdot 3H_2O$), trisodium citrate, NaBH4, ascorbic acid, cetyltrimethylammonium bromide (CTAB), $AgNO_3$, and bovine serum albumin (BSA) were purchased from Sigma-Aldrich (USA). Methoxypoly(ethylene glycol)-thiol (mPEG-SH, MW 5000) was purchased from Laysan Bio, Inc. Cell penetrating peptide (RGD) and nuclear localization signal (NLS) peptides were obtained from GenScript, Inc. Dulbecco's phosphate buffered saline (PBS), RPMI-1640 cell culture media, fetal bovine serum (FBS), antibiotic solution, and 0.25% trypsin/2.2 mM EDTA solution were purchased from VWR. 8.0 µm polycarbonate membrane inserts were bought from Costar. Hoechst 33342 solution was purchased from Thermo Fisher Scientific (20 mM solution).

Instrumentation.

Gold nanoparticles were imaged using a JEOL 100CX-2 transmission electron microscope (TEM) microscope and their average size was then measured by ImageJ software. UV-vis spectra were obtained using an Ocean Optics HR4000CG UV-NIR spectrometer. Cell stiffness was obtained using a MFP-3D AFM (Asylum Research, Santa Barbara, Calif.) with a combined Nikon Ti inverted optical microscope (Nikon, Melville, N.Y.) for optically aligning the probe (MCST-AUHW, Bruker, Camarillo, Calif.) with a nominal spring constant of 0.03 N/m) to the cells. Confocal images were taken with a Zeiss LSM 700-405 confocal microscope.

Gold Nanoparticle Synthesis, Conjugation and Characterization.

Gold nanospheres (AuNSs) with an average diameter of 35 nm were synthesized using the citrate reduction method. Briefly, 100 mL of 0.254 mM $HAuCl_4 \cdot 3H_2O$ solution was heated until boiling, and then reduced by adding 2.5 mL of 0.35% of trisodium citrate. The solution was then left heating until it turned wine red, followed by cooling under water flow. The citrate stabilized AuNSs were centrifuged under 5000 g for 10 min and redispersed in deionized (DI) water to remove extra citrate and be ready for conjugation.

Gold nanorods (AuNRs) with an average size of 25×6 nm (length×width) were synthesized using a seedless growth method (35). Briefly, 5 mL of 1.0 mM $HAuCl_4$ was added to a mixture of 5 mL of 0.20 M CTAB, 250 µl of 4.0 mM $AgNO_3$ and 8 µl of 37% HCl. For reduction, 70 µl of 78.8 mM ascorbic acid was added, followed by immediate injection of 15 µL of 0.01 M of ice-cold $NaBH_4$. The solution was left undisturbed for 12 h, then centrifuged at 21,000 rpm for 50 min and redispersed in DI water followed by a second centrifugation at 19,000 rpm for 40 min to remove the extra CTAB. TEM was used to measure the sizes and homogeneity of the nanoparticles.

AuNSs and AuNRs were then conjugated according to previous work to achieve nuclear and cytoplasmic targeting. For nuclear targeting, first, mPEG-SH (1 mM) was added to the nanoparticles for overnight to achieve about 1000 ligands on each particle. Then, the PEGylated nanoparticles (1 nM) were treated with RGD (1 mM) and NLS (1 mM) to achieve $10^4$ and $10^5$ molar excess, respectively. The solution was then allowed to shake overnight at room temperature. Excess ligands were removed by centrifugation. For preparing BSA conjugated nanoparticles, BSA (4.5 mM) was added to the nanoparticles and left for 3 h to incubate. UV-vis spectrometer and zetasizer was used to test the conjugation. Surface modification causes red shift of UV-vis spectra due to the change in the dielectric constant of the surrounding environment of Au nanoparticles.

Cell Culture and AuNPs Incubation.

The ovarian cancer HEY A8 cell lines were provided by Dr. G. Mills (MD Anderson Cancer Center, Houston, Tex.) and were grown in RPMI-1640 media supplemented with 10% FBS and 1% antibiotic-antimycotic solution. Cells were kept in a humidified incubator at 37° C. and under 5% CO2. After achieving 50% confluence, the cells were incubated with functionalized AuNSs or AuNRs in supplemented DMEM cell culture medium for 24 h. The concentration of nanoparticles was carefully chosen to avoid cytotoxicity or perturbation to the cell cycle.

Apoptosis/Necrosis Assay.

The HEY A8 cells were collected by trypsinization and washed with cold PBS twice. Then, cells were the dispersed in 493 µL of Annexin V binding buffer before labeling by 5 µL of Annexin V FITC (BioLegend) and 2 µL of PI (BioLegend, 100 µg/mL) according to previous reports. The mixture was then incubated for 15 min at room temperature. The cells were subjected to flow cytometry analysis using a BSR LSR II flow cytometer (BD Biosciences). For excitation, a 488 nm laser was applied. FITC and PI were detected in FL-1 and FL-2 using 525/30 and 575/30 BP filters, separately. Standard compensation using unstained and single-stained cells was conducted before performing actual experiments. FlowJo software (Tree Star Inc.) was used for data analysis. At least 10,000 events were collected for each experiment.

Cell Motility Assay.

HEY A8 cells were seeded on uncoated 24-well plate at a subconfluent density for 24 h. Then the cells were treated with nanoparticles of varying shapes and conjugated motifs before returning them to incubator for 12 h to facilitate particle uptake. After the incubation period, cells were stained with nuclear dye Hoechst 33342 (dilution 1:10,000) for 30-60 min. Cells were maintained at 37° C. and 5% carbon dioxide throughout the experiment using an environmental cell chamber (InViva Scientific). For observation, a Nikon Eclipse Ti inverted epifluorescent microscope was used and both bright field (BF) and DAPI images were taken at multiple xy positions at 12 min time interval for 6-8 h at 10× magnification. The locations of cell nuclei, segmented from fluorescent images, were tracked in MATLAB to define cell traces. The cell migration coefficients and directional velocities were determined by fitting the traces to the persistent random walk model. Briefly, mean square displacements were calculated from the two-dimensional tracking data and was used for fitting the following equation:

$$\langle d^2(\tau)\rangle = 4\mu\{t - P[1 - e^{-t/P}]\}$$

where P=persistence time and µ=migration coefficient.

Transwell Invasion Assay.

The Cultured 24 Well BME Cell Invasion Assay kit (Trevigen) was used according to the manufacturer's instructions. For these studies, HEY A8 cells were seeded and grown in a 6 well plate to 60-80% confluency before treating with nanoparticles in serum free media for 24 h. Cells were then detached, spun down and resuspended in serum free media. The inventors also counted the cell number at this time to adjust the density to 500,000 cells/mL. Then 50,000 cells (100 µL) were added for each condition to the top surface of transwell inserts with 8 µm membrane pores coated with basement membrane matrix (BME). Cells were allowed to migrate toward the 10% PBS containing media in bottom chamber acting as the chemo attractant for a period of 32 h. After the desired incubation time, nonmigratory cells were gently removed from the top of each transwell using q-tips and the migrated cells at the bottom surface were detached using detaching buffer and incubated with Calcein AM. A plate reader was used to measure the fluorescence intensity, which is positively related to the number of transwell cells.

Atomic Force Microscopy.

AFM mechanical measurements of HEY A8 cells were obtained using an MFP 3-D AFM (Asylum Research, Santa Barbara, Calif.) on a vibration isolation table (Henan, Laguna Hills, Calif.). A silicon nitride cantilever (Bruker, Camarillo, Calif.) was used for the experiments. The pyramidal tip had a half angle of 35° and the radius of curvature of the point of the tip was 20 nm. Measurements were performed on cells plated to the glass bottom of the Fluorodish and in culture media at room temperature. For eliminating the effect of the overlapping neighboring cells on the stiffness, single cells were measured. Thermal calibration yielded the cantilever spring constant, k=28.01pN/nm. A measurement rate of 0.39 Hz was used. The 5 nN force trigger resulted in indentations of approximately 4 µm for typical cells. Cells were optically located using a Nikon Eclipse Ti microscope (Nikon, Melville, N.Y.). Force-displacement curves were recorded to obtain the Young's modulus of each cell. Two distinct sets of measurements were performed with the APM. The first investigated changes in mean cell stiffness between populations treated with AuNPs@NLS and an untreated control population. The second set of measurements investigated subcellular elasticity of nucleus. For the first set of measurements, the cantilever probe was positioned over the individual cells for indentation and measurement. For the second set, the probe was positioned over the perinuclear region.

Cell Imaging Using DIC Microscopy.

An inverted Nikon Eclipse Ti-E microscope equipped with Perfect Focus System (PFS, 25 nm zaxial resolution) was used for imaging and z-stacks acquisitions under differential interference contrast (DIC) microscopy. The DIC mode utilized a pair of DIC polarizer and analyzer, a high resolution 100×I-R DIC slider, a high numerical aperture (NA, 1.40) oil immersion condenser lens, a Nikon CFI Apo TIRF 100× (NA, 1.49) oil immersion objective, and a 12 V/100 W halogen lamp as light source. Appropriate bandpass filters were placed in the light path. The z-stack movies were taken by a Hamamatsu ORCA-Flash 4.0 V2 CMOS camera (C11440-22CU, pixel size: 6.5/Am×6.5 µm) with Camera Link interface using Micro-Manager and analyzed using NMI ImageJ and reconstructed in Amira. Fixed HEY A8 cells on 22 mm×22 mm glass coverslips were rinsed with DPBS at pH 7.4 and fabricated into a sandwiched chamber with two pieces of double-sided tape and a cleaned glass slide. PBS solution was added into the chamber to fill the space and the chamber was then sealed by clear nail polish. The so-formed sample slide was then placed under the microscope for observation. Z-stacks were acquired using the Multi-Dimensional Acquisition function in Micro-Manger. More specifically, the DIC optical sectioning through the whole cell thickness was achieved by moving the objective on the motorized nosepiece using PFS at 65 nm/step at 33 ms (30 fps) exposure time.

Scratch Assay.

The scratch assay has been performed according to former report. Cells were cultured in a 6 well plate to a confluent monolayer. A p200 pipet tip was used to scrape the cell monolayer in a straight line to create an empty gap. The debris was then removed by washing the cells once with culture medium and then replace with 2 mL of fresh medium. Then the cells were imaged shortly after and 12 h after scratch.

Western Blot.

Briefly, cells were lysed in RIPA buffer (20 mM Tris pH 7.4, 150 mM NaCl, 2 mM EDTA, 2 mM EGTA, 0.1% Sodium Deoxycholate, 1% Triton X-100, 0.1% SDS) containing protease inhibitors (Sigma-Aldrich). BCA assay (Pierce) was performed to measure the protein concentration and equal amounts of protein were loaded on a SDS-PAGE gel. After SDS-PAGE, the resulting gels were transferred to PVDF membranes (Millipore) overnight. Afterward, the gel was blocked with 5% milk in TBS (20 mM Tris, 150 mM NaCl). A rabbit polyclonal antibody to Lamin A/C was used as the primary antibody (Bethyl Laboratories, Inc.) overnight in 4° C. with shaking. A goat anti rabbit HRP labeled antibody was used as the secondary antibody (Jackson Immuno Research Laboratories). Blots were washed 3 times for 20 m in TBS after primary and secondary antibodies. Konica Minolta developer and Hyglo enhanced chemiluminescence (Denville) were used to develop the immunoblots.

Immunofluorescence Labeling and Confocal Microscopy.

Cells were cultured on confocal chamber slides (MATECH Co. USA). After gold nanoparticle treatment (17), cells were fixed in 4% Paraformaldehyde/0.1% Glutaraldehyde for 10 min at room temperature the wash with PBS. Cells were then permeabilized with 0.1% Triton X-100 for 5 min at room temperature. Cells were then blocked with 5% BSA and incubated with the primary antibody as stated in the Western-blot method for overnight. Cells were then incubated for 1 h with an Alexa Fluor 488 secondary antibody (Invitrogen) for 1 h before mounting with Prolong Gold (Invitrogen). Lastly images were taken with a Zeiss LSM 700-405 confocal microscope and the fluorescence intensity was quantified in ImageJ.

Data Analysis.

To determine the Young's modulus, IGOR Pro software (Wavemetrics, Portland, Oreg.) was used to apply the Hertzian contact model from 10 to 90% of the maximum indentation of the extension force-displacement curve. Due to the unequal sample size and heteroscedasticity of the AFM data, overall statistical significance of differences in mean cell stiffness and nuclear stiffness between cells treated with AuNPs@NLS was tested using Welch's analysis of variance (ANOVA). Posthoc analysis was performed using the Games-Howell test. For the rest of the studies, the inventors used the t test. The analyses were performed with the alpha type error set at 0.05.

Example 3—Gold Nanorods Assisted Photothermal Therapy Decreases Bleeding During Breast Cancer Surgery on Dogs and Cats In this example, the inventors have focused on introducing a new treatment regime featuring the combination of PPTT and surgery in dogs and cats with large tumors and examining the efficacy of this new regime. Surprisingly, the inventors observed that AuNRs PPTT before surgery could significantly decrease the bleeding which could potentially avoid the risk of metastasis caused by surgery. This observation supports the explanation that AuNRs-based PPTT could assist surgical processes in preventing tumor recurrence and metastasis.

Materials and methods.

Synthesis and Surface Modification of AuNRs.

AuNRs having dimensions of approximately 26×5 nm was prepared according to the seedless method. Briefly, 5 mL of 1 mM $HAuCl_4$ (Sigma-Aldrich, St. Louis, Mo., USA) were mixed with 5 mL of 0.20 M cetyltrimethylammonium bromide (CTAB; Sigma-Aldrich), followed by adding 250 µL of 4 mM $AgNO_3$ (Sigma-Aldrich) and adjusting the pH of the solution to be 1-1.15 by 37% HCl. Then, 70 µL of 78.8 mM ascorbic acid (Sigma-Aldrich) was added to the solution until the solution became clear. 15 µL of 0.01 M ice-cold $NaBH_4$ (Sigma-Aldrich) was injected into the growth solution immediately and the solution was left unstirred for 6 hours. To remove the extra CTAB and prepare for surface modification, the AuNRs were centrifuged at 19,000 rcf for 1 h, pellet was redispersed in deionized water and centrifuged again at 14,000 rcf for 15 minutes. For surface modification, methoxy polyethylene glycol (PEG) thiol (m-PEG-Th, PEG; Laysan Bio, Arab, AL, USA) was added to AuNRs and stirred overnight to achieve a concentration of around 1000 PEG molecules per AuNR. After rinsing them with water, AuNRs were then conjugated with different surface ligands (PEG and RGD). For AuNRs@PEG, mPEG-SH (1 mM) was added to the nanoparticles overnight to achieve about 1,000 ligands PEG on each particle. To prepare AuNRs@RGD, first, mPEG-SH (1 mM) was added to the nanoparticles overnight to achieve about 1,000 ligands on each particle. Then, the PEGylated nanoparticles (1 nM) were treated with RGD (1 mM) to achieve 10,000 molar excess. The solution was then allowed to shake overnight at room temperature. Excess of ligands was removed by centrifugation. UV-vis spectrometer a were used to test the conjugation.

Characterization of AuNRs.

A JEOL 100 CX transmission electron microscope (TEM) (JEOL Ltd., Tokyo, Japan) was used to measure the size and homogeneity of the samples. A Cary 500 UV-Vis Spectrometer (Agilent Technologies, Santa Clara, Calif., USA) was used for measuring the absorbance of the AuNRs. To characterize the surface conjugation with PEG, a ZetaSizer 3000 HAS (Malvern Instruments, Worcestershire, UK) was used for measuring the surface Zeta potentials. In addition, Ellman's reagents (Sigma-Aldrich), which react with react with free —SH group (calorimetrically measured at 412 nm), were used to quantify the number of PEG molecules bound to the surface of the AuNRs.

Animal Diagnosis, and X-Ray Examination.

All animals were handled in accordance with Association for Assessment and Accreditation of Laboratory Animal Care and Office of Laboratory Animal Welfare guidelines under the direction of the Institutional Animal Care and Use Committee (IACUC) in Cairo University (Supplementary information). The pet animals were admitted to the Department of Surgery clinic of the Faculty of Veterinary Medicine, Cairo University. All pets' owners claimed that their animals did not receive any treatment before their arrival at the university. 8 female animals were treated in this study, including 2 canines and 6 felines, with a total of 21 tumors with varied grades (I to III). Individual animal reports which stating the diagnosis (number of tumors, tumor grades, etc.), and general information are provided. Histopathology tests were used to diagnose the tumors as adenocarcinoma without any skin invasion. At the tumor site, the animal's hair was clipped and shaved, and subsequently, Radiographic recordings were taken with an X-ray machine (Fischer, Berlin, Germany). The radiographic setting factors were 58 to 70 kVp, 10 mAs, and 90 cm focal spot-film distance. The radiographic exposures were conducted, dorsoventrally and right laterally. The tumor dimensions were measured using calipers. The blood loss was quantified by measuring the blood and weighing surgical sponges used for blood collection throughout surgery.

Performing PPTT in Animals.

Each animal was subjected to three sessions of PPTT treatment in 2-week intervals using an 808 nm diode laser with a power of 5.8 W/cm$^2$ and a spot size of around 5.6 mm$^2$. An effective dose of AuNRs solution (7.5 nM AuNRs) for each 100 cm$^3$ was used, and the amount used was scaled up based on the volume of the tumor and injected directly into the tumor. Five minutes after injection, the entirety of the tumor was irradiated with the laser. The AuNRs concentration was decreased by 50% for each subsequent treatment. The temperature increase of a tumor during the laser irradiation was measured by placing a 33-gauge hypodermic thermocouple (OMEGA Engineering, Inc., Stamford, Conn., USA) needle directly inside the tumor (42° C.-44° C.).

Histopathology Evaluation of the Animal Tumor.

The detailed pathologic evaluation of tumors was conducted by members of the pathology department of the Faculty of Veterinary Medicine in Cairo University. Histopathological analysis was performed on 5 μm sections from tumor tissue that were fixed in 10% buffered formalin. The samples were stained with hematoxylin and eosin to assess pathology.

Results

Preparation and characterization of the AuNRs

Figure 23A:
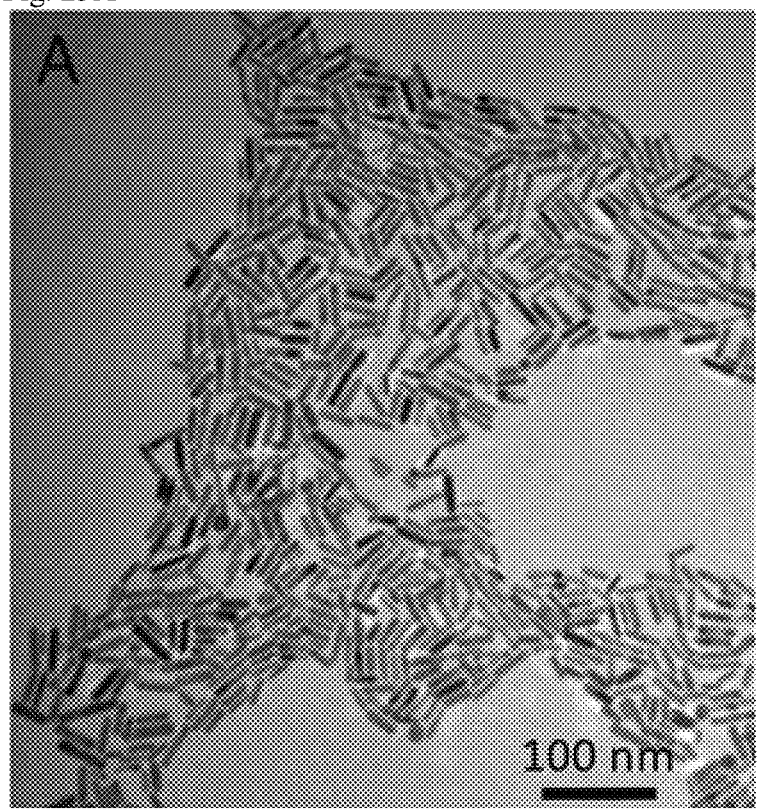
FIG. 23A-23B. Characterization of Gold nanorods (Length 26±3, width 5±0.8 nm). (23A) TEM image with 100 nm scale bar. (23B) UV-Vis absorbance spectra showing the SPR peaks of AuNRs before and after conjugation.
Figure 23B:
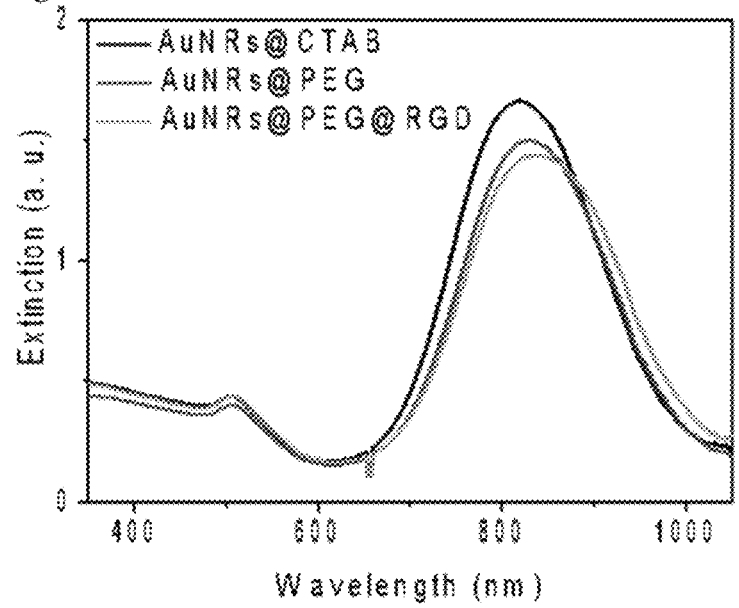

AuNRs with average length×width (26×5 nm) was used in this study, as they showed enhanced efficacy of PPTT. AuNRs were synthesized using the inventors' reported method and these AuNRs are shown in the TEM image (FIG. 23A). To absorb the near-IR laser light for performing PPTT, AuNRs were generated with an aspect ratio of about 5 and with a surface plasmon resonance wavelength of ~800 nm (FIG. 23B). The approximate length and width were 26±3 nm and 5±0.8 nm, respectively. After synthesis, AuNRs were successfully coated with mPEG-SH as evidenced by the red-shift of the surface plasmon peak (FIG. 23B). The as-synthesized AuNRs had a positive surface charge. The average number of mPEG-SH on each particle was quantified to be 1,000 and 10,000 RGD on each particle.

PPTT Decrease Bleeding During Surgery

In the inventors' earlier studies, the PPTT conditions were optimized including the dosage and the laser conditions (2.5 nM of AuNRs irradiated by near-Infrared laser with 0.5 w/cm$^2$ intensity for 2 minutes). The PPTT optimized conditions were conducted multiple times (at 0, 2, and 4 weeks apart) until complete regression via apoptosis as shown better results than necrosis. Herein, the inventors developed a new treatment regime for treating animal with tumor volumes more than 20 cm$^3$ by combining surgery with PPTT.

Figure 24A:
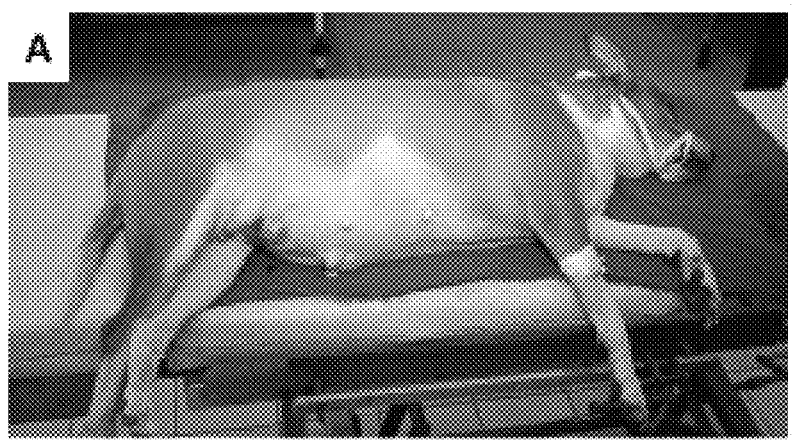
FIG. 24A-24D. (24A) A photo for control case treated with Surgery only without any treatment. (24B) A magnified figure of A for the tumor area. (24C) Photo of case during surgery with high amount of bleeding. (24D) Photo-micrograph of tumor tissue showing ductal carcinoma in situ grade II (H&E X 100).
Figure 24B:
Figure 24C:
Figure 24D:
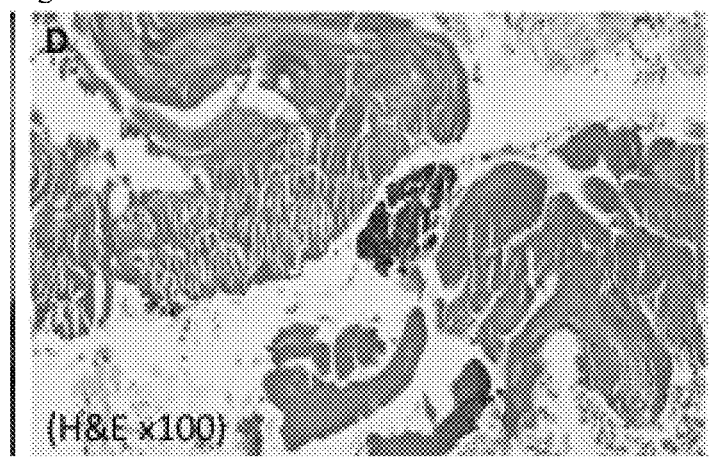

Before any treatment, tumors of all the animals showed variant growth, as shown in detail in Tables 2 and 3. Representing Group (I): 3 cases with 10 tumors, were solely treated by mastectomy (control group), or laser, or AuNRs treatment alone. As shown in FIGS. 24A and 24B, photographic images of animal of case 1 has 3 large tumors located at cranioabdominal and inguinal lymph node, all the three connected to form one chain. FIG. 24C is a picture of tumor during surgery with obvious bleeding (over 100 gram). FIG. 24D shows the histopathology of the tumor tissue showing ductal carcinoma in situ grade II.

TABLE 2

(Control Group I, GI) Three cases (2 dogs and 1 cat with 10 tumors) have been Treated with either surgery only, Laser only, or AuNRs only. All cases had metastasis then died.

| No. # | Case details | Species & age | Site of tumors | Size of tumors | Grade | Metastasis | Survival | Therapy | Extent of bleeding |
|---|---|---|---|---|---|---|---|---|---|
| GI-1 | Dia | Dog Mixed Boxer 14 Yrs | 1-R. caudoabdominal large ulcerated 2-R. cranioabdominal 3-R. inguinal L. N All the three connected to form one chain | T3 18 × 4 | II | Lymph node & chest metastasis | Died 3 months | Only Mastectomy | High bleeding +++ |
| GI-2 | Amany 25 Oct. 2016 | Dog Griffon 7 yrs | R. Cranioinquinal | T3 (4.1 × 2.9) | II | Lymph node &chest metastasis | Died 1 month | Laser only followed by mastectomy | 66.5 gm of blood |
| GI-3 | Sameha | Cat 15 yrs | 1-R. caudo abdominal 2-R. inguinal L. N 3-L. cranioabdominal | T2 (4 × 4.5). reacted ((5 × 2)) | II | Lymph node metastasis | 1 month | Laser only followed by mastectomy 1 + 2 + 3 tumors form chain laser only | 47.5 gm |
|  |  |  | 4- R. inguinal 5- L. inguinal 6-L. caudothoracic | (1 × 2)T3 (1 × 1)T1 (1 × 1)T1 | I |  |  | 4 + 5 + 6 tumors treated by AuNRs only followed by mastectomy | 45 gm |

TABLE 3

(Group II, GII) Five cases (4 dogs and 1 cat with 11 tumors) have been treated with
PPTT for 3 sessions followed by Surgery all cured one case had metastasis then died.

| No. # | Case details | Species & age | Site of tumors | Size of tumors | Grade | Metastasis | Survival | Therapy | Extent of bleeding |
|---|---|---|---|---|---|---|---|---|---|
| GII-1 | Afaf | Cat 9 yrs | L. caudothoracic R. caudothoracic 4 × 4 | T2 T1 | III | No | Survival months 24 months | 3 sessions of PPTT | Very low |
| GII-2 | Magdy Fawzy | Dog Griffon 10 yrs | R. Caudoquinal 3.1 × 3.65 | T2 | III | No | 48 months | 3 session of PPTT followed by surgery | Very low |
| GII-3 | Norhan 28 Jul. 2016 | Dog Griffon 11 yrs | 1- L. inguinal (5 × 5) 2- inguinal XXX 3 small tumors | | | No | 3 months | 3 session of PPTT followed by surgery PPTT Complete ablation | Very low |
| GII-4 | Mostafa abdo 13 Jul. 2016 | Dog Griffon 5 yrs | 1- R. caudo thoracic 2- R. cranio abdominal both tumors form chain (8 × 6.5) | T3 | II | Lymph node &chest metastasis | Died, 1 month | 3 sessions of PPTT followed by surgery | Low+ |
| GII-5 | Morais case 28 Jul. 2016 | Dog Griffon 8 yrs | 1-L. inguinal large calcified (5 × 5). 2-small caudal abdomenial (2 × 1.5). 3-two small tumors | T3 | III | No | 6 months | Three session of PPTT followed by surgery. 2&3 treated by PPTT only | Low+ |

Figure 25A:
FIG. 25A-25D. Left side (25A, 25B) shows case 1 in GI (surgery only). Right side (25C, 25D) shows a case in GII (treated with PPTT for three sessions (2-weeks intervals) before the surgery). (25A and 25C) Photographic images indicating decrease of bleeding after PPTT (25C), compared with control (25A). (25B and 25D) Photo-micrograph of tumor bed vasculature showing (25B) normal intact blood vessels with surgery only and (25D) swelling and sloughing of endothelial lining and destruction of blood vessel wall (arrow) after PPTT (H&E X 400).
Figure 25B:
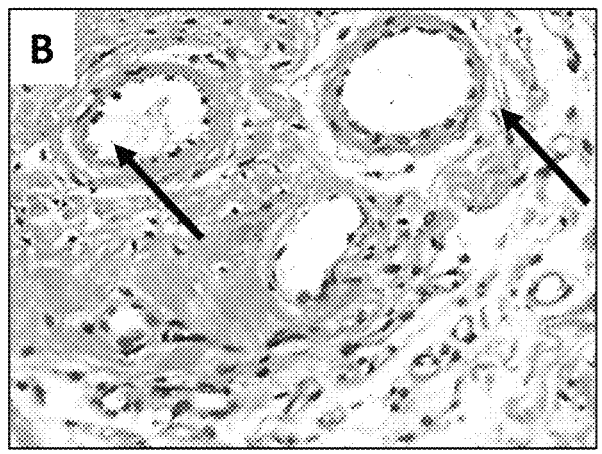
Figure 25C:
Figure 25D:
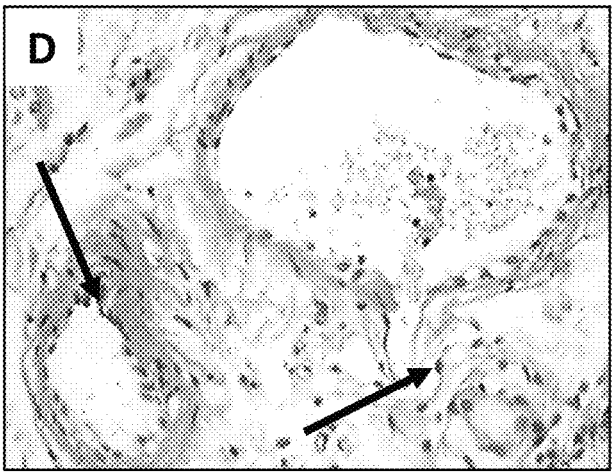

In Group (II), 5 cases with 11 tumors were treated with 3 sessions of PPTT (2 weeks' intervals) and followed by surgery after the last PPTT session. FIG. 25 A-25B show case 1 which treated with surgery only and FIG. 25C-25D show another with surgery after PPTT. Interestingly, the inventors observed that when applying PPTT before surgery, no bleeding during the surgery were observed for all treated tumors in group II when compared with Group I (FIGS. 25A and 25C (surgery only versus surgery after PPTT).

Without wishing to be bound by theory, the decrease of the bleeding might be explained by the histopathology of the tumor bed vasculature, with surgery only, the blood vessels are normal and intact (FIG. 25B), while after PPTT, tumor bed vasculature shows swelling and sloughing of endothelial lining and destruction of blood vessel wall (H&E X 400) (FIG. 25D).

PPTT before surgery regime was shown to be effective for achieving complete tumor recession as shown in Table 3.

Figure 26A:
FIG. 26A-26F. (26A) Case 1 of 9 years old mixed breed cat suffering from mammary neoplasm. (26B) the site of tumors left axillary lymph node (black arrow) and left cranial thoracic (blue arrow) (26C) after surgical excision and (26D) Subcutaneous layer showing well developed granulation tissue at the site of suture (arrow) (H&E X 100). (26E) the case after 12 months showed complete recovery of the surgery without evidence of recurrence. (26F) X-ray shows no metastasis in the chest.
Figure 26B:
Figure 26C:
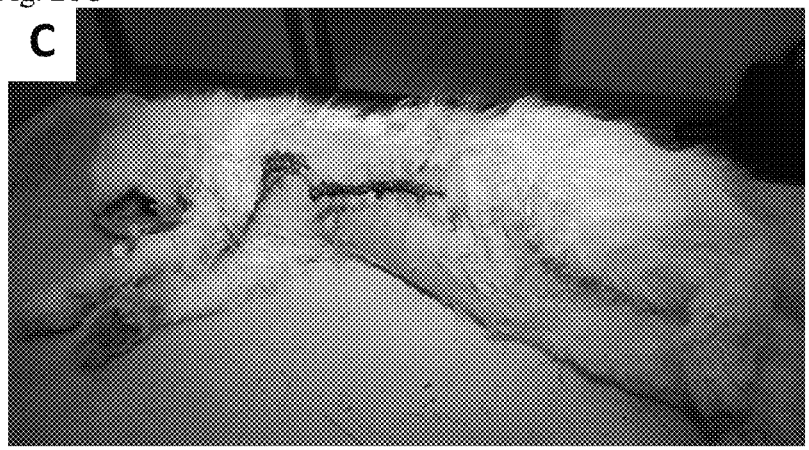
Figure 26D:
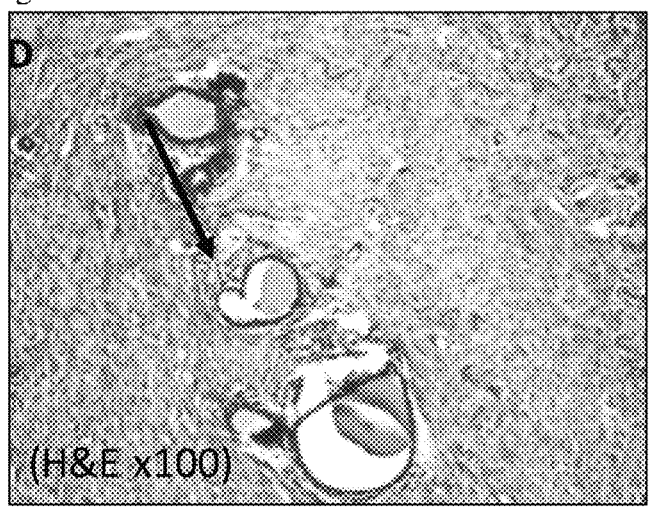
Figure 26E:
Figure 26F:
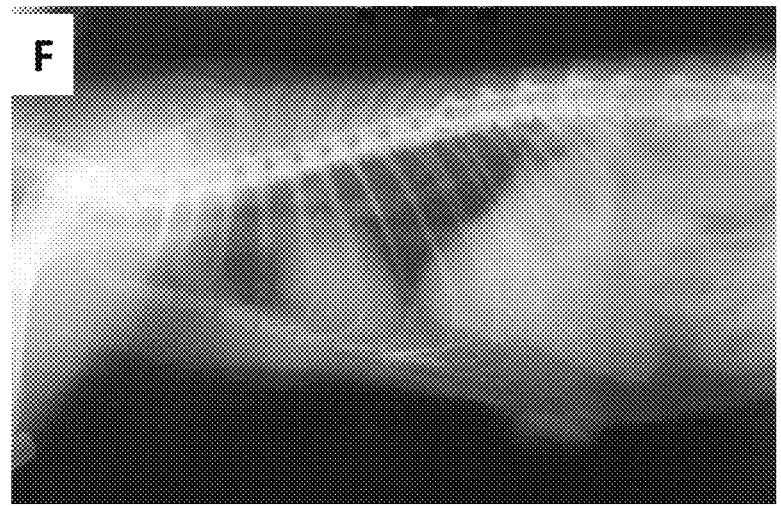

As seen in case 1 from group 2, a 9 years old mixed breed cat suffered from mammary neoplasms as shown in FIG. 26A. The site of 2 tumors located at her left axillary lymph node (black arrow) and left cranial thoracic (blue arrow) in FIG. 26B. After PPTT, followed by surgical excision of the tumors (FIG. 26C), tumor recession was achieved. The histopathology showed after PPTT, well-developed granulation tissues was observed, indicating the tumor recovery (FIG. 26D). After 12 months, this case showed complete recovery of the surgery (FIG. 26E) without evidence of recurrence or chest metastasis (FIG. 26F).

Discussion

Surgery is often used for tumor removal; however, it might trigger metastasis. PPTT could be a good alternative to replace traditional chemotherapy and radiotherapy for localized tumors especially for tumors with (volume ≤20 cm$^3$). Herein, for effective treatment of large tumors (volume ≥20 cm$^3$), the inventors applied PPTT before surgical resection to naturally occurring tumors in mammary glands of dogs and cats. 5 cases were treated with this regime, showed complete remission without any recurrence after therapy. 3 cases died in few months after treatment. However, no tumors were found, and the animals appeared to have died for other reasons (such as pneumonia). Histopathology results showed a decrease of cancer grades before (variant grades from 1-4) and after two weeks of treatment via PPTT and surgery (grade 0), X-ray diffraction showed no metastasis 1-2 years after treatment. In conclusion, this example demonstrates the feasibility of applying PPTT before surgery for large tumors in dogs and cats. AuNRs-PPTT before surgery, including in treatment of large tumors, could significantly affect blood vessels inside the tumor, which potentially avoids the risk of bleeding during surgery such as blood loss and metastasis. This example demonstrates that it is likely that PPTT has affected the tumor blood vessels, which decreased the blood flow inside the tumor. Previously, it has been reported that photothermal ablation of breast cancer in mice models using doxorubicin-loaded DNA wrapped gold nanorods could disturb the blood vessels.

Example 4—Gold Nanorod-Photothermal Therapy Alters Cell Junctions and Cytoskeletal Proteins in Inhibiting Cancer Cell Collective Migration In this example, quantitative mass spectrometry (MS)-based phosphoproteomics was employed to examine the signaling pathways upon the stimulation of AuNRs and PPTT. A primary signaling pathway map has been constructed to display a large number of identified alterations. Furthermore, super-resolution microscopy imaging techniques were used to visualize the changes of key cytoskeletal and cell junction proteins. Both phosphoproteomics and super-resolution imaging results indicated possible functions of the AuNRs and PPTT in regulating and changing the architecture of the cytoskeletal filaments and cell junctions, contributing to the inhibition of collective cancer cell migration.

Results

Figure 33A:
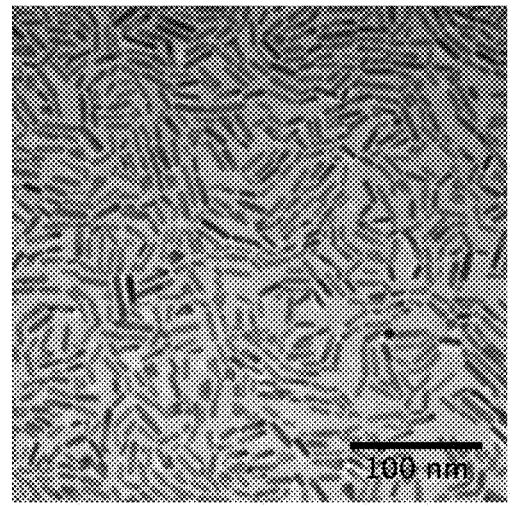
FIG. 33A-33C. AuNR synthesis and characterization. (33A) TEM image of AuNRs. (33B) UV-Vis spectra of AuNRs with different surface ligands. Black, the as-synthesized AuNRs with CTAB on the surface; red, AuNRs conjugated with PEG and RGD. (33C) Zeta potential of AuNRs before/after conjugations (n=3).
Figure 33B:
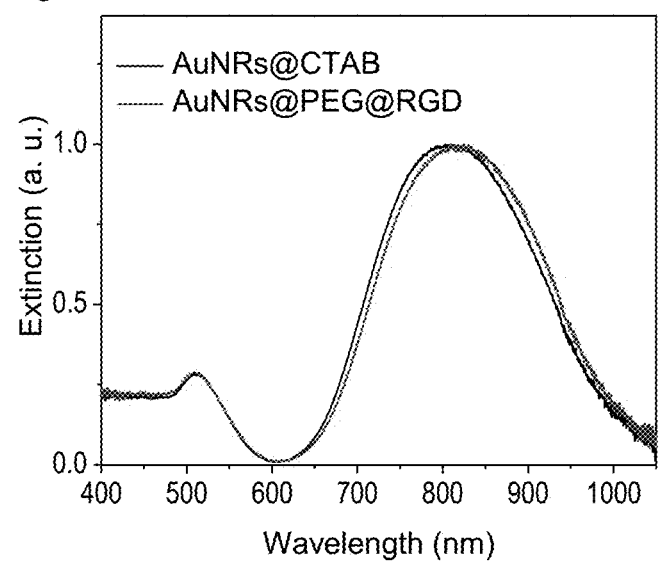
Figure 33C:
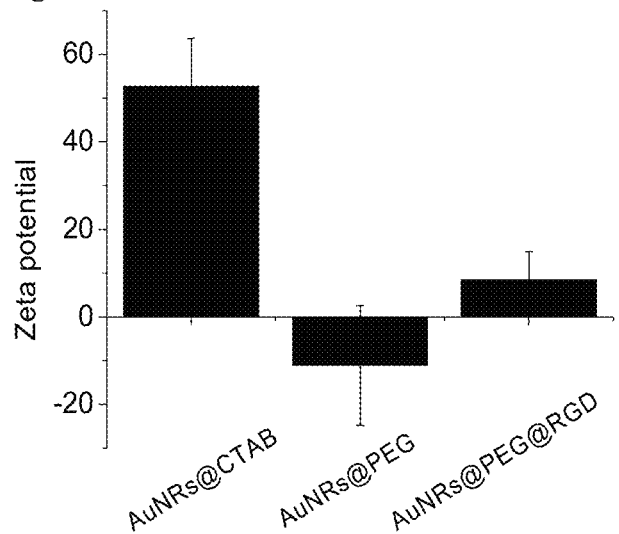

Gold Nanorods and NIR Light Attenuate the Migration and Invasion of Cancer Cells The preparation of integrin targeted AuNRs was stated in the inventors' previous work. Briefly, AuNRs with a size of 25 (±3)×6 (±1) nm (length×width) and an aspect ratio of 4.2 (FIG. 33A, transmission electron microscopy (TEM) image) were synthesized using the seedless growth method. Optimal heat-generating efficacy in PPTT with these AuNRs has been demonstrated previously. To remove the cytotoxic cetyltrimethylammonium bromide (CTAB), the as-synthesized AuNRs were washed twice with D.I. water. Then, the AuNRs were functionalized with polyethylene glycol thiol (PEG) and Arg-Gly-Asp (RGD) peptides to increase the biocompatibility and obtain integrin targeting, respectively. The surface conjugations were confirmed by the red-shift of the longitudinal surface plasmon resonance (SPR) band (FIG. 33B) and surface charge changes of the AuNRs (FIG. 33C), consistent with the previous reports.

Figure 27A:
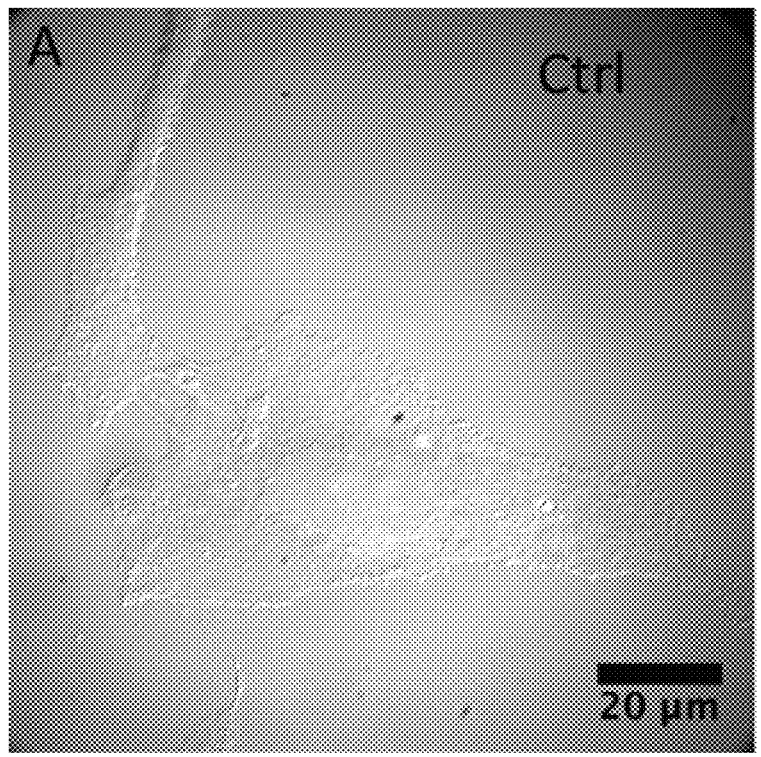
FIG. 27A-27F. Cellular uptake, cytotoxicity and motility upon AuNRs treatments (the results of MCF-7 cells are in FIG. 34-36). (27A-27B) Differential interference contrast (DIC) microscopic images of HeLa cells without (27A) and with AuNRs@RGD (27B). The red arrows identify the locations of AuNRs. (27C) Cell viability of HeLa cells after AuNRs and AuNRs+NIR treatments (n=3). (27D) Western blotting for the BAX protein upon different treatments. (27E) Scratch assay images of HeLa cells (control, AuNRs treatment, and AuNRs/PPTT treatment) at 0 and 12 h (n=6). (27F) Percent wound healing. Student's t test was used for statistical analysis. All values are expressed as means±standard errors of the mean (SEM). *p<0.001, p<0.01, *p<0.05.
Figure 27B:
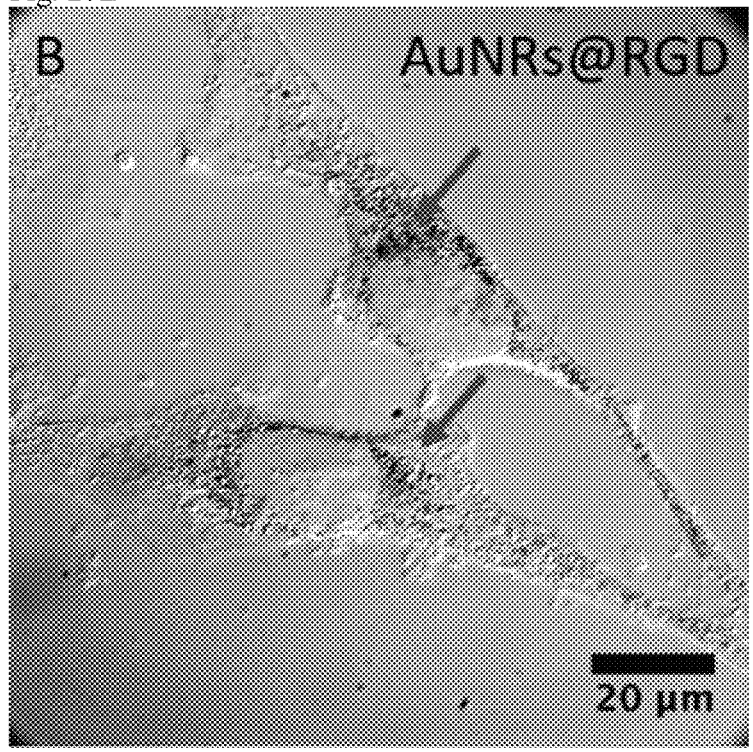
Figure 27C:
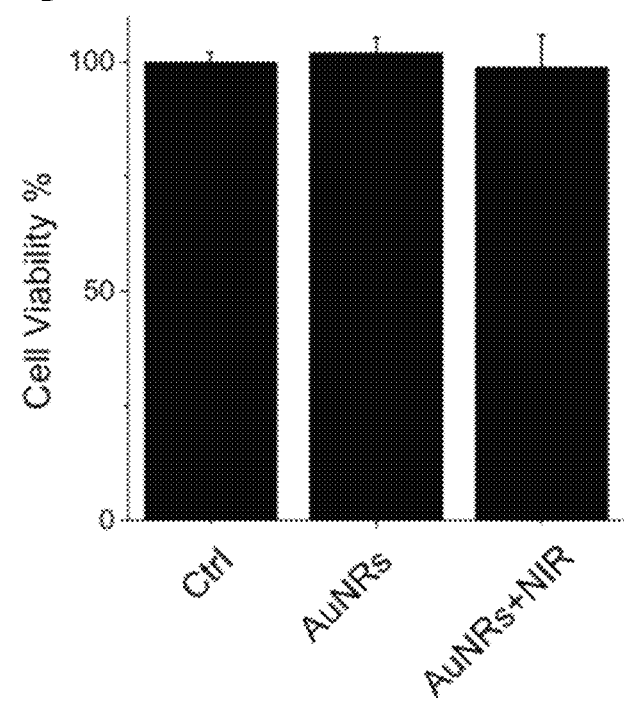
Figure 27D:
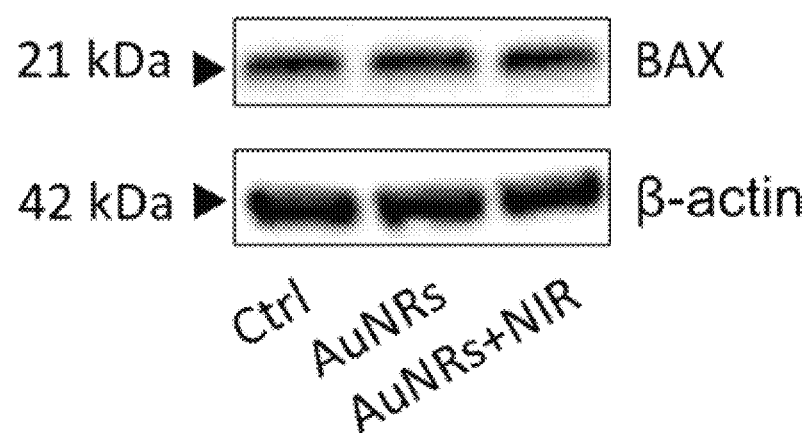
Figure 34A:
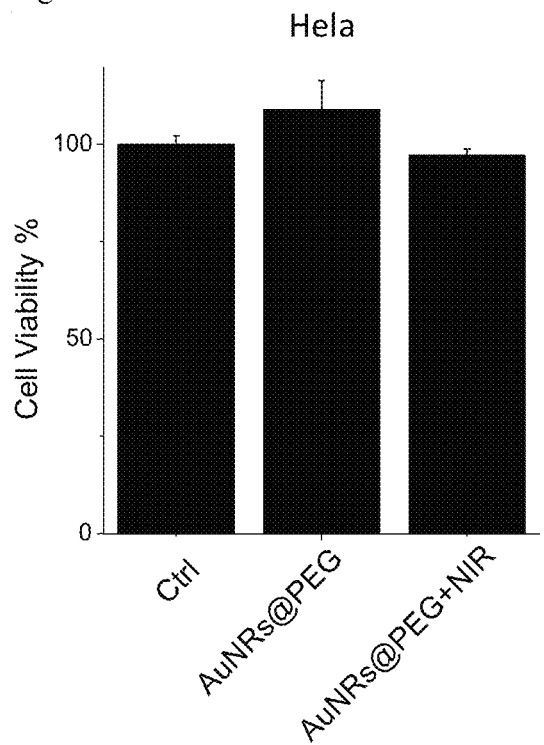
FIG. 34A-34B. Cytotoxicity of non-specifically targeted AuNRs (AuNRs@PEG) on HeLa (34A) and MCF-7 cells (34B) (n=3).
Figure 34B:
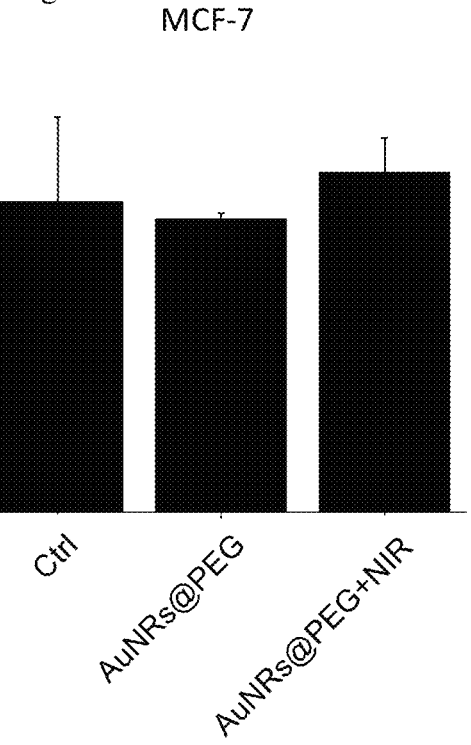
Figure 35D:
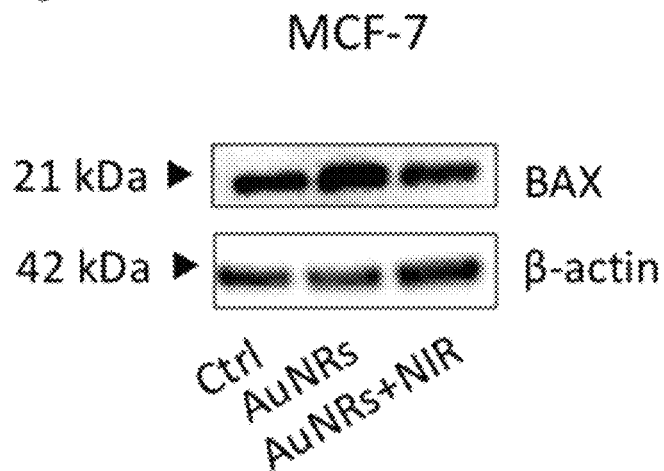

The binding of RGD peptide to the cell surface integrin could enhance the endocytosis of AuNRs. The internalization of AuNRs within the cervical cancer cell line HeLa, was observed under a differential interference contrast (DIC) microscope (FIGS. 27A and 27B). The cell viability (XTT) assay revealed that the cells remained viable and had similar proliferation rates after incubation with AuNRs and after PPTT for 24 h (FIG. 27C and FIG. 34 for nonspecifically targeted AuNRs (AuNRs@PEG) treatments). In addition, no observable change of the apoptosis regulator Bcl-2-associated X (BAX) protein indicates no apoptosis after treatment (FIG. 27D). The inventors performed the same assays with the breast cancer cell line MCF-7, and similar results were obtained (FIG. 35).

Figure 27E:
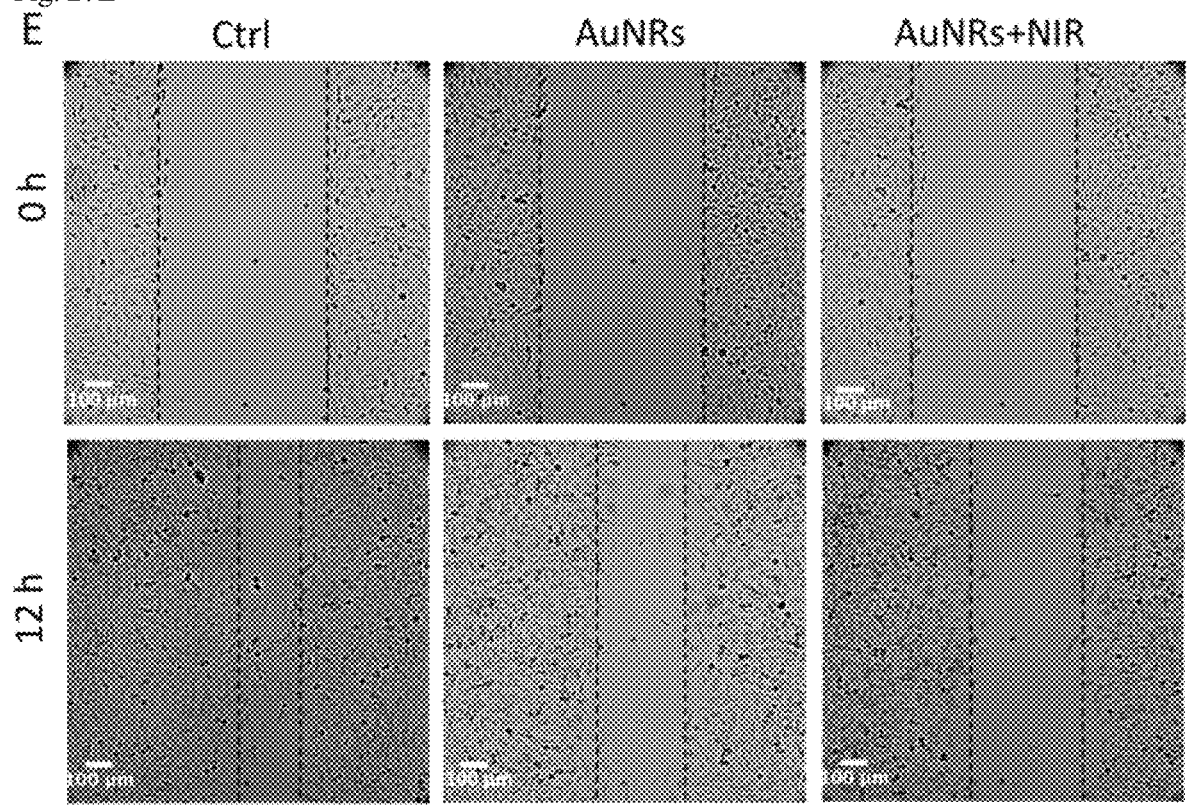
Figure 27F:
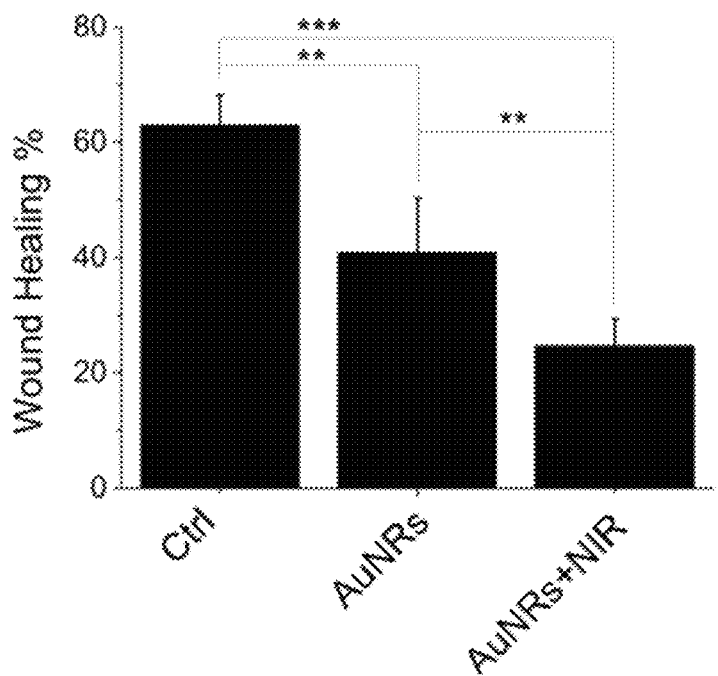
Figure 36:
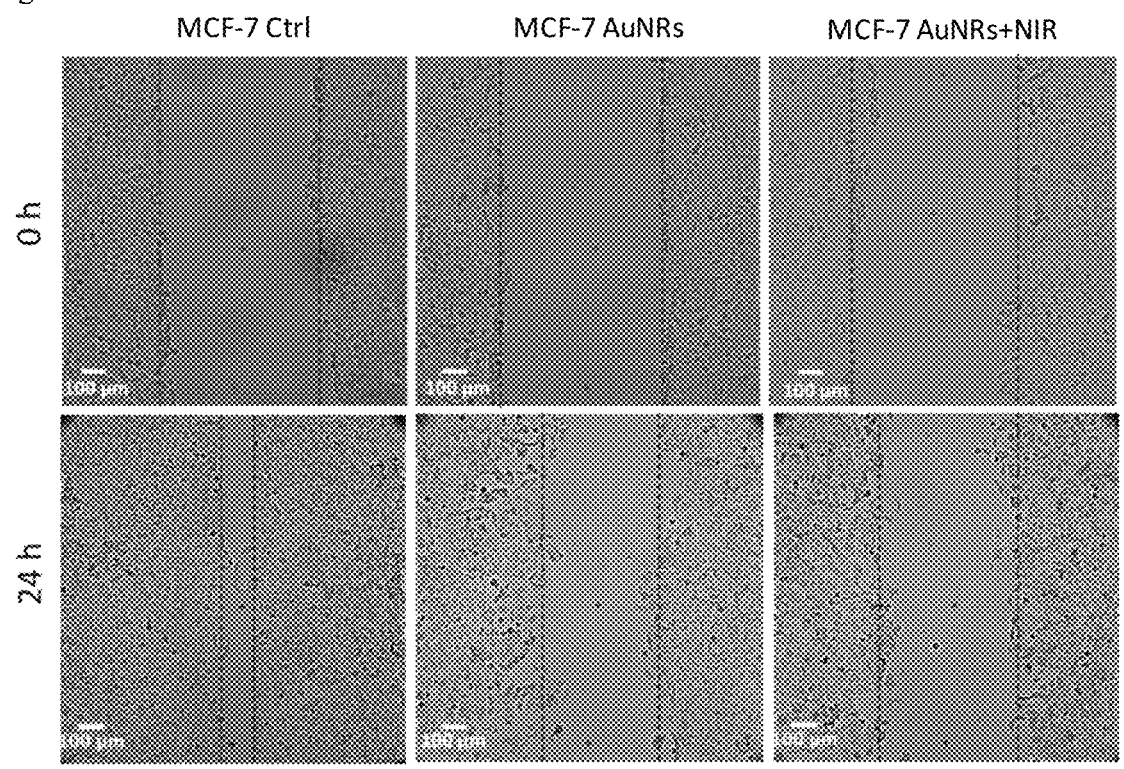
FIG. 36. Scratch assay images of MCF-7 cells (control, AuNRs treatment, and AuNRs/PPTT treatment) at 0 and 24 h (n=6). Student's t test was used for statistical analysis. All values are expressed as means±standard errors of the mean (SEM). *p<0.001, p<0.01, *p<0.05.
Figure 36:
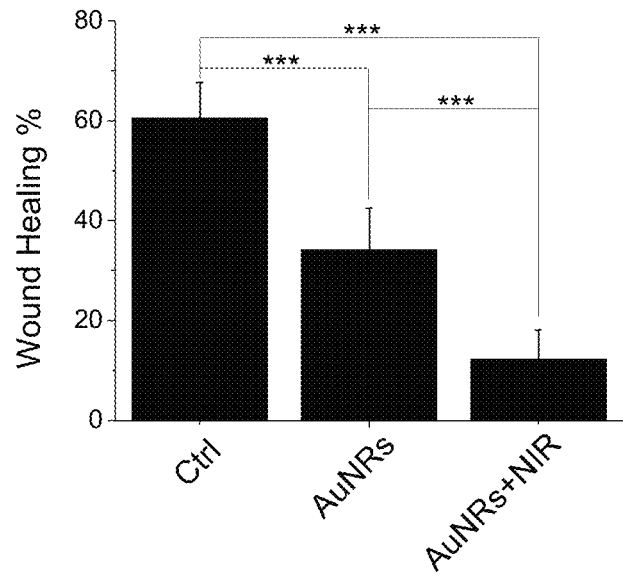

To evaluate the effects of AuNRs on cancer cell collective migration, the inventors conducted a 2D scratch assay on the monolayers of MCF-7 and HeLa cells that were incubated with or without the treatments. After introducing a "scratch" or "wound" into a cell culture, the cancer cells migrate collectively to the empty space, and images were captured immediately and 12 hours after the scratch of HeLa cells in FIG. 27E (or 24 hours of MCF-7 cells in FIG. 36). The statistics (FIG. 27F) indicates that cells have exhibited significantly different wound-healing ability in the control groups compared with those treated with AuNRs, while the introduction of NIR light to generate PPTT further decreases the wound-healing ability of cancer cells.

Figure 28A:
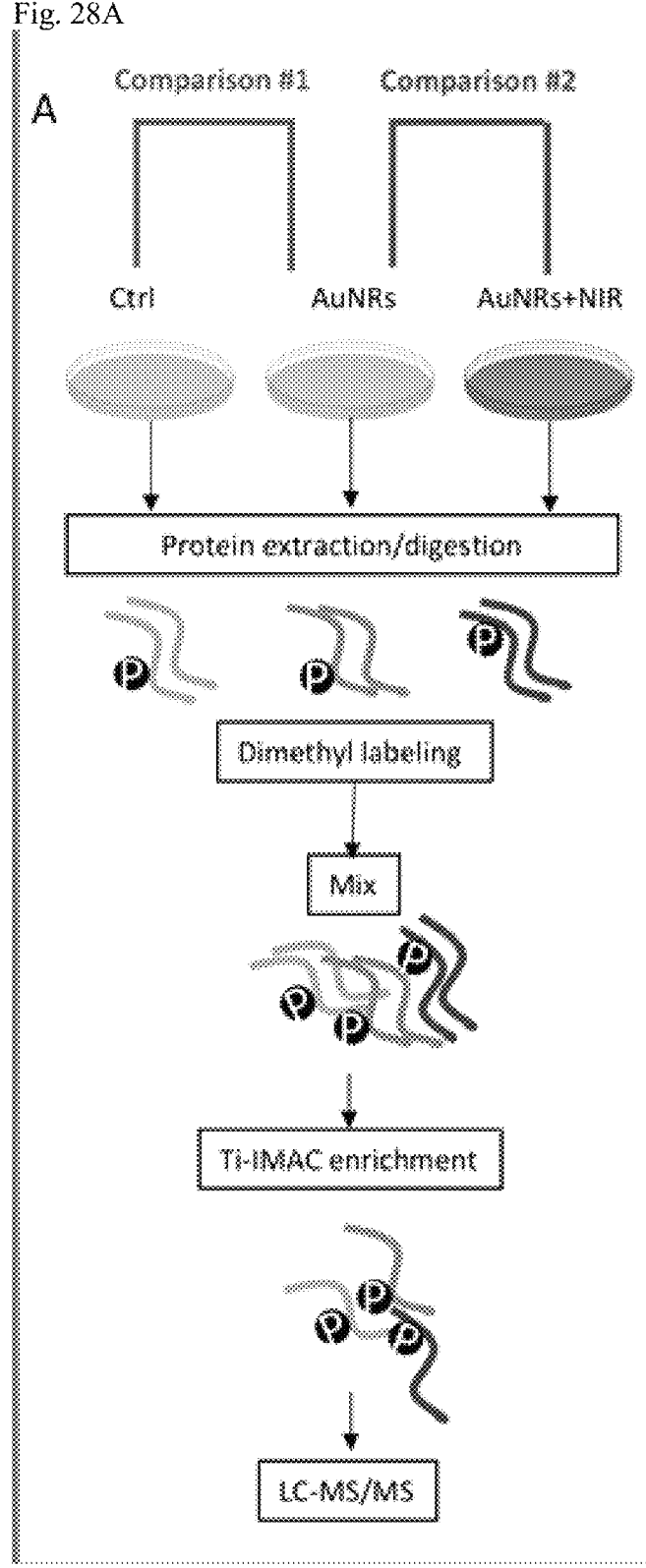
FIG. 28A-28I. Phosphoproteomics results. (28A) Experimental workflow. Two comparisons were performed in data analysis. Comparison #1 (AuNRs vs. control): (28B) Heatmap and (28C) pathway analysis after AuNRs treatment. (28D) Western blotting showing the altered phosphorylation sited in p120 Catenin (HeLa cells). (28E) Altered phosphorylation sited in p120 Catenin (pS268) indicated by phosphoproteomics (HeLa cells). Comparison #2 (AuNRs+NIR vs. AuNRs): (28F) Heatmap and (28G) pathway analysis after AuNRs+NIR treatment. (28H) Western blotting showing the altered phosphorylation sited in GSK3 (HeLa cells). (28I) Altered phosphorylation sites GSK3 (pY216) indicated by phosphoproteomics (HeLa cells). Mean values in are shown in the heatmaps (n=3).
Figure 32A:
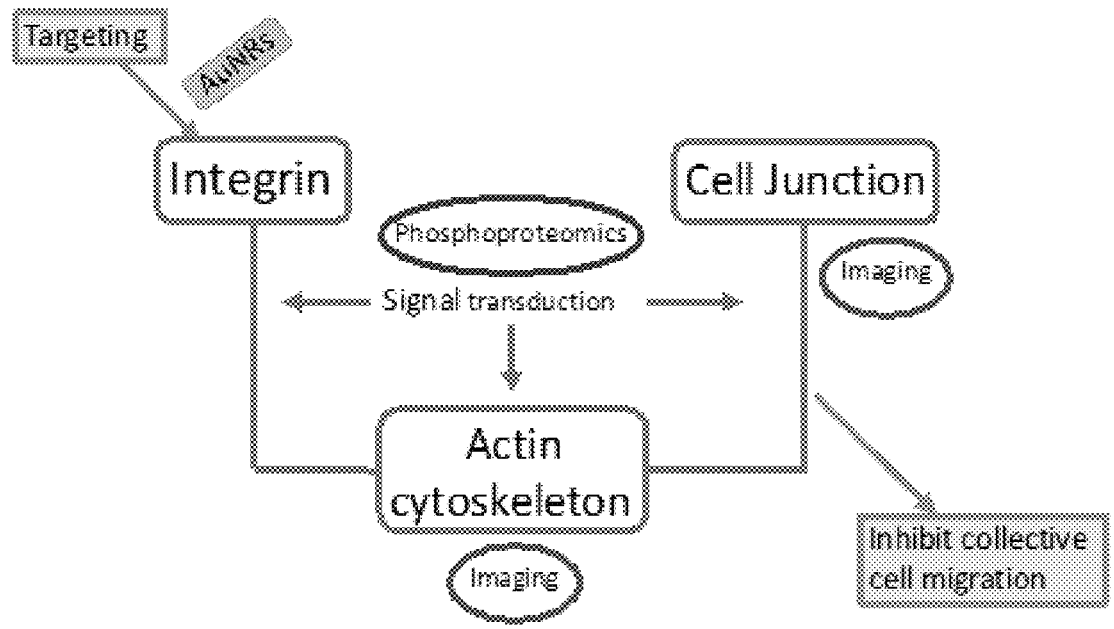
FIG. 32A-32B. Experimental design (31A) and proposed mechanism (31B) of AuNRs and PPTT in inhibiting cancer collective migration. Targeting integrin could affect the actin cytoskeleton and cell junctions to result in the inhibition of cancer cell collective migration. Phosphoproteomics and super-resolution fluorescence imaging, as well as Western blot, were the main experimental tools used in the current study.
Figure 32B:
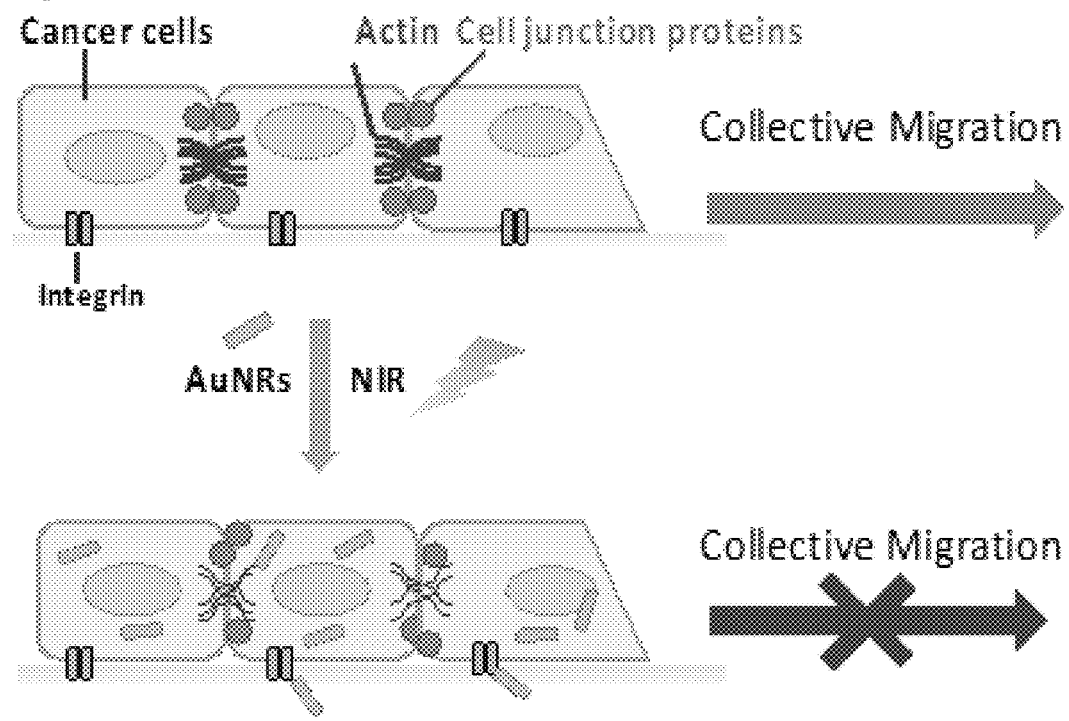
Figure 37A:
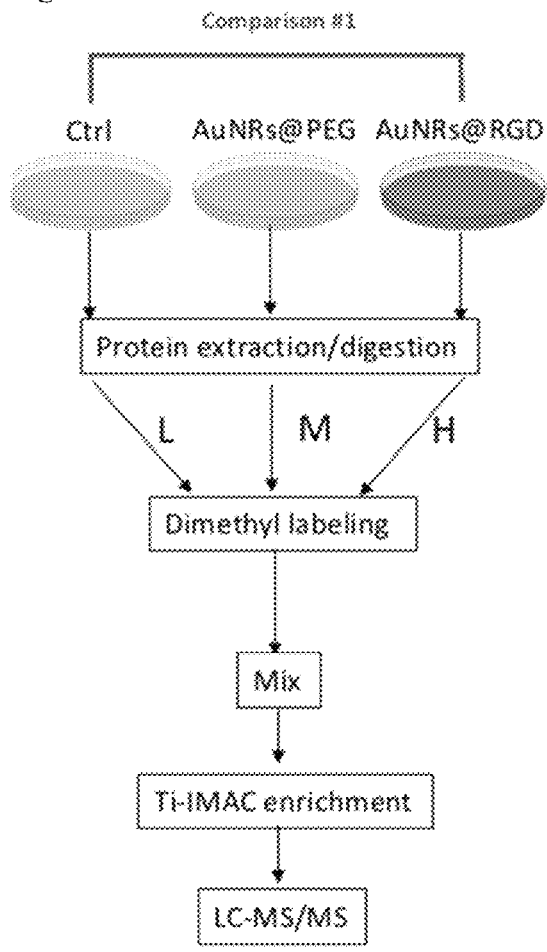
FIG. 37A-37B. Experimental design of quantitative phosphoproteomics. Two sets of experiments were performed to examine the AuNRs and the photothermal effects separately. (37A) Studying the protein phosphorylation upon treatments of AuNRs@PEG (30 min stimulation) and AuNRs@RGD (30 min stimulation). (37B) Studying the protein phosphorylation upon photothermal effects (30 min stimulation) after overnight incubating the cells with AuNRs@RGD. The comparisons #1 and #2 are indicated in FIG. 2.
Figure 37B:
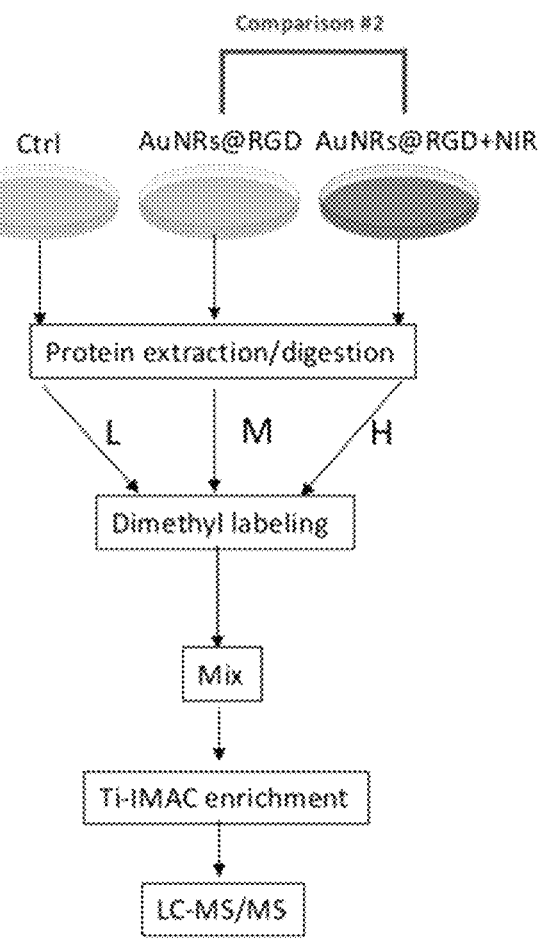
Figure 38A:
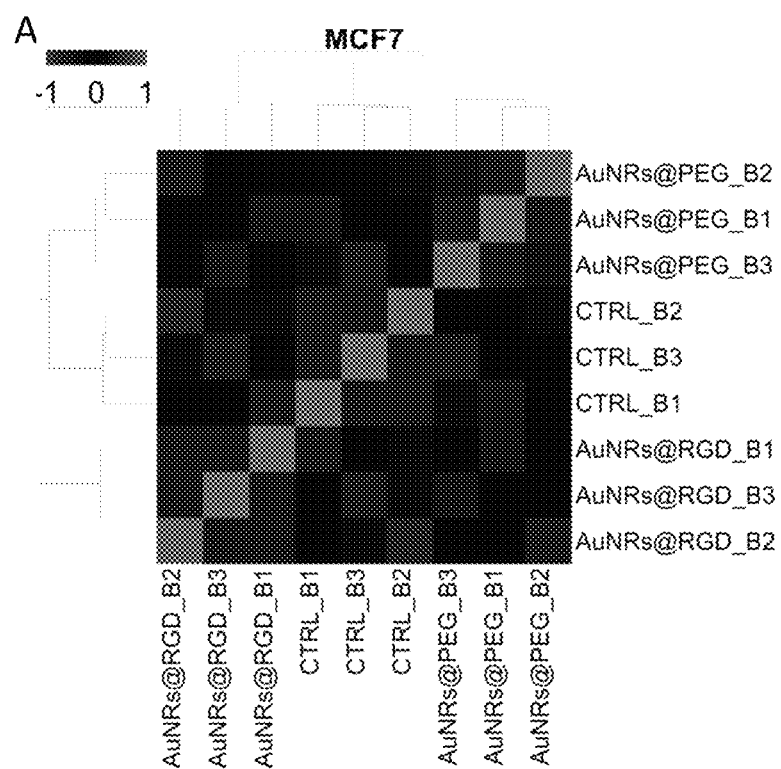
FIG. 38A-38D. Clustering analysis of the samples. (38A) AuNRs@PEG, AuNRs@RGD and control for MCF-7. (38B) AuNRs@PEG, AuNRs@RGD and control for HeLa. (38C) AuNRs@RGD, AuNRs@RGD+NIR, and control for MCF-7. (38D) AuNRs@RGD, AuNRs@RGD+NIR, and control for HeLa. B1, B2, and B3 in the figures indicate the three biological replications.
Figure 38B:
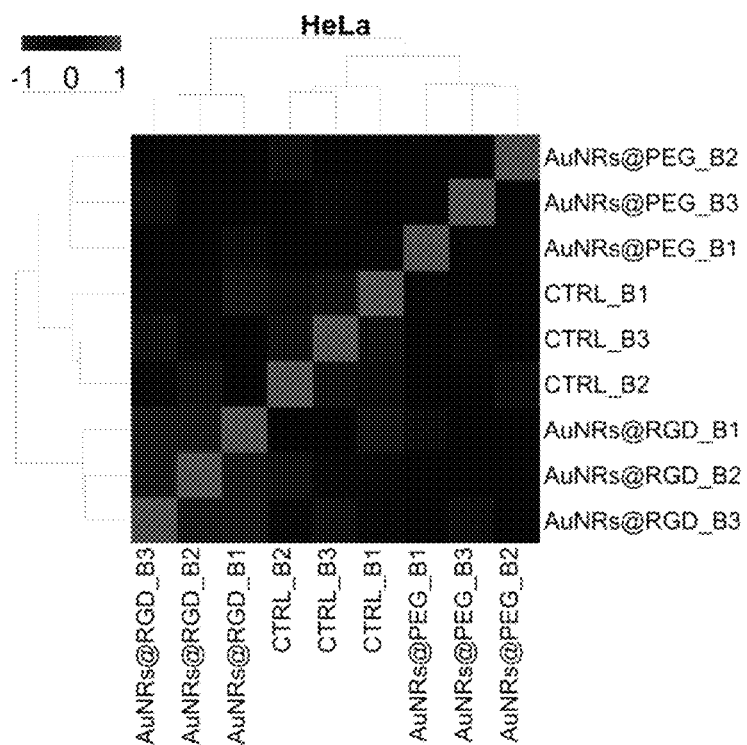
Figure 38C:
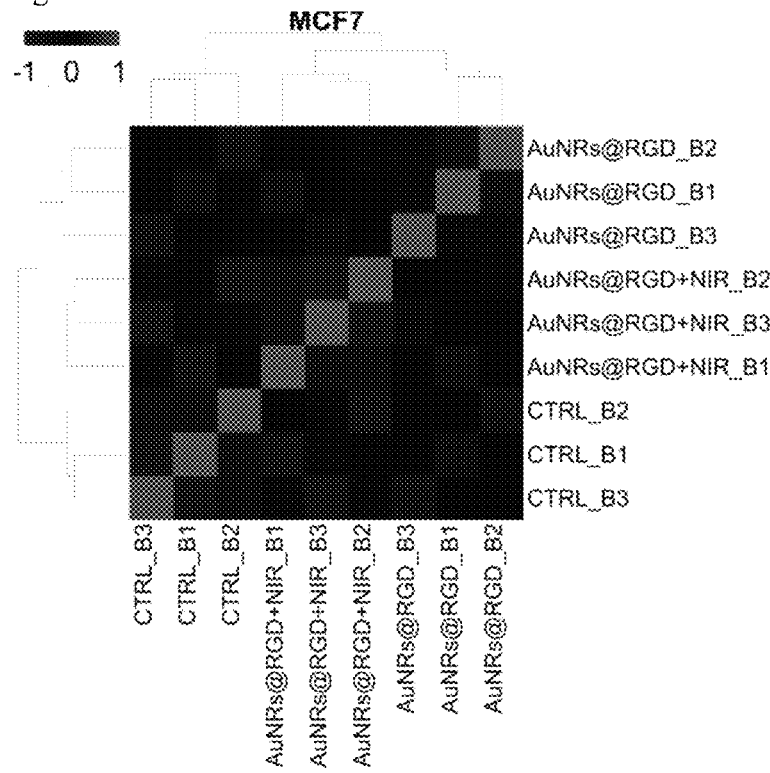
Figure 38D:
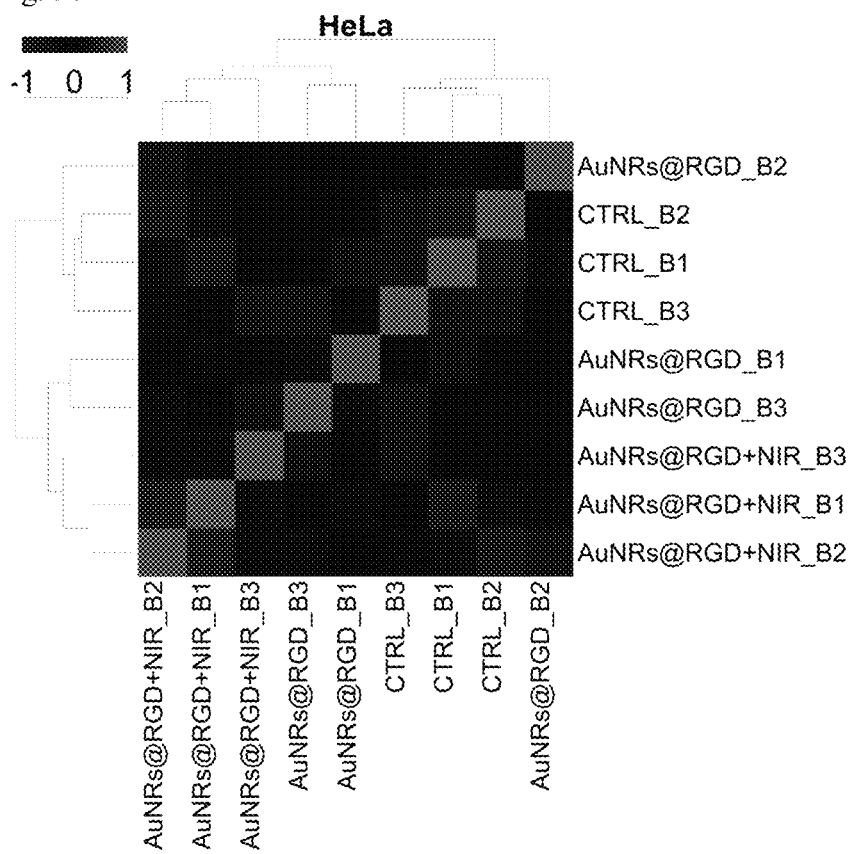
Figure 39A:
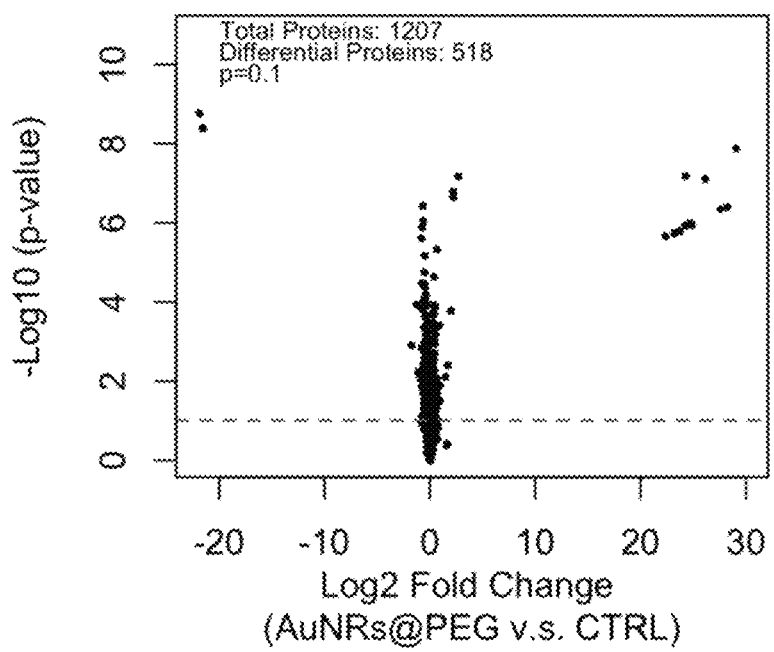
FIG. 39A-39F. Volcano plots of proteins under perturbation by (39A) AuNRs@PEG for MCF-7, (39B) AuNRs@PEG for HeLa, (39C) AuNRs@RGD for MCF-7, (39D) AuNRs@RGD for HeLa, (39E) AuNRs@RGD+NIR for MCF-7 and (39F) AuNRs@RGD+NIR for HeLa.
Figure 39B:
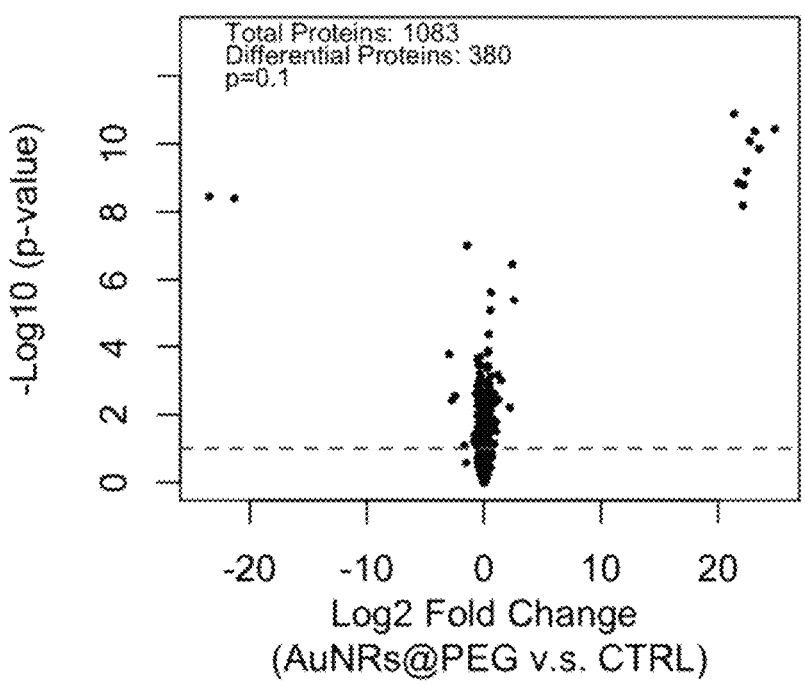
Figure 39C:
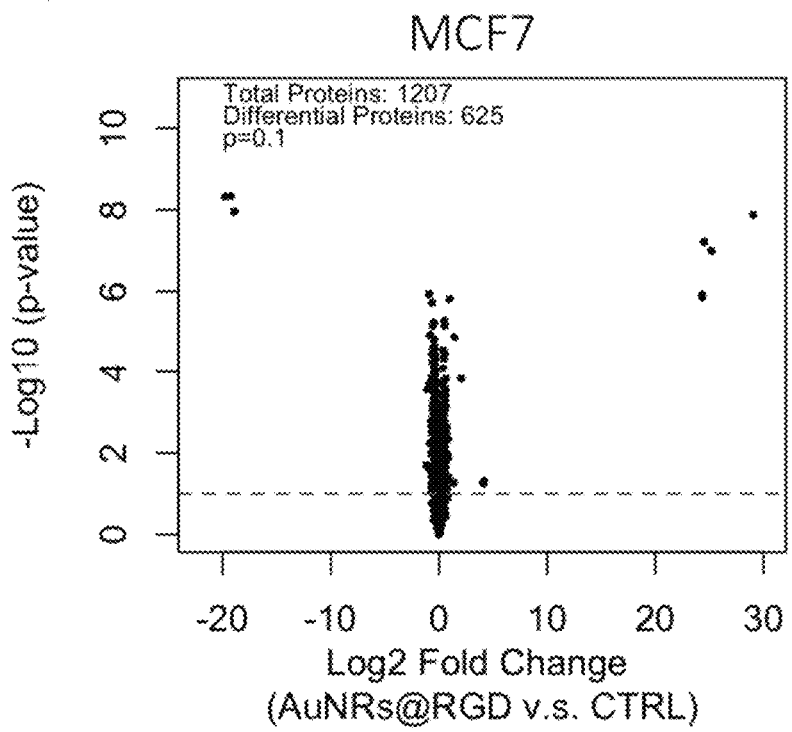
Figure 39D:
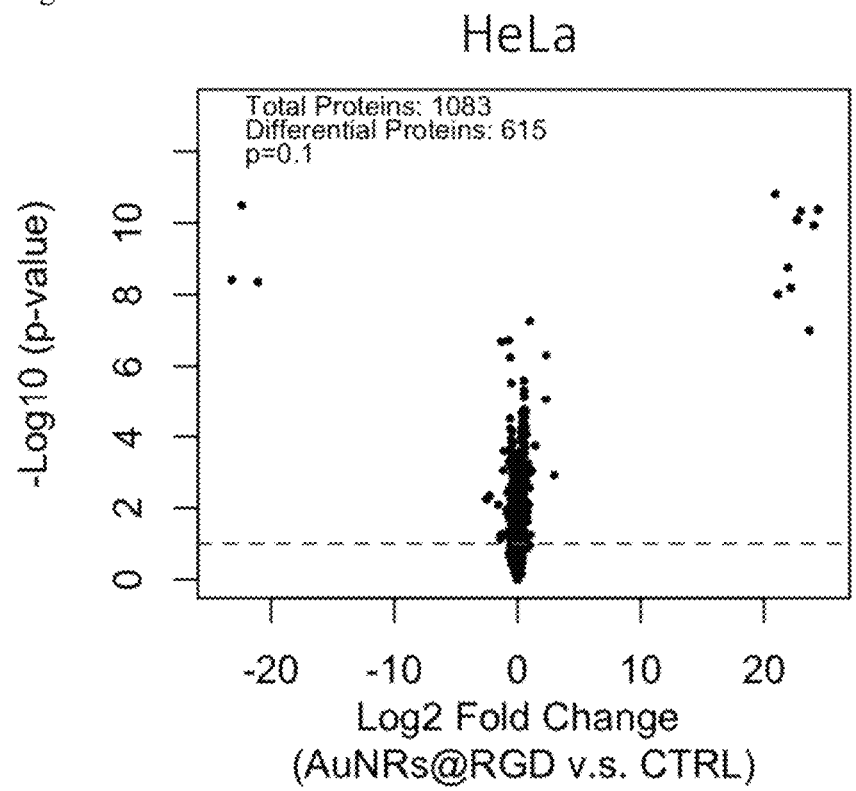
Figure 39E:
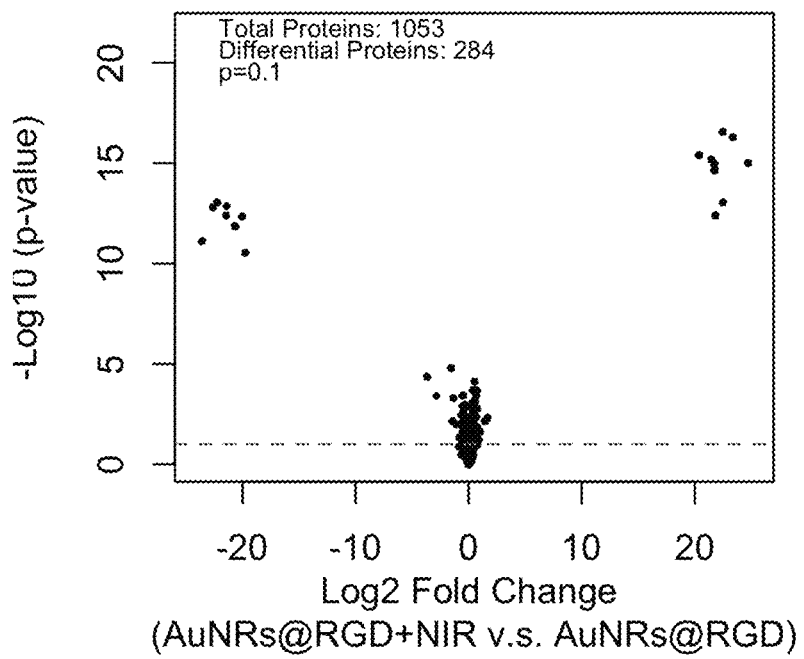
Figure 39F:
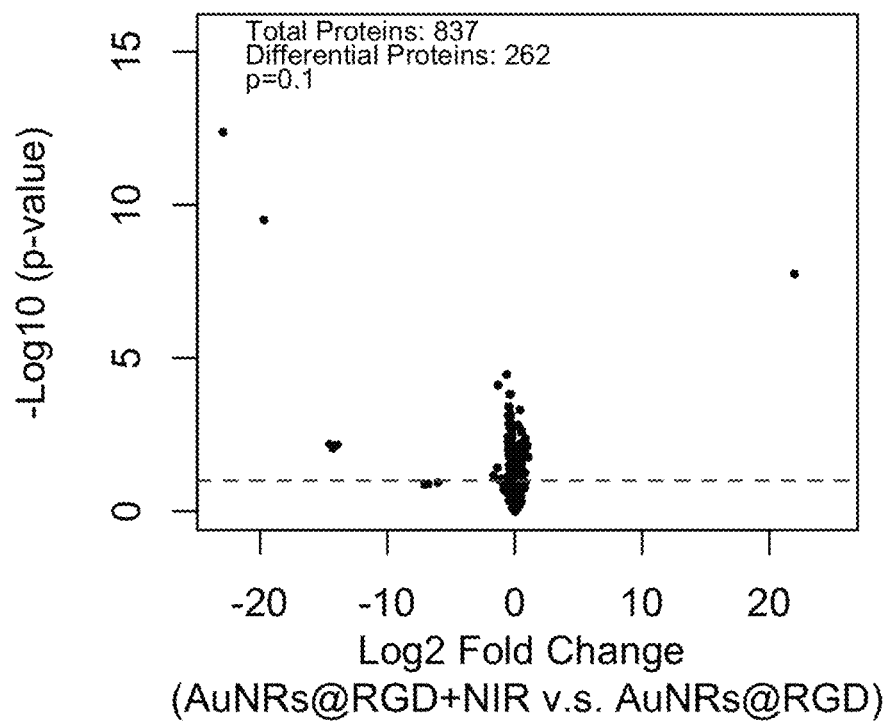
Figure 40A:
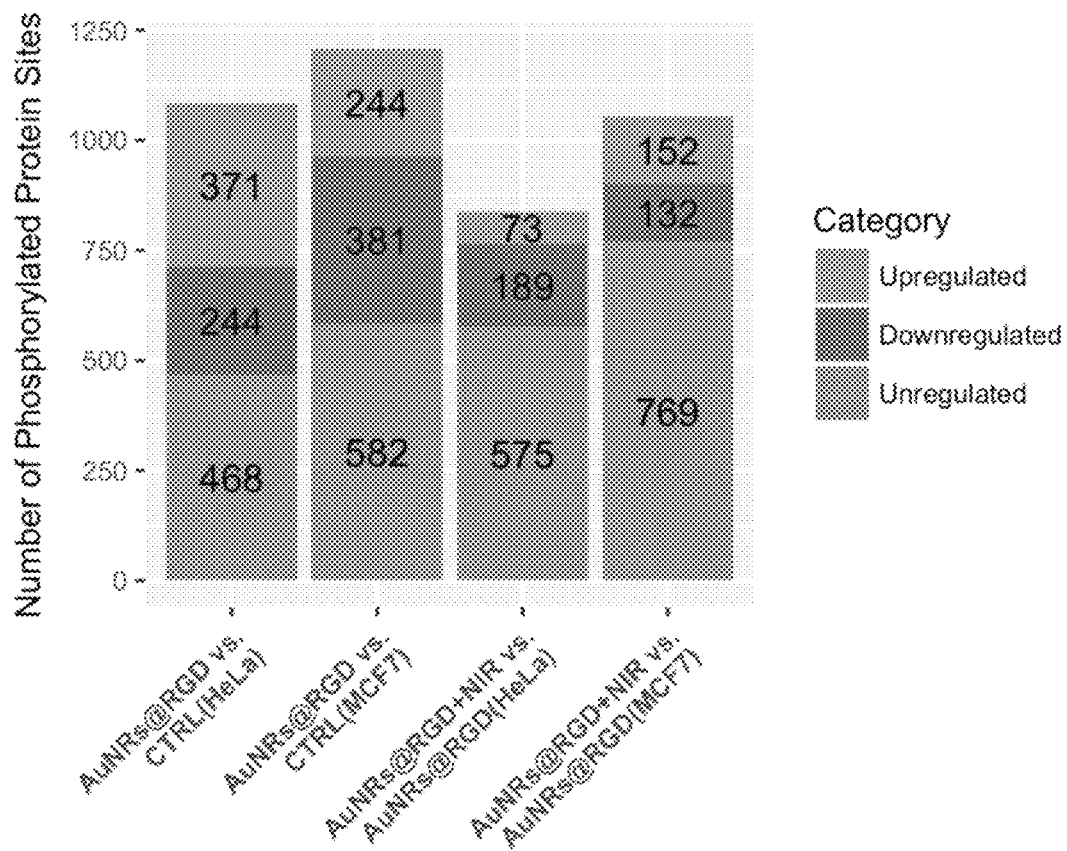
FIG. 40A-40C. (40A) Numbers of regulated/unregulated phosphorylated sites identified in each experiment. (40B-40C) Venn diagram showing the comparison of differentially phosphorylated sites identified in each experiment.
Figure 40B:
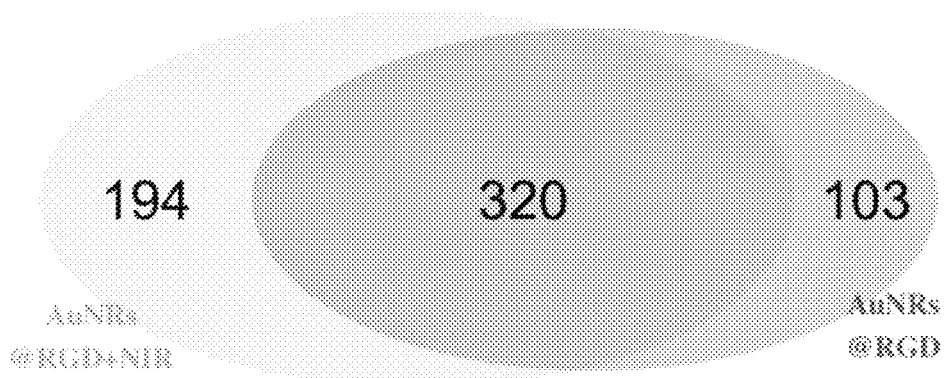
Figure 40C:
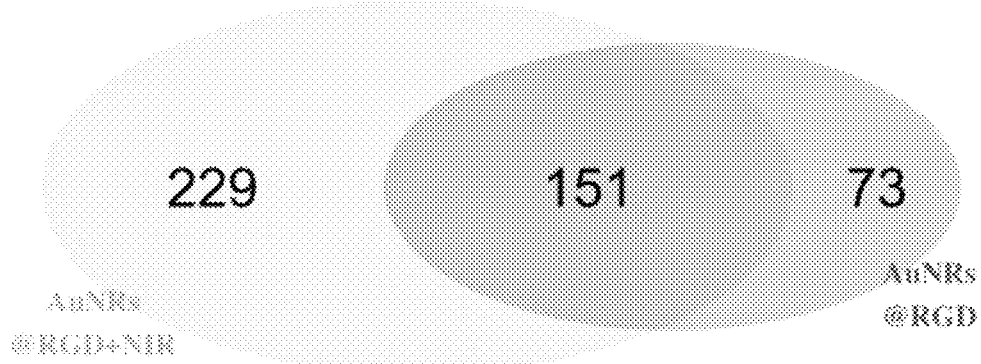
Figure 41A:
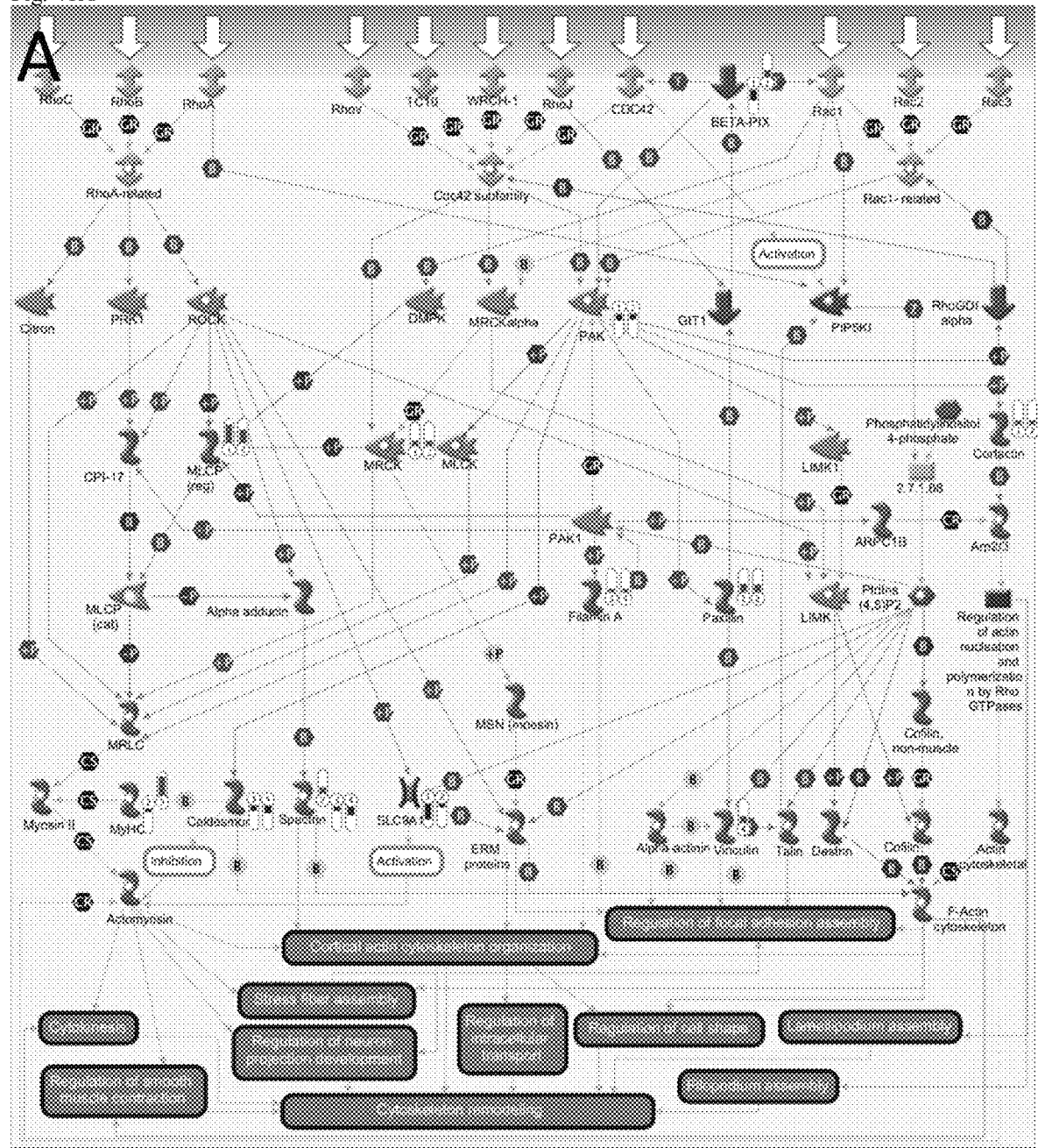
FIG. 41A-41D. Key pathways perturbed by AuNRs (vs control group) identified with MetaCore from Thomson Reuters. In the thermometer sign, red means up-regulation and blue means down-regulation.1 refers to AuNRs@PEG (MCF-7), 2 refers to AuNRs@RGD (MCF-7), 3 refers to AuNRs@PEG (HeLa) and 4 refers to AuNRs@RGD (HeLa). The thermometers are filled to various degrees, corresponding to the amount by which the markers were up-regulated or down-regulated. (41A) Pathway map of "Cytoskeleton remodeling_Regulation of actin cytoskeleton organization by the kinase effectors of Rho GTPases" (41B) Pathway map of "Cytoskeleton remodeling_Keratin filaments." (41C) Pathway map of "Cell adhesion_Endothelial cell contacts by junctional mechanisms." (41D) Pathway map of "Cell adhesion_Histamine H1 receptor signaling in the interruption of cell barrier integrity."
Figure 41B:
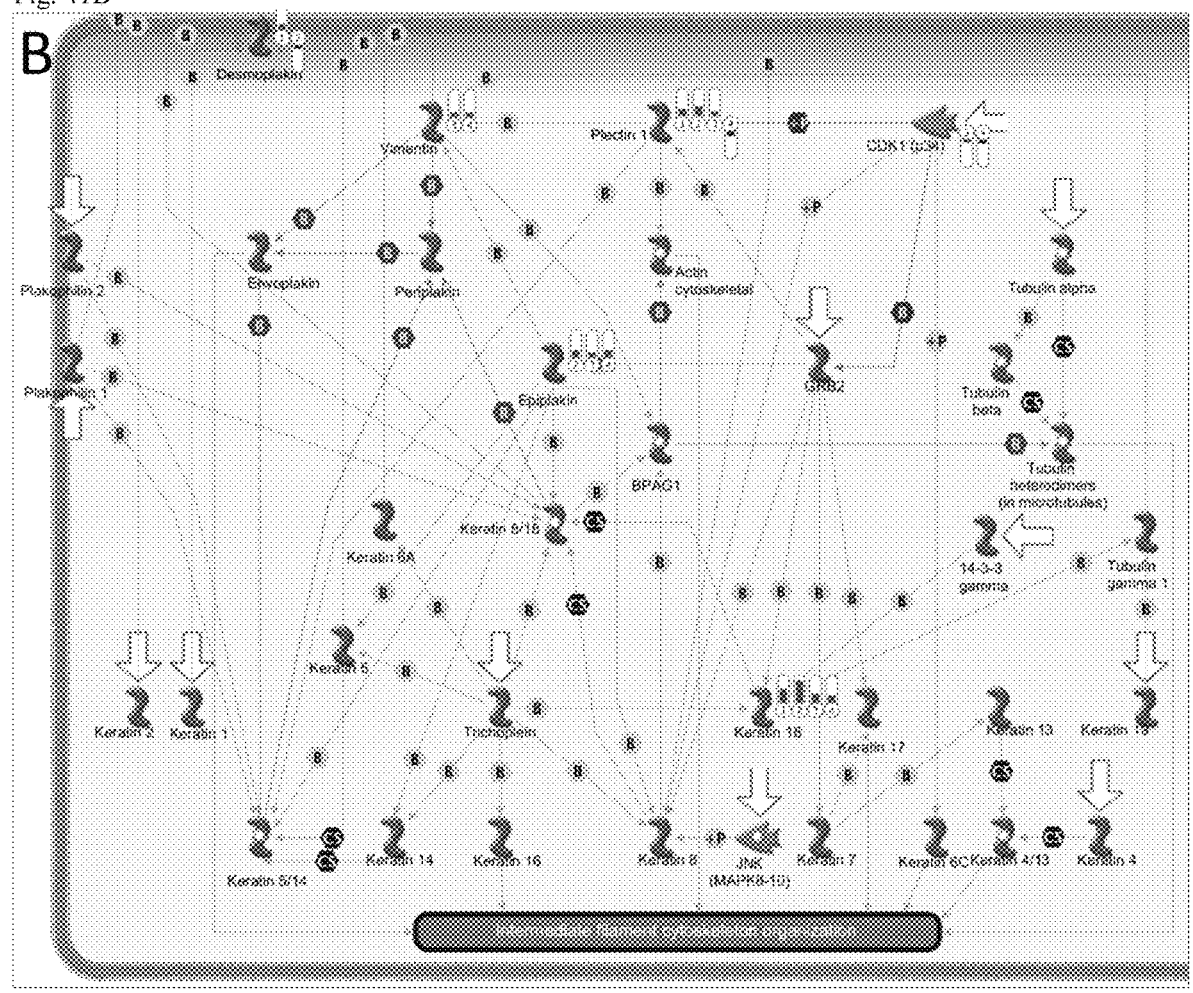
Figure 41C:
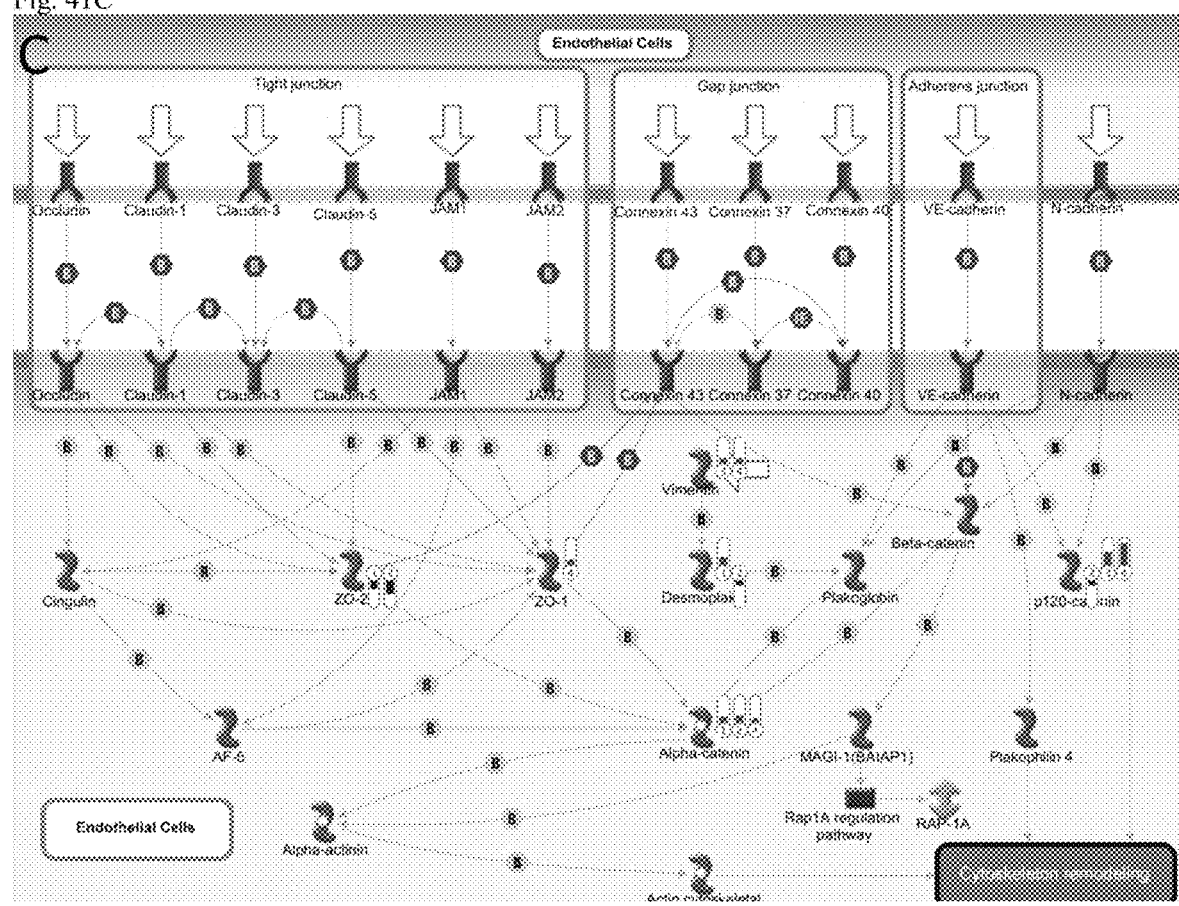
Figure 41D:
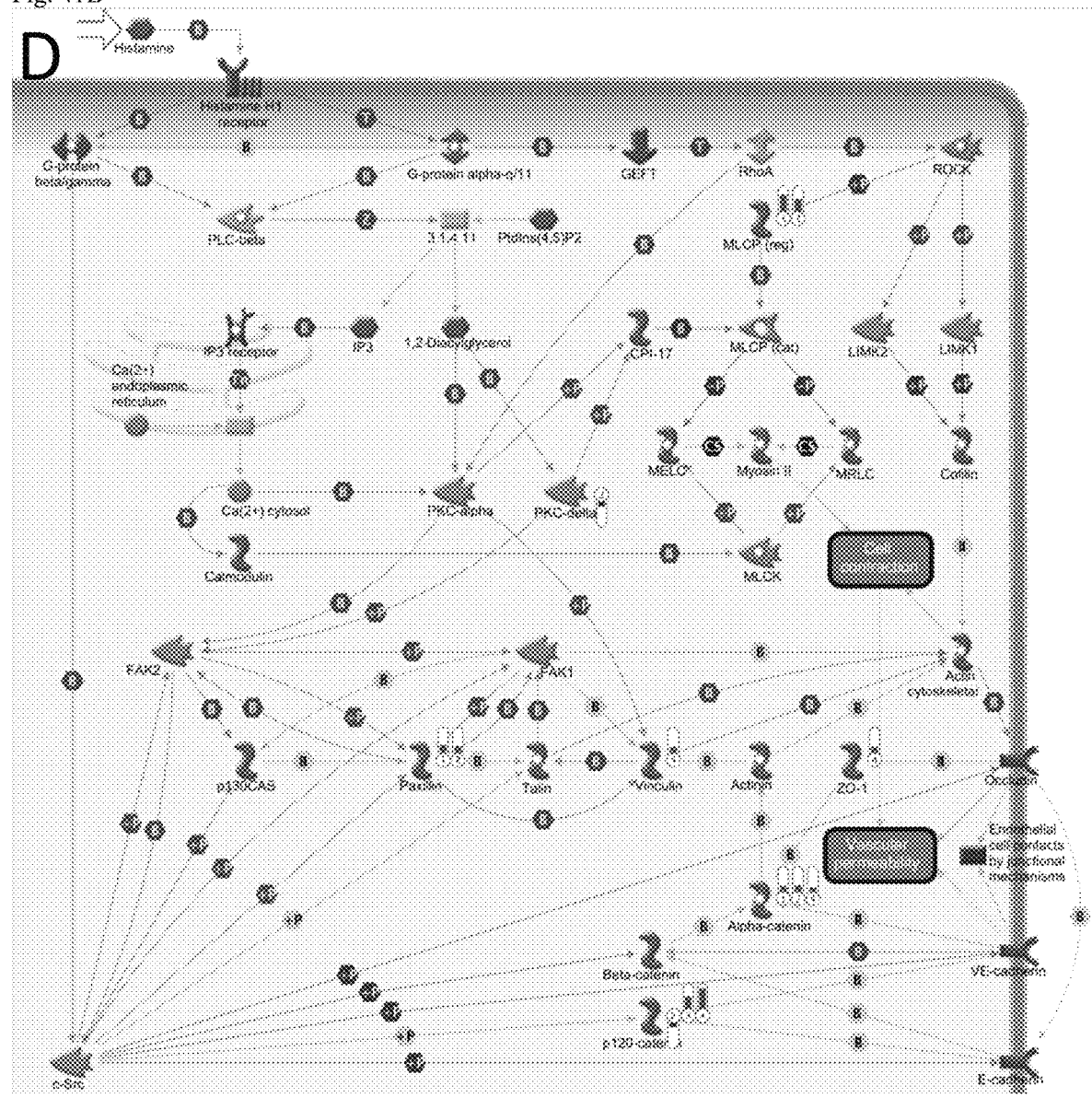

Mass Spectrometry-Based Phosphoproteomics Analysis Reveals Perturbations of the Signal Transduction of the Cytoskeletal and Junction Proteins To elucidate the effects of AuNRs and PPTT treatments on cytoskeleton filaments and cell junctions, the inventors examined the phosphoproteomics of cancer cells using quantitative mass spectrometry (MS) as a tool to explore the changes of the cytoskeleton filaments and cell junctions. A simplified experimental procedure is shown in FIG. 28A (detailed and complete experimental procedure in FIG. 32, and FIG. 37, including conditions of non-specific targeting AuNRs@PEG). Protein phosphorylation was identified and quantified in both HeLa and MCF-7 cells after incubation with AuNRs for 30 min or after AuNRs-PPTT treatment for 30 min. Three-plex dimethyl labeling was used for phosphoproteomic quantification, and titanium (IV) based immobilized metal ion affinity chromatography (Ti-IMAC) was used to enrich the phosphorylated peptides from the protein digest of cell lysate. The enriched phosphorylated peptides were analyzed by an on-line liquid chromatography-mass spectrometry (LC-MS) system. Three replications of each condition were conducted and about 1200 common phosphorylation sites (where the phosphorus group binds to the protein) were quantified. The clustering analysis (FIG. 38) shows that the control and experimental groups were separately clustered with good reproducibility. Differential analysis identified proteins with significant changes in AuNRs-treated groups compared to the control group (FIG. 39). The numbers of dysregulated phosphorylation sites of different treatments and their overlap in the Venn diagrams are shown in FIG. 40. For instance, compared with the control group, the phosphorylation levels of 371 and 244 sites are significantly up- and down-regulated, respectively, for HeLa cells upon AuNRs treatment. Further changes from PPTT were observed, with 73 and 189 phosphorylated sites up- and down-regulated.

Figure 28B:
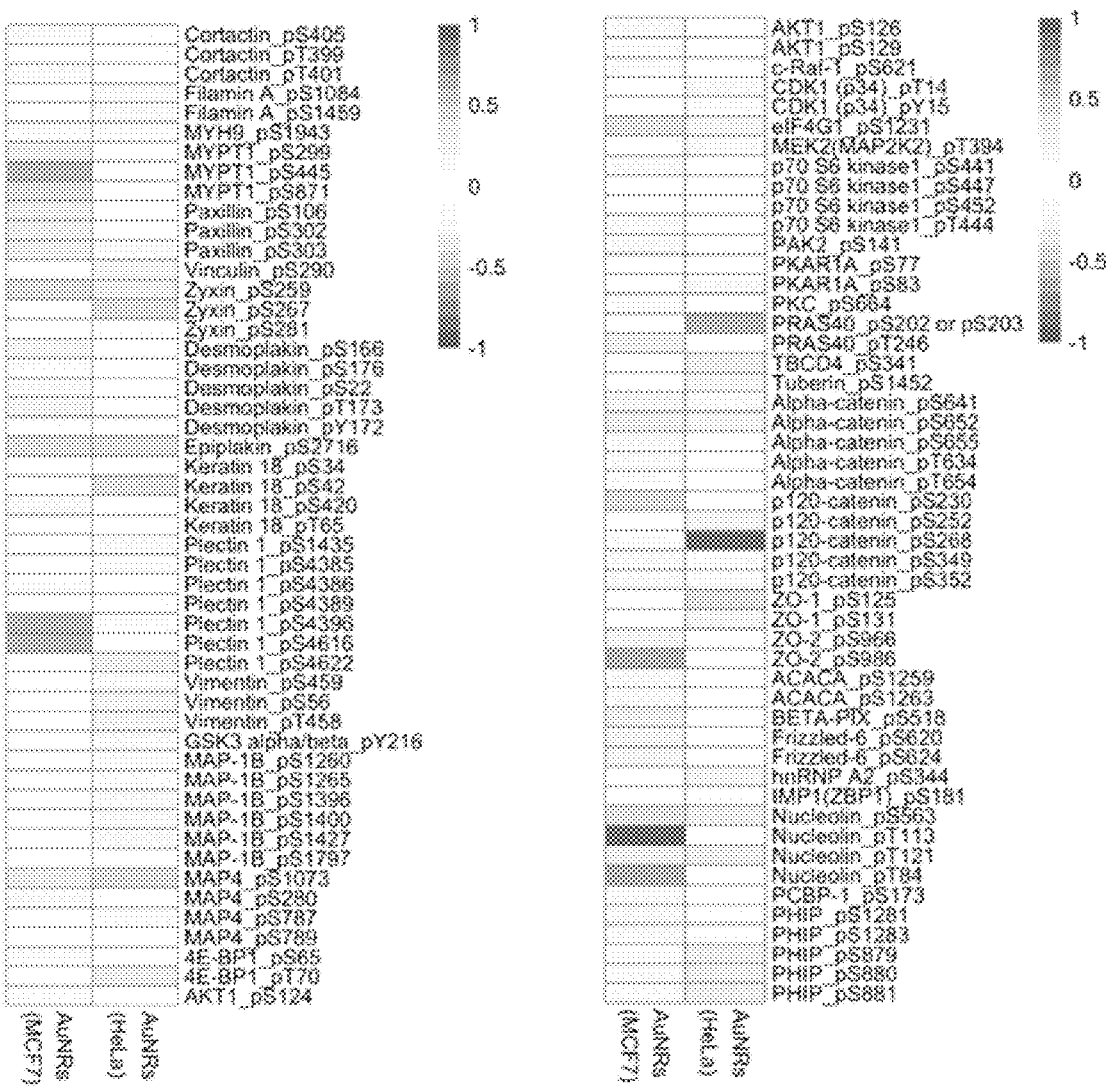
Figure 28C:
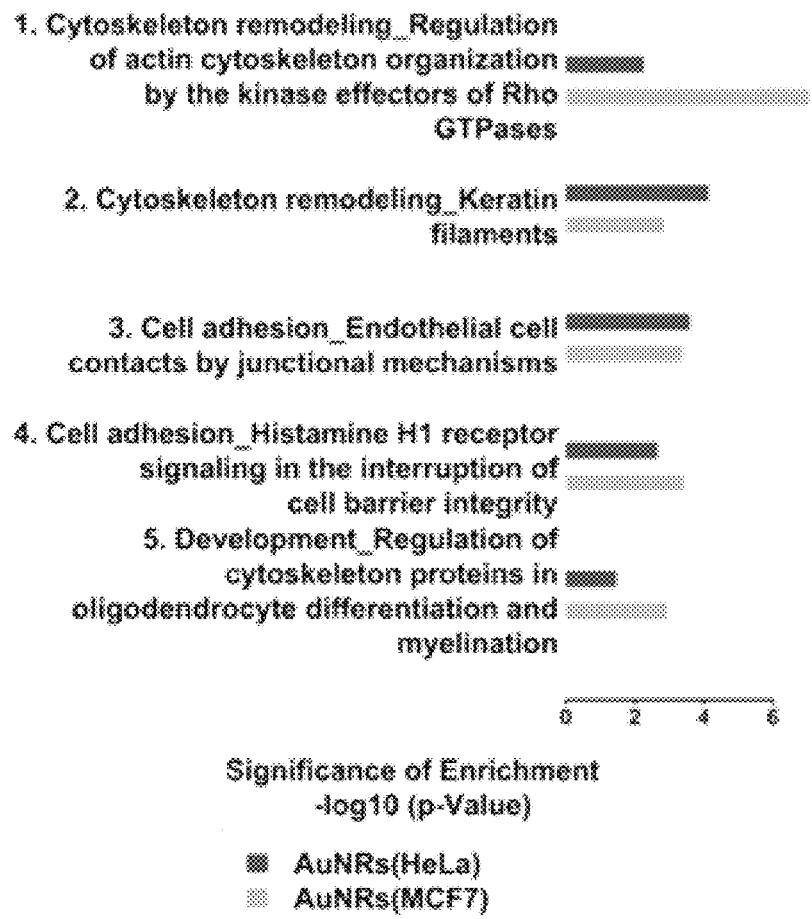
Figure 28D:
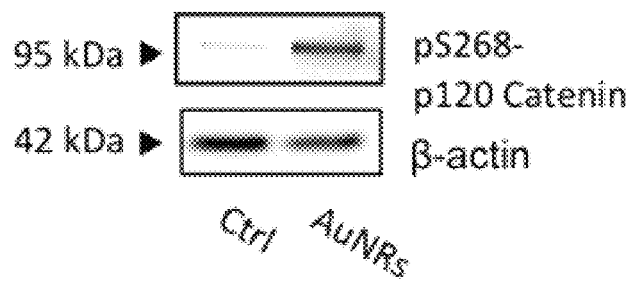
Figure 28E:
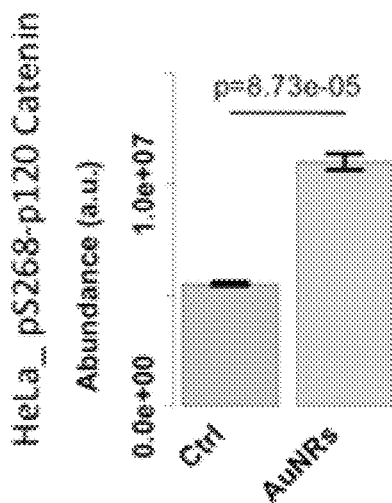
Figure 28G:
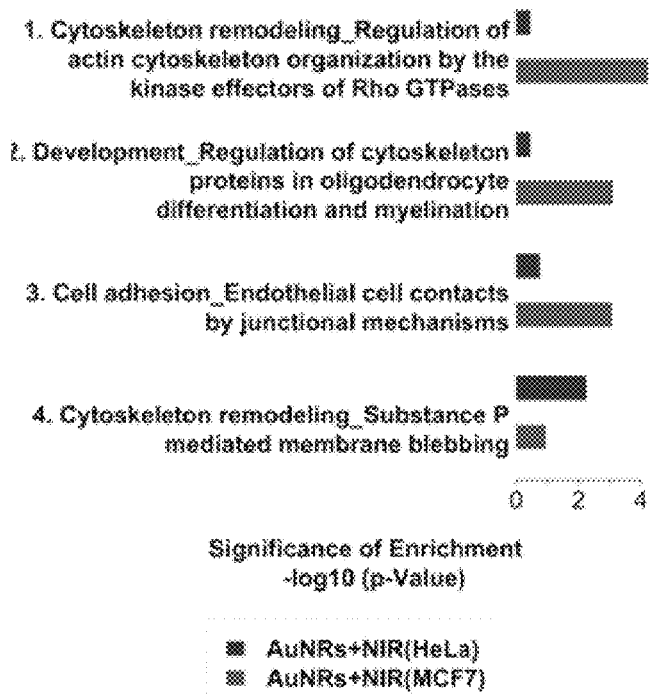
Figure 28H:
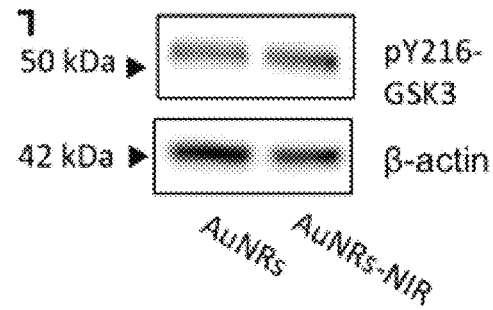
Figure 28F:
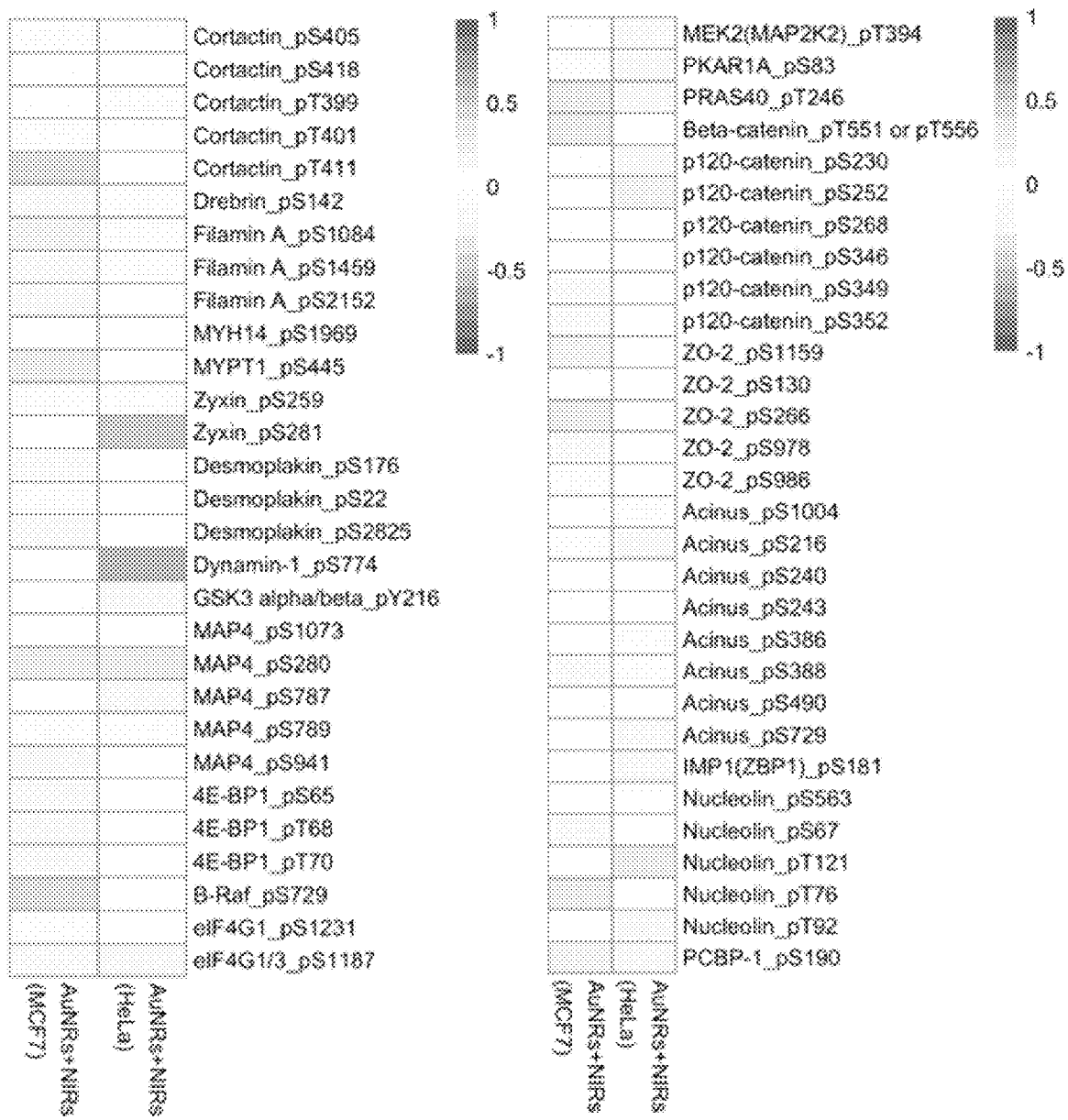
Figure 28I:
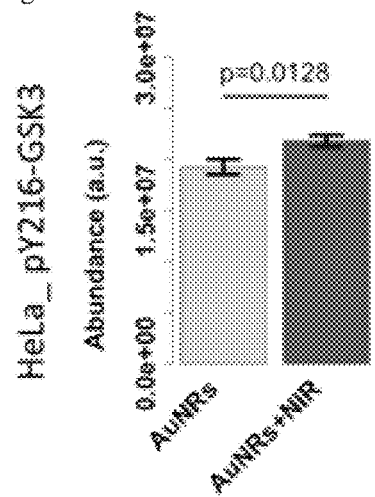

Proteins with their significantly altered phosphorylation sites are listed in heatmaps (FIGS. 28B and 28F) and Table 4. In order to understand the biological meanings of these phosphorylation changes, the inventors performed pathway analysis (FIG. 28C for AuNRs and 28G for AuNRs-PPTT), which revealed the significant perturbations to the signaling pathways related to the cytoskeleton and cell junctions. To further confirm the mass spectrometric results, the varied phosphorylated sites of p120 catenin (pS268), and glycogen synthase kinase (GSK3, pY216), which are highly related to cell adhesive junctions, Rho signaling and cell migration, and microtubule dynamics, respectively, have been validated by Western blot results (FIGS. 28D, 28E, 28H, and 28I).

TABLE 4

Selected significantly dysregulated phosphorylation sites of the cytoskeletal and junction proteins, specifying the phosphorylation sites and biological functions.

| Category | Protein | Protein Function | Phosphorylation sites altered | Phosphorylation sites function |
|---|---|---|---|---|
| Cytoskeleton | Paxillin | Form focal adhesions | pS303, pS302, pS106, pS85 | Increase of pS85 has an important function in cell adhesion |
| | MYH9 | Form stress fibers and create a contraction force in cell migration | pS1943 | pS1943 could alter cell motility |
| | MLCP | | pS299, pS445, pS871 | pS445 is closely related to cell adhesion |

TABLE 4-continued

Selected significantly dysregulated phosphorylation sites of the cytoskeletal and junction proteins, specifying the phosphorylation sites and biological functions.

| Category | Protein | Protein Function | Phosphorylation sites altered | Phosphorylation sites function |
|---|---|---|---|---|
| | MAP4 | Promotes microtubule assembly | pS1073, pS787, pS280, pS789 | pS1073 is related to cancer cell metastasis potential and pS787 could promote tubulin polymerization thereby changing the microtubule organization. |
| Cells junctions | α-catenin | Form cell-cell adhesion complexes, anchoring actin cytoskeleton and interacting with cadherins. | pT654, pS641, pT634, pS652, pS655 | S641 affects cell motility |
| | ZO-2 | Connect cytoskeletons of adjacent cells and act as barriers for the passage of molecules and ions | pS966, pS986, pS978, pS266, pS986, pS1159, pS130 | — |
| | Vimentin | A hallmark protein of epithelial to mesenchymal transition (EMT), which is related to the increase of migration and invasive properties | pS459, pS56, pT458 | pS56 was reported with the function of cytoskeleton reorganization |
| | Keratin 18 | Keratin 18 and its filament partner keratin 8 are regarded as the most commonly found members of the intermediate filament family. | pS34, pT65, pS420, pS42 | pS34 affects cell motility and cytoskeleton |

Firstly, the inventors observed that the treatment can change the phosphorylation of actin cytoskeletal proteins, including i) proteins forming the focal adhesions (FAs), such as paxillin, zyxin, vinculin; ii) the myosin related proteins, such as MYH9 and MLCP; iii) the actin-binding proteins, such as filamin, cortactin and drebrin. Secondly, the phosphorylation of several microtubule (MT)-related proteins were changed, including microtubule associated proteins MAP4, microtubule associated protein 1B (MAP1B) and glycogen synthase kinase-3 alpha (GSK3A). Thirdly, phosphorylation states intermediate filaments (also desmosome related) have been changed, such as Keratin 18 and vimentin. Besides, phosphorylation changes of many protein kinases that could regulate the cytoskeleton filaments and cell motility were observed, such as RAF proto-oncogene serine/threonine-protein kinase (Raf1), mitogen-activated protein kinase kinase 2 (MAP2K2), cyclin-dependent kinase (CDK1), AKT1, 4E-BP1, eIF4G1, PKA, PKC-delta, etc.

TABLE 5

List of selected proteins with their altered phosphorylation sites.

| Category | | Protein | Protein Function | Phosphorylation sites altered | Phosphorylation sites function |
|---|---|---|---|---|---|
| Actin | Focal adhesions | Paxillin | Form focal adhesions | pS303, pS302, pS106, pS85 | Increase of pS85 of paxillin could have an important function in cell adhesion |
| | | Zyxin | | pS258, pS288, and pS267 | — |
| | | Vinculin | | pS290 | — |
| | Myosin related proteins | MYH9 | Form stress fibers and create a contraction force in cell migration | pS1943 | Phosphorylation status of MYH9 at Ser 1943 could alter cell motility, relating to cell junction |
| | | MLCP | | pS299, pS445, pS871 | The Ser 445 of MLCP is closely related to cell adhesion |
| | Actin-binding protein | Filamin | Actin filament crosslinking protein | pS1084, pS1459, pS1432, pS2112 | — |
| | | Cortactin | Actin-nucleation-promoting factor | pS39, pS52, pT33, pT35 pT45 | — |
| | | Drebrin | Induce stabilization of actin filaments | pS142 | — |

TABLE 5-continued

List of selected proteins with their altered phosphorylation sites.

| Category | Protein | Protein Function | Phosphorylation sites altered | Phosphorylation sites function |
|---|---|---|---|---|
| Microtubule | MAP4 | Promoting microtubule assembly, regulating cell invasion/migration | pS1073, pS787, pS280, pS789 | MAP4 pS1073 is related to cancer cell metastasis potential and pS787 could promote tubulin polymerization thereby changing the MT organization. |
| | MAP1B | Microtubule assembly | pS248, pS250, pS345, pS352, pS367, pS552 | — |
| | GSK3 | Regulate microtubule dynamics | pY279 | — |
| Desmosome related intermediate filaments | Keratin | Keratin 18 and its filament partner keratin 8 are regarded as the most commonly found members of the intermediate filament family. | pS34, pT65, pS420, pS42 | — |
| | Vimentin | A hallmark protein of epithelial to mesenchymal transition (EMT), which is related to the increase of migration and invasive properties | pS459, pS56, pT458 | pS56 was reported with the function of cytoskeleton reorganization |
| Kinases | Raf1 | A MAP kinase kinase kinase (MAP3K), egulates Rho signaling and cell migration | pS621 | — |
| | MAP2K2 | MAP kinase kinase family | pT394 | — |
| | CDK1 | Regulation of cell cycle progression and greatly related to cancer development | pT14, pY15 | — |
| Junction proteins | Tight junction proteins | ZO-1 ZO-2 | Connect cytoskeletons of adjacent cells and act as barriers for the passage of molecules and ions | pS125, pS131 pS966, pS986, pS978, pS266, pS986, pS1159, pS130 | — |
| | Catenins | α-Catenin β-Catenin p120-Catenin | Form cell-cell adhesion complexes, anchoring actin cytoskeleton and interacting with cadherins. | pT654, pS641, pT634, pS652, pS655 pT551 or pT556 pS230, pS268, pS349, pS352, pS252 | S641 affects cell motility — — |
| | Desmosomes | Desmoplakin | Desmosome protein, confer strong cell-cell adhesion, | pS22, pY172, pT173, pS166, pS176, pS2821, pS2825 | — |
| | | Epiplakin Plectin | Epiplakin, and plectin connect and reorganize the intermediate filaments, such as keratins to the desmosome, which are also closely related to cell motility | pS2716 pS4386, pS4385, pS4616, pS4396, pS4389 | — |

Changes of tight junction proteins ZO-1 and ZO-2 were also observed upon AuNRs stimulation. After PPTT, more changes were observed to ZO-2, indicating an enhanced perturbation in the tight junctions. In addition, catenins, including alpha, beta, and p120 catenins, have altered phosphorylated sites upon treatment. Furthermore, phosphorylation change of desmosomes related proteins, including desmoplakin, epiplakin, and plectin, were observed.

Figure 29:
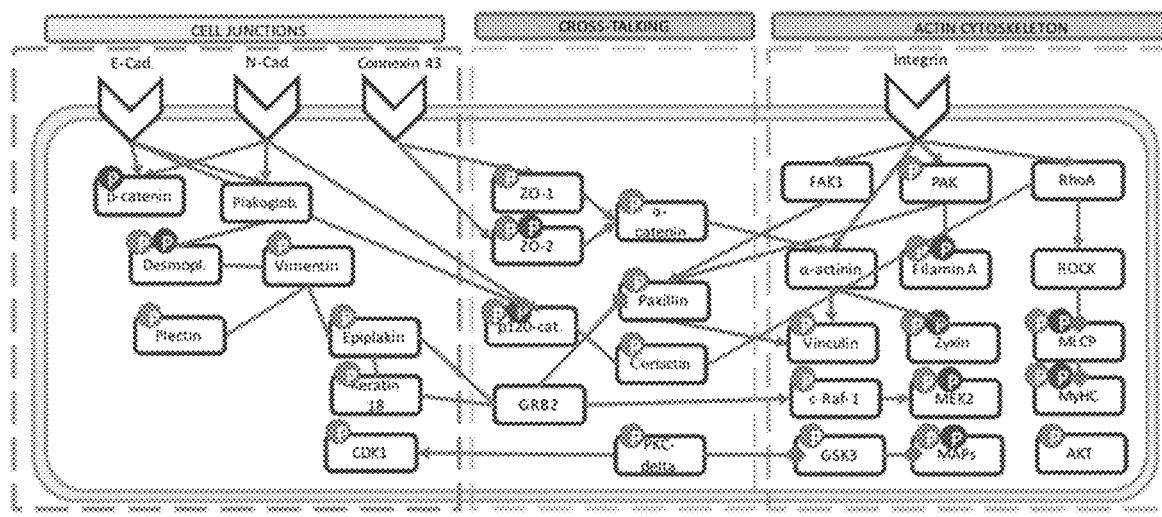
FIG. 29. Schematic diagram of the signaling pathways that are engaged with the cytoskeleton and cell junctions upon the AuNRs and PPTT treatment. The blue and red "P"s indicate the altered phosphorylation level upon AuNRs treatment and PPTT treatment (AuNRs+NIR), respectively.
Figure 42A:
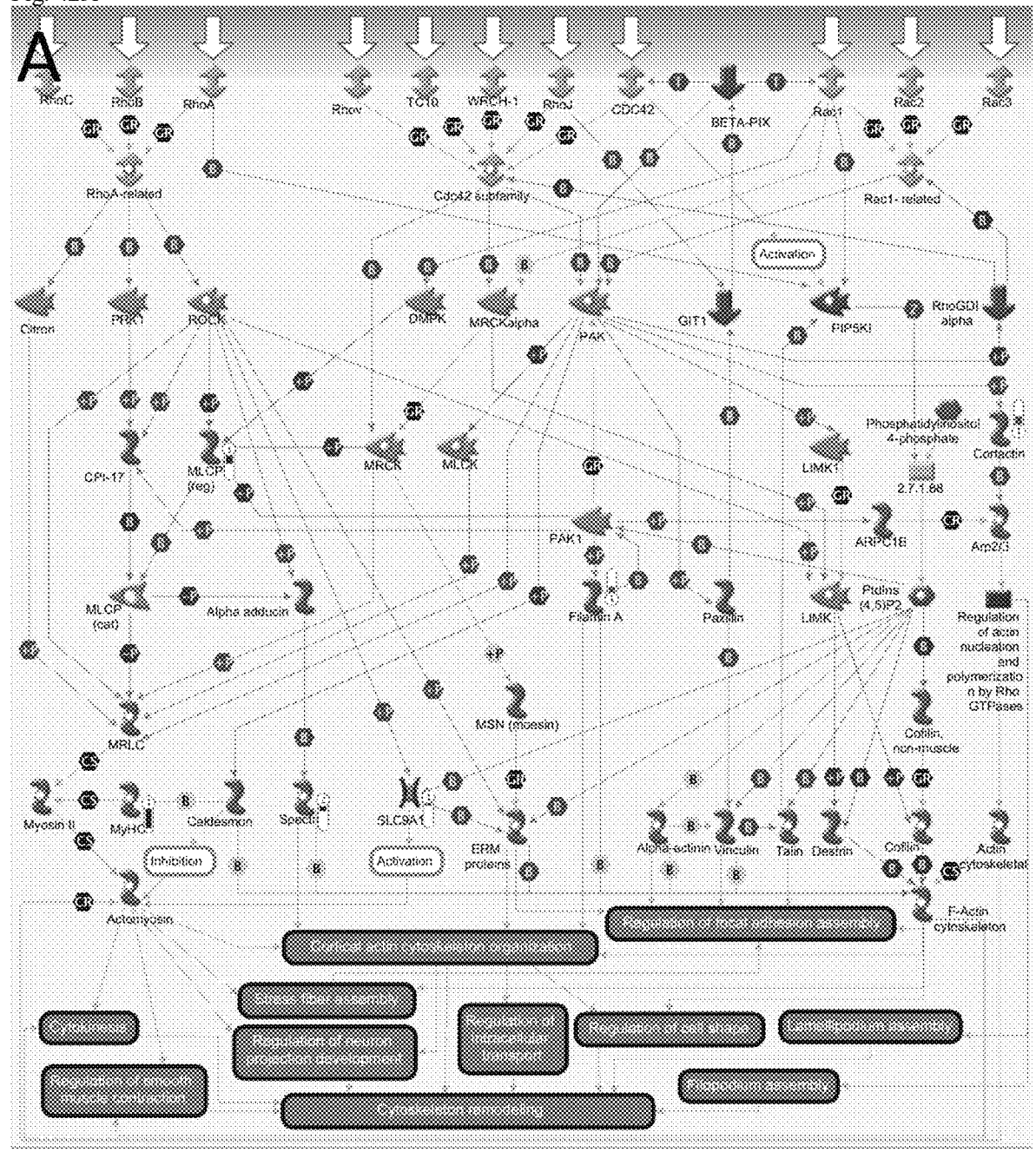
Figure 42B:
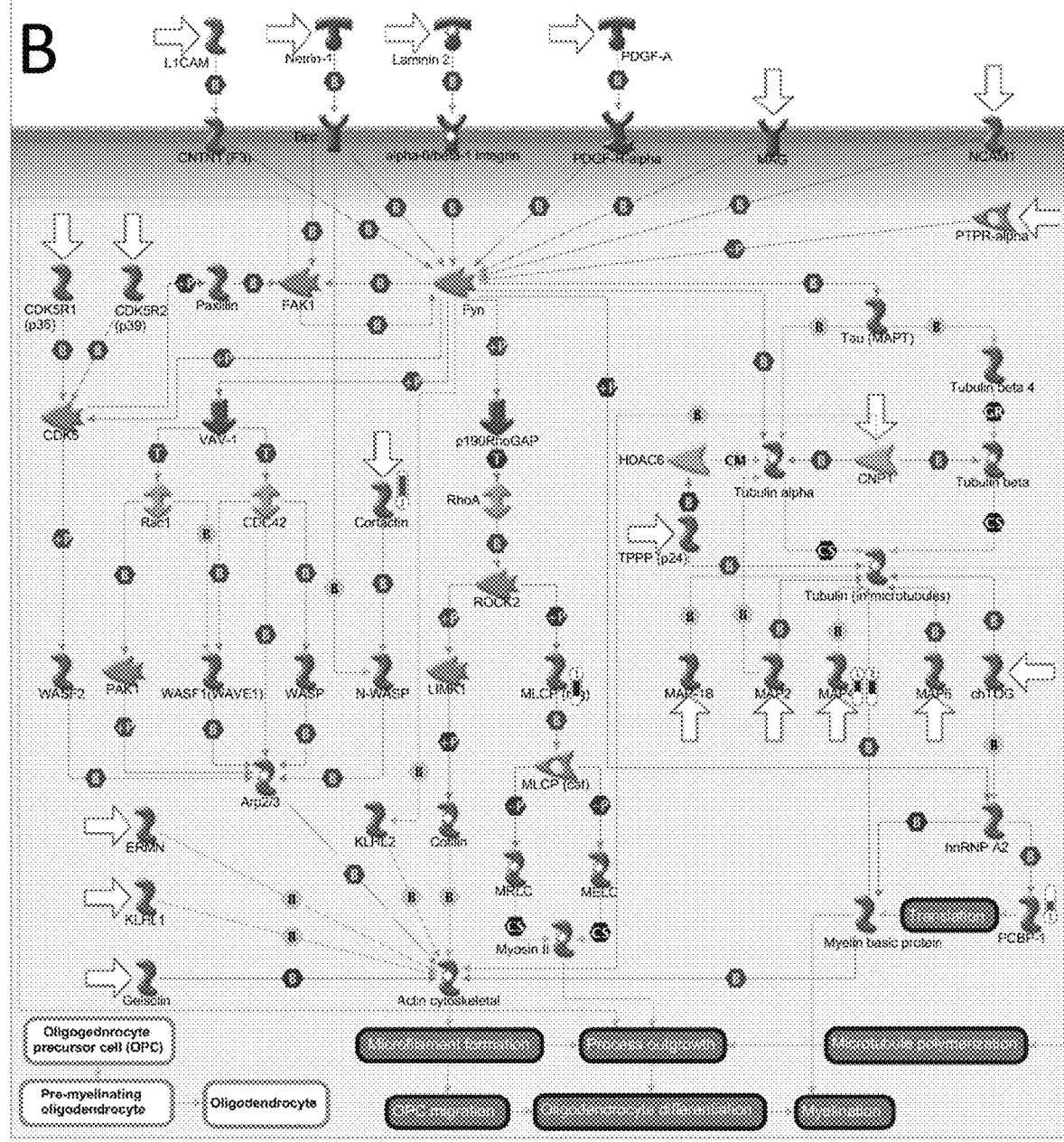
Figure 42C:
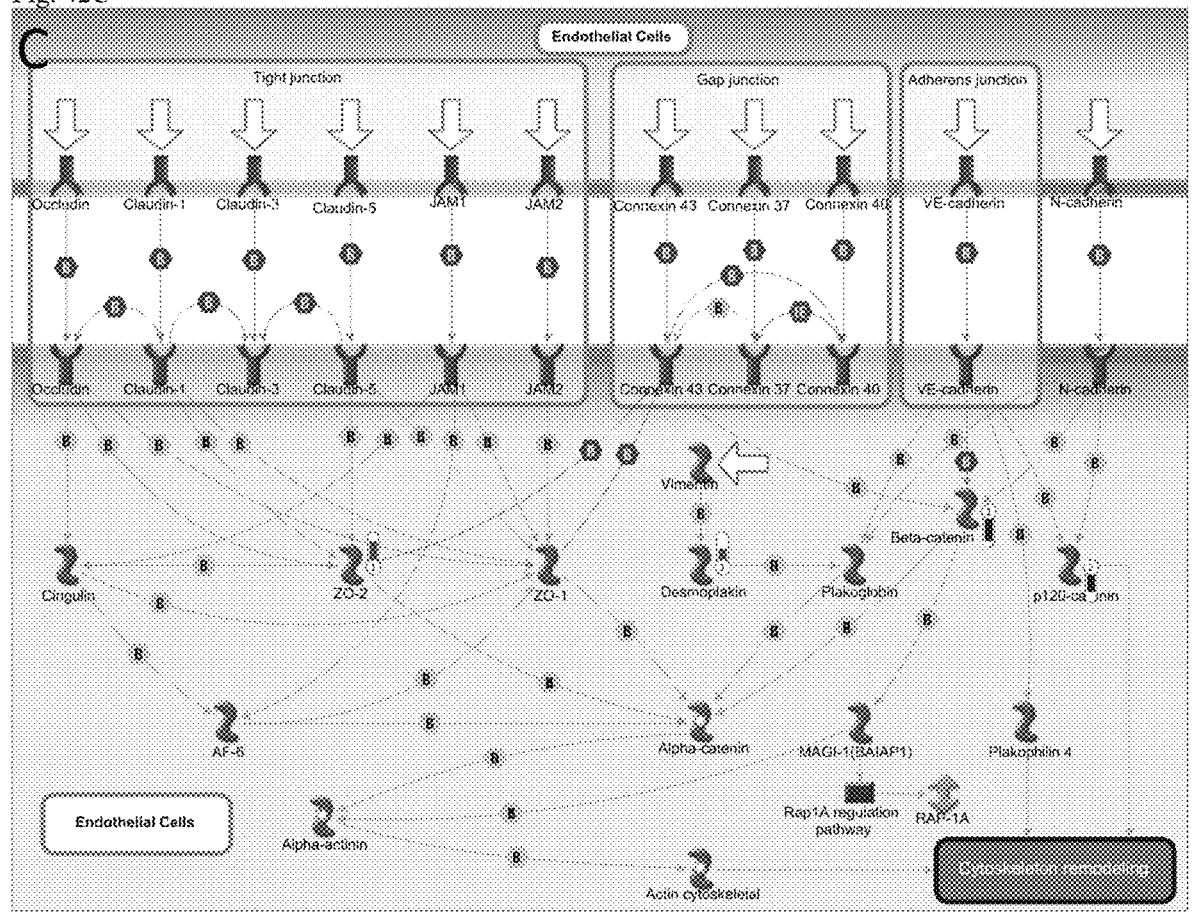

Integrins are adhesive molecules located in the cell membrane and responsible of transporting signals and cell-cell communications. The ability of integrin-targeted AuNRs to alter the junction proteins is linked to the coordination and interdependence manner of integrin and cell junction to form adhesive networks, by connecting through the actin cytoskeleton and sharing common signaling molecules. For instance, integrin-induced signaling molecules FAK and paxillin regulate the N-cadherin junctions in Hela cells; α-catenin links cadherin to the actin cytoskeleton; and p120 catenin cooperates with cortactin to regulate lamellipodial dynamics and cell adhesion. Here, the inventors observed possible signal cross-talk between the cytoskeleton and cell junctions, such as the altered phosphorylation of paxillin, α-, β-, and p120-catenin, as well as cortactin. Based on the phosphoproteomics results, a schematic diagram is constructed to show the signal transduction upon AuNRs and PPTT stimulation (FIG. 29, and more details in FIGS. 41 and 42). By targeting integrins, these treatments induced the protein phosphorylation change of the downstream cytoskeletal and junction proteins.

Super-Resolution Imaging for Confirming Disturbed Cytoskeletal and Cell Junction Proteins.

Figure 30A:
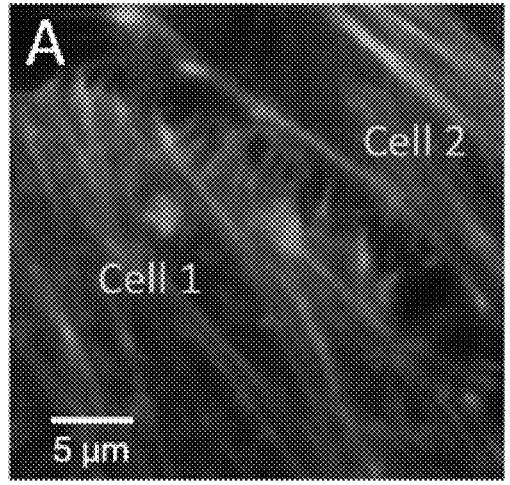
FIG. 30A-30F. STORM images of actin filaments in the cell-cell junction upon different treatments: (30A, 30D) Control; (30B, 30E) AuNRs; (30C, 30F) AuNRs+NIR. After NIR exposure, the actin filaments at cell junctions exhibited clearly altered morphology (scale bar=5 μm).
Figure 30B:
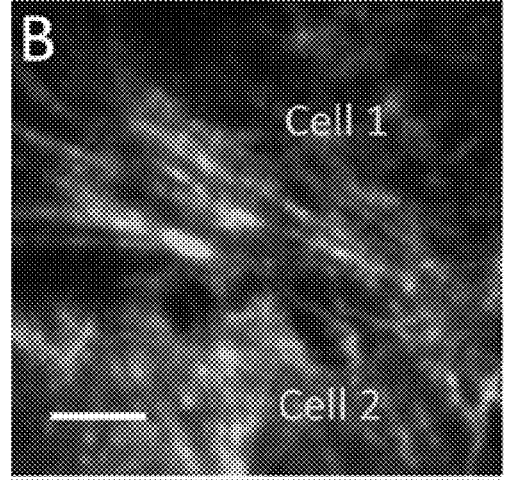
Figure 30C:
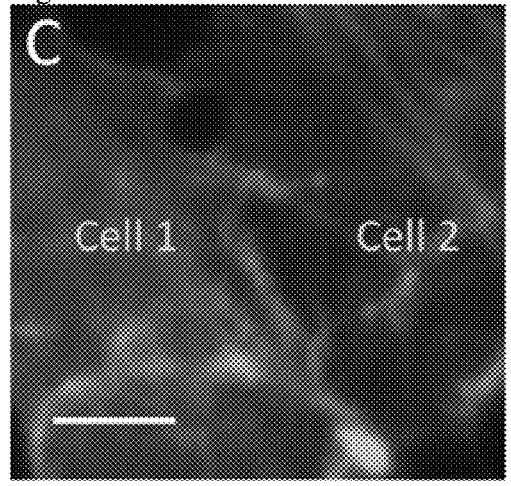
Figure 30D:
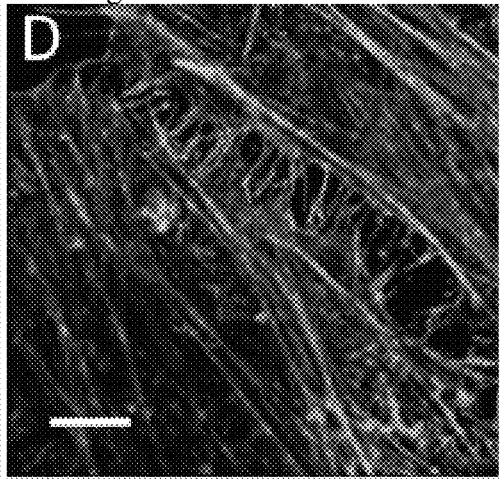
Figure 30E:
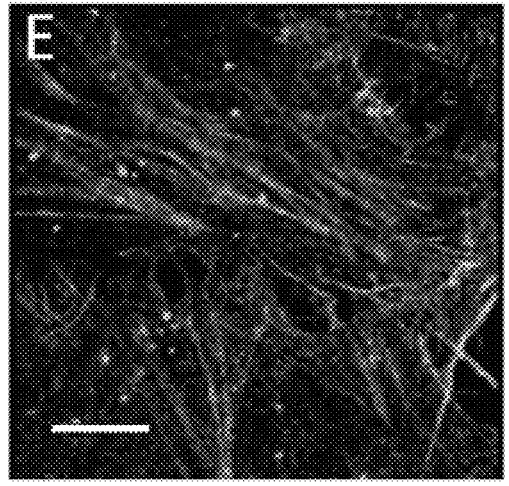
Figure 30F:
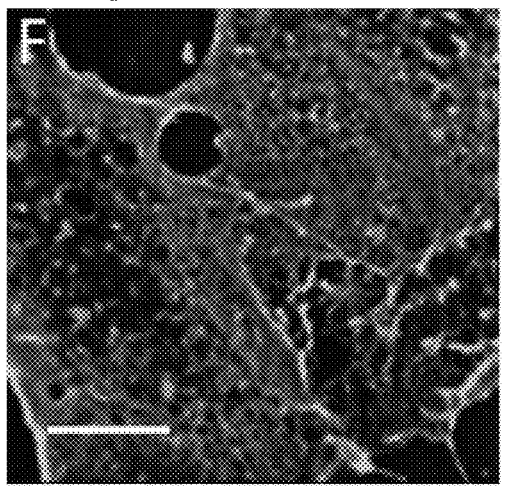
Figure 31A:
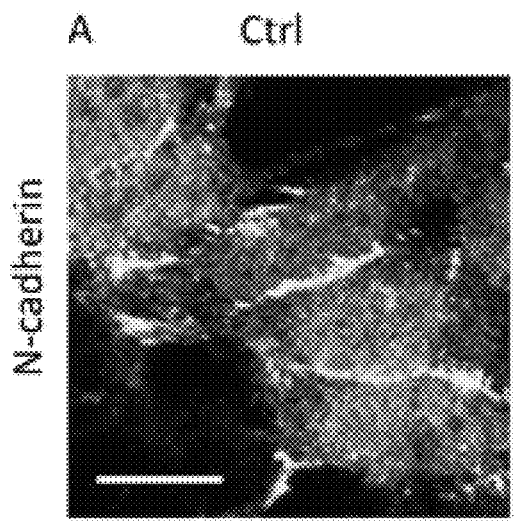
Figure 31B:
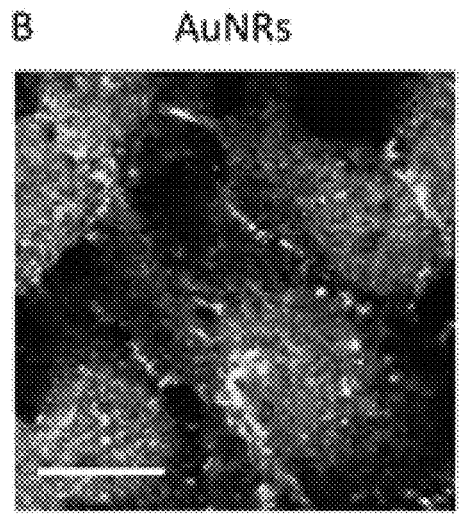
Figure 31C:
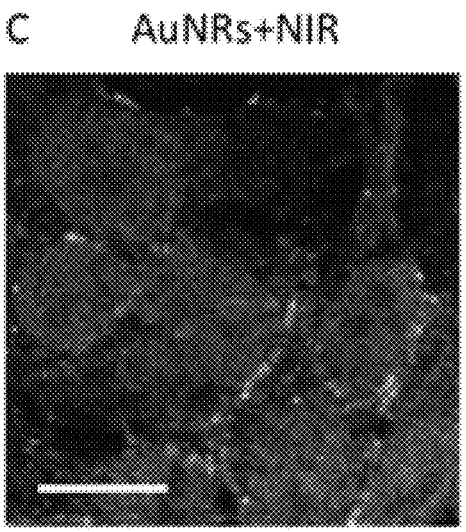
Figure 31D:
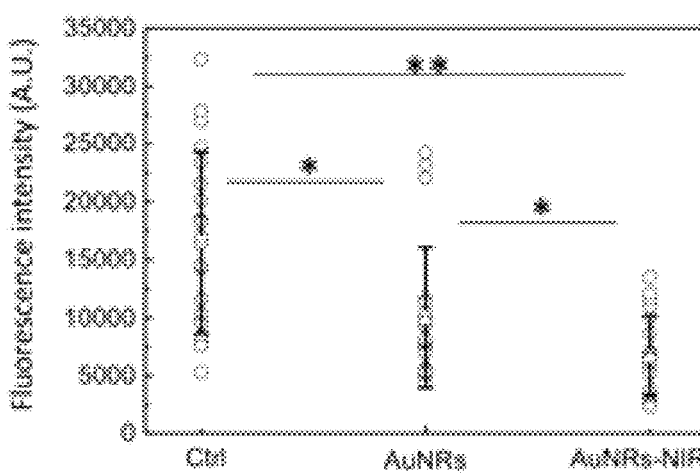
Figure 31E:
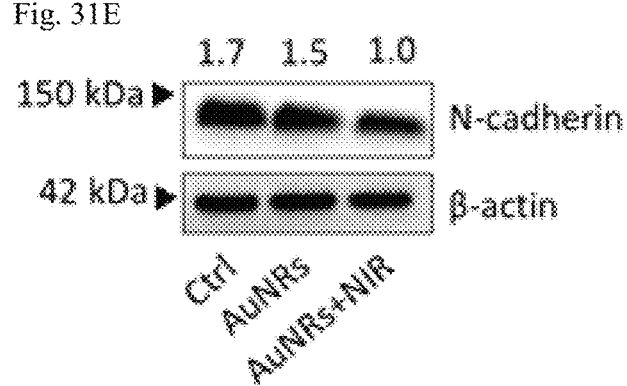
Figure 44A:
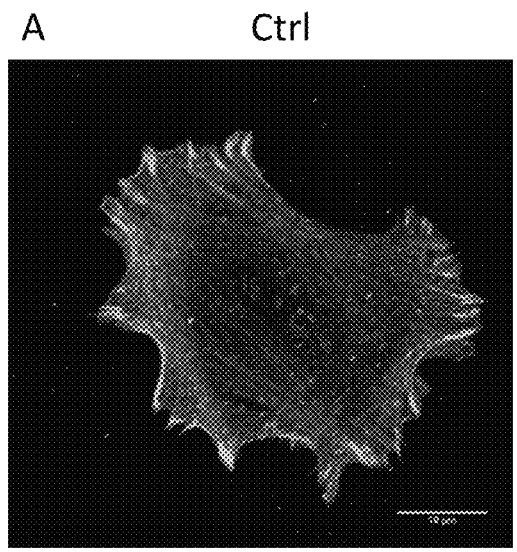
FIG. 44A-44C. STORM images of actin filaments in individual HeLa cells. (44A) Control; (44B) AuNRs; (44C) AUNRs plus NIR.
Figure 44B:
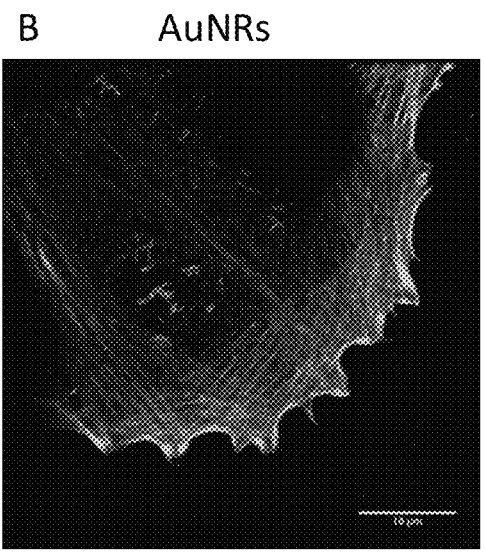
Figure 44C:
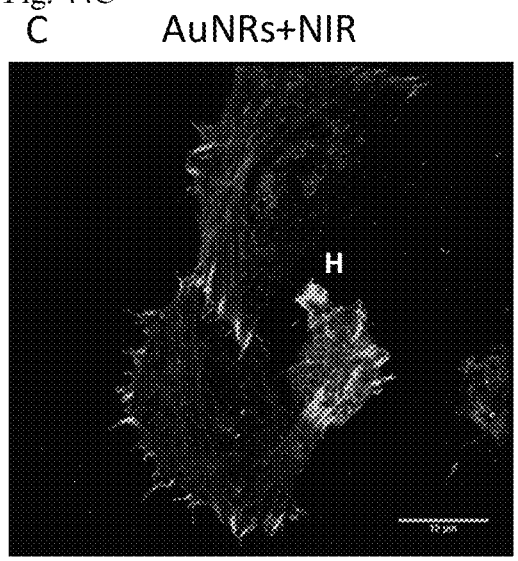

Collective cell migration requires the cells are effectively coupled by cell junctions, coordinating their actin dynamics and intracellular signaling thereby forming a functioning unit. The actin cytoskeletons of neighboring cells are coupled by the cell junctions. The drag force between the cells is provided by actomyosin contractility, which is important in maintaining effective cell junction and collective migration. Although the phosphorylation signal transduction takes place within a few minutes, the protein expression level may take hours to change. Therefore, to clearly observe the protein expression level changes, the inventors monitored the actin filament structures after 24 hours of AuNRs incubation with or without PPTT (FIG. 30A-30F). Under a normal fluorescence microscope, it is difficult to differentiate changes of actin structure before and after treatments due to the insufficient resolution, as shown in FIG. 30A-30C. Stochastic optical reconstruction microscopy (STORM) provides superior spatial resolution than conventional fluorescence microscopy to reveal the detailed actin cytoskeletal structures (FIG. 43). By using STORM, the inventors observed the morphological changes of the circumferential actin filaments at the cell-cell junctions. Before AuNRs treatment, the well-aligned stress fibers (contractile actin bundles) are clearly visualized, with polymerized and stable structure (FIG. 30D). However, after AuNRs treatment, the actin bundles became thinner, showing a clear sign of disturbance (FIG. 30E). Furthermore, after NIR exposure, the circumferential actin filaments at cell junctions exhibited obvious changes (FIG. 30F): the stress fibers were greatly decreased, while coil, depolymerized and reorganized structures appeared, which possibly indicated the heating effect on harming the actin filaments polymerization at the junction sites. In addition, the actin structure at the cell leading edges (filopodia and lamellipodia) was also imaged (FIG. 44), and the observed decrease in stress fibers in the cell leading edges hinted a decrease in cell motility.

Figure 45:
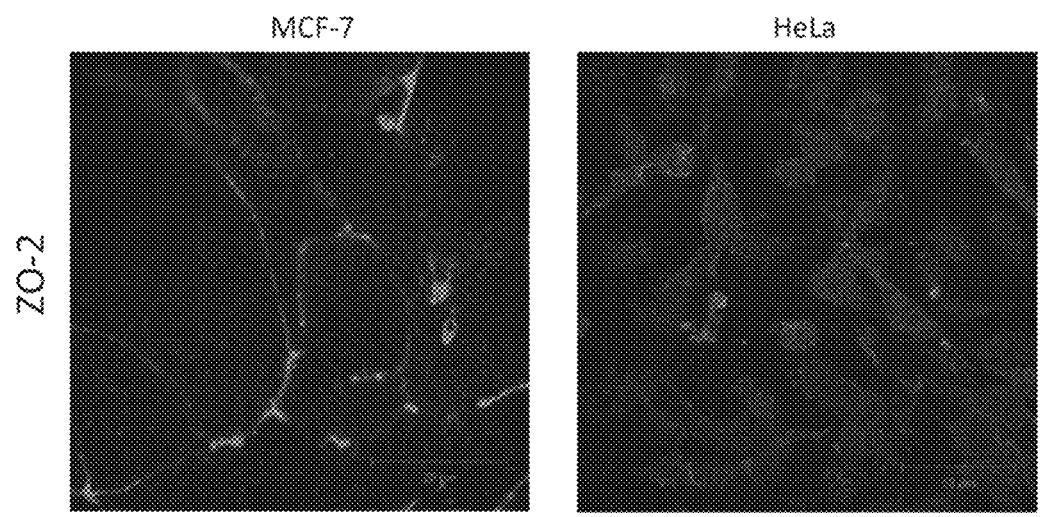
FIG. 45. Low expression of tight junctions in HeLa cells compared with MCF-7 cells.
Figure 46:
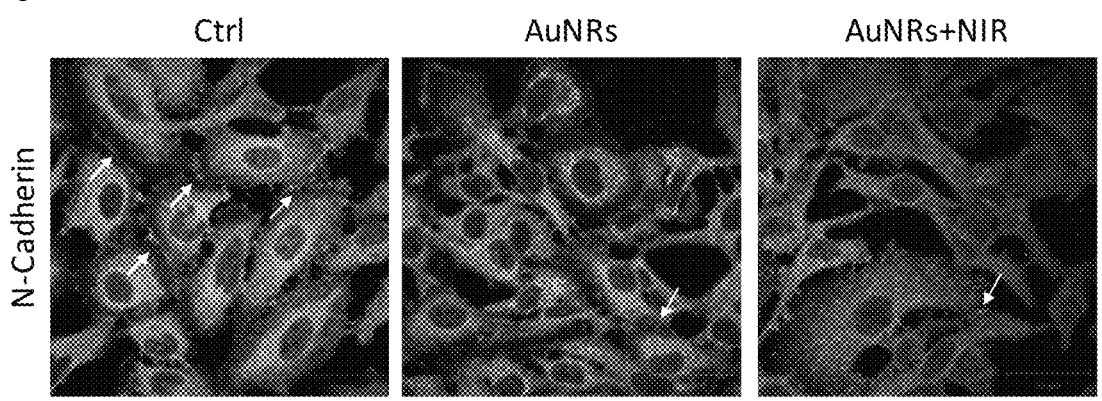
FIG. 46. Immunofluorescence images of N-cadherin in HeLa cells before and after AuNRs or AuNRs/PPTT treatments. The arrows indicate the N-cadherin junctions.

The inventors further examined the AuNRs and PPTT effects on cell junctions in faster-migrating HeLa cells and slower-migrating MCF-7 cells. Different cell lines could have highly diverse populations of cell junction proteins. The expression level of neural (N)-cadherin in HeLa was found to be much higher than that in the MCF-7 cells (not detectable in MCF-7 cells in this study). On the other hand, MCF-7 cells show significantly higher expression levels of tight junction proteins than HeLa cells (FIG. 45). Therefore, the inventors used HeLa cells as a model for studying the N-cadherin junction and MCF-7 cells for the tight junction (FIG. 46).

The N-cadherin junction is well known to be highly expressed in many aggressive tumors and promote metastasis. It is reported that N-cadherin holds the cohesive cell clusters together, which tend to migrate persistently, a key role in collective migration. The expression level of N-cadherin junction is largely known as a marker for cancer motility and invasiveness. The inventors observed a decreased expression level of N-cadherin (FIG. 31A-31E) upon the AuNRs treatments by fluorescence intensity and Western blot analysis.

Tight junctions create strong intercellular links at the invasion zone of tumors. During tumor development, tight junctions are remodeled, enabling cancer cells to adopt a migratory behavior. It has been reported that tight junction protein Zonula occludens ZO-1 can directly bind to integrin and regulate the mechanical properties of integrin-fibronectin links. In addition, the tight junction proteins ZO-1, ZO-2 and ZO-3 can bind to the cytoskeleton. Here, the inventors studied the tight junction changes by labeling ZO-2. The inventors observed the morphology of ZO-2 change from a normal and continuous line-like structure in the control group to a discontinuous dot-like structure after treatment, indicating possible impaired tight junctions (FIG. 31F).

Discussion

In this example, the inventors investigated the mechanism of integrin-targeted AuNRs and PPTT with NIR light in inhibiting collective cancer cell migration. The phosphoproteomics results revealed the phosphorylation changes to many cytoskeletal and cell junction proteins, setting the foundation for current and future studies of the underlying mechanism at the molecular level.

Using super-resolution fluorescence microscopy and Western blotting, the inventors verified the changes to selected key proteins related to the actin cytoskeleton and cell junctions. The morphological changes of actin filaments and extensive phosphorylation changes to actin-associated proteins, such as filamin, paxillin, vinculin, zyxin, PAK, MLCP, MyHC, et al., upon integrin-targeted AuNRs and PPTT treatment also indicated weakened cell adhesion and stress fiber generation. Furthermore, in HeLa cells, the inventors found a significantly lower expression level of N-cadherin, as well as the phosphorylation changes to α-, β- and p120-catenin that connect N-cadherin to the actin cytoskeleton, while in MCF-7 cells, a discontinuation and altered morphology of the tight junction protein ZO-2.

All of the current experimental evidence has led to a proposed mechanism that the interactions between the integrin-targeted AuNRs and cells could trigger the phosphorylation changes of essential components associated with cytoskeleton filaments and cell-cell junctions, and cause their morphological or expression level changes, therefore inhibiting cancer collective migration. Further studies of the perturbations to individual related proteins will be carried out to provide a more complete understanding of the inhibition effect.

Methods

Experimental Design.

The experiment is based the inventors' hypothesis that integrin-targeting AuNRs and PPTT treatment could affect the cytoskeleton and cell junctions, thus result in the inhibition of cancer cell collective migration. To test this hypothesis, phosphoproteomics was performed to understand the signal transduction among the integrin, cytoskeleton and cell junctions. Super-resolution imaging tools, as well as Western blot, were used to observe the changes of the actin cytoskeleton and cell junctions.

Materials.

Dulbecco's modified Eagle's medium (DMEM), phosphate buffered saline (PBS), fetal bovine serum (FBS), antibiotic/antimycotic solution, and 0.25% trypsin/2.2 mM EDTA solution were purchased from VWR. Methoxypolyethylene glycol-thiol (mPEG-SH, MW 5000) was purchased from Laysan Bio, Inc. Cell penetrating peptide RGD (RGDRGDRGDRGDPGC) was purchased from GenScript, Inc. Mammalian cell protease inhibitors and phosphatase inhibitors were purchased from Roche Applied Sciences, and sequencing grade trypsin was purchased from Promega. Tetrachloroauric acid trihydrate ($HAuCl_4 \cdot 3H_2O$), ascorbic acid, cetyltrimethylammonium bromide (CTAB), $AgNO_3$, $NaBH_4$, 4-(2-hydroxyethyl)-1-piperazineethanesulfonic acid (HEPES), NaCl, sodium deoxycholate, sodium dodecyl sulfate (SDS), paraformaldehyde, glutaraldehyde, formaldehyde-D2 (DCDO), sodium cyanoborohydride ($NaBH_3CN$), formic acid (FA), trypsin (TPCK treated), iodoacetamide (IAA), dithiothreitol (DTT), trifluoroacetic acid (TFA) and triethylammonium bicarbonate buffer (TEAB), Triton X-100, 2-(N-Morpholino)ethanesulfonic acid hemisodium salt (MES), NaCl, EGTA, glucose, $MgCl_2$, $NaBH_4$, BSA, Anti-BAX and anti-beta-actin primary antibody, (H+L) HRP conjugate, Alexa 647-phalloidin, 100 mM Tris pH 8.0, glucose oxidase, catalase, β-mercaptoethanol were purchased from Sigma (St. Louis, Mo.). Urea were from Shanghai Sangon Biotech (Shanghai, China). BCA protein assay kit was from Beyotime Institute of Biotechnology (Shanghai, China). HPLC-grade acetonitrile (ACN) was from Merck (Darmstadt, Germany). Fused silica capillaries with dimensions of 75 and 200 μm i.d. were obtained from Yongnian Optical Fiber Factory (Hebei, China). C18 AQ beads (3 and 5 μm, 120 Å) were purchased from Daiso (Osaka, Japan). Anti-ZO-2 (Cell Signaling Technology) and Anti-N-Cadherin (ABclonal) Alexa Fluor-568 conjugated anti-rabbit IgG (H+L) (Abcam), goat anti-rabbit IgG Antibody. All the water used in experiments was purified with a Milli-Q system from Millipore (Milford, Mass.).

Instrumentation.

Gold nanorods were imaged using a JEOL 100CX-2 transmission electron microscope (TEM) microscope, with their average size being measured by ImageJ software (NIH). UV-vis spectra were obtained by an Ocean Optics HR4000CG UV-NIR spectrometer. A Nikon Eclipse 80i upright microscope and a back-illuminated scientific complementary metal oxide semiconductor (sCOMS) camera (Dhyana 400BSI, Tucsen) were used to record high magnification (up to 200×) differential interference contrast (DIC) images. Phosphoproteomics analysis was performed on a hybrid dual-cell quadrupole linear ion trap-Orbitrap mass spectrometer LTQ Orbitrap Elite (Thermo Fisher) with XCalibur 3.0.63 software. An 808 nm cw laser (0.7 W/cm$^2$) was used for PPTT. STORM imaging was conducted on modified Zeiss Axiovert 100 TV microscope equipping with a high sensitive back-illuminated sCOMS camera (Dhyana 95, Tucsen).

Synthesis, Conjugation and Characterization of AuNRs.

AuNRs with an average size of 25×6 nm (length×width) were synthesized using a seedless growth method according to our previous reports. Briefly, 5 ml of 1.0 mM $HAuCl_4$ was added to a solution of 5 mL of 0.2 M cetyltrimethylammonium bromide (CTAB), 250 μL of 4.0 mM $AgNO_3$, and 8 μL of 37% HCl. Then, 70 μL of 78.8 mM ascorbic acid was added, followed by immediate injection of 15 μL of 0.01M of ice-cold $NaBH_4$. The solution was left undisturbed for 12 hours. To remove extra cytotoxic CTAB, the AuNRs were centrifuged at 21000 g for 1 hour and dispersed in DI water, followed by a second centrifugation at 19000 g for 40 min. The sizes and homogeneity of the AuNRs were measured by TEM. AuNRs were then conjugated with surface ligands PEG and RGD. For first-step preparation of AuNRs@PEG, mPEG-SH (1 mM in $H_2O$) was added to the nanoparticles overnight to achieve about 1000 ligands per AuNR. Then, RGD (1 mM) was added to achieve 10000 molar excess per AuNR. The solution was allowed to shake overnight at room temperature. Excess of ligands were removed by centrifugation. UV-vis spectrometer and zetasizer were used to test the successful conjugation of the ligands.

Cell Culture, AuNR Treatments, and PPTT.

HeLa and MCF-7 cells were grown in Dulbecco's modified Eagles' medium DMEM containing 10% (v/v) fetal bovine serum and 1% antibiotic solution at 37° C. in a humidified incubator under 5% CO2. Cells were cultured for 24 hours followed by incubation with AuNRs (5 nM) for 24 hours. Then, a cw 808 nm laser (0.75 W/cm$^2$) was applied to the cells for 2 minutes.

Toxicity and Uptake of AuNRs to Cancer Cells.

In order to examine the nanoparticle cytotoxicity in cells, XTT assay was performed. The uptake of AuNRs to HeLa and MCF-7 cells was visualized under a DIC microscope. Plasmonic AuNRs can be easily discerned from the cellular features as they appeared with high DIC contrast at/near SPR wavelength.

Measuring Cell Migration Speed Upon AuNRs Treatment.

The 2D scratch assay was performed according to previous report. For measuring cell migration rate, a scratch assay will be used where cells will be cultured in a 6 well plate to form a confluent monolayer. A p200 pipet tip will be used to scrape the cell monolayer in a straight line to create an empty gap. Then the cells will be allowed for migration into the gap and imaged to track their migration rates. The cells were imaged on an inverted Nikon Eclipse Ti-E microscope using bright field microscopy. A Nikon Plan Fluor 10× objective (Numerical aperture: 0.30, working distance: 16.0 mm) and a 12 V/100 W halogen lamp as light source was used. The output power of the light source was kept constant for all the imaging experiments and the exposure time of 30 ms was used to provide optimal contrast and brightness. Images were then recorded by a sCOMS camera (Dhyana 400BSI, Tucsen).

Super-Resolution Imaging Setup:

The STORM imaging system was integrated into an inverted microscope (Zeiss Axiovert 100 TV, Jena, Germany). 405 nm and 660 nm lasers (Newport Excelsior one 405 nm, 200 mW, Irvine, Calif.; Laser Quantum Gem 660, 200 mW, Stockport, Cheshire, England) were collimated into a single light path after the beam expander (Thorlabs BE03M-A, Newton, N.J.) with 3× magnification. Collimation of multicolor lasers was done by using a dichroic mirror (Thorlabs, DMLP425T), thus allowing simultaneous illumination of the sample at multi-wavelengths. Uniblitz mechanical shutters (Vincent Associates, LS2Z2, Rochester, N.Y.) in front of each laser were used to control the illumination conditions, either pulsed or continuous illumination profiles. The collimated light was expanded by a telescope of a pair of achromatic lenses (Thorlabs, AC127-025-A & AC254-150-A) and then focused at the back focal plane of a high refractive index oil immersion objective (Olympus, 60× Oil, N.A. 1.49) using another achromatic lens (Thorlabs, AC508-300-A). The incident angle of illumination light is controlled by the lateral shift of the light path, through a three-dimensional stage (Sigma KOKI, SGSP-20-20, Tokyo, Japan), before entering the objective. A multi-edge beam splitter (Semrock, DC-405-388-543-635, Rochester, N.Y.) was used to reflect the light into the working objective to excite the sample. The emission light is collected by the same objective. After the tube lens, provided with the microscope, a pair of relay lenses (Thorlabs, AC127-125-A & AC127-150-A) was used to focus emission light onto an sCMOS chip (Tucsen, Dhyana 95) enabling a pixel size of ~110 nm. A combination of filters (Semrock, 664 nm RazorEdge long-pass edge filter (LP02-664RU-25), 658 nm StopLine single-notch filter (NF03-658E-25), 708/75 nm BrightLine single-band bandpass filter (FF01-708/75-25)) were inserted in front of the camera to reduce the background noise. Both epi-fluorescence images and STORM images were performed using the customized system.

Briefly, cells were cultured in an 8-well glass chamber (ibidi) and washed once with pre-warmed PBS buffer (Invitrogen). Cells were then fixed and permeabilized with 0.3% glutaraldehyde (Sigma) and 0.25% Triton X-100 (Sigma) in a cytoskeleton buffer containing 10 mM MES pH 6.1 (Sigma), 150 mM NaCl (Sigma), 5 mM EGTA (Sigma), 5 mM glucose (Sigma), and 5 mM $MgCl_2$ (Sigma). Freshly prepared 0.1% $NaBH_4$ (Sigma) in a PBS buffer was used to reduce the autofluorescence background generated during the cell fixation. The cells were then washed with a PBS buffer three times followed by applying a blocking buffer (3% BSA (Sigma)+0.2% Triton-X100 in PBS buffer) for 60 min. The cells were first incubated with beta-catenin primary antibody in blocking buffer over 1 h, washed three times with PBS buffer, incubated in Alexa Fluor-568 conjugated goat anti-mouse IgG (H+L) (Invitrogen) at 2 µg $mL^{-1}$ in blocking buffer over 60 min and washed three times with PBS buffer again. To label the actin, cells were stained with 0.5 µM Alexa 647-phalloidin (Invitrogen) in a PBS buffer, wrapped with aluminum foil to protect from light and incubated at 4° C. overnight. Remove the staining solution and briefly wash once with a PBS buffer. Immediately mount the sample for STORM imaging in an imaging buffer containing 100 mM Tris pH 8.0 (Invitrogen), 10 mM NaCl (Sigma), 0.5 mg/mL glucose oxidase (Sigma), 40 µg/mL catalase (Sigma), 10% (w/v) glucose (Sigma) and 1% (v/v) β-mercaptoethanol (Sigma) for STORM imaging.

STORM Imaging Data Processing.

In these experiments, an imaging sequence of 30,000-40,000 frames recorded at 60 Hz was used to reconstruct a high resolution STORM image. In each frame, individual molecules were identified and fit by an elliptical Gaussian function to determine their centroid positions, widths, intensities and ellipticities. Molecules that were too dim, too wide or too elliptical to yield high localization accuracy were eliminated in order to generate high resolution images. Furthermore, positions for those molecules that were appealing continuously in several imaging frames were determined using the weighted centroid positions in all consecutive frames. To generate the super-resolution images, molecular positions were assigned as one point and their sizes were rendered as a normalized 2D Gaussian distribution. The width of 2D rendered spot depends the localization accuracy calculated from the number of photons detected for that localization event. The reconstructed STORM images have a pixel size of 10 nm.

Sample Preparation for Phosphoproteomics Experiment.

Cells were cultured in 100 mm dishes (Corning). The cells were then harvested for MS analysis, with a final confluence about 80-90%. After AuNRs treatment for 30 min, cells were washed twice with PBS before directly adding the lysis buffer (50 mM HEPES (pH=7.4), 150 mM NaCl, 0.1% SDC, 10 units/mL benzonase, protease inhibitor cocktail and phosphatase inhibitors) to the cells followed by scraping and collecting the cell lysate on ice. Lysates were vortexed and sonicated on ice, followed by centrifugation at 18000 g for 20 min at 4° C. to remove cell debris. The proteins in the supernatant were precipitated by adding 4× excess volumes of ice-cold precipitation solvents (acetone:ethanol:acetic acid=50:50:0.1) and kept at −20° C. for overnight. The proteins were obtained after centrifugation, and were re-dissolved in 8 M urea and 50 mM HEPES (pH=8). The protein concentration was determined by Bradford assay. For mass spectrometry analysis, the disulfide bonds of proteins were firstly reduced by 1 mM dithiothreitol (DTT), followed by alkylation with 5.5 mM iodoacetamide. Then, trypsin (1:50 w/w) was used for protein digestion overnight.

Stable-isotope dimethyl labeling was performed according to previous reports. Briefly, for light, intermediate and heavy dimethyl labeling, 4 µL of $CH_2O$ (4%, v/v), $CD_2O$ (4%, v/v) or $^{13}CD_2O$ (4%, v/v) was added into 100 µg cell protein digest, respectively. Then 4 µL of freshly prepared $NaBH_3CN$ (0.6 M), $NaBH_3CN$ (0.6 M), and $NaBD_3CN$ (0.6 M) was added. The mixtures were then incubated for 1 h at room temperature for labeling reaction. For quenching the reaction, 16 µL of ammonia (1%, v/v) and 8 µL formic acid (5% v/v) were successively added.

Phosphorylation enrichment was conducted according to previous reports by using $Ti^{4+}$-IMAC microspheres after dimethyl labeling. Briefly, the microspheres were suspended in the sample loading buffer containing 80% (vol/vol) ACN and 6% (v/v) TFA, and mixed with protein digest with a ratio of 10:1 (w/w), followed by violent vibration for 30 min. After removing the supernatant by centrifugation, the microspheres were washed with washing buffer 1 (50% (v/v) ACN, 6% (v/v) TFA containing 200 mM NaCl) and washing buffer 2 (30% (v/v) ACN and 0.1% (v/v) TFA) for 20 min, respectively. Finally, the phosphopeptides were eluted by adding 10% (v/v) ammonia-water and lyophilized to powder for following analysis.

RPLC-MS/MS Analysis for Quantitative Phosphoproteomics.

LTQ-Orbitrap Elite (Thermo Scientific) coupled with Dionex UltiMate 3000 RSLCnano system (Thermo Scientific) was used for all proteomic analyses. The lyophilized phosphopeptide samples were re-dissolved in aqueous solution with 1% FA and loaded onto a 4 cm×200 µm i.d. C18 trap column packed with C18 AQ beads (5 µm, 120 Å) and separated by a 50 cm×75 µm i.d C18 (5 µm, 120 Å) capillary column kept in 50° C. with a flow rate 300 nL/min. Aqueous solution with 0.1% FA (solvent A) and 80% ACN with 0.1% FA (solvent B) were used for the reversed phase (RP) binary gradient separation, and the RP binary gradient was set as: from 0-3% solvent B in 3 min, from 3-30% solvent B in 135 min, from 30-45% solvent B in 15 min, from 45%-100% solvent B in 2 min, after flush with 100% solvent B for 11 min the whole system was equilibrated by using solvent A for 13 min. The MS full scan was acquired from m/z 350 to 1650 in an LTQ-Orbitrap Elite with a mass resolution of 60 000 at m/z 400, and the MS/MS scan was acquired in ion trap. All MS and MS/MS spectra were acquired in the data dependent analysis (DDA) mode, in which the 20 most intense ions in the MS scan were selected for MS/MS scan by collision induced dissociation (CID) with the normalized collision energy at 35%. The dynamic exclusion function was: repeat count 1, repeat duration 30 s, and exclusion duration 90 s.

Phosphoproteomics Data Processing.

MS data were processed using MaxQuant (version 1.5.3.30, www.maxquant.org) using Andromeda as search engine against the Uniprot human protein database (69712 sequences, downloaded from www.uniprot.org) with precursor mass tolerance of 4.5 ppm and fragment mass deviation of 0.5 Da. Variable modifications consisted of methionine oxidation, acetylation of protein N-term and phosphorylation (STY). Fixed modification contained cysteine carbamidomethylation. Trypsin was set as specific proteolytic enzyme. Peptides with a minimum of six amino acids and a maximum of two missed cleavages were allowed for the analysis. For peptide and protein identification, the false discovery rate (FDR) cutoffs were both set to 0.01. Triplets were selected as the quantification mode with the dimethyl Lys 0 and N-term 0 as light labels, dimethyl Lys 4 and N-term 4 as median labels and dimethyl Lys 8 and N-term 8 as heavy labels. All other parameters are the default setting in MaxQuant.

Western-Blot Analysis.

Cells were lysed in RIPA buffer (20 mM Tris pH 7.4, 150 mM NaCl, 2 mM EDTA, 2 mM EGTA, 0.1% sodium deoxycholate, 1% Triton X-100, 0.1% SDS) supplemented with protease inhibitors (Sigma-Aldrich) and phosphatase inhibitors (25 mM sodium fluoride, 10 mM sodium pyrophosphate, 50 mM β-glycerophosphate, 1 mM sodium orthovanadate). Protein concentrations were measured by BCA assay (Pierce), and equal amounts of protein were loaded on a SDS-PAGE gel. After SDS-PAGE, the resulting gels were transferred to PVDF membranes (Millipore) by Bio-Rad trans blot turbo (Bio-Rad). Afterwards, the membranes were treated with blocking buffer (5% BSA in TBS (20 mM Tris, 150 mM NaCl)). The primary antibodies p120 catenin (pS268), GSK3 (pY216), N-Cadherin, and BAX were incubated with the membranes for different sets of experiments overnight in 4° C. with shaking, followed by adding the secondary antibodies (Goat Anti-Rabbit IgG Antibody, (H+L) HRP conjugate, purchased from Millipore Sigma). Blots were washed three times for 10 m in TBS after primary and secondary antibodies.

Immunofluorescence Labeling and Confocal Microscopy.

Cells were cultured on 8 well μ-Slide with glass bottom (Ibidi). After treatment, cells were fixed in 3% Paraformaldehyde/0.1% Glutaraldehyde for 7 min at room temperature, followed by treated with 0.1% (m/v) NaBH$_4$ for 7 min and the wash three times with PBS. Cells were then blocked with 3% (w/v) BSA and 0.5% (v/v) Triton-X100 in PBS for 30 minutes at room temperature with mild shaking. Primary antibody was diluted to a working concentration in a blocking solution, and incubated at 4° C. overnight. After three times washing with PBS, secondary antibody (Goat Anti-Rabbit IgG H&L (Alexa Fluor® 568) from abcam) was added for 1 h, followed by wash 3× with PBS before mounting with Prolong Gold (Invitrogen). Images were taken with a Zeiss LSM 700-405 confocal microscopes.

Statistical Information.

Bioinformatics analysis of phosphoproteomics study was performed. Three biological replications for each condition (control, AuNRs@RGD, AuNRs@RGD+NIR) in MCF7 and HeLa cells were conducted. Raw data from phosphoproteomics was normalized using supervised normalization of the microarray (SNM). In the SNM procedure, variance due to biological replicates was adjusted by setting them as variables in the model. Variance explained by different experimental treatments (control, AuNRs@RGD, and AuNRs@RGD+NIR) was fitted as a biological variable in the model. Hierarchical clustering was done with statistical software R. Phosphoproteomics data were log 2-transformed before analysis of variance (ANOVA), which was used to detect differential phosphorylated proteins between two treatment groups (e.g., AuNRs@RGD vs. AuNRs@RGD+NIR), with treatment conditions set as fixed effects. P value threshold at 0.1 was set to select differential phosphorylated proteins. The proteins identified as being affected were subjected to pathway analysis using the MetaCore pathway analysis software ("MetaCore from Thomson Reuters"). For the other experiments in this study, two-tailed t-tests were performed and the differences between data sets were considered significant when P<0.05.

The invention claimed is:

1. A method of inhibiting cancer cell motility comprising:
   targeting a cancer cell having a pre-targeting stiffness and a pre-targeting migration coefficient with gold nanoparticles (AuNPs);
   aggregating the AuNPs on and around the membrane of the cancer cell resulting in the cancel cell having a post-aggregating stiffness and a post-aggregating migration coefficient;
   wherein the post-aggregating stiffness is greater than the pre-targeting stiffness;
   wherein the post-aggregating migration coefficient is lower than the pre-targeting migration coefficient;
   wherein the cancer cell is live and viable and part of a tumor in a subject; and
   wherein after the targeting and aggregating, the cancer cell maintains its viability.

2. The method of claim 1 further comprising conjugating only one or more Rifampicin (RF) moieties to the AuNPs.

3. The method of claim 1, wherein the AuNPs are selected from the group consisting of gold nanorods and gold nanospheres.

4. The method of claim 1, wherein the AuNPs are gold nanorods having a length dimension of from about 20 nm to about 50 nm and a width dimension of from about 3 nm to about 10 nm.

5. The method of claim 1 further comprising conjugating ligands to the AuNP.

6. The method of claim 5, wherein the ligands are targeting moieties that increase biocompatibility of the AuNPs.

7. The method of claim 5, wherein conjugating comprises conjugating ligands selected from the group consisting of Nuclear Localization Signal (NLS), Bovine Serum Albumin (BSA), Rifampicin (RF), and polyethylene glycol (PEG) to the AuNPs.

8. The method of claim 6, wherein a concentration of the targeting moieties on the AuNPs is from about 1,000 to about 50,000 moieties per particle of AuNPs.

9. The method of claim 1 further comprising irradiating the AuNPs with an irradiation source.

10. The method of claim 9, wherein irradiating comprises irradiating the AuNPs with the irradiation source for from about 30 seconds to about four minutes with the irradiation source.

11. The method of claim 9, wherein the irradiation source is a laser comprising a single emission wavelength of from about 750 nm to about 1250 nm.

12. The method of claim 9, wherein the irradiation source is an 808 nm diode laser.

13. The method of claim 9, wherein irradiating comprises irradiating the AuNPs with the irradiation source for about 1 minute.

14. The method of claim 1, wherein aggregating the AuNPs is on and around the nuclear membrane of the cancer cell; and
wherein aggregating the AuNPs increases the mechanical stiffness of the nucleus of the cancer cell.

15. The method of claim 1, wherein aggregating the AuNPs is on and around the nuclear membrane of the cancer cell; and
wherein aggregating the AuNPs results in an overexpression of lamin A/C located around the nuclear membrane.

16. The method of claim 1, wherein targeting the cancer cell with the AuNPs comprises functionalizing the AuNPs with ligands to modify the surfaces of the AuNPs.

17. The method of claim 16, wherein the functionalized AuNPs comprise methoxy-polyethylene glycol thiol, arginylglycylaspartic acid (RGD) and nuclear localization signal (NLS).

18. The method of claim 17, wherein the methoxy-polyethylene glycol thiol increases the biocompatibility of the AuNPs.

19. The method of claim 17, wherein the RGD binds to surface integrin of the cancer cell and enhances endocytosis.

20. The method of claim 17, wherein the NLS is recognized by importin and enhances accumulating the AuNPs at the nuclear membrane.

21. A method of inhibiting cancer cell motility using plasmonic photothermal therapy (PPTT) comprising:
targeting a cancer cell having a pre-targeting motility with gold nanoparticles (AuNPs);
irradiating the AuNPs with an irradiation source; and
regulating with the irradiated AuNPs one or more cytoskeletal proteins of the cancer cell having a post-regulating motility;
wherein the post-regulating motility is lower than the pre-targeting motility; and
wherein at least one of:
both a concentration of the AuNPs and the temperature of the AuNPs from irradiating are maintained below a threshold to avoid negative effects on the cancer cell viability or proliferation;
both a concentration of the AuNPs and the temperature of the AuNPs from irradiating are maintained below a threshold to avoid cancer cell apoptosis/necrosis; and
the cancer cell is live and viable and part of a tumor in a subject, and after the targeting, irradiating and regulating, the cancer cell maintains its viability.

22. The method of claim 21, wherein regulating comprises changing the cancer cell morphology.

23. The method of claim 21, wherein regulating comprises morphological changes of integrin-rich lamellipodia and filopodia of the cancer cell.

24. The method of claim 21, wherein regulating inhibits cancer cell motility by disrupting cellular contractility.

25. The method of claim 21, wherein targeting the cancer cell with the AuNPs comprises functionalizing the AuNPs with ligands to modify the surfaces of the AuNPs.

26. The method of claim 21 further comprising conjugating ligands to the AuNPs.

27. The method of claim 21, wherein the AuNPs are selected from the group consisting of gold nanorods and gold nanospheres.

28. The method of claim 21, wherein the AuNPs are gold nanorods having a length dimension of from about 20 nm to about 50 nm and a width dimension of from about 3 nm to about 10 nm.

29. The method of claim 21 further comprising conjugating only one or more Rifampicin (RF) moieties to the AuNPs.

30. The method of claim 21, wherein irradiating comprises irradiating the AuNPs with the irradiation source for from about 30 seconds to about four minutes.

31. The method of claim 21, wherein irradiating comprises irradiating the AuNPs with the irradiation source for about 1 minute.

32. The method of claim 21, wherein the irradiation source is a laser comprising a single emission wavelength of from about 750 nm to about 1250 nm.

33. The method of claim 21, wherein the irradiation source is an 808 nm diode laser.

34. The method of claim 25, wherein the ligands are targeting moieties that increase biocompatibility of the AuNPs.

35. The method of claim 25, wherein the ligands selected from the group consisting of Nuclear Localization Signal (NLS), Bovine Serum Albumin (BSA), Rifampicin (RF), and polyethylene glycol (PEG).

36. The method of claim 25, wherein the functionalized AuNPs comprise methoxy-polyethylene glycol thiol, arginylglycylaspartic acid (RGD) and nuclear localization signal (NLS).

37. The method of claim 26, wherein conjugating comprises conjugating ligands selected from the group consisting of Nuclear Localization Signal (NLS), Bovine Serum Albumin (BSA), Rifampicin (RF), and polyethylene glycol (PEG) to the AuNPs.

38. The method of claim 34, wherein a concentration of the targeting moieties on the AuNPs is from about 1,000 to about 50,000 moieties per particle of AuNPs.

39. The method of claim 36, wherein the methoxy-polyethylene glycol thiol increases the biocompatibility of the AuNPs.

40. The method of claim 36, wherein the RGD binds to surface integrin of the cancer cell and enhances endocytosis.

41. The method of claim 36, wherein the NLS is recognized by importin and enhances accumulating the AuNPs at the nuclear membrane.

42. A method of inhibiting cancer cell motility using plasmonic photothermal therapy (PPTT) comprising:
targeting a cancer cell having a pre-targeting motility with gold nanoparticles (AuNPs);
irradiating the AuNPs with an irradiation source; and
regulating with the irradiated AuNPs one or more cytoskeletal proteins of the cancer cell having a post-regulating motility;
wherein the post-regulating motility is lower than the pre-targeting motility; and
wherein both a concentration of the AuNPs and the temperature of the AuNPs from irradiating are maintained below a threshold to avoid negative effects on the cancer cell viability or proliferation.

43. The method of claim 42, wherein regulating comprises changing the cancer cell morphology.

44. The method of claim 42, wherein regulating comprises morphological changes of integrin-rich lamellipodia and filopodia of the cancer cell.

45. The method of claim 42, wherein regulating inhibits cancer cell motility by disrupting cellular contractility.

46. A method of inhibiting cancer cell motility using plasmonic photothermal therapy (PPTT) comprising:
targeting a cancer cell having a pre-targeting motility with gold nanoparticles (AuNPs);
irradiating the AuNPs with an irradiation source; and
regulating with the irradiated AuNPs one or more cytoskeletal proteins of the cancer cell having a post-regulating motility;
wherein the post-regulating motility is lower than the pre-targeting motility; and
wherein both a concentration of the AuNPs and the temperature of the AuNPs from irradiating are maintained below a threshold to avoid cancer cell apoptosis/necrosis.

47. The method of claim 46, wherein regulating comprises changing the cancer cell morphology.

48. The method of claim 46, wherein regulating comprises morphological changes of integrin-rich lamellipodia and filopodia of the cancer cell.

49. The method of claim 46, wherein regulating inhibits cancer cell motility by disrupting cellular contractility.

50. A method of inhibiting cancer cell motility using plasmonic photothermal therapy (PPTT) comprising:
targeting a cancer cell having a pre-targeting motility with gold nanoparticles (AuNPs);
irradiating the AuNPs with an irradiation source; and
regulating with the irradiated AuNPs one or more cytoskeletal proteins of the cancer cell having a post-regulating motility;
wherein the post-regulating motility is lower than the pre-targeting motility;
wherein the cancer cell is live and viable and part of a tumor in a subject; and
wherein after the targeting, irradiating and regulating, the cancer cell maintains its viability.

51. The method of claim 50, wherein regulating comprises changing the cancer cell morphology.

52. The method of claim 50, wherein regulating comprises morphological changes of integrin-rich lamellipodia and filopodia of the cancer cell.

53. The method of claim 50, wherein regulating inhibits cancer cell motility by disrupting cellular contractility.

54. The method of claim 1 further comprising:
irradiating the AuNPs with an irradiation source; and
conjugating ligands to the AuNPs;
wherein the AuNPs are gold nanorods having a length dimension of from about 20 nm to about 50 nm and a width dimension of from about 3 nm to about 10 nm;
wherein aggregating the AuNPs on and around the nuclear membrane of the cancer cell increases the mechanical stiffness of the nucleus of the cancer cell and results in an overexpression of lamin A/C located around the nuclear membrane;
wherein targeting the cancer cell with the AuNPs comprises functionalizing the AuNPs with ligands to modify the surfaces of the AuNPs;
wherein the functionalized AuNPs comprise methoxy-polyethylene glycol thiol that increases the biocompatibility of the AuNPs, arginylglycylaspartic acid (RGD) that binds to surface integrin of the cancer cell and enhances endocytosis, and nuclear localization signal (NLS) that is recognized by importin and enhances accumulating the AuNPs at the nuclear membrane;
wherein irradiating comprises irradiating the AuNPs with the irradiation source for from about 30 seconds to about four minutes; and
wherein the irradiation source is a laser comprising a single emission wavelength of from about 750 nm to about 1250 nm.

* * * * *